US008039506B2

(12) United States Patent
Wurtz et al.

(10) Patent No.: US 8,039,506 B2
(45) Date of Patent: Oct. 18, 2011

(54) BICYCLIC LACTAM FACTOR VIIA INHIBITORS USEFUL AS ANTICOAGULANTS

(75) Inventors: Nicholas Ronald Wurtz, Pennington, NJ (US); Eldon Scott Priestley, Yardley, PA (US); Daniel L. Cheney, Ringoes, NJ (US); Xiaojun Zhang, Furlong, PA (US); Brandon Parkhurst, Twin Rivers, NJ (US); Vladimir Ladziata, Ewing, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 158 days.

(21) Appl. No.: 12/519,365

(22) PCT Filed: Dec. 17, 2007

(86) PCT No.: PCT/US2007/087704
§ 371 (c)(1),
(2), (4) Date: Sep. 22, 2009

(87) PCT Pub. No.: WO2008/079759
PCT Pub. Date: Jul. 3, 2008

(65) Prior Publication Data
US 2010/0041664 A1    Feb. 18, 2010

Related U.S. Application Data

(60) Provisional application No. 60/870,867, filed on Dec. 20, 2006.

(51) Int. Cl.
*A61K 31/4035* (2006.01)
(52) U.S. Cl. .......... 514/416; 548/471; 548/472
(58) Field of Classification Search .......... 548/471, 548/472
See application file for complete search history.

(56) References Cited

U.S. PATENT DOCUMENTS

| 6,642,252 | B2 | 11/2003 | Bisacchi et al. |
| 7,122,559 | B2 | 10/2006 | Glunz et al. |
| 7,144,895 | B2 | 12/2006 | Bisacchi et al. |
| 7,456,195 | B2 | 11/2008 | Zhang et al. |
| 2006/0166997 | A1 | 7/2006 | Zhang et al. |
| 2007/0208054 | A1 | 9/2007 | Priestley et al. |
| 2009/0131473 | A1 | 5/2009 | Nirschl et al. |

FOREIGN PATENT DOCUMENTS

| WO | WO2006/076246 A | 7/2006 |
| WO | WO2007/146719 A | 12/2007 |
| WO | WO2008/079836 A | 7/2008 |

OTHER PUBLICATIONS

Carson, S.D. et al., "The role of tissue factor in the production of thrombin", Blood Coagulation and Fibrinolysis, vol. 4, pp. 281-292 (1993).
Giesen, P. et al., "Blood-borne tissue factor: Another view of thrombosis", PNAS, vol. 96, pp. 2311-2315 (1999).
Himber, J. et al., "Inhibition of tissue factor limits the growth of venous thrombus in the rabbit", J. of Thrombosis and Haemostasis, vol. 1, pp. 889-895 (2003).
Hoffman, M., "A cell-based model of coagulation and the role of factor VIIa", Blood Reviews, vol. 17, pp. S1-S5 (2003).
Kranjc A. et al., "recent Advances in the Discovery of Tissue Factor/Factor VIIA inhibitors and Dual Inhibitors of Factor VIIA/Factor XA", Current Pharmaceutical Design, vol. 11(32), pp. 4207-4227 (2005).
Lazarus, R. et al., "Inhibitors of tissue factor, Factor VIIA for Anticoagulant therapy", Current Medicinal Chemistry, vol. 11(18), pp. 2275-2290 (2004).
Morrissey, JH., "Tissue factor: in at the start . . . and the finish?", Journal of Thrombosis and Haemostasis, vol. 1 pp. 878-880 (2003).
Morrissey, JH. et al., "Quantitation of activated factor VII levels in plasma using a tissue factor mutant selectively deficient in promoting factor VII activation", Blood, vol. 81, pp. 734-744 (1993).

*Primary Examiner* — James O Wilson
*Assistant Examiner* — Brian McDowell
(74) *Attorney, Agent, or Firm* — Jing G. Sun

(57) ABSTRACT

The present invention provides novel bicyclic lactams derivatives, and analogues thereof, of Formula (I):

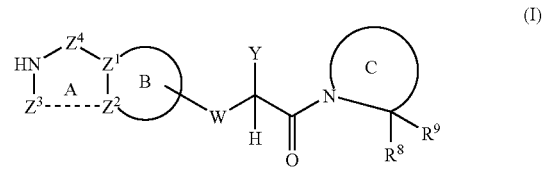

or a stereoisomer, tautomer, pharmaceutically acceptable salt, solvate, or prodrug thereof, wherein the variables A, B, C, W, Y, $Z^1$, $Z^2$, $Z^3$, $Z^4$, $R^8$, and $R^9$ are as defined herein. These compounds are selective inhibitors of factor VIIa which can be used as medicaments.

16 Claims, No Drawings

BICYCLIC LACTAM FACTOR VIIA INHIBITORS USEFUL AS ANTICOAGULANTS

CROSS-REFERENCE TO RELATED APPLICATIONS

The present application is a 371 application of PCT/US2007/087704 filed Dec. 19, 2007, which claims priority benefit of U.S. provisional application Ser. No. 60/870,867, filed Dec. 20, 2006, which is incorporated by reference herein.

FIELD OF THE INVENTION

The present invention provides novel bicyclic lactam derivatives, and analogues thereof, which are selective inhibitors of the serine protease blood coagulation factor VIIa. This invention also relates to pharmaceutical compositions comprising these compounds and methods of using the same.

BACKGROUND OF THE INVENTION

Thromboembolic diseases remain the leading cause of death in developed countries despite the availability of anticoagulants such as warfarin (Coumadin®), heparin, low molecular weight heparins (LMWH), and synthetic pentasaccharides and antiplatelet agents such as aspirin and clopidogrel (Plavix®). The oral anticoagulant warfarin, inhibits the post-translational maturation of coagulation factors VII, IX, X and prothrombin, and has proven effective in both venous and arterial thrombosis. However, its usage is limited due to its narrow therapeutic index, slow onset of therapeutic effect, numerous dietary and drug interactions, and a need for monitoring and dose adjustment. Thus discovering and developing safe and efficacious oral anticoagulants for the prevention and treatment of a wide range of thromboembolic disorders has become increasingly important.

One approach is to inhibit thrombin generation by targeting the inhibition of coagulation factor VIIa (FVIIa). Factor VII is a plasma serine protease involved in the initiation of the coagulation cascade. It is present in human blood at a concentration of approximately 500 ng/mL, with about 1% of the total amount in the proteolytically active form factor VIIa (Morrissey, J. H. et al. *Blood* 1993, 81, 734-744). Factor VIIa binds with high affinity to its cofactor, tissue factor, in the presence of calcium ions to form a complex with enhanced proteolytic activity (Carson, S. D. and Brozna, J. P. *Blood Coag. Fibrinol.* 1993, 4, 281-292). Tissue factor is normally expressed in cells surrounding the vasculature, and is exposed to factor VIIa in blood by vessel injury or atherosclerotic plaque rupture. Once formed, the tissue factor/factor VIIa complex initiates blood coagulation by proteolytic cleavage of factor X to factor Xa, factor IX to factor IXa and autoactivation of additional factor VII to VIIa. Factor Xa, generated either directly by tissue factor/factor VIIa or indirectly through action of factor IXa, catalyzes the conversion of prothrombin to thrombin. Thrombin converts fibrinogen to fibrin, which polymerizes to form the structural framework of a blood clot, and activates platelets, which are a key cellular component of coagulation (Hoffman, M. *Blood Reviews* 2003, 17, S1-S5). In addition, there is evidence that tissue factor is present in blood, likely in an encrypted, form that is de-encrypted during clot formation. (Giesen, P. L. A. et al. *Proc. Natl. Acad. Sci* 1999, 96, 2311-2315; Himber, J. et al. *J. Thromb. Haemost.* 2003, 7, 889-895). The tissue factor/factor VIIa complex derived from blood borne tissue factor may play an important role in propagation of the coagulation cascade (clot growth) and in thrombus formation in the absence of vessel wall injury (i.e., stasis induced deep vein thrombosis or sepsis). The source of blood borne tissue factor is an area of active research (Morrissey, J. H. *J. Thromb. Haemost.* 2003, 1, 878-880). Therefore, factor VIIa plays a key role in propagating this amplification loop and is thus an attractive target for antithrombotic therapy.

SUMMARY OF THE INVENTION

The present invention provides bicyclic lactam derivatives, and analogues thereof, which are useful as selective inhibitors of factor VIIa, including stereoisomers, tautomers, pharmaceutically acceptable salts, solvates, or prodrugs thereof.

The present invention also provides processes and intermediates for making the compounds of the present invention or stereoisomers, tautomers, pharmaceutically acceptable salts, solvates, or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for the treatment or prophylaxis of a thromboembolic disorder comprising administering to a patient in need of such treatment or prophylaxis a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment or prophylaxis of a thromboembolic disorder.

These and other features of the invention will be set forth in the expanded form as the disclosure continues.

DETAILED DESCRIPTION OF THE INVENTION

In a first aspect, the present invention provides, inter alia, a compound of Formula (I):

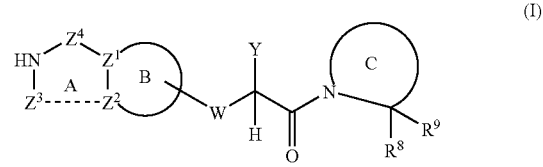

or stereoisomers, tautomers, pharmaceutically acceptable salts, solvates, or prodrugs thereof, wherein:

$Z^1$ is C or N;
$Z^2$ is C or N;
provided that when $Z^1$ is N, then $Z^2$ is C; or $Z^2$ is N, then $Z^1$ is C;
for the definition of $Z^3$, as they are written from left to right, the atom connectivity is in the order —NH-$Z^3$-$Z^2$-;
$Z^3$ is —$CR^{11}R^{11}$—, —$NR^{12}$—, —O—, —$S(O)_p$—, —C(=NH)—, —$CR^{11}CR^{11}$—, —$CR^{11}R^{11}CR^{11}R^{11}$—, —CR$^{11}$═N—, —C(O)NR$^{12}$, —CR$^{11}$R$^{11}$NR$^{12}$—, NR$^{12}$CR$^{11}$R$^{11}$—, C(O)CR$^{11}$R$^{11}$—, —CR$^{11}$R$^{11}$C(O)—, —C(O)C(O)—, —SO$_2$—, —SO$_2$CR$^{11}$R$^{11}$—, —CR$^{11}$R$^{11}$SO$_2$—, —CR$^{11}$R$^{11}$CR$^{11}$R$^{11}$CR$^{11}$R$^{11}$—,
—CR$^{11}$═CR$^{11}$CR$^{11}$R$^{11}$—, —CR$^{11}$R$^{11}$CR$^{11}$═CR$^{11}$—, —N═CR$^{11}$CR$^{11}$R$^{11}$—, —CR$^{11}$R$^{11}$CR$^{11}$═N—, —CR$^{11}$R$^{11}$CR$^{11}$O—, —NR$^{12}$CR$^{11}$R$^{11}$CR$^{11}$R$^{11}$—, —CR$^{11}$R$^{11}$CR$^{11}$R$^{11}$NR$^{12}$—, —C(O)CR$^{11}$R$^{11}$CR$^{11}$R$^{11}$—, —CR$^{11}$R$^{11}$C(O)CR$^{11}$R$^{11}$—, CR$^{11}$R$^{11}$CR$^{11}$R$^{11}$C(O)—, CR$^{11}$═CR$^{11}$C(O)—, —C(O)CR$^{11}$═CR$^{11}$—, —N═CR$^{11}$C(O)—, —C(O)CR$^{11}$═N—, —C(O)CR$^{11}$R$^{11}$O—, —NR$^{12}$C(O)CR$^{11}$R$^{11}$—, —CR$^{11}$R$^{11}$C(O)NR$^{12}$—, —NR$^{12}$CR$^{11}$R$^{11}$C(O)—, —C(O)CR$^{11}$R$^{11}$NR$^{12}$—, —C(O)NR$^{12}$CR$^{11}$R$^{11}$, —SO$_2$CR$^{11}$R$^{11}$CR$^{11}$R$^{11}$—, —CR$^{11}$R$^{11}$SO$_2$CR$^{11}$R$^{11}$—, —CR$^{11}$R$^{11}$CR$^{11}$R$^{11}$SO$_2$—, —CR$^{11}$═CR$^{11}$SO$_2$—, —SO$_2$CR$^{11}$═CR$^{11}$—, —N═CR$^{11}$SO$_2$—, —SO$_2$CR$^{11}$═N—, —SO$_2$CR$^{11}$R$^{11}$O—, —NR$^{12}$SO$_2$CR$^{11}$R$^{11}$—, —CR$^{11}$R$^{11}$SO$_2$NR$^{12}$—, —NR$^{12}$CR$^{11}$R$^{11}$SO$_2$—, —SO$_2$CR$^{11}$R$^{11}$NR$^{12}$—, or —SO$_2$—NR$^{12}$CR$^{11}$R$^{11}$—;

$Z^4$ is C(O), CR$^{13}$R$^{13}$ or SO$_2$;

ring B, including the two atoms $Z^1$ and $Z^2$ which are fused to ring A, is phenyl substituted with 0-3 R$^6$ or a 5-6 membered heteroaryl consisting of: carbon atoms and 1-4 heteroatoms selected from the group consisting of N, O, and S, wherein said heteroaryl is substituted with 0-2 R$^6$;

ring C is a 4- to 8-membered heterocycle comprising: the nitrogen atom shown in the ring, carbon atoms and 0-1 additional heteroatom selected from n, NR$^c$, O, and S(O)$_p$, 0-1 carbonyl, and 0-2 double bonds, wherein said heterocycle is substituted with 0-2 R$^7$;

W is NR$^j$, O or S;

Y is selected from:

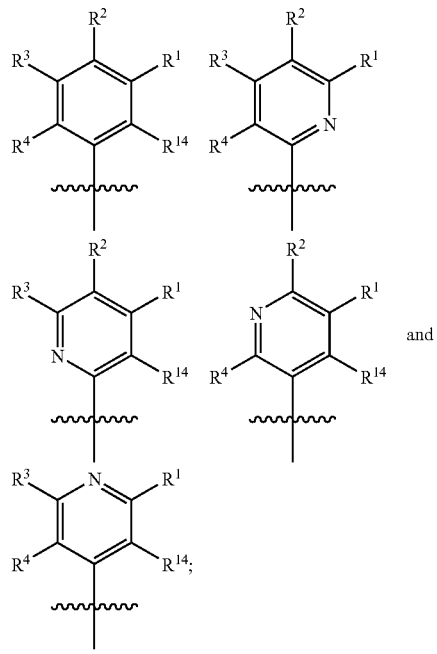

R$^1$ is, independently at each occurrence, H, F, Cl, Br, I, C$_{1-5}$alkyl substituted with 0-1 OH, C$_{1-5}$ haloalkyl, C$_{2-5}$ alkenyl, C$_{2-5}$ alkynyl, —O—C$_{1-5}$ alkyl, —O—C$_{1-5}$ haloalkyl, —S—C$_{1-5}$ alkyl, or C$_{3-6}$ cycloalkyl;

R$^2$, R$^3$ and R$^4$ are, independently at each occurrence, H, F, Cl, Br, I, —(CH$_2$)$_s$OR$^a$, —(CH$_2$)$_s$SR$^b$, —(CH$_2$)$_s$CF$_3$, —(CH$_2$)$_s$OCF$_3$, —(CH$_2$)$_s$OCHF$_2$, —(CH$_2$)$_s$OCH$_2$F, —(CH$_2$)$_s$CN, —(CH$_2$)$_s$NO$_2$, (CH$_2$)$_s$NR$^b$R$^c$, (CH$_2$)$_s$C(O)R$^a$, (CH$_2$)$_s$CO$_2$R$^a$, —(CH$_2$)$_s$NR$^d$C(O)R$^a$, —(CH$_2$)$_s$C(O)NR$^c$R$^d$, —(CH$_2$)$_s$NR$^c$C(O)OR$^a$, —(CH$_2$)$_s$OC(O)R$^a$, (CH$_2$)$_s$OC(O)OR$^a$, —(CH$_2$)$_s$NR$^c$C(O)NR$^c$R$^d$, —(CH$_2$)$_s$OC(O)NR$^c$R$^d$, —(CH$_2$)$_s$SO$_2$NR$^c$R$^d$, —(CH$_2$)$_s$NR$^c$SO$_2$NR$^c$R$^d$, —(CH$_2$)$_s$NR$^c$SO$_2$R$^i$, —(CH$_2$)$_s$NR$^c$SO$_2$CF$_3$, —(CH$_2$)$_s$SO$_2$CF$_3$, —(CH$_2$)$_s$S(O)$_p$R$^i$, —O(CH$_2$)$_n$CO$_2$R$^a$, —(CH$_2$)$_s$SO$_2$NHCOR$^a$, —(CH$_2$)$_s$CONHSO$_2$R$^i$, —(CF$_2$)$_r$CF$_3$), C$_{1-6}$ alkyl substituted with 0-2 R$^e$, C$_{1-4}$ haloalkyl, C$_{2-6}$ alkenyl substituted with 0-2 R$^e$, C$_{2-6}$alkynyl substituted with 0-2 R$^e$, —O(benzyl substituted with CO$_2$R$^a$), —(CH$_2$)$_s$C$_{3-10}$ carbocycle substituted with 0-3 R$^f$; —(CH$_2$)$_s$-(5- to 10-membered heterocycle), comprising: carbon atoms and 1-4 heteroatoms selected from N, NR$^c$, O, and S(O)$_p$, wherein said heterocycle is substituted with 0-3 R$^f$;

alternatively, R$^2$ and R$^3$ may combine to form a 5- to 7-membered carbocycle or heterocycle comprising: carbon atoms and 0-4 heteroatoms selected from N, NR$^c$, O, and S(O)$_p$, wherein said carbocycle and heterocycle are substituted with 0-3 R$^f$;

alternatively, R$^3$ and R$^4$ may combine to form a 5- to 7-membered carbocycle or heterocycle comprising: carbon atoms and 0-4 heteroatoms selected from N, NR$^c$, O, and S(O)$_p$, wherein said carbocycle and heterocycle are substituted with 0-3 R$^f$;

R$^6$ is, independently at each occurrence, F, Cl, Br, I, CN, OH, CF$_3$, C$_{1-4}$ alkyl, C$_{1-4}$ haloalkyl, C$_{1-4}$ alkoxy, or C$_{3-6}$ cycloalkyl;

R$^7$ is, independently at each occurrence, F, Cl, Br, I, —(CH$_2$)$_r$OR$^a$, —(CH$_2$)$_r$SR$^b$, —(CH$_2$)$_r$CF$_3$, —(CH$_2$)$_s$OCF$_3$, —(CH$_2$)$_r$OCHF$_2$, —(CH$_2$)$_r$OCH$_2$F, —(CH$_2$)$_s$CN, —(CH$_2$)$_s$NO$_2$, —(CH$_2$)$_r$NR$^b$R$^c$, (CH$_2$)$_s$C(O)R$^a$, (CH$_2$)$_s$CO$_2$R$^a$, —(CH$_2$)$_r$NR$^d$C(O)R$^a$, —(CH$_2$)$_s$C(O)NR$^c$R$^d$, —SO$_2$NR$^c$R$^d$, —NR$^c$SO$_2$R$^i$, —(CH$_2$)$_r$NR$^c$C(O)OR$^b$, —(CH$_2$)$_r$OC(O)OR$^b$, (CH$_2$)$_r$NR$^c$C(O)NR$^c$R$^d$, —(CH$_2$)$_r$OC(O)NR$^c$R$^d$, —(CH$_2$)$_r$SO$_2$NR$^c$R$^d$, —(CH$_2$)$_r$NR$^c$SO$_2$NR$^c$R$^d$, —(CH$_2$)$_r$NR$^c$SO$_2$R$^b$, —(CH$_2$)$_r$NR$^c$SO$_2$CF$_3$, —(CH$_2$)$_r$SO$_2$CF$_3$, —(CH$_2$)$_r$S(O)$_2$R$^b$, —SO$_2$NHC(O)R$^b$, —C(O)NHSO$_2$R$^b$, —NR$^c$SO$_2$CF$_3$, —SO$_2$CF$_3$, —S(O)$_p$R$^i$, —(CF$_2$)$_r$CF$_3$, tetrazole, —(CH$_2$)$_r$-phenyl substituted with 0-3 R$^f$ or —(CH$_2$)$_r$-5- to 6-membered heterocycle comprising: carbon atoms and 1-4 heteroatoms selected from N, NR$^c$, O, and S(O)$_p$, wherein said heterocycle is substituted, with 0-3 R$^f$;

R$^8$ is H, CN, —CO$_2$R$^a$ —C(O)NR$^c$R$^d$, tetrazolyl, or C$_{1-4}$ alkyl substituted with 0-2 R$^{8a}$;

R$^{8a}$ is, independently at each occurrence, ═O, OR$^a$, F, Cl, Br, I, CN, NO$_2$, SR$^b$, CF$_3$, OCF$_3$, —OCHF$_2$, —OCH$_2$F, NR$^b$R$^c$, —C(O)R$^a$, —CO$_2$R$^a$, —OC(O)R$^a$, —OC(O)NR$^c$R$^d$, —NR$^d$C(O)R$^a$, —C(O)NR$^c$R$^d$, —NR$^c$C(O)NR$^c$R$^d$, —NR$^c$C(O)OR$^b$, —SO$_2$NR$^c$R$^d$, —NR$^c$SO$_2$R$^i$, —NR$^c$SO$_2$NR$^c$R$^d$, —SO$_2$NHC(O)R$^b$, —C(O)NHSO$_2$R$^b$, —NR$^c$SO$_2$CF$_3$, —SO$_2$CF$_3$, —S(O)$_p$R$^i$, —O(CH$_2$)$_n$CO$_2$R$^a$, —(CF$_2$)$_r$CF$_3$, tetrazole, C$_{3-6}$cycloalkyl substituted with 0-3 R$^f$, phenyl substituted with 0-3 R$^f$, or 5 to 6-membered heterocycle comprising: carbon atoms and 1-4 heteroatoms selected from N, NR$^c$, O, and S(O)$_p$, wherein said heterocycle is substituted with 0-3 R$^f$;

R$^9$ is phenyl or pyridyl substituted with 1-3 R$^{10}$;

R$^{10}$ is, independently at each occurrence, F, Cl, Br, I, —(CH$_2$)$_r$OR$^a$, —(CH$_2$)$_r$SR$^b$, —(CH$_2$)$_s$CF$_3$, —(CH$_2$)$_s$OCF$_3$, —(CH$_2$)$_s$OCHF$_2$, —(CH$_2$)$_s$OCH$_2$F, (CH$_2$)$_s$CN, —(CH$_2$)$_s$NO$_2$, —(CH$_2$)$_s$SCF$_3$, —(CH$_2$)$_s$NR$^b$R$^c$, —(CH$_2$)$_s$C(O)R$^a$, —(CH$_2$)$_s$CO$_2$R$^a$, —(CH$_2$)$_s$NR$^c$CO$_2$R$^a$, —(CH$_2$)$_s$NR$^d$C(O)R$^a$, —(CH$_2$)$_s$C(O)NR$^c$R$^d$, —(CH$_2$)$_s$NR$^c$C(O)OR$^b$, —(CH$_2$)$_s$OC(O)OR$^b$, —(CH$_2$)$_s$NR$^c$C(O)NR$^c$R$^d$, —(CH$_2$)$_s$SO$_2$NR$^c$R$^d$ —(CH$_2$)$_s$OSO$_2$NR$^c$R$^d$, —(CH$_2$)$_s$NR$^c$SO$_2$NR$^c$R$^d$, —(CH$_2$)$_s$NR$^c$SO$_2$R$^i$; —(CH$_2$)$_s$NR$^c$SO$_2$CF$_3$, —(CH$_2$)$_s$SO$_2$CF$_3$, —(CH$_2$)$_s$S(O)$_p$R$^i$, (CF$_2$)$_r$CF$_3$, C$_{1-6}$ alkyl substituted with 0-2 R$^e$, haloalkyl, C$_{2-6}$ alkenyl substituted, with 0-2 R$^e$, C$_{2-6}$ alkynyl substituted with 0-2 R$^e$, —(CH$_2$)$_r$—C$_{3-10}$ carbocycle substituted with 0-3 R$^f$, or —(CH$_2$)$_r$-5- to 10-membered heterocycle comprising: carbon atoms and 1-4 heteroatoms selected from N, NR$^c$, O, and S(O)$_p$, wherein said heterocycle are substituted with 0-3 R$^f$;

R$^{11}$ is, independently at each occurrence, H, F, Cl, Br, I, CF$_3$, OCF$_3$, OCHF$_2$, OCH$_2$F, CN, C$_{1-4}$ alkyl, C$_{1-4}$ alkoxy, C$_{1-4}$ haloalkyl, C$_{2-4}$ alkenyl, C$_{2-4}$ alkynyl, or C$_{3-6}$ cycloalkyl;

R$^{12}$ is, independently at each occurrence, H, C$_{1-4}$ alkyl, C$_{2-4}$ alkenyl, or C$_{2-4}$ alkynyl;

R$^{13}$ is, independently at each occurrence, H, CF$_3$, CN, —C(O)R$^a$, —CO$_2$R$^a$, —C(O)NR$^c$R$^d$, C$_{1-6}$ alkyl substituted with 0-2 R$^e$, C$_{1-4}$ haloalkyl, C$_{2-4}$ alkenyl substituted with 0-2 R$^e$, C$_{2-4}$ alkynyl substituted with 0-2 R$^e$, —(CH$_2$)$_s$—C$_{3-6}$ carbocycle substituted with 0-2 R$^f$, —(CH$_2$)$_s$-(5- to 6-membered heterocycle), —NR$^c$(5- to 6-membered heterocycle), or —O-(5- to 6-membered heterocycle); wherein said heterocycle comprises carbon atoms and 1-3 heteroatoms selected from N, NR$^c$, O, and S(O)$_p$ and is substituted with 0-2 R$^f$;

R$^{14}$ is, independently at each occurrence, H, F, Cl, Me, Et, or OMe;

R$^a$ is, independently at each occurrence, H, C$_{1-6}$ alkyl substituted with 0-4 R$^h$, fluoroalkyl, —(CH$_2$)$_r$—C$_{3-7}$ carbocycle substituted with 0-4 R$^f$, or (CH$_2$)$_r$-5- to 10-membered heterocycle comprising: carbon atoms and 1-4 heteroatoms selected from N, NR$^g$, O, and S(O)$_p$, wherein said heterocycle is substituted with 0-4 R$^f$;

R$^b$ is, independently at each occurrence, H, C$_{1-6}$ alkyl, fluoroalkyl, —(CH$_2$)$_n$-phenyl, (C$_{1-6}$ alkyl)C(O)—, (C$_{3-6}$ cycloalkyl)-C$_{0-4}$ alkyl-C(O)—, (C$_{6-10}$ aryl)-(C$_{0-4}$ alkyl)-C(O)—, (5- to 10-membered heteroaryl)-C$_{0-4}$ alkyl-C(O)—, (C$_{1-6}$ alkyl)-NHC(O)—, (C$_{1-6}$ alkyl)$_2$-NHC(O)—, (C$_{6-10}$ aryl)-C$_{0-4}$ alkyl-NHC(O)—, (5- to 10-membered heteroaryl)-C$_{0-4}$ alkyl-NHC(O)—, (C$_{1-6}$ alkyl)-SO$_2$—, (C$_{6-10}$ aryl)-C$_{0-4}$ alkyl-SO$_2$—, or (5- to 10-membered heteroaryl)-C$_{0-4}$ alkyl-SO$_2$—, wherein said, phenyl, aryl and heteroaryl are substituted with 0-2 R$^f$;

R$^c$ is, independently at each occurrence, H, C$_{1-6}$ alkyl substituted with 0-3 R$^h$, fluoroalkyl, —(CH$_2$)$_n$—C$_{3-7}$ cycloalkyl substituted with 0-3 R$^h$, or —(CH$_2$)$_n$-phenyl substituted with 0-3 R$^h$;

alternatively, R$^b$ and R$^c$, when attached to the same nitrogen atom, may be taken together with the nitrogen atom to form a 4- to 10-membered heterocycle comprising: carbon atoms and 1-4 heteroatoms selected from N, NR$^g$, O, and S(O)$_p$, wherein heterocycle are substituted with 0-3 R$^f$;

R$^d$ is, independently at each occurrence, H, C$_{1-6}$ alkyl, fluoroalkyl, —(CH$_2$)$_r$—C$_{3-10}$ carbocycle substituted, with 0-3 R$^f$, or a —(CH$_2$)$_r$-5- to 12-membered heterocycle comprising: carbon atoms and 1-4 heteroatoms selected from N, NR$^g$, O, and S(O)$_p$, wherein said, heterocycle is substituted with 0-3 R$^f$;

alternatively, R$^c$ and R$^d$, when attached to the same nitrogen atom, may be taken together with the nitrogen atom to form a 4- to 10-membered heterocycle comprising: carbon atoms and 1-4 heteroatoms selected from N, NR$^g$, O, and S(O)$_p$, wherein heterocycle are substituted with 0-3 R$^f$;

R$^e$ is, independently at each occurrence, =O, OR$^a$, F, Cl, Br, I, CN, NO$_2$, —SR$^a$, —OCF$_3$, —NR$^b$R$^c$, —C(O)R$^a$, —CO$_2$R$^a$, —NR$^d$C(O)R$^a$, —C(O)NR$^c$R$^d$, —OC(O)R$^a$, —NR$^d$C(O)OR$^a$, —NR$^d$C(O)NR$^c$R$^d$, —OC(O)NR$^c$R$^d$, —SO$_2$NR$^c$R$^d$, —NC(O)OR$^a$, —NR$^c$SO$_2$NR$^c$R$^d$, NR$^c$SO$_2$R$^i$, —CONHSO$_2$R$^i$, —CH$_2$CONHSO$_2$R$^i$, —NR$^c$SO$_2$CF$_3$, —SO$_2$CF$_3$, —S(O)$_p$R$^i$, —(CF$_2$)$_r$CF$_3$, C$_{3-10}$ carbocycle substituted with 0-3 R$^f$, or a 5- to 12-membered heterocycle comprising: carbon atoms and 1-4 heteroatoms selected from N, NR$^g$, O, and S(O)$_p$, wherein said heterocycle is substituted with 0-3 R$^f$;

R$^f$ is, independently at each occurrence, =O, OR$^g$, F, Cl, Br, I, CN, NO$_2$, —SR$^g$, —OCF$_3$, —NR$^c$R$^c$, —C(O)R$^g$, —CO$_2$R$^g$, —NR$^c$C(O)R$^g$, —C(O)NR$^c$R$^c$, —OC(O)R$^g$, —NR$^c$C(O)ORS, —NR$^c$C(O)NR$^c$R$^c$, —OC(O)NR$^c$R$^c$, —SO$_2$NR$^c$R$^c$, —NR$^c$SO$_2$NR$^c$R$^c$, —NR$^c$SO$_2$R$^i$, —CONHSO$_2$R$^i$, —CH$_2$CONHSO$_2$R$^i$, —NR$^c$SO$_2$CF$_3$, —SO$_2$CF$_3$, —S(O)$_p$R$^i$, —(CF$_2$)$_r$CF$_3$, C$_{1-6}$ alkyl, C$_{2-6}$ alkenyl, C$_{2-6}$ alkynyl, C$_{3-10}$ carbocycle substituted with 0-3 R$^h$, or a 5- to 12-membered heterocycle comprising: carbon atoms and 1-4 heteroatoms selected from N, NR$^g$, O, and S(O)$_p$, and substituted with 0-3 R$^h$;

R$^g$ is, independently at each occurrence, H, C$_{1-6}$ alkyl, or —(CH$_2$)$_n$-phenyl;

R$^h$ is, independently at each occurrence, =O, —(CH$_2$)$_r$OR$^g$, F, Cl, Br, I, CN, NO$_2$, —OCF$_3$, —NR$^g$R$^g$, —C(O)R$^g$, —CO$_2$R$^g$, —NR$^g$C(O)R$^g$, —C(O)NR$^g$R$^g$, —SO$_2$NR$^g$R$^g$, —NR$^g$SO$_2$NR$^g$R$^g$, —NR$^g$SO$_2$—C$_{1-4}$ alkyl, —NR$^g$SO$_2$CF$_3$, —NR$^g$SO$_2$-phenyl, —SO$_2$CF$_3$, —S(O)$_p$—C$_{1-4}$ alkyl, —S(O)$_p$-phenyl, (CF$_2$)$_r$CF$_3$, C$_{1-6}$ alkyl, C$_{2-6}$ alkenyl, C$_{2-6}$ alkynyl, (C$_{1-6}$ alkyl)C(O)—, (C$_{3-6}$ cycloalkyl)-C$_{0-4}$ alkyl-C(O)—, (C$_{6-10}$ aryl)-(C$_{0-4}$ alkyl)-C(O)—, (5-10 membered heteroaryl)-C$_{0-4}$ alkyl-C(O)—, C$_{1-6}$ alkyl)-NHC(O)—, (C$_{1-6}$ alkyl)$_2$-NHC(O)—, (C$_{6-10}$ aryl)-C$_{0-4}$ alkyl-NHC(O)—, (5-10 membered heteroaryl)-C$_{0-4}$ alkyl-NHC(O)—, (C$_{1-6}$ alkyl)-SO$_2$—, (C$_{6-10}$ aryl)-C$_{0-4}$ alkyl-SO$_2$—, (5-10 membered heteroaryl)-C$_{0-4}$ alkyl-SO$_2$—, —(CH$_2$)$_r$C$_{3-10}$ carbocycle, or a (CH$_2$)$_r$-5- to 12-membered heterocycle comprising: carbon atoms and 1-4 heteroatoms selected from N, NR$^g$, O, and S(O)$_p$;

R$^i$ is, independently at each occurrence, H, C$_{1-6}$ alkyl substituted with 0-3 R$^h$, C$_{3-6}$ cycloalkyl substituted with 0-3 R$^h$, —(CH$_2$)$_n$-phenyl substituted with 0-3 R$^h$, —(CH$_2$)$_r$-5- to 10-membered heterocycle comprising: carbon atoms and 1-4 heteroatoms selected from N, NR$^g$, O, and S(O)$_p$, wherein said heterocycle is substituted with 0-3 R$^h$;

R$^j$ is, independently at each occurrence, H or C$_{1-3}$ alkyl;
n, at each occurrence, is selected from 0, 1, 2, 3, and 4;
p, at each occurrence, is selected from 0, 1, and 2;
r, at each occurrence, is selected from 0, 1, 2, 3, and 4; and
s, at each occurrence, is selected from 0, 1, and 2.

In a second aspect, the present invention includes the compounds of Formula (I) or stereoisomers, tautomers, pharmaceutically acceptable salts, solvates, or prodrugs thereof, within the scope of the first aspect wherein:

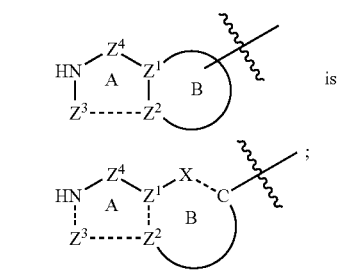

wherein X is selected from CR$^6$, S, O and N when Z$^1$=C; alternately, X is CR$^6$ when Z$^1$=N.

In a third aspect, the present invention includes the compounds of Formula (I) or stereoisomers, tautomers, pharmaceutically acceptable salts, solvates, or prodrugs thereof, within the scope of the first aspect wherein:

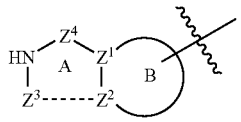

is selected from:

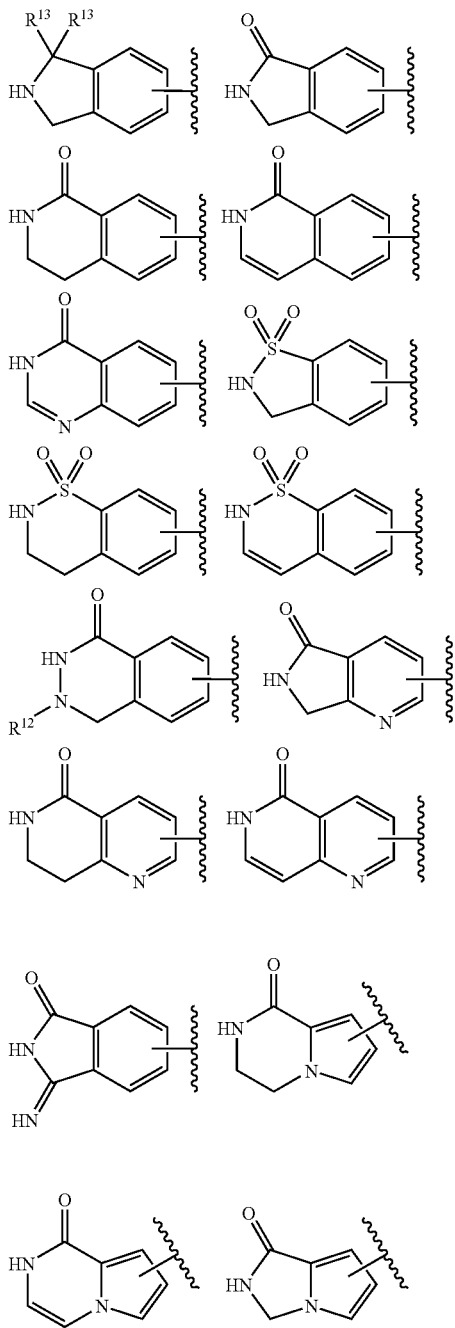

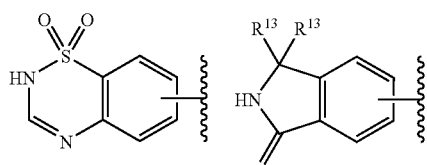
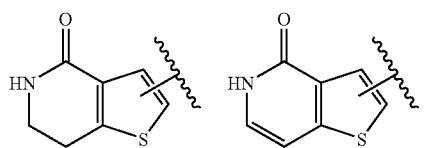
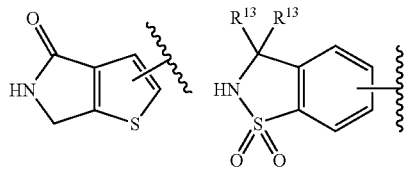
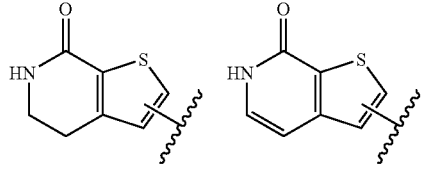
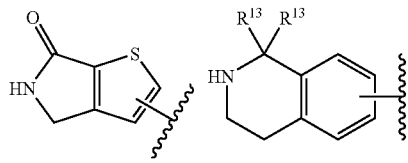
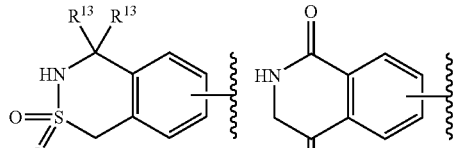
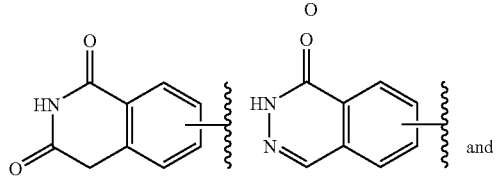
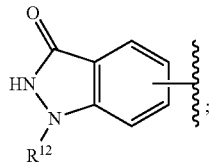

;

wherein ring A is substituted with 0-2 $R^{11}$; and ring B is substituted with 0-2 $R^6$;

ring C is a 5- or 6-membered heterocycle comprising: the nitrogen atom shown in the ring, carbon atoms and 0-1 additional heteroatom selected from N, $NR^c$, O, and $S(O)_p$, wherein said heterocycle is substituted with 0-2 $R^7$;

W is NH or O; and $R^1$ is, independently at each occurrence, H, F, Cl, Br, $C_{1-3}$ alkyl substituted with 0-1 OH, $C_{1-3}$ haloalkyl, $C_{2-3}$ alkenyl, $C_{2-3}$ alkynyl, —O—$C_{1-3}$ alkyl, or $C_{3-5}$ cycloalkyl.

In a fourth aspect, the present invention includes a compound of Formula (II):
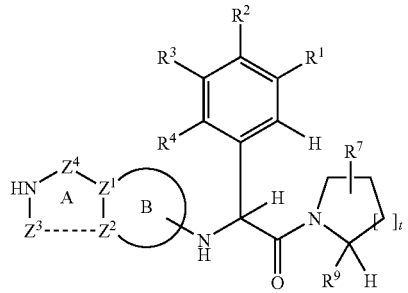
(II)
or stereoisomers, tautomers, pharmaceutically acceptable salts, solvates, or prodrugs thereof, wherein:
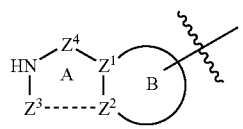
is selected from:
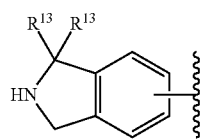 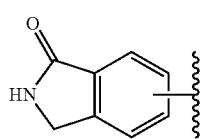
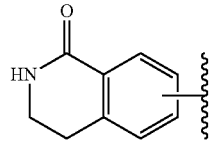 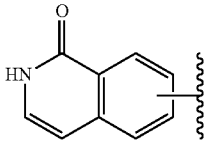
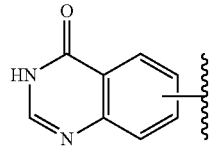 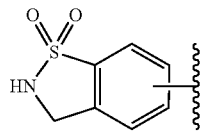
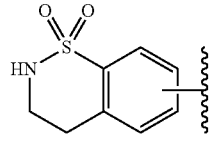 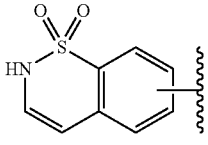
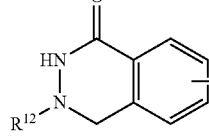 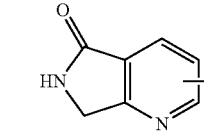
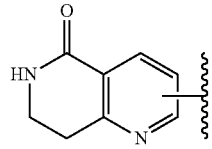 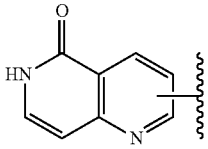
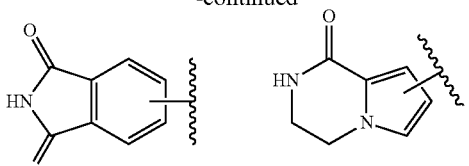
-continued
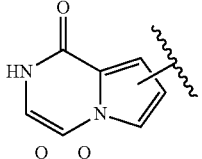 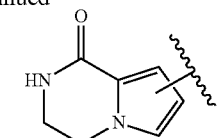
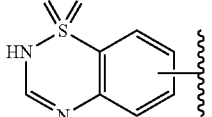 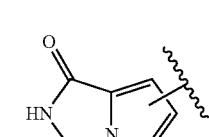
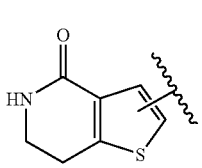 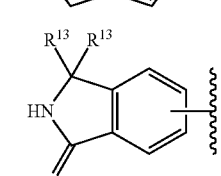
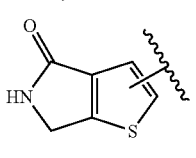 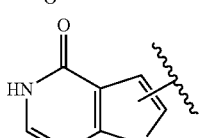
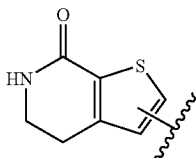 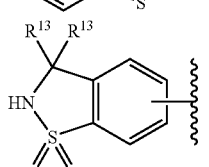
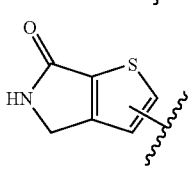 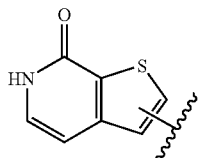
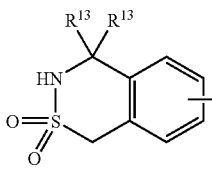 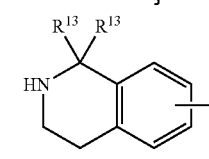
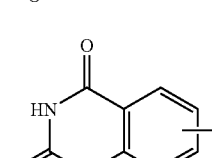 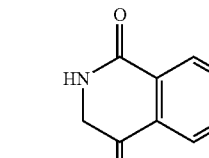
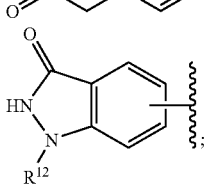 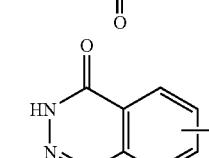
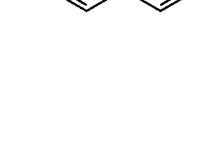
and
;
wherein ring A is substituted with 0-2 $R^{11}$; and ring B is substituted with 0-2 $R^6$;

$R^1$ is H, F, Cl, Br, $C_{1-2}$ alkyl substituted with 0-1 OH, $C_{1-2}$ haloalkyl, $C_{2-3}$ alkenyl, $C_{2-3}$ alkynyl, —O—$C_{1-2}$ alkyl, or $C_{3-5}$ cycloalkyl;

$R^2$, $R^3$ and $R^4$ are, independently at each occurrence, H, F, Cl, Br, I, $OR^a$, $SR^a$, $OCF_3$, $OCHF_2$, $OCH_2F$, CN, $NO_2$, —$NR^bR^c$, —$C(O)R^a$, —$CO_2R^a$, —$NR^dC(O)R^a$, —$C(O)NR^cR^d$, —$NR^cC(O)OR^a$, —$NR^cC(O)NR^cR^d$, —$SO_2NR^cR^d$, —$NR^cSO_2NR^cR^d$, $NR^cSO_2R^i$, —$NR^cSO_2CF_3$, —$SO_2CF_3$, —$S(O)_pR^i$, —$(CF_2)_rCF_3$, $C_{1-6}$ alkyl substituted with 0-2 $R^e$, $C_{1-4}$ haloalkyl, $C_{2-6}$ alkenyl substituted with 0-2 $R^e$, $C_{2-6}$ alkynyl substituted with 0-2 $R^e$, $C_{3-10}$ carbocycle substituted with 0-3 $R^f$, or a 5- to 10-membered heterocycle comprising: carbon atoms and 1-4 heteroatoms selected from N, $NR^c$, O, and $S(O)_p$, wherein said heterocycle are substituted with 0-3 $R^f$;

alternatively, $R^2$ and $R^3$ may combine to form a 5- to 7-membered carbocycle or heterocycle comprising: carbon atoms and 0-4 heteroatoms selected from N, $NR^c$, O, and $S(O)_p$, wherein said carbocycle and heterocycle are substituted with 0-3 $R^f$;

alternatively, $R^3$ and $R^4$ may combine to form a 5- to 7-membered carbocycle or heterocycle comprising: carbon atoms and 0-4 heteroatoms selected from N, $NR^c$, O, and $S(O)_p$, wherein said carbocycle and heterocycle are substituted with 0-3 $R^f$;

$R^6$ is, independently at each occurrence, F, Cl, OH, $CF_3$, $C_{1-2}$ alkyl, or $C_{1-2}$ alkoxy;

$R^7$ is, independently at each occurrence, $OR^a$, F, Cl, Br, I, CN, $NO_2$, —$OCF_3$, —$NR^bR^c$, —$C(O)R^a$, —$CO_2R^a$, —$NR^dC(O)R^a$, —$C(O)NR^cR^d$, —$SO_2NR^cR^d$, —$NR^cSO_2R^i$, —$SO_2NHC(O)R^b$ —$C(O)NHSO_2R^b$, —$NR^cSO_2CF_3$, —$SO_2CF_3$, —$S(O)_pR^i$, —$(CF_2)_rCF_3)$ tetrazole, —$(CH_2)_r$-phenyl substituted with 0-3 $R^f$, or a —$(CH_2)_r$-5- to 6-membered heterocycle comprising: carbon atoms and 1-4 heteroatoms selected from N, $NR^c$, O, and $S(O)_p$, wherein said heterocycle is substituted with 0-3 $R^f$;

$R^9$ is selected from:

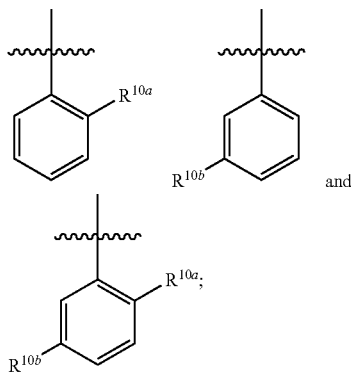

and $R^{10a}$ and $R^{10b}$ are, independently at each occurrence, H, F, Cl, Br, I, —$(CH_2)_rOR^a$, —$(CH_2)_rSR^a$, $OCF_3$, $SCF_3$, CN, $NO_2$, —$(CH_2)_r$—$NR^bR^c$, —$C(O)R^a$, —$(CH_2)_rCO_2R^a$, —$(CH_2)_r$—$NR^cCO_2R^a$, —$NR^dC(O)R^a$, —$(CH_2)_rC(O)NR^cR^d$, —$NR^cC(O)NR^cR^d$, $SO_2NR^cR^d$, —$OSO_2NR^cR^d$ —$NR^cSO_2NR^cR^d$, —$NR^cSO_2R^i$, —$NR^cSO_2CF_3$, —$SO_2CF_3$, —$S(O)_pR^i$, —$(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, —$(CH_2)_rC_{3-10}$ carbocycle substituted with 0-3 $R^f$, or —$(CH_2)_r$-5- to 10-membered heterocycle comprising: carbon atoms and 1-4 heteroatoms selected from N, $NR^c$, O, and $S(O)_p$, wherein said heterocycle are substituted with 0-3 $R^f$;

t is selected from 1 and 2; and $R^{11}$, $R^{12}$, $R^{13}$, $R^a$, $R^b$, $R^c$, $R^d$, $R^e$, $R^f$, $R^g$, $R^h$, $R^i$, n, p, and r are each the same as defined in the first aspect.

In a fifth aspect, the present invention includes a compound of Formula (II) or stereoisomers, tautomers, pharmaceutically acceptable salts, solvates, or prodrugs thereof, within the scope of the fourth aspect wherein:

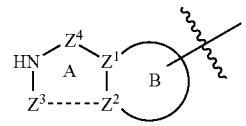

is selected from:

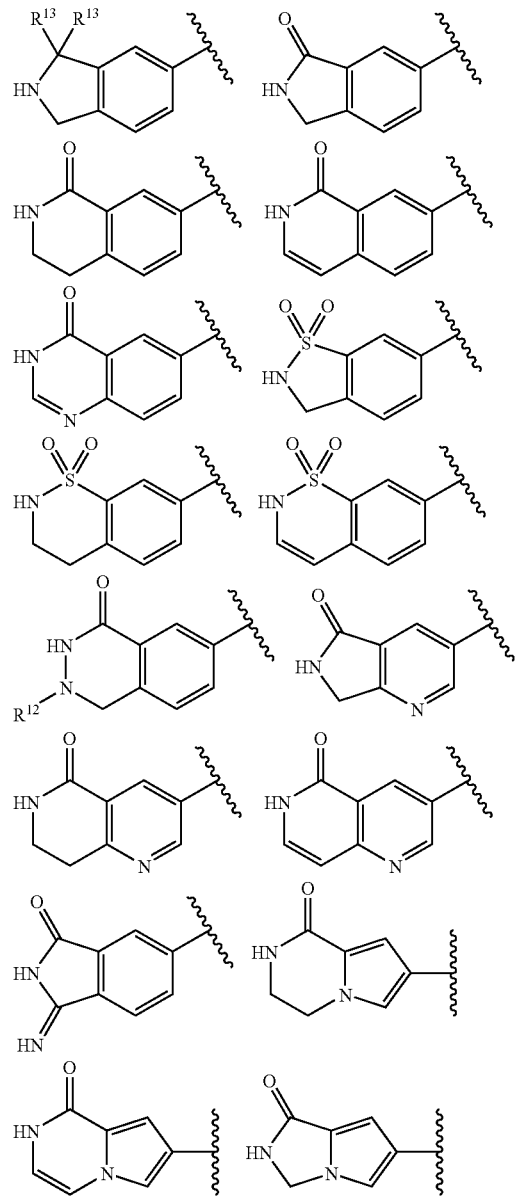

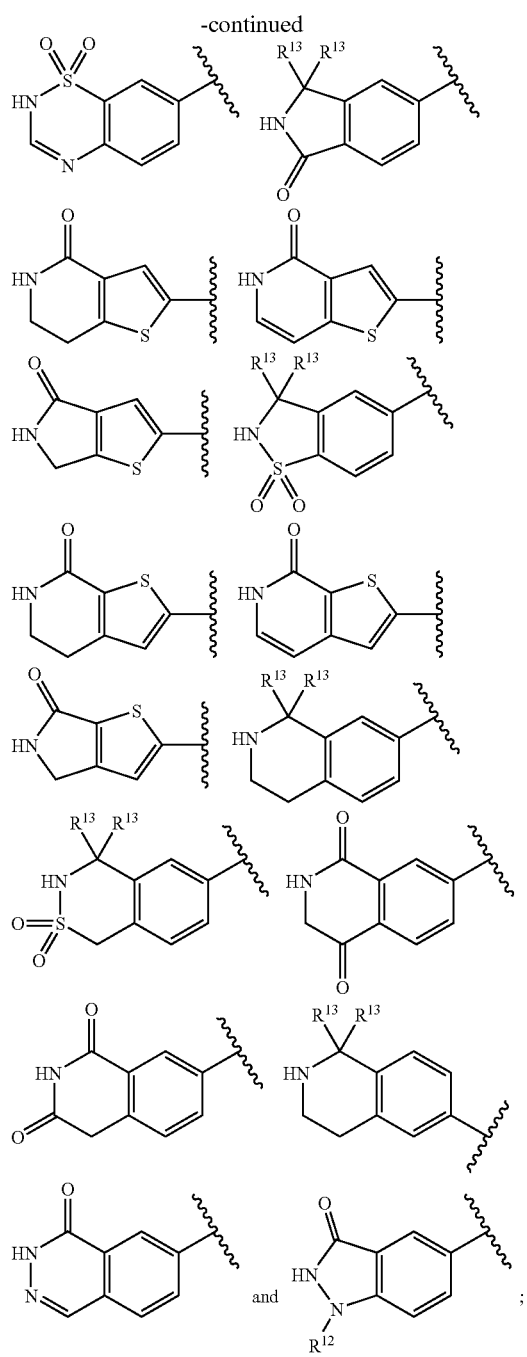
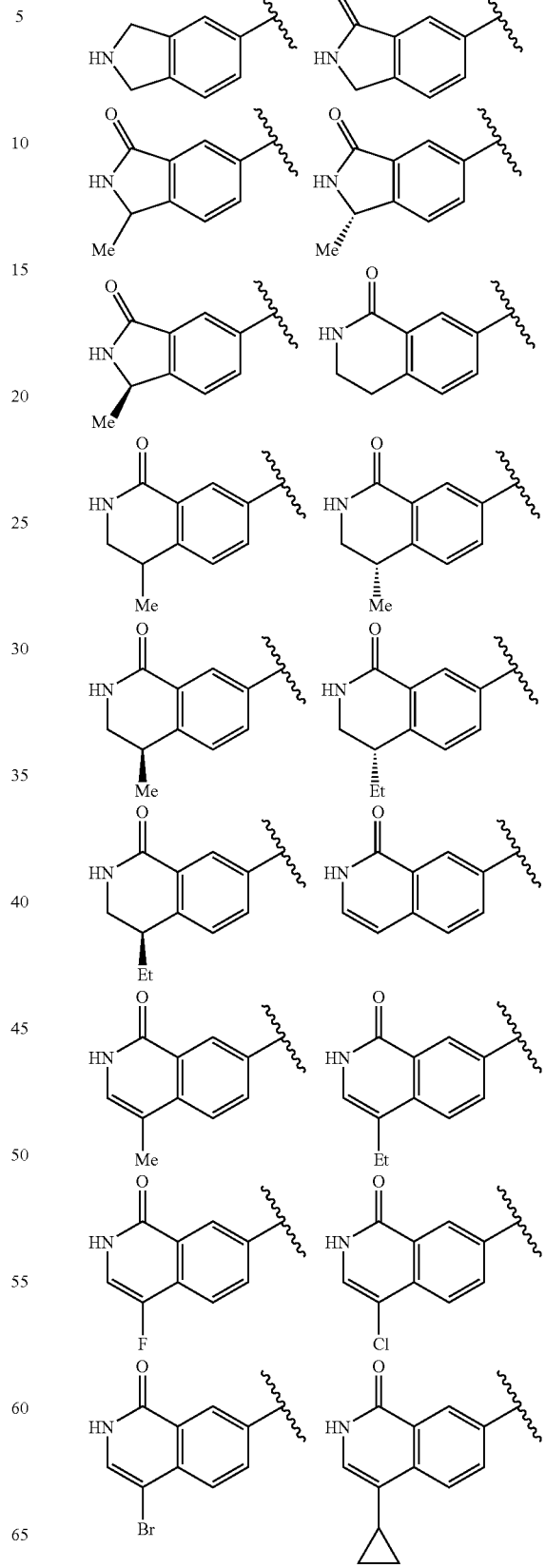
wherein ring A is substituted with 0-2 $R^{11}$; and ring B is substituted with 0-2 $R^6$.
In a sixth aspect, the present invention includes a compound of Formula (II) or stereoisomers, tautomers, pharmaceutically acceptable salts, solvates, or prodrugs thereof, within the scope of the fourth aspect wherein:
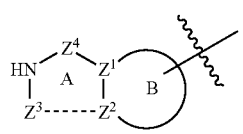
is selected from:

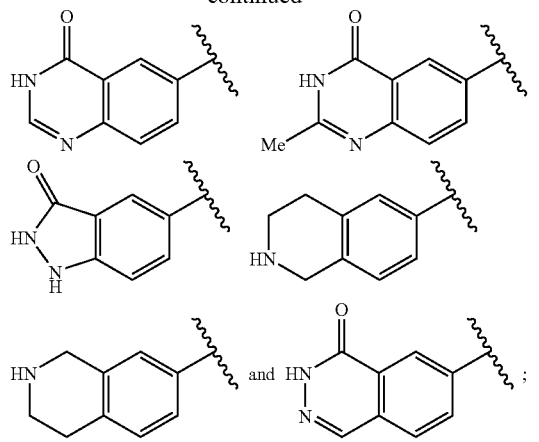
wherein ring B is substituted with 0-1 $R^6$; and
$R^6$ is, independently at each occurrence, F, Cl, Me or Et.
In a seventh aspect, the present invention includes a compound of Formula (II) or stereoisomers, tautomers, pharmaceutically acceptable salts, solvates, or prodrugs thereof, within the scope of the fourth aspect wherein:
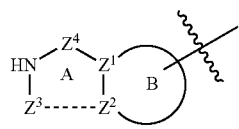
is selected from:
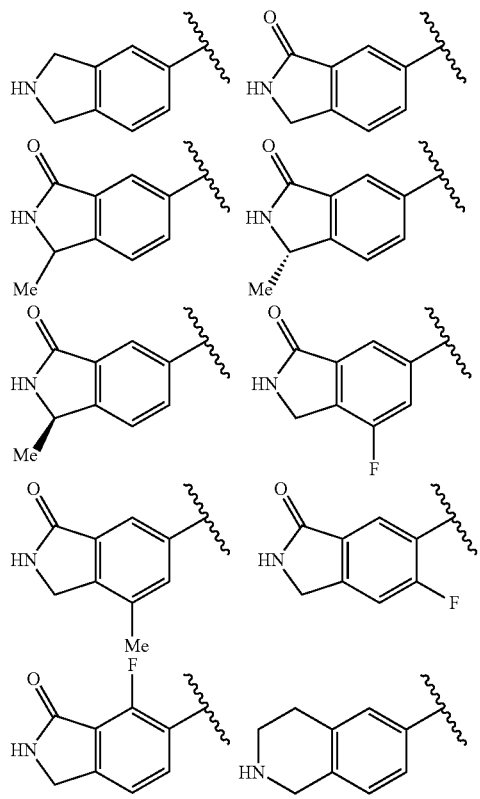
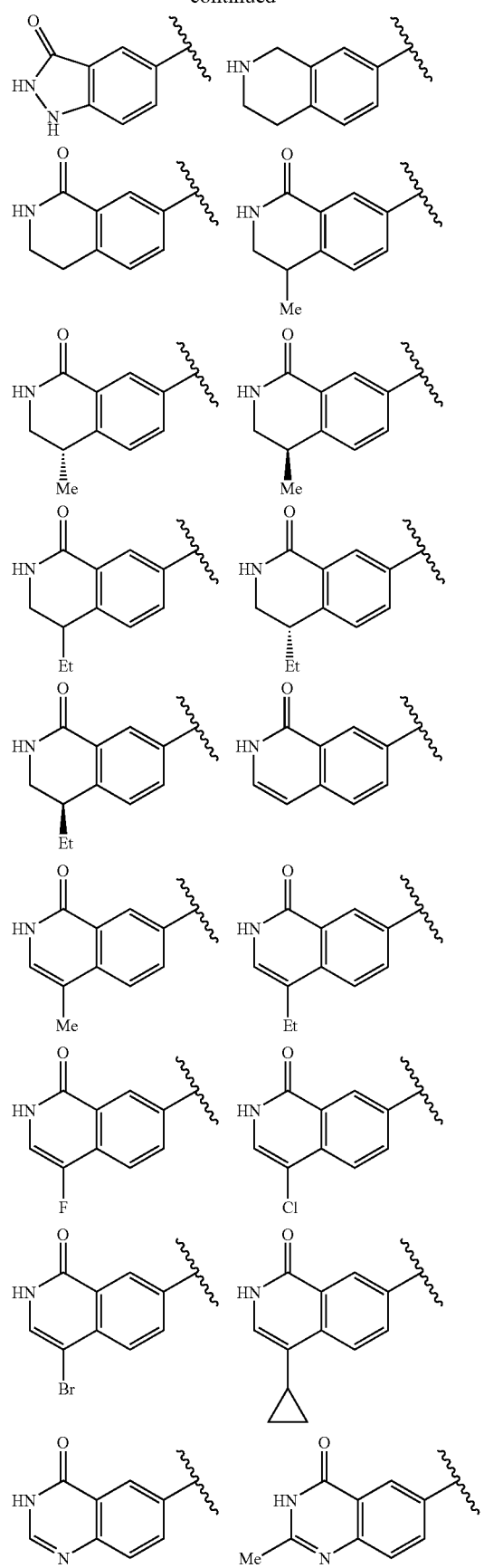

-continued

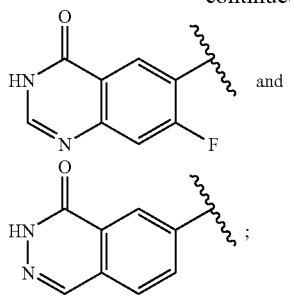
and

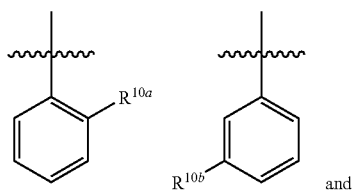
;

R$^1$ is Cl, Br, Me, Et, vinyl, 2-propenyl, ethynyl, —CH(OH)Me, OMe, OEt, cyclopropyl, —OCHF$_2$, or —OCF$_2$CHF$_2$;

R$^2$ is H, F, Cl, C$_{1-4}$ alkyl, C$_{1-4}$ alkoxy, or —OCHF$_2$;

R$^3$ is H, C$_{1-4}$ alkyl, or C$_{1-4}$ alkoxy;

R$^4$ is H or F;

R$^7$ is H, CO$_2$H, CO$_2$Me, CO$_2$Et, or CONMe$_2$;

R$^9$ is selected from:

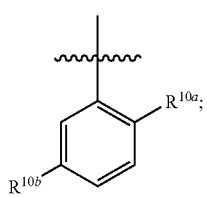

R$^{10a}$ is, independently at each occurrence, H, —SO$_2$Me, —SO$_2$Et, —SO$_2$Pr, —SO$_2$(i-Pr), SO$_2$(i-Bu), —SO$_2$-cyclopropyl, —SO$_2$-cyclobutyl, —SO$_2$-cyclopentyl, —SO$_2$Ph, —SO$_2$-(1-pyrrolidinyl), —SO$_2$-(1-piperidyl), —SO$_2$-(1-azepanyl), SO$_2$-(4-morpholinyl), —SO$_2$-(4-thiamorpholinyl), SO$_2$-(4-Me-1-piperazinyl), —SO$_2$NH$_2$, —SO$_2$NHMe, SO$_2$NHEt, —SO$_2$NH(i-Pr), —SO$_2$NH-cyclopropyl, —SO$_2$NH-cyclohexyl, —SO$_2$NH(t-Bu), —SO$_2$N(Me)Bn, —SO$_2$NMe$_2$, —OSO$_2$NH$_2$, O—NHSO$_2$NH$_2$, —NHSO$_2$Me, Ph, 4-F-Ph, 1-piperidyl, 4-morpholinyl, 3,5-diethyl-1H-pyrazol-1-yl, NO$_2$, or —B(OH)$_2$; and R$^{10b}$ is, independently at each occurrence, H, CONH$_2$, NH$_2$, NHMe, NHEt, NMe$_2$, —NHCOH, —NHCOMe, —NHCOEt, —NHCOPr, —NHCO(i-Pr), —NHCO(i-Bu), —NHCO-cyclopropyl, —N(Me)COMe, NHCO$_2$Me, NHCO$_2$Et, —NHCONH$_2$, —NHCONHMe, NHCONMe$_2$, NHCON(Me)Et, —NHCON(Me)(i-Pr), —NHCO-(1-azetidinyl), —NHCO-(1-pyrrolidinyl), or —NHCO-(3-thiazolidinyl).

In an eighth aspect, the present invention includes a compound of Formula (II) or stereoisomers, tautomers, pharmaceutically acceptable salts, solvates, or prodrugs thereof, within the scope of the fourth aspect wherein:

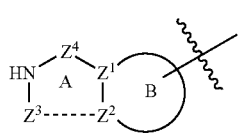

is selected from:

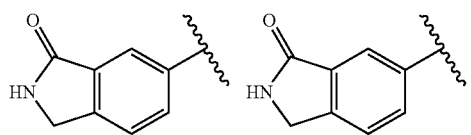

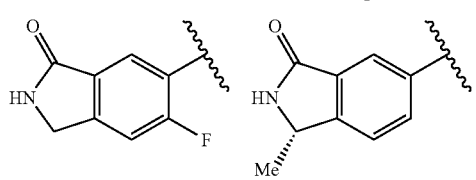

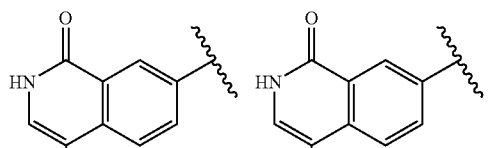

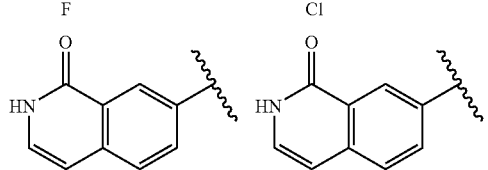

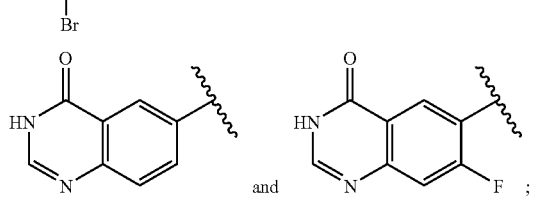
and
;

R$^1$ is Cl, Br, Me, Et, vinyl, 2-propenyl, ethynyl, —CH(OH)Me, OMe, OEt, cyclopropyl, —OCHF$_2$, or —OCF$_2$CHF$_2$;

R$^2$ is H, F, Cl, C$_{1-4}$ alkyl, C$_{1-4}$ alkoxy, or —OCHF$_2$;

R$^3$ is H, C$_{1-4}$ alkyl, or C$_{1-4}$ alkoxy;

R$^4$ is H or F;

R$^7$ is H, CO$_2$H, CO$_2$Me, CO$_2$Et, or CONMe$_2$;

R$^9$ is selected from:

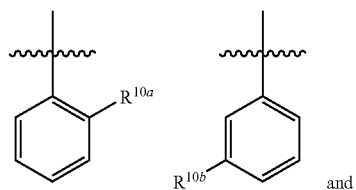
and

-continued

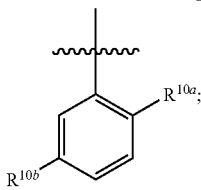

R$^{10a}$ is, independently at each occurrence, H, —SO$_2$Me, —SO$_2$Et, —SO$_2$Pr, —SO$_2$(i-Pr), —SO$_2$(i-Bu), —SO$_2$-cyclopropyl, —SO$_2$-cyclobutyl, —SO$_2$-cyclopentyl, O—SO$_2$Ph, —SO$_2$-(1-pyrrolidinyl), —SO$_2$-(1-piperidyl), —SO$_2$-(1-azepanyl), SO$_2$(4-morpholinyl), —SO$_2$-(4-thiamorpholinyl), —SO$_2$-(4-Me-1-piperazinyl), —SO$_2$NH$_2$, —SO$_2$NHMe, —SO$_2$NHEt, —SO$_2$NH(i-Pr), —SO$_2$NH-cyclopropyl, —SO$_2$NH-cyclohexyl, —SO$_2$NH(t-Bu), —SO$_2$N(Me)Bn, —SO$_2$NMe$_2$, —OSO$_2$NH$_2$, —NHSO$_2$NH$_2$, —NHSO$_2$Me, Ph, 4-F-Ph, 1-piperidyl, 4-morpholinyl, 3,5-diethyl-1H-pyrazol-1-yl, NO$_2$, or —B(OH)$_2$; and R$^{10b}$ is, independently at each occurrence, H, CONH$_2$, NH$_2$, NHMe, NHEt, NMe$_2$, —NHCOH, —NHCOMe, —NHCOEt, —NHCOPr, —NHCO(i-Pr), —NHCO(i-Bu), —NHCO-cyclopropyl, N(Me)COMe, —NHCO$_2$Me, —NHCO$_2$Et, —NHCONH$_2$, —NHCONHMe, NHCONMe$_2$, —NHCON(Me)Et, —NHCON(Me)(i-Pr), —NHCO-(1-azetidinyl), —NHCO-(1-pyrrolidinyl), or —NHCO-(3-thiazolidinyl).

In a ninth aspect, the present invention includes a compound of Formula (II) or stereoisomers, tautomers, pharmaceutically acceptable salts, solvates, or prodrugs thereof, within the scope of the fourth, fifth, or sixth aspect wherein:

R$^1$ is Cl, Me, Et, OMe, or OEt;
R$^2$ is F, Cl, OMe or O(i-Pr);
R$^3$ is H;
R$^4$ is H or F;
R$^7$ is H, CO$_2$H, CO$_2$Me, or CO$_2$Et;
R$^9$ is:

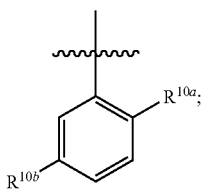

R$^{10a}$ is, independently at each occurrence, H, —SO$_2$—C$_{1-4}$ alkyl, SO$_2$-cyclopropyl, —SO$_2$-cyclobutyl, —SO$_2$-cyclopentyl, —SO$_2$Ph, —SO$_2$-(1-pyrrolidinyl), —SO$_2$-(1-piperidyl), —SO$_2$-(1-azepanyl), —SO$_2$NH—C$_{1-4}$ alkyl, —SO$_2$NH-cyclopropyl, —SO$_2$NMe$_2$, CONMe$_2$, CO(1-pyrrolidinyl), CO(1-piperidinyl), 1-piperidyl, 4-morpholinyl, or 3,5-diethyl-1H-pyrazol-1-yl;

R$^{10b}$ is, independently at each occurrence, H, OH, NH$_2$, —NHCOH, —NHCOMe, —NHCOEt, —NHCO$_2$Me, —NHCO$_2$Et, —NHCONHMe, —NHCONH$_2$; —NHCONMe$_2$, —NHCON(Me)Et, —NHCON(Me)(i-Pr), —NHCO-(1-azetidinyl), —NHCO-(1-pyrrolidinyl), —NHCO-(3-thiazolidinyl), —OSO$_2$NH$_2$, —NHSO$_2$NH$_2$, NHSO$_2$Me, —SO$_2$NH$_2$, or NO$_2$; and t is 1, In a tenth aspect, the present invention includes a compound of Formula (IIa);

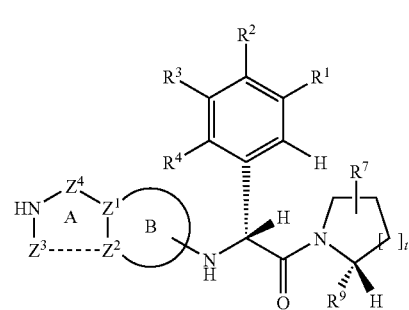

or stereoisomers, tautomers, pharmaceutically acceptable salts, solvates, or prodrugs thereof, wherein: ring A-ring B, R$^1$, R$^2$, R$^3$, R$^4$, R$^7$ and R$^9$ are the same as defined in the fourth aspect.

In an eleventh aspect, the present invention provides a compound selected from the exemplified examples and stereoisomers, tautomers, pharmaceutically acceptable salts, solvates, and prodrugs thereof.

In another embodiment, the present invention includes a compound of Formula (II) or stereoisomers, tautomers, pharmaceutically acceptable salts, solvates, or prodrugs thereof, within the scope of the fourth aspect wherein:

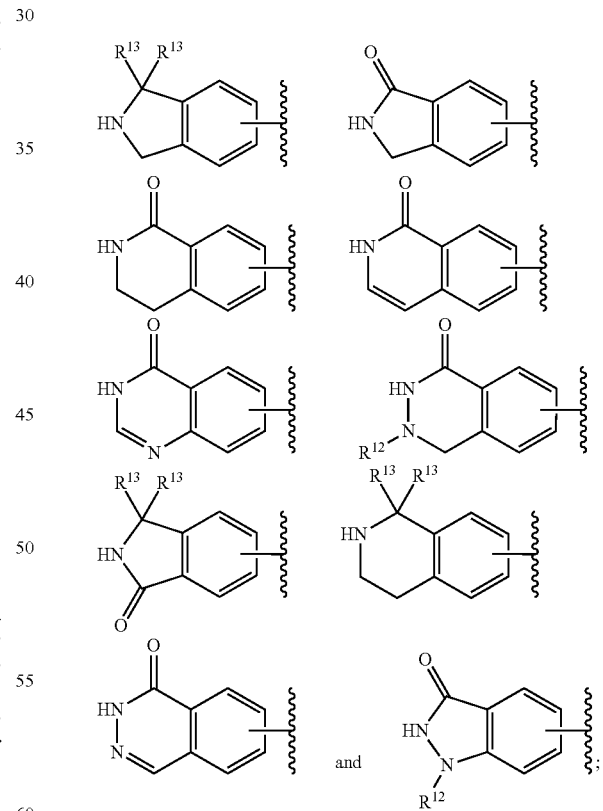

wherein ring A is substituted with 0-2 R$^{11}$; and ring B is substituted with 0-2 R$^6$.

In another embodiment, the present invention includes a compound of Formula (II) or stereoisomers, tautomers, pharmaceutically acceptable salts, solvates, or prodrugs thereof, within the scope of the fourth aspect wherein:

$R^2$, $R^3$ and $R^4$ are, independently at each occurrence, H, F, Cl, Br, I, $OR^a$, $SR^a$, $OCF_3$, $OCHF2$, $OCH_2F$, CN, $NO_2$, $-NR^bR^c$, $-C(O)R^a$, $-CO_2R^a$, $-NR^dC(O)R^a$, $-C(O)NR^cR^d$, $-NR^cC(O)OR^a$, $-NR^cC(O)NR^cR^d$, $-SO_2NR^cR^d$, $-NR^cSO_2NR^cR^d$, $-NR^cSO_2R^i$, $-NR^cSO_2CF_3$, $-SO_2CF_3$, $-S(O)_pR^i$, $-(CF_2)_rCF_3$, $C_{2-6}$ alkyl substituted with 0-2 $R^e$, $C_{1-4}$ haloalkyl, $C_{2-6}$ alkenyl substituted with 0-2 $R^e$, $C_{2-6}$ alkynyl substituted with 0-2 $R^e$, $C_{3-10}$ carbocycle substituted with 0-3 $R^f$, or a 5- to 10-membered heterocycle comprising: carbon atoms and 1-4 heteroatoms selected from N, $NR^c$, O, and $S(O)_p$, wherein said heterocycle are substituted with 0-3 $R^f$.

In another embodiment, the present invention includes a compound of Formula (II) or stereoisomers, tautomers, pharmaceutically acceptable salts, solvates, or prodrugs thereof, within the scope of the first or fourth aspect wherein:

$R^{11}$ is, independently at each occurrence, H, F, Cl, $CF_3$, $OCF_3$, $OCHF_2$, $OCH_2F$, CN, $C_{1-4}$ alkoxy, $C_{1-4}$ haloalkyl, $C_{2-4}$ alkenyl, or $C_{2-4}$ alkynyl.

II. OTHER EMBODIMENTS OF THE INVENTION

In another embodiment the present invention provides a composition comprising at least one of the compounds of the present invention or a stereoisomer, tautomer, pharmaceutically acceptable salt, solvate, or prodrug thereof.

In another embodiment the present invention provides a pharmaceutical composition comprising a pharmaceutically acceptable carrier and at least one of the compounds of the present invention or a stereoisomer, tautomer, pharmaceutically acceptable salt, solvate, or prodrug thereof.

In another embodiment the present invention provides a pharmaceutical composition comprising a pharmaceutically acceptable carrier and a therapeutically effective amount of at least one of the compounds of the present invention or a stereoisomer, tautomer, pharmaceutically acceptable salt, solvate, or prodrug thereof.

In another embodiment, the present invention provides a process for making a compound of the present invention or a stereoisomer, tautomer, pharmaceutically acceptable salt, solvate or prodrug thereof.

In another embodiment, the present invention provides an intermediate for making a compound of the present invention or a stereoisomer, tautomer, pharmaceutically acceptable salt, solvate or prodrug thereof.

In another embodiment, the present invention provides a pharmaceutical composition further comprising additional therapeutic agent(s). In a preferred embodiment, the present invention provides a pharmaceutical composition, wherein the additional therapeutic agent(s) are an anti-platelet agent or a combination thereof. Preferably, the anti-platelet agent(s) are clopidogrel and/or aspirin, or a combination thereof.

In another embodiment, the present invention provides a method for the treatment or prophylaxis of a thromboembolic disorder comprising: administering to a patient in need of such treatment or prophylaxis a therapeutically effective amount of at least one of the compounds of the present invention or a stereoisomer, tautomer, pharmaceutically acceptable salt, solvate, or prodrug thereof. In another embodiment, the present invention provides a compound of the present invention or a stereoisomer, tautomer, pharmaceutically acceptable salt, solvate or prodrug thereof, for use in therapy for the treatment or prophylaxis of a thromboembolic disorder. In another embodiment, the present invention also provides the use of a compound of the present invention or a stereoisomer, tautomer, pharmaceutically acceptable salt, solvate or prodrug thereof, for the manufacture of a medicament for the treatment or prophylaxis of a thromboembolic disorder. Preferably, in these embodiments, the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders. Preferably, the thromboembolic disorder is selected from unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention provides a compound of the present invention or a stereoisomer, tautomer, pharmaceutically acceptable salt, solvate or prodrug thereof, for use in therapy.

In another embodiment, the present invention provides a method for treating a thromboembolic disorder, comprising: administering to a patient in need thereof a therapeutically effective amount of a first and second therapeutic agent, wherein the first therapeutic agent is a compound of the present invention or a stereoisomer, tautomer, pharmaceutically acceptable salt, solvate or prodrug thereof, and the second therapeutic agent is at least one agent selected from a Xa inhibitor, an anti-coagulant agent, an anti-platelet agent, a thrombin inhibiting agent, a thrombolytic agent, and a fibrinolytic agent. In another embodiment, the present invention provides a first and second therapeutic agent for use in treating treating a thromboembolic disorder, wherein the first therapeutic agent is a compound of the present invention or a stereoisomer, tautomer, pharmaceutically acceptable salt, solvate or prodrug thereof, and the second therapeutic agent is at least one agent selected from a Xa inhibitor, an anti-coagulant agent, an anti-platelet agent, a thrombin inhibiting agent, a thrombolytic agent, and a fibrinolytic agent. Preferably, in these embodiments, the second therapeutic agent is at least one agent selected from warfarin, unfractionated heparin, low molecular weight heparin, synthetic pentasaccharide, hirudin, argatrobanas, aspirin, Ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase. Preferably, the second therapeutic agent is at least one anti-platelet agent. Preferably, the anti-platelet agent(s) are clopidogrel and/or aspirin, or a combination thereof.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment or prophylaxis of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

III. CHEMISTRY

Compounds of this invention may have one or more asymmetric centers. Compounds of the present invention containing an asymmetrically substituted atom may be isolated in optically active or racemic forms. It is well known in the art how to prepare optically active forms, such as by resolution of racemic forms or by synthesis using optically active starting materials or optically active catalysts. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, (enantiomeric and diastereomeric) racemic forms and all geometric isomeric forms of a structure are intended, unless the specific stereochemistry or isomeric form is specifically indicated. When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The molecular weight of compounds of the present invention is preferably less than about 800 grams per mole.

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_{1-6}$ alkyl" denotes alkyl having 1 to 6 carbon atoms. Alkyl group can be unsubstituted or substituted with at least one hydrogen being replaced by another chemical group. Examples of alkyl include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl.

"Alkenyl" or "alkenylene" is intended to include hydrocarbon chains of either a straight or branched configuration having the specified number of carbon atoms and one or more unsaturated carbon-carbon bonds which may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either a straight or branched configuration having one or more carbon-carbon triple bonds which may occur in any stable point along the chain. For example, "$C_{2-6}$alkynyl" (or alkynylene), is intended to include $C_2$, $C_3$, $C_4$, $C_5$, and alkynyl groups; such as ethynyl, propynyl, butynyl, pentynyl, and hexynyl.

"Alkoxy" or "alkyloxy" represents an alkyl group as defined above with the indicated number of carbon atoms attached through an oxygen bridge. For example, "$C_{1-6}$ alkoxy" (or alkyloxy), is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" or "thioalkoxy" represents an alkyl group as defined above with the indicated number of carbon atoms attached through a sulphur bridge; for example methyl-S—, and ethyl-S—.

"Halo" or "halogen" as used herein refers to fluoro, chloro, bromo, and iodo. "Haloalkyl" is intended to include both branched, and straight-chain saturated aliphatic hydrocarbon groups having the specified number of carbon atoms, substituted with 1 or more halogen. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated, number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle" is intended to mean any stable 3-, 4-, 5-, 6-, 7-, or 8-membered monocyclic or bicyclic or 7-, 8-, 9-, 10-, 11-, 12-, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge, As used herein, the term "bicyclic carbocycle" or "bicyclic carbocyclic group" is intended to mean a stable 9 or 10-membered carbocyclic ring system that contains two fused rings and consists of carbon atoms. Of the two fused rings, one ring is a benzo ring fused to a second ring; and the second ring is a 5 or 6 membered carbon ring which is saturated, partially unsaturated, or unsaturated. The bicyclic carbocyclic group may be attached, to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in *Hawley's Condensed Chemical Dictionary* (13 ed.), R. J. Lewis, ed., J. Wiley & Sons, Inc., New York (1997). "$C_{6-10}$ aryl" refers to phenyl or naphthyl. Unless otherwise specified, "aryl", "$C_{6-10}$ aryl" or "aromatic residue" may be unsubstituted or substituted with 1 to 3 groups selected from H, OH, OCH$_3$, Cl, F, Br, I, CN, NO$_2$, NH$_2$, N(CH$_3$)H, N(CH$_3$)$_2$, CF$_3$, OCF$_3$, C(=O)CH$_3$, SCH$_3$, S(=O)CH$_3$, S(=O)$_2$CH$_3$, CH$_3$, CH$_2$CH$_3$, CO$_2$H, and CO$_2$CH$_3$.

As used herein, the term "heterocycle" or "heterocyclic group" is intended to mean a stable 3-, 4-, 5-, 6-, or 7-membered monocyclic or polycyclic or 7-, 8-, 9-, 10-, 11-, 12-, 13-, or 14-membered polycyclic heterocyclic ring that is saturated, partially unsaturated or fully unsaturated, and that consists of carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized to —NO—, —SO—, or —SO$_2$—. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl, Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl.

As used herein, the term "bicyclic heterocycle" or "bicyclic heterocyclic group" is intended to mean a stable 9 or 10-membered heterocyclic ring system which contains two fused rings and consists of carbon atoms and 1, 2, 3, or 4 heteroatoms independently selected from the group consisting of N, O and S. Of the two fused rings, one ring is a 5 or 6-membered monocyclic aromatic ring comprising a 5 membered heteroaryl ring, a 6-membered heteroaryl ring or a benzo ring, each fused to a second ring. The second ring is a 5 or 6 membered monocyclic ring which is saturated, partially unsaturated, or unsaturated, and comprises a 5 membered heterocycle, a 6 membered heterocycle or a carbocycle (provided the first ring is not benzo when the second ring is a carbocycle).

The bicyclic heterocyclic group may be attached, to its pendant group at any heteroatom or carbon atom which, results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted.

Bridged rings are also included in the definition of heterocycle. A bridged ring occurs when one or more atoms (i.e., C, O, N, or S) link two non-adjacent carbon or nitrogen atoms. Examples of bridge rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a small, negatively charged species such as chloride, bromide, hydroxide, acetate, and sulfate.

When a dotted ring is used within a ring structure, this indicates that the ring structure may be saturated, partially saturated or unsaturated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. When a ring system (e.g., carbocyclic or heterocyclic) is said to be substituted with a carbonyl group or a double bond, it is intended that the carbon atom of the carbonyl group or one carbon atom of the double bond be part of (i.e., within) the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative. In cases wherein there are quarternary carbon atoms on compounds of the present invention, these may be replaced by silicon atoms, provided they do not form Si—N or Si—O bond.

When any variable occurs more than one time in any constituent or formula for a compound, its definition at each occurrence is independent of its definition at every other occurrence. Thus, for example, if a group is shown to be substituted with 0-3 $R^f$, then said group may optionally be substituted with up to three Regroups and $R^f$ at each occurrence is selected independently from the definition of $R^f$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th Edition, Mack Publishing Company, Easton, Pa., 1990, the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) *Design of Prodrugs*, edited by H. Bundgaard, (Elsevier, 1985), and *Methods in Enzymology*, Vol. 42, at pp. 309-396, edited by K, Widder, et. al. (Academic Press, 1985);

b) *A Textbook of Drug Design and Development*, edited by Krosgaard-Larsen and H. Bundgaard, Chapter 5, "Design and Application of Prodrugs" by H. Bundgaard, at pp. 113-191 (1991);

c) H. Bundgaard, *Advanced Drug Delivery Reviews*, Vol. 8, p. 1-38 (1992);

d) H. Bundgaard, et al., *Journal of Pharmaceutical Sciences*, Vol. 77, p. 285 (1988); and e) N. Kakeya, et. al, *Chem Phar Bull*, Vol. 32, p. 692 (1984).

Compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$alkanoyloxy-$C_{1-6}$alkyl (e.g. acetoxymethyl, pivaloyloxymethyl or propionyloxymethyl), $C_{1-6}$ alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Preparation of Prodrugs is Well Known in the Art and Described in, for example, *Medicinal Chemistry: Principles and Practice*, ed. F. D. King, The Royal Society of Chemistry, Cambridge, UK, 1994.

Isotopically labeled compounds of the present invention, i.e., wherein one or more of the atoms described are replaced by an isotope of that atom (e.g., $^{12}C$ replaced by $^{13}C$ or by $^{14}C$; and isotopes of hydrogen include tritium and deuterium), are also provided herein. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

Compounds of the present invention are, subsequent to their preparation, preferably isolated and purified to obtain a composition containing an amount by weight equal to or greater than 98%, preferably 99%, compound of the present invention ("substantially pure"), which is then used or formulated as described herein. Such "substantially pure" compounds are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates and the like. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

AcOH or HOAc is acetic acid,
AIBN is 2,2'-azo-bis-isobutyrlnitrile,
$BH_3.SMe_2$ is borane-dimethyl sulfide complex,
$BH_3.THF$ is borane-tetrahydrofuran complex,
BHT is butylated hydroxytoluene,
BINAP is 2,2'-bis(diphenylphosphino)-1,1'-binaphthalene,
Bn is benzyl,
Boc is tert-butyl oxycarbonyl,
BOP is benzotriazol-1-yloxy-tris(dimethylamino)phosphonium hexafluorophosphate,
Bu is butyl,
iBu or i-Bu is isobutyl,
t-Bu is tert-butyl,
Cbz is carbonylbenzyloxy,
CbzSerOtBu is (S) -2-tert-butoxycarbonylamino-3-hydroxy-propionic acid tert-butyl ester,
CDI is 1,1'-carbonyldiimidazole,
$CH_2Cl_2$ is dichloromethane,
$CH_3CN$ is acetonitrile,
Davis oxaziridine is 2-benzenesulfonyl-3-phenyl-oxaziridine,
DABCO is 1,4-diazabicyclo[2.2.2]octane,
DBU is 1,8-diazabicyclo[5.4.0]undec-7-ene,
DCE is 1,2-dichloroethane,
DEAD is diethyl azodicarboxylate,
DIBAL is diisobutylaluminium,
DIBAH is diisobutylaluminum hydride,
DIC is 1,3-diisopropylcarbodiimide,
DIEA or DIPEA is N,N-diisopropylethyl amine,
DMA is N,N-dimethylacetamide,
DMAP is dimethylaminopyridine,
DME is dimethyl ether,
DMF is dimethylformamide,
DMPU is 1,3-dimethyl-3,4,5,6-tetrahydro-2(1H)-pyrimidone,
DMSO is dimethyl sulfoxide,
DPPA is diphenylphosphoryl azide,
EDCI or EDC is 1-(3-dimethylaminopropyl)-3-ethylcarbodiimide hydrochloride,
Et is ethyl,
EtOH is ethanol,
EtOAc is ethyl acetate,
$Et_2O$ is diethyl ether,
HATU is O-(7-azabenzotriazol-1-yl)-N,N,N',N'-tetramethyluronium,
HBTU is O-benzotriazol-1-yl-N,N,N',N'-tetramethyluronium hexafluorophosphate,
HCl is hydrochloric acid,
HOAt or HOAT is 1-hydroxy-7-azabenzotriazole,
HOBt or HOBT is 1-hydroxybenzotriaole,
$H_3PO_4$ is phosphoric acid,
$K_2CO_3$ is potassium carbonate,
LAH is lithium aluminum hydride,
LDA is lithium diisopropylamide,
LiHMDS is bis(trimethylsilyl)amide,
LiOH is lithium hydroxide,
mCPBA or MCPBA is meta-chloroperbenzoic acid,
Me is methyl,
MeOH is methanol,
$MgSO_4$ is magnesium sulfate,
$MnO_2$ is manganese dioxide, MoOPH is oxodiperoxymolybdenum(pyridine)(hexamethylphosphoric triamide),
MsCl is methanesulfonyl chloride,
Na is sodium,
NaH is sodium hydride,
NaHCO$_3$ is sodium bicarbonate,
NaHSO$_3$ is sodium thiosulfite,
NaOAc is sodium actetate,
NaOH is sodium hydroxide,
Na$_2$SO$_4$ is sodium sulfate,
NBS is N-bromosuccinimide,
NCS is N-chlorosuccinimide,
Ni is nickel,
OAc is acetate,
Pd/C is palladium on carbon,
Pd(PPh$_3$)$_4$ is tetraks (triphenylphosphine) palladium,
Ph is phenyl,
Pr is propyl,
iPr or i-Pr is isopropyl,
i-PrOH or IPA is isopropanol,
PyBroP or Py-BroP is bromotripyrrolidinophosphonium hexafluorophosphate, Selectfluor™ is [1(chloromethy)-4-fluoro-1,4-diazoniabicyclo[2,2,2]octanebis(tetrafluoroborate)],
TBAF is tetrabutylammoniumfluoride,
TBAI is tetrabutylammonium iodide,
tBME is tert-butyl methyl ether,
TEA is triethylamine,
TFA is trifluoroacetic acid,
TFAA is trifluoroacetic anhydride,
THF is tetrahydrofuran.

The compounds of the present invention can be prepared in a number of ways blown to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C. *Comprehensive Organic Transformations*, VCH: New York, 1989. Preferred methods include, but are not limited to, those described below. All references cited herein are hereby incorporated in their entirety herein by reference.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley-Interscience, 3 nd Edition, 1999).

Compounds having the general Formula (I):

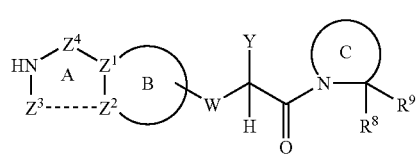

(I)

wherein A, B, C, W, Y, Z$^1$, Z$^2$, Z$^3$, Z$^4$, R$^8$, and R$^9$ are each as defined above, can be prepared by coupling an acid of Formula (Ia):

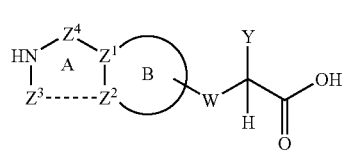

(Ia)

with an amine of Formula (Ib):

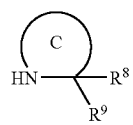

(Ib)

under conditions suitable for forming an amide bond between the acid and the amine. Coupling conditions can be found in Bodanszky, "Principles of Peptide Synthesis, Second Edition" Springer Verlag Ed, Berlin (1993). Coupling reagents include CDI, DIC, and EDCI. Optionally, an intermediate activated ester can be prepared by adding one equivalent of 1-hydroxybenzotriazole or 1-hydroxy-7-azabenzotriazole. Other coupling reagents include HATU, HBTU, and Py-Brop which are usually reacted in the presence of one equivalent of a tertiary base such as DIEA or TEA. Protection and deprotection of functional groups may be required before or after the amide formation step to afford a compound of Formula (I).

The intermediate acid of Formula (Ia) can be prepared in several different ways. For example, it can be prepared according to the steps described in Scheme 1. Thus, amines 1 (prepared following the methods shown in later Schemes and in the Examples) react with phenyl or pyridyl acetate derivatives 2 (Y is substituted phenyl or pyridyl) under basic conditions to give 3. X is a leaving group such as Cl, Br, OSO$_2$Me or OSO$_2$CF$_3$ and P is a protecting group such as methyl or benzyl. Deprotection of P in 3 by hydrolysis or hydrogenation gives acid intermediates Ia.

Scheme 1

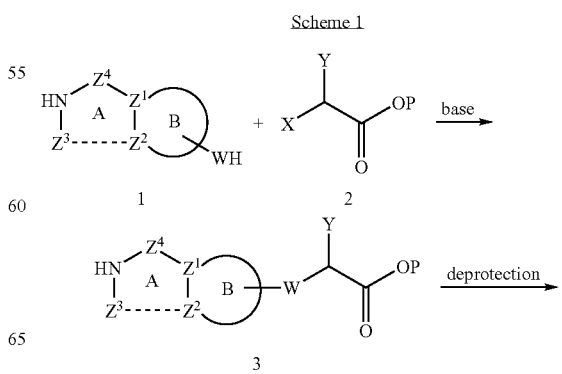

-continued

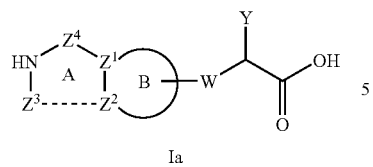

W = NH, O
Y = substituted phenyl or pyridyl

Acids Ia with Y as substituted phenyl and W as NH can be prepared by a Petasis boronic acid Mannich reaction (*J. Am. Chem. Soc.* 1997, 119, 445-446) shown in Scheme 2. Amines 1 react with phenyl boronic acid, derivatives 4 and glyoxylic acid 5 in a suitable solvent such as 1,2-dichloroethane and toluene or acetonitrile and DMF to give the acids 6 directly. Many phenyl boronic acid derivatives are commercial available. They can also be prepared by methods known in the art.

Scheme 2

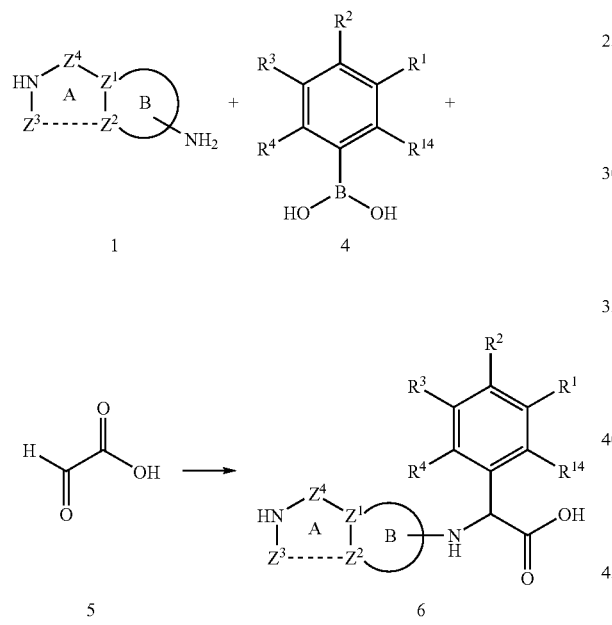

Acids 6 can also be prepared by reductive amination (*Tetrahedron*, 1996, 52, 9777-9784) of α-keto acids 7 with amines 1 as shown in Scheme 3.

Scheme 3

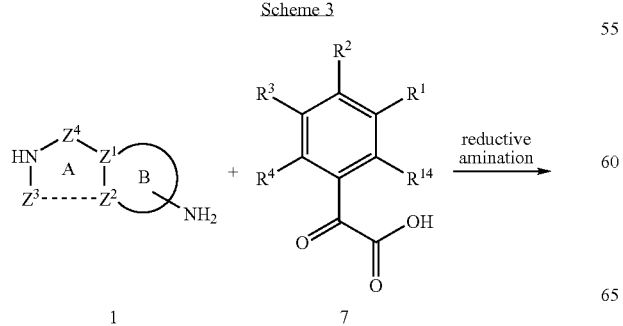

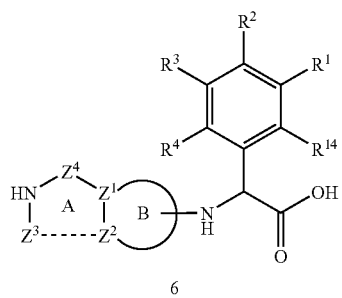

Alternatively to Schemes 2 and 3, as exemplified in Scheme 4, acids 6 can be prepared from amino-esters 9. Amino-esters 9 can be accessed through a Strecker type synthesis, by condensation of aldehydes 8 with trimethylsilylcyanide in presence of ammonia, followed by treatment with hydrochloric acid in MeOH. Compounds 9 can be converted to 11 via coupling with aryl halides or sulfonates 10 by methods known in the art (Huang, X. et al. *J. Am. Chem. Soc.* 2003, 125, 6653-6655). For example, amino-esters 9 may be coupled to aryl halides 10 in the presence of a palladium catalyst, an appropriate ligand, for example, BINAP, and a base such as cesium carbonate to provide esters 11. Deprotection of 11 under controlled condition gives 6.

Scheme 4

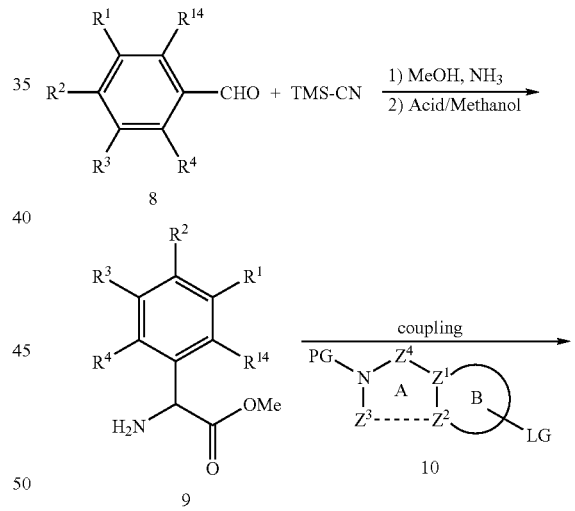

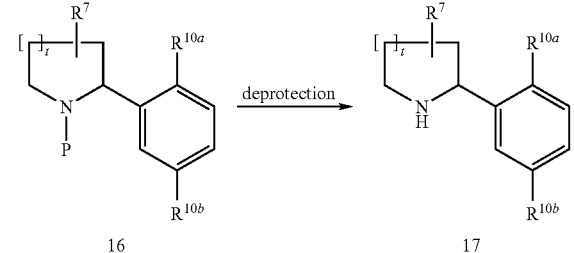

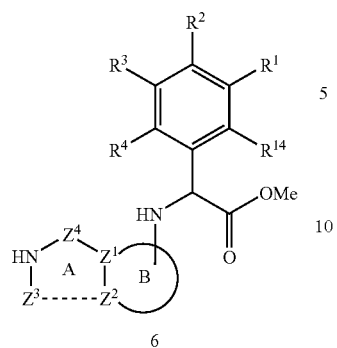

6

Amines of Formula (Ib) may be prepared in different ways depending on the ring size and substituents. A general method to prepare N-heterocycles of formula Ib may be via palladium catalyzed coupling of lactam-derived ketene animal with aryl boronic acids, as shown in Scheme 5. Thus, treatment of properly protected lactam 12 with base such as LDA at low temperature and trapping the enolate with diphenylphosphoryl chloride gives the ketene aminal diphenylphosphate 13. Diphenylphosphate 13 undergoes palladium catalyzed coupling with arylboronic acid 14 to give the coupled intermediate 15. Hydrogenation of the double bond in 15 and removal of the protecting group in 16 should give rise to α-aryl substituted N-heterocycle 17. The sequences described in scheme 5 are particularly useful for preparation of 5-, 6-, 7- and 8-membered N-heterocycles.

Scheme 6 illustrate another general method to prepare N-heterocycles of Formula (Ib), particularly for the preparation of α-aryl substituted pyrrolidine and piperidine. Condensation of benzylamine 18 with diphenylketone gives Shiff base 19. Treatment of the Schiff base 19 with 1.0 equivalent of base such as LDA and mono-alkylation with a dielectrophile 20 gives intermediate amine 21 after acid hydrolysis. Intramolecular cyclization of 21 in the presence of base such as $K_2CO_3$ should, give rise to α-aryl substituted N-heterocycle 22.

Scheme 5

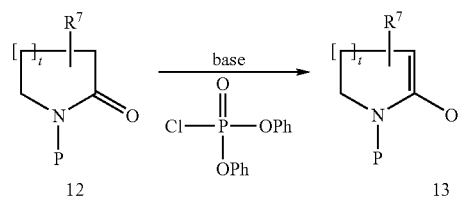

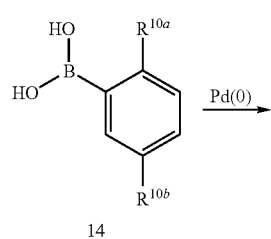

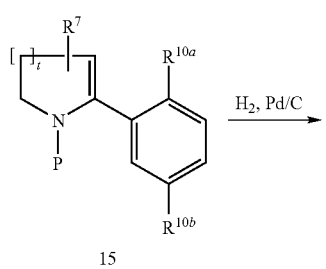

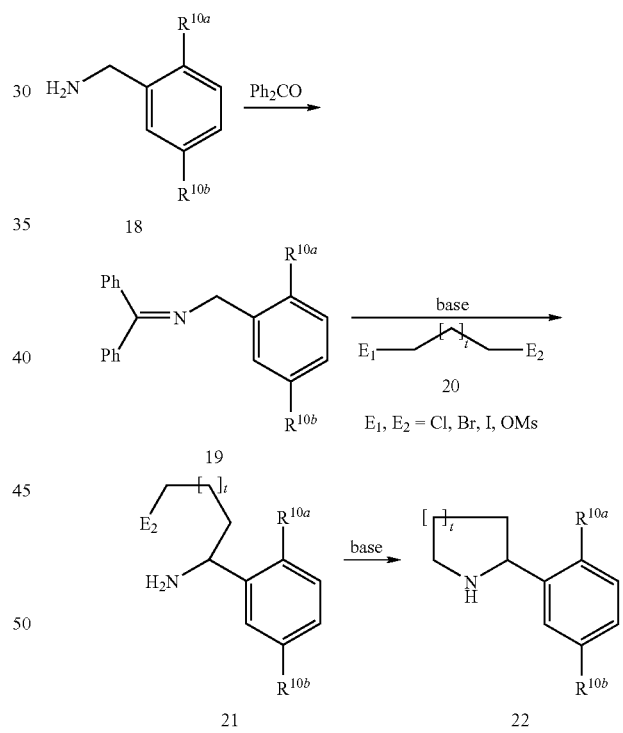

Functionalized phenylpyrrolidines can be prepared by the procedures described in Schemes 7-11. In Scheme 7, palladium catalyzed coupling of Boc protected 2-pyrrole boronic acid 23 with substituted phenyl halide 24 (X=Br or I) gives α-aryl pyrrole 25. Aryl pyrrole 25 can be hydrogenated with a catalyst such as Pt/C, $PtO_2$/C and $Pd(OH)_2$/C in a solvent such as MeOH to Boc-protected aryl pyrrolidine 26. At this stage, the $R^{10a}$ and $R^{10b}$ groups can be manipulated to the desired functional groups. Treatment of the Boc protected 2-aryl pyrrolidine 26 with acid, such as HCl in dioxane or TFA gives the pyrrolidine 27.

Scheme 7

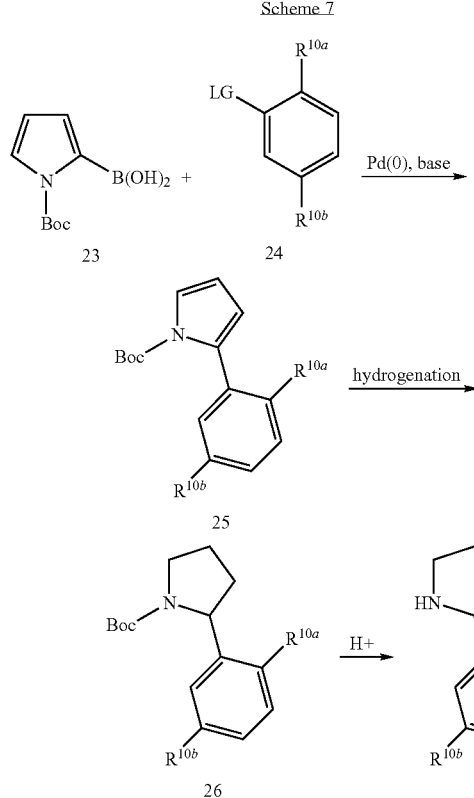

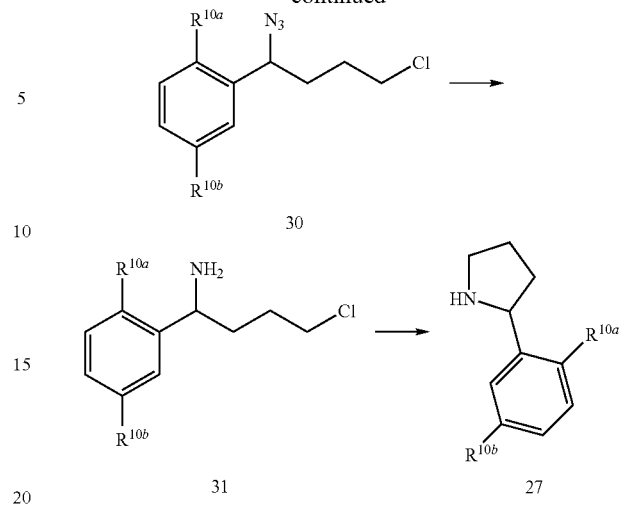

In Scheme 8, reduction of chloro ketone 28 gives hydroxy chlorides 29. Hydroxy chloride 29 can be converted to azides 30, e.g. by the action of DPPA/DBU, Reduction of the azides with PPh₃ to amines 31, followed by base-promoted intramolecular cyclization gives the functionalized phenylpyrrolidines 27. It is known that the reduction of the aryl ketones like 28 can be achieved enantioselectively with chiral boranes, e.g. B-chlorodiisopinocamphenyl borane (Dip-Cl, Brown, H. C. et al, *Tetrahedron Lett.* 1994, 35, 2141-2144). It is possible that both enantiomers of 27 can be prepared with the proper choice of chiral borane reagent.

Scheme 8

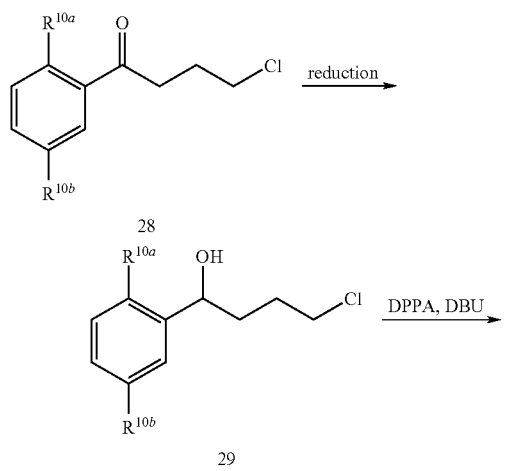

Scheme 9 illustrate the preparation of arylpyrrolidine carboxylate. Condensation of aryl aldehyde 32 with γ-aminobutyric ester 33 (R=Me, Et) gives imine 34. Intramolecular cyclization of 34 in the presence of catalyst such as TiCl₄ and base Et₃N gives rise to arylpyrrolidine carboxylate 35.

Scheme 9

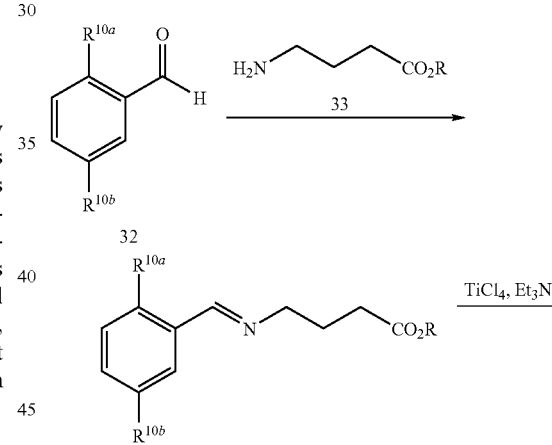

Scheme 10 illustrates a ring closing metathesis (RCM) route to functionalized phenylpyrroldine derivative 43. Condensation of aldehyde 32 with sulfinamide 36 (racemic or chiral, R is tert-butyl or p-tolyl) in the presence of titanium tetraethoxide gives activated imine 37. Sulfinimine 37 is then treated with vinyl Grignard reagent to give intermediate 38. High diastereoselectivity towards 38 may be achieved with a chiral sulfinamide 36 and with a proper choice of reaction condition. N-allylation of 38 with a substituted allylbromide 39 gives a diene intermediate 40 which can undergo ring closing metathesis (RCM) to give dihydropyrrole 41. Sulfinamide in 41 can be removed under acidic condition and the dihydropyrrole re-protected with a more common protecting group, e.g. a Boc to intermediate 42. Hydrogenation and deprotection of 42 gives rise to functionalized phenylpyrrolidine 43.

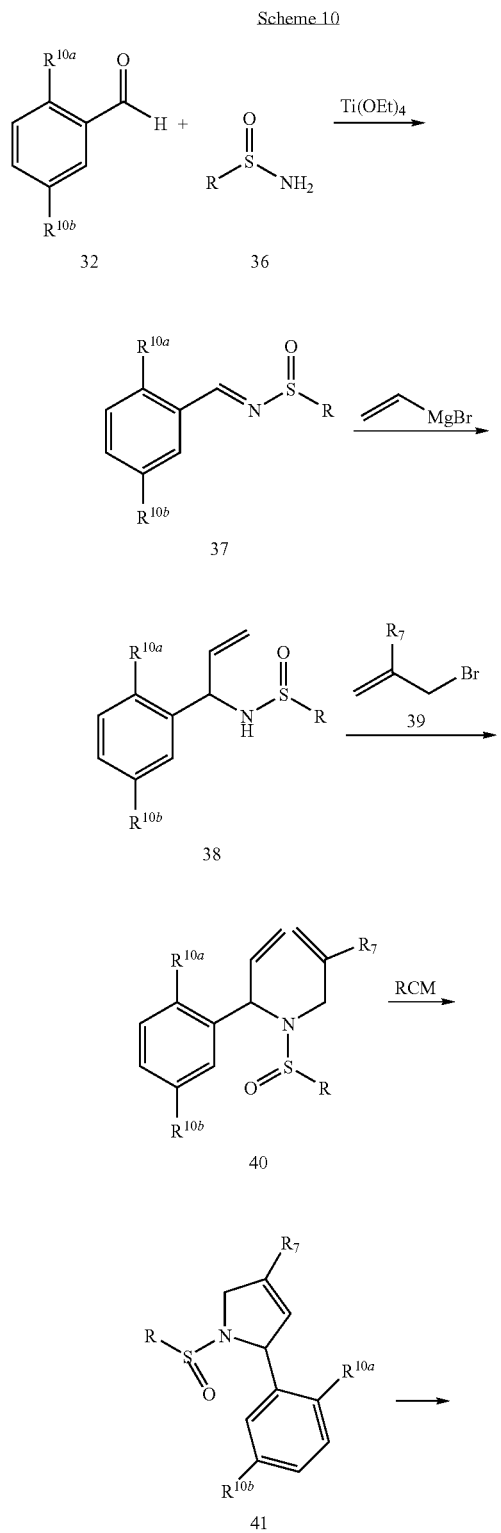

Scheme 11 illustrate a variation of scheme 10 using RCM to the synthesis of phenylpyrrolidine derivative 50 from Baylis-Hillman adduct 46. Thus three component condensation of aldehyde 32, sulfonamide 44 (R is tert-butyl or p tolyl) and acrylate or vinyl ketone 45 in the presence of a base, e.g. DABCO, gives Baylis-Hillman adduct 46. N-allylation of 46 with allylbromide gives a diene intermediate 47 which can undergo ring closing metathesis (RCM) to give dihydropyrrole 48. Sulfonamide in 48 can be removed and the dihydropyrrole re-protected with a more common protecting group, e.g. a Boc to intermediate 49. Hydrogenation and deprotection of 49 gives rise to functionalized phenylpyrrolidine 50.

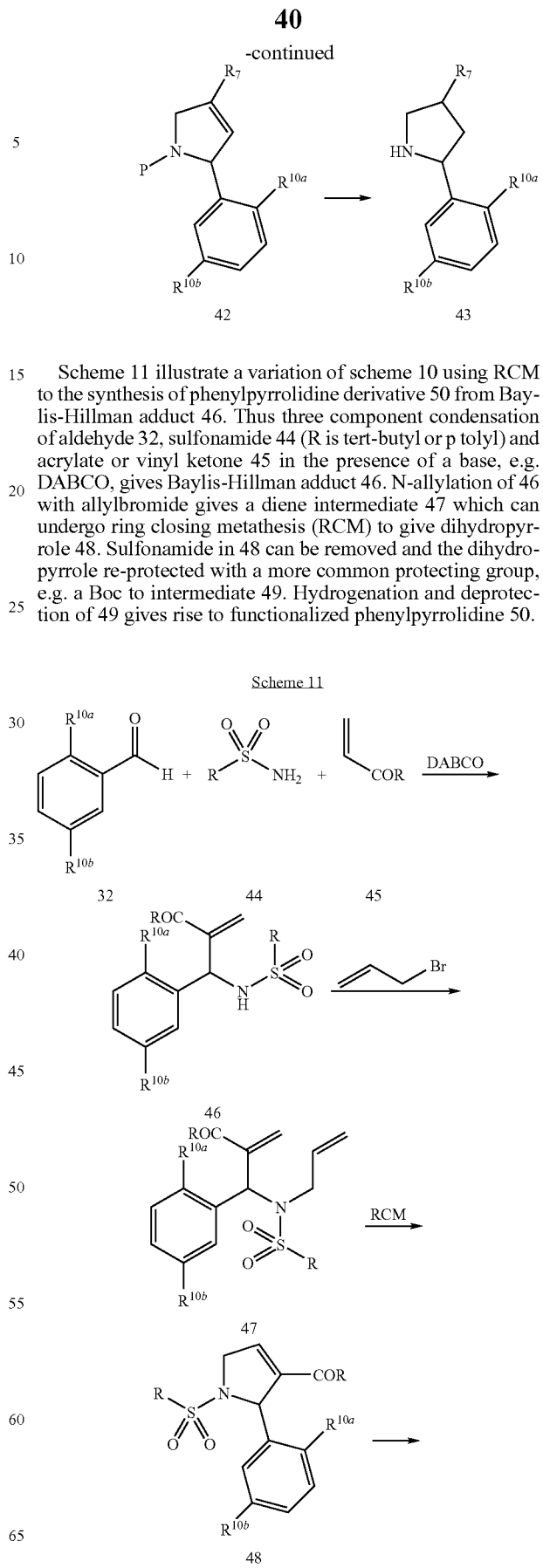

-continued

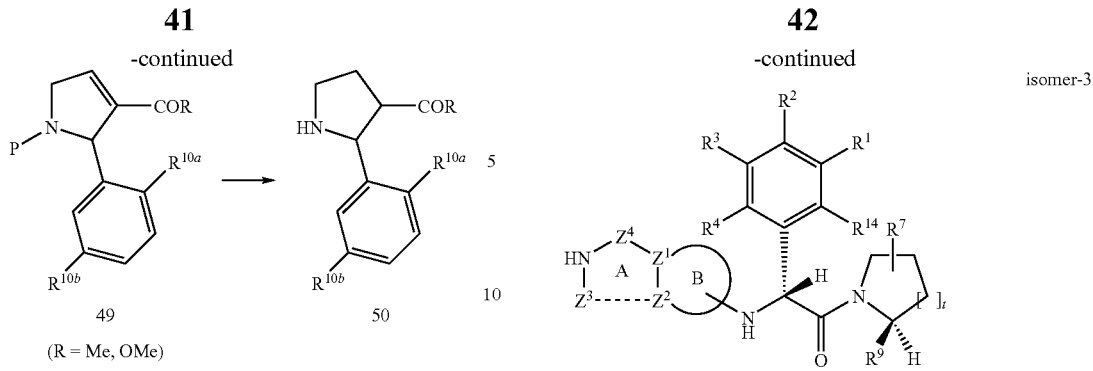

49　　　50

(R = Me, OMe)

The compound of the instant invention herein described may have asymmetric centers. For example, the chiral carbon atoms in Formula (I) as indicated below, exist in either as S or R configuration.

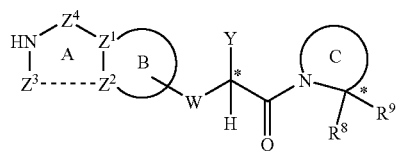

(I)

Thus, the stereoisomeric configurations of each compound of the present invention are considered part of the invention. For example, but not limited to therein, in compounds of Formula (II), the following four stereoisomeric configurations are possible:

isomer-1

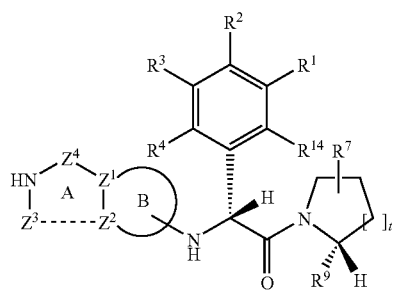

isomer-2

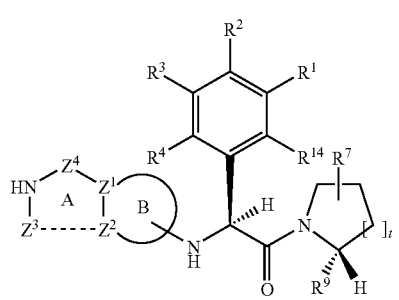

They are collectively, as well as individually, considered part of the invention. In a preferred stereoisomeric embodiment the present invention provides for a stereoisomeric configuration of isomer-1 for all embodiments of Formula (I), (II) or (III), or tautomer, pharmaceutically acceptable salt, solvate, or prodrug form thereof.

In the following experimental procedures, solution ratios express a volume relationship, unless stated otherwise. NMR chemical shifts ($\delta$) are reported in parts per million (ppm).

Products were analyzed by reverse phase analytical HPLC carried out on a Shimadzu Analytical HPLC system running DiscoveryVP software using Method A: Phenomenex Luna C18 column (4.6×50 mm or 4.6×75 mm) eluted at 4 mL/min with a 4 or 8 min gradient from 100% A to 100% B (A: 10% methanol, 89.9% water, 0.1% TFA; B: 10% water, 89.9% methanol, 0.1% TFA, UV 220 nm), or Method B: Phenomenex Luna C18 column (4.6×50 mm) eluted at 4 mL/min with a 4 min gradient from 100% A to 100% B (A: 10% acetonitrile, 89.9% water, 0.1% TFA; B: 10% water, 89.9% acetonitrile, 0.1% TFA, UV 220 nm). Purification of intermediates and final products was carried out via either normal or reverse phase chromatography. Normal phase chromatography was carried out on an ISCO CombiFlash™ System using prepacked $SiO_2$ cartridges eluted with gradients of hexanes and ethyl acetate. Reverse phase preparative HPLC was carried out using a Shimadzu Preparative HPLC system running DiscoveryVP software using Method A: YMC Sunfire 5 μm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm), Method B: Phenomenex AXIA Luna 5 μm C18 30×75 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), Method C; Phenomenex Luna 5 μm C18 30×100 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), or Method D: Phenomenex Luna 5 μm C18 30×100 mm column with a 10 min gradient at 40 mL/min from 100%, A to 100% B (A: 10% methanol, 89.9% water, 0.1% TFA; B: 10% water, 89.9% methanol, 0.1% TFA, UV 220 ran). LCMS chromatograms were obtained on a Shimadzu HPLC system running DiscoveryVP software, coupled with a Waters ZQ mass spectrometer running MassLynx version 3.5 software using the same columns and conditions as utilized for analytical described above.

IV. BIOLOGY

While blood coagulation is essential to the regulation of an organism's hemostasis, it is also involved in many pathological conditions. In thrombosis, a blood clot, or thrombus, may form and obstruct circulation locally, causing ischemia and organ damage. Alternatively, in a process known as embolism, the clot may dislodge and subsequently become trapped in a distal vessel, where it again causes ischemia and organ damage. Diseases arising from pathological thrombus formation are collectively referred to as thromboembolic disorders and include acute coronary syndrome, unstable angina, myocardial infarction, thrombosis in the cavity of the heart, ischemic stroke, deep vein thrombosis, peripheral occlusive arterial disease, transient ischemic attack, and pulmonary embolism, hi addition, thrombosis occurs on artificial surfaces in contact with blood, including catheters, stents, and artificial heart valves.

Some conditions contribute to the risk of developing thrombosis. For example, alterations of the vessel wall, changes in the flow of blood, and alterations in the composition of the vascular compartment. These risk factors are collectively known as Virchow's triad. (Hemostasis and Thrombosis, Basic Principles and Clinical practice, page 853, 5$^{th}$ Edition, 2006, edited by Colman, R. W. et al. Published by Lippincott Williams & Wilkins)

Antithrombotic agents are frequently given to patients at risk of developing thromboembolic disease because of the presence of one or more predisposing risk factors from Virchow's triad to prevent formation of an occlusive thrombus (primary prevention). For example, in an orthopedic surgery setting (e.g., hip and knee replacement), an antithrombotic agent is frequently administered prior to a surgical procedure. The antithrombotic agent counterbalances the prothrombotic stimulus exerted by vascular flow alterations (stasis), potential surgical vessel wall injury, as well as changes in the composition of the blood due to the acute phase response related to surgery. Another example of the use of an antithrombotic agent for primary prevention is dosing with aspirin, a platelet activation inhibitor, in patients at risk for developing thrombotic cardiovascular disease. Well recognized risk factors in this setting include age, male gender, hypertension, diabetes mellitus, lipid alterations, and obesity.

Antithrombotic agents are also indicated for secondary prevention, following an initial thrombotic episode. For example, patients with mutations in factor V (also known as factor V Leiden) and additional risk factors (e.g., pregnancy), are dosed with anticoagulants to prevent the reoccurrence of venous thrombosis. Another example entails secondary prevention of cardiovascular events in patients with a history of acute myocardial infarction or acute coronary syndrome. In a clinical setting, a combination of aspirin and clopidogrel (or other thienopyridines) may be used to prevent a second thrombotic event.

Antithrombotic agents are also given to treat the disease state (i.e., by arresting its development) after it has already started. For example, patients presenting with deep vein thrombosis are treated with anticoagulants (i.e. heparin, warfarin, or LMWH) to prevent further growth of the venous occlusion. Over time, these agents also cause a regression of the disease state because the balance between prothrombotic factors and anticoagulant/profibrinolytic pathways is changed in favor of the latter. Examples on the arterial vascular bed include the treatment of patients with acute myocardial infarction or acute coronary syndrome with aspirin and clopidogrel to prevent further growth of vascular occlusions and eventually leading to a regression of thrombotic occlusions.

Thus, antithrombotic agents are used widely for primary and secondary prevention (i.e., prophylaxis or risk reduction) of thromboembolic disorders, as well as treatment of an already existing thrombotic process. Drugs that inhibit blood coagulation, or anticoagulants, are "pivotal agents for prevention and treatment of thromboembolic disorders" (Hirsh, J, et al. *Blood* 2005, 105, 453-463).

Because of its key role in the coagulation cascade, researchers have postulated that inhibition of factor VIIa could be used to treat or prevent thromboembolic diseases. (Girard, T. J.; Nicholson, N. S. *Curr. Opin. Pharmacol.* 2001, 1, 159-463; Lazarus, R. A., et al. *Curr. Med. Chem.* 2004, 11, 2275-2290; Frederick, R. et al. *Curr. Med. Chem.* 2005, 12, 397-417.) Several studies have confirmed that various biological and small molecule inhibitors of factor VIIa have in vivo antithrombotic efficacy with a low bleeding liability. For instance, it has been demonstrated that a biological factor VIIa inhibitor XK1, comprising a hybrid of Factor X light chain and tissue factor pathway inhibitor first kunitz domain, prevents thrombus formation in a rat model of arterial thrombosis, with no change in bleeding time or total blood loss (Szalony, J. A, et al. *J. Thrombosis and Thrombolysis* 2002, 14, 113-121). In addition, small molecule active site directed, factor VIIa inhibitors have demonstrated, antithrombotic efficacy in animal models of arterial thrombosis (Suleymanov, O., et al. *J Pharmacology and Experimental Therapeutics* 2003, 306, 1115-1121; Olivero, A. G. et al. *J. Biol. Chem.* 2005, 280, 9160-9169; Young, W. B., et al. *Bioorg. Med. Chem. Lett.* 2006, 16, 2037-2041; Zbinden, K. G. et al. *Bioorg. Med. Chem.* 2006, 14, 5357-5369) and venous thrombosis (Szalony, J. A., et al, Thrombosis Research 2003, 112, 167-174; Arnold, C. S., et al. *Thrombosis Research* 2006, 117, 343-349), with little impact on bleeding time or blood loss. Moreover, the biological factor VIIa inhibitor recombinant nematode anticoagulant protein c2(rNAPc2) is currently under clinical investigation for treatment of acute coronary syndromes. Results of initial clinical trials demonstrate that rNAPc2 prevents deep vein thrombosis in patients undergoing total knee replacement (Lee, A., et al. *Circulation* 2001, 104, 74-78), reduces systemic thrombin generation in patients undergoing coronary angioplasty (Moons, A. H. M. *J. Am. Coll. Cardiol.* 2003, 41, 2147-2153) and reduces magnitude and duration of ischemic events in patients with acute coronary syndromes (Giugliano, R. P. et al. World Congress of Cardiology 2006, Barcelona, Poster #3897).

Work has accordingly been performed to identify and optimize factor VIIa inhibitors. For example, U.S. Pat. No. 5,866, 542 describes recombinant nematode anticoagulant proteins which inhibit factor VIIa. U.S. Pat. No. 5,843,442 discloses monoclonal antibodies or antibody fragments possessing factor VIIa inhibitory activity, and U.S. Pat. No. 5,023,236 presents tripeptides and tripeptide derivatives that inhibit factor VIIa.

While a number of factor VIIa inhibitors have been discussed in the art, improved inhibitors, especially non-peptide inhibitors, of serine proteases for the treatment of thromboembolic disorders are always desirable. The present invention discloses bicyclic lactam derivatives, and analogues thereof, as inhibitors of coagulation Factor VIIa and, as such, their utility in the treatment of thromboembolic disorders.

Also, it is preferred to find new compounds with improved activity in in vitro clotting assays, compared with known serine protease inhibitors, such as the activated partial thromboplastin time (aPTT) or the prothrombin time (PT) assay. (For a description of the aPTT and PT assays see, Goodnight, S. H.; Hathaway, W. E. Screening Tests of Hemostasis. *Disorders of Thrombosis and Hemostasis: a clinical guide*, $2^{nd}$ edition, McGraw-Hill: New York, 2001 pp. 41-51).

It is also desirable to find new compounds with improved pharmacological characteristics compared with known factor VIIa inhibitors. For example, it is preferred to find new compounds with improved factor VIIa inhibitory activity and improved selectivity for factor VIIa versus other serine proteases. It is also desirable and preferable to find compounds with advantageous and improved characteristics in one or more of the following categories that are given as examples, and not intended to be limiting: (a) pharmacokinetic properties, including oral bioavailability, half life, and clearance; (b) pharmaceutical properties; (c) dosage requirements; (d) factors which decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) factors that improve manufacturing costs or feasibility.

As used herein, the term "patient" encompasses all mammalian species.

As used herein, "treating" or "treatment" cover the treatment of a disease-state in a mammal, particularly in a human, and include: (a) inhibiting the disease-state, i.e., arresting its development; and/or (b) relieving the disease-state, i.e., causing regression of the disease state.

As used herein, "prophylaxis" or 'prevention' cover the preventive treatment of a subclinical disease-state in a mammal, particularly in a human, aimed at reducing the probability of the occurance of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurance of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination with other active ingredients to inhibit factor VIIa or to prevent or treat the disorders listed herein. When applied to a combination, the term refers to combined amounts of the active ingredients that result in the preventive or therapeutic effect, whether administered in combination, serially or simultaneously.

The term "thrombosis", as used herein, refers to formation or presence of a thrombus (pl. thrombi); clotting within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined vide supra).

The term "thromboembolic disorders (or conditions)" as used herein includes arterial or venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolisms, pulmonary embolisms, and thrombosis resulting from medical implants, devices, of procedures in which blood is exposed to an artificial surface that promotes thrombosis. The medical implants or devices include, but are not limited to: prosthetic valves, artificial valves, indwelling catheters, stents, blood oxygenators, shunts, vascular access ports, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid communis, carotid interna, or intracerebral arteries.

It is noted that thrombosis includes vessel occlusion (e.g. after a bypass) and reocclusion (e.g., during or after percutaneous transluminal coronary angioplasty). The thromboembolic disorders may result from conditions including but not limited to atherosclerosis, surgery or surgical complications, prolonged immobilization, atrial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, arterial fibrillation is frequently associated with thromboembolic disorders. Risk factors for arterial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to are family history, obesity, physical inactivity, race/ethnicity, previously impaired fasting glucose or glucose tolerance test, history of gestational diabetes mellitus or delivery of a 'big baby', hypertension, low HDL cholesterol, and polycystic ovary syndrome.

Risk factor for congenital thrombophilia include gain of function mutations in coagulation factors or loss of function mutations in the anticoagulant- or fibrinolytic pathways.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population. (Levitan, N. et al. *Medicine* (Baltimore) 1999, 78(5):285-291; Levine M. et al *N Engl J Med* 1996, 334(11):677-681; Blom, J. W. et al. *JAMA:* 2005, 293(6); 715-722.) Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e. presence of metastases), (ii) the presence of central vein catheters, (iii) surgery and anticancer therapies including chemotherapy, and (iv) hormones and antiangiogenic drugs. Thus, it is common clinical practice to dose patients having advanced tumors with heparin or low molecular heparin to prevent thromboembolic disorders. A number of low molecular heparin preparations have been approved by the FDA for these indications.

There are three main clinical situations when considering the prevention of VTE in a medical cancer patient: (i) the patient is bedridden for prolonged periods of time; (ii) the ambulatory patient is receiving chemotherapy or radiation; and (iii) the patient is with indwelling central vein catheters. Unfractionated heparin (UFH) and low molecular weight heparin (LMWH) are effective antithrombotic agents in cancer patients undergoing surgery. (Mismetti, P. et al. *British Journal of Surgery* 2001, 88:913-930.)

A. In Vitro Assays

The effectiveness of compounds of the present invention as inhibitors of the coagulation factors VIIa, IXa, Xa, XIa, XIIa or thrombin, can be determined using a relevant purified serine protease, respectively, and an appropriate synthetic substrate. The rate of hydrolysis of the chromogenic substrate by the relevant serine protease was measured both in the absence and presence of compounds of the present invention. Hydrolysis of the substrate resulted, in the release of para-nitroaniline (pNA), which was monitored spectrophotometrically by measuring the increase in absorbance at 405 nM, or the release of aminomethylcoumarin (AMC), which was monitored spectrofluorometrically by measuring the increase in emission at 460 nM with excitation at 380 nM. A decrease in the rate of absorbance change at 405 nM in the presence of inhibitor is indicative of enzyme inhibition. Such methods are known to one skilled in the art. The results of this assay are expressed as inhibitory constant, $K_i$.

Factor VIIa determinations were made in 0.005 M calcium chloride, 0.15 M sodium chloride, 0.05 M HEPES buffer containing 0.5% PEG 8000 at a pH of 7.5. Determinations were made using purified human Factor VIIa (Haematologic Technologies) or recombinant human Factor VIIa (Novo Nordisk) at a final assay concentration of 1-5 nM, recombinant soluble tissue factor at a concentration of 10-40 nM and the synthetic substrate H-D-Ile-Pro-Arg-pNA (S-2288; Chromogenix or BMPM-2; AnaSpec) at a concentration of 0.001-0.0075 M.

Factor IXa determinations were made in 0.005 M calcium chloride, 0.1M sodium chloride, 0.0001 M Refludan (Berlex), 0.05 M TRIS base and 0.5% PEG 8000 at a pH of 7.4. Refludan was added to inhibit small amounts of thrombin in the commercial preparations of human Factor IXa. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Phe-Gly-Arg-AMC; CenterChem) at a concentration of 0.0004-0.0005 M.

Factor Xa determinations were made in 0.1 M sodium phosphate buffer at a pH of 7.4 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu(gamma-OMe, 50%)-Gly-Arg-pNA; Chromogenix) at a concentration of 0.0002-0.00035 M.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 75-200 pM (Haematologic Technologies) and the synthetic substrate S-2366 (pyroGlu-Pro-Arg-pNA; Chromogenix) at a concentration of 0.0002-0.001 M.

Factor XIIa determinations were made in 50 mM HEPES buffer at pH 7.4 containing 145 mM NaCl, 5 mM KCl, and 0.1% PEG 8000. Determinations were made using purified human Factor XIIa at a final concentration of 4 nM (American Diagnostica) and the synthetic substrate Spectrozyme #312 (pyroGlu-Pro-Arg-pNA; American Diagnostica) at a concentration of 0.00015 M.

Thrombin determinations were made in 0.1 M sodium phosphate buffer at a pH of 7.5 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; Chromogenix) at a concentration of 0.0002-0.00026 M.

The Michaelis constant, $K_m$, for substrate hydrolysis by each protease was determined at 25° C. using the method of Lineweaver and Burk. Values of $K_i$ were determined by allowing the protease to react with the substrate in the presence of the inhibitor. Reactions were allowed to go for periods of 20-180 minutes (depending on the protease) and the velocities (rate of absorbance change vs time) were measured. The following relationship was used to calculate $K_i$ values:

$$(v_O - v_s)/v_S = I/(K_i(1 + S/K_m))$$ for a competitive inhibitor with one binding site; or $$v_S/v_O = A + ((B - A)/1 + (IC_{50}/(I)^n)))$$ and $$K_i = IC_{50}/(1 + S/K_m)$$ for a competitive inhibitor where:
$v_O$ is the velocity of the control in the absence of inhibitor;
$v_S$ is the velocity in the presence of inhibitor;
I is the concentration of inhibitor;
A is the minimum activity remaining (usually locked at zero);
B is the maximum activity remaining (usually locked at 1.0);
n is the Hill coefficient, a measure of the number and cooperativity of potential inhibitor binding sites;
$IC_{50}$ is the concentration of inhibitor that produces 50% inhibition under the assay conditions;
$K_i$ is the dissociation constant of the enzyme:inhibitor complex;
S is the concentration of substrate; and
$K_m$ is the Michaelis constant for the substrate.

The selectivity of a compound may be evaluated by taking the ratio of the $K_i$ value for a given protease with the $K_i$ value for the protease of interest (i.e., selectivity for FVIIa versus protease P=$K_i$ for protease P/$K_i$ for FVIIa). Compounds with selectivity ratios >20 are considered selective. Compounds with selectivity ratios >100 are preferred, and compounds with selectivity ratios >500 are more preferred.

The effectiveness of compounds of the present invention as inhibitors of coagulation can be determined using a standard or modified clotting assay. An increase in the plasma clotting time in the presence of inhibitor is indicative of anticoagulation. Relative clotting time is the clotting time in the presence of an inhibitor divided by the clotting time in the absence of an inhibitor. The results of this assay may be expressed as IC1.5× or IC2×, the inhibitor concentration required to increase the clotting time by 50 or 100 percent, respectively. The IC1.5× or IC2× is found by linear interpolation from relative clotting time versus inhibitor concentration plots using inhibitor concentration that spans the IC1.5× or IC2×.

Clotting times are determined using citrated normal human plasma as well as plasma obtained from a number of laboratory animal species (e.g., rat, or rabbit). A compound is diluted into plasma beginning with a 10 mM DMSO stock solution. The final concentration of DMSO is less than 2%. Plasma clotting assays are performed in an automated coagulation analyzer (Sysmex, Dade-Behring, Ill.). Similarly, clotting times can be determined from laboratory animal species or humans dosed with compounds of the invention.

Activated Partial Thromboplastin Time (aPTT) is determined using Alexin (Trinity Biotech, Ireland) following the directions in the package insert. Plasma (0.05 mL) is warmed to 37° C. for 1 minute. Alexin (0.05 mL) is added to the plasma and incubated for an additional 2 to 5 minutes. Calcium chloride (25 mM, 0.05 mL) is added to the reaction to initiate coagulation. The clotting time is the time in seconds from the moment calcium chloride is added until a clot is detected.

Prothrombin Time (PT) is determined using thromboplastin (Thromboplastin C Plus, Dade-Behring, Illinois) following the directions in the package insert. Plasma (0.05 mL) is warmed to 37° C. for 1 minute. Thromboplastin (0.1 mL) is added to the plasma to initiate coagulation. The clotting time is the time in seconds from the moment thromboplastin is added until a clot is detected.

B. In Vivo Assays

The effectiveness of compounds of the present invention as antithrombotic agents can be determined using relevant in vivo thrombosis models, including In Vivo Electrically-induced Carotid Artery Thrombosis Models and In Vivo Rabbit Arterio-venous Shunt Thrombosis Models.

a. In Vivo Electrically-induced Carotid Artery Thrombosis (ECAT) Model

The rabbit ECAT model, described by Wong et al. (*J Pharmacol Exp Ther* 2000, 295, 212-218), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. An electromagnetic flow probe is placed on a segment of an isolated carotid artery to monitor blood flow. Test agents or vehicle will be given (i.v., i.p., s.c., or orally) prior to or after the initiation of thrombosis. Drug treatment prior to initiation of thrombosis is used to model the ability of test agents to prevent and reduce the risk of thrombus formation, whereas dosing after initiation is used to model the ability to treat existing thrombotic disease. Thrombus formation is induced by electrical stimulation of the carotid artery for 3 min at 4 mA using an external stainless-steel bipolar electrode. Carotid blood flow is measured continuously over a 90-min period to monitor thrombus-induced occlusion. Total carotid blood flow over 90 min is calculated by the trapezoidal rule. Average carotid flow over 90 min is then determined by converting total carotid blood flow over 90 min to percent of total control carotid blood flow, which would result if control blood flow had been maintained continuously for 90 min. The $ED_{50}$ (dose that increased average carotid blood flow over 90 min to 50% of the control) of compounds are estimated by a nonlinear least square regression program using the Hill sigmoid $E_{max}$ equation (DeltaGraph; SPSS Inc., Chicago, Ill.).

b. In Vivo Rabbit Arterio-venous (AV) Shunt Thrombosis Model

The rabbit AV shunt model, described by Wong et al. (Wong, P. C. et al. *J Pharmacol Exp Ther* 2000, 292, 351-357), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. The femoral artery, jugular vein and femoral vein are isolated and catheterized. A saline-filled AV shunt device is connected between the femoral arterial and the femoral venous cannulae. The AV shunt device consists of an outer piece of tygon tubing (length=8 cm; internal diameter=7.9 mm) and an inner piece of tubing (length=2.5 cm; internal diameter=4.8 mm). The AV shunt also contains an 8-cm-long 2-0 silk thread (Ethicon, Somerville, N.J.). Blood flows from the femoral artery via the AV-shunt into the femoral vein. The exposure of flowing blood to a silk thread induces the formation of a significant thrombus. Forty minutes later, the shunt is disconnected and the silk thread covered with thrombus is weighed. Test agents or vehicle will be given (i.v., i.p., s.c, or orally) prior to the opening of the AV shunt. The percentage inhibition of thrombus formation is determined for each treatment group. The $ID_{50}$ values (dose which produces 50% inhibition of thrombus formation) are estimated by a nonlinear least square regression program using the Hill sigmoid $E_{max}$ equation (DeltaGraph; SPSS Inc., Chicago, Ill.).

V. PHARMACEUTICAL COMPOSITIONS, FORMULATIONS AND COMBINATIONS

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutical acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 18th Edition, 1990.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intraveneously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intra-musculary, or sub-cutaneously. When administered intra-venous or intra-arterial, the dose can be given continuously or intermittend. Furthermore, formulation can be developed for intramusculary and subcutaneous delivery that ensure a gradual release of the active pharmaceutical ingredient.

Compounds of this invention can be administered in intra-nasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, Mack Publishing Company, a standard reference text in this field.

Where the compounds of this invention are combined, with other anticoagulant agents, for example, a daily dosage may be about 0.1 to about 100 milligrams of the compound of the present invention and about 0.1 to about 100 milligrams per kilogram of patient body weight. For a tablet dosage form, the compounds of this invention generally may be present in an amount of about 5 to about 100 milligrams per dosage unit, and the second anti-coagulant in an amount of about 1 to about 50 milligrams per dosage unit.

Where the compounds of the present invention are administered in combination with an anti-platelet agent, by way of general guidance, typically a daily dosage may be about 0.01 to about 25 milligrams of the compound of the present invention and about 50 to about 150 milligrams of the anti-platelet agent, preferably about 0.1 to about 1 milligrams of the compound of the present invention and about 1 to about 3 milligrams of antiplatelet agents, per kilogram of patient body weight.

Where the compounds of the present invention are administered in combination with thrombolytic agent, typically a daily dosage may be about 0.1 to about 1 milligrams of the compound of the present invention, per kilogram of patient body weight and, in the case of the thrombolytic agents, the usual dosage of the thrombolyic agent when administered alone may be reduced by about 50-80% when administered with a compound of the present invention.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

In another embodiment, the present invention provides a pharmaceutical composition further comprising additional therapeutic agent(s) selected from potassium channel openers, potassium channel blockers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phosphodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a pharmaceutical composition further comprising additional therapeutic agent(s) selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a potassium channel blocker, a cholesterol/lipid lowering agent, or a combination thereof.

In another embodiment, the present invention provides a pharmaceutical composition further comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In another embodiment, the present invention provides a pharmaceutical composition wherein the additional therapeutic agent is an antihypertensive agent selected from ACE inhibitors, AT-1 receptor antagonists, beta-adrenergic receptor antagonists, ETA receptor antagonists, dual ETA7AT-1 receptor antagonists, renin inhibitors (alliskerin) and vasopepsidase inhibitors, an antiarrythmic agent selected from IKur inhibitors, an anticoagulant selected from thrombin inhibitors, antithrombin-III activators, heparin co-factor II activators, other factor VIIa inhibitors, other kallikrein inhibitors, plasminogen activator inhibitor (PAI-1) antagonists, thrombin activatable fibrinolysis inhibitor (TAFI) inhibitors, factor XIa inhibitors, factor IXa inhibitors, and factor Xa inhibitors, or an antiplatelet agent selected from GPIIb/IIIa blockers, GP Ib/IX blockers, protease activated receptor 1 (PAR-1) antagonists, protease activated receptor 4 (PAR-4) antagonists, prostaglandin E2 receptor EP3 antagonists, collagen receptor antagonists, phosphodiesterase-III inhibitors, $P2Y_1$ receptor antagonists, $P2Y_{12}$ antagonists, thromboxane receptor antagonists, cyclooxygense-1 inhibitors, and aspirin, or a combination thereof.

In another embodiment, the present invention provides pharmaceutical composition, wherein the additional therapeutic agent(s) are an anti-platelet agent or a combination thereof.

In another embodiment, the present invention provides a pharmaceutical composition, wherein the additional therapeutic agent is the anti-platelet agent clopidogrel.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

Compounds that can be administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Other anticoagulant agents (or coagulation inhibitory agents) that may be used in combination with the compounds of this invention include warfarin, heparin (either unfractionated heparin or any commercially available low molecular weight heparin, for example LOVENOX™), synthetic pentasaccharide, direct acting thrombin inhibitors including hirudin and argatroban, as well as other factor VIIa inhibitors, factor IXa inhibitors, factor Xa inhibitors (e.g., Arixtra™, apixaban, rivaroxaban, LY-517717, DU-176b, DX-9065a, and those disclosed in WO 98/57951, WO 03/026652, WO 01/047919, and WO 00/076970), factor XIa inhibitors, and inhibitors of activated TAFI and PAI-1 known in the art.

The term anti-platelet agents (or platelet inhibitory agents), as used herein, denotes agents that inhibit platelet function, for example, by inhibiting the aggregation, adhesion or granule-content secretion of platelets. Such agents include, but are not limited to, the various known non-steroidal anti-inflammatory drugs (NSAIDS) such as acetaminophen, aspirin, codeine, diclofenac, droxicam, fentaynl, ibuprofen, indomethacin, ketorolac, mefenamate, morphine, naproxen, phenacetin, piroxicam, sufentanyl, sulfinpyrazone, sulindac, and pharmaceutically acceptable salts or prodrugs thereof. Of the NSAIDS, aspirin (acetylsalicylic acid or ASA) and piroxicam are preferred. Other suitable platelet inhibitory agents include glycoprotein IIb/IIIa antagonists (e.g., tirofiban, eptifibatide, abciximab, and integrelin), thromboxane-A2-receptor antagonists (e.g., ifetroban), thromboxane-A-synthetase inhibitors, phosphodiesterase-III (PDE-III) inhibitors (e.g., dipyridamole, cilostazol), and PDE-V inhibitors (such as sildenafil), protease-activated receptor 1 (PAR-1) antagonists (e.g., E-5555, SCH-530348, SCH-203099, SCH-529153 and SCH-205831), and pharmaceutically acceptable salts or prodrugs thereof.

Other examples of suitable anti-platelet agents for use in combination with the compounds of the present invention, with or without aspirin, are ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include clopidogrel, ticlopidine, prasugrel, and AZD-6140, cangrelor, and pharmaceutically acceptable salts or prodrugs thereof. Ticlopidine and clopidogrel are also preferred compounds since they are known to be more gentle than aspirin on the gastrointestinal tract in use. Clopidogrel is an even more preferred agent.

A preferred example is a triple combination of a compound of the present invention, aspirin, and another anti-platelet agent. Preferably, the anti-platelet agent is clopidogrel or prasugrel, more preferably clopidogrel.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the secretion of platelet granule contents including serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, dabigatran, AZD-0837, and those disclosed in WO 98/37075 and WO 02/044145, and pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, thrombin inhibitors, inhibitors of factors IXa, Xa, and XIa, PAI-I inhibitors (i.e., inactivators of tissue plasminogen activator inhibitors), inhibitors of activated TAFI, alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable cholesterol/lipid lowering agents and lipid profile therapies for use in combination with the compounds of the present invention include HMG-CoA reductase inhibitors (e.g., pravastatin, lovastatin, simvastatin, fluvastatin, atorvsatatin, rosuvastatin, and other statins), low-density lipoprotein (LDL) receptor activity modulators (e.g., HOE-402, PCSK9 inhibitors), bile acid sequestrants (e.g., cholestyramine and colestipol), nicotinic acid or derivatives thereof (e.g., NIASPAN®), GPR109B (nicotinic acid receptor) modulators, fenofibric acid derivatives (e.g., gemfibrozil, clofibrate, fenofibrate and benzafibrate) and other peroxisome proliferator-activated receptors (PPAR) alpha modulators, PPARdelta modulators (e.g., GW-501516), PPAR-gamma modulators (e.g., rosiglitazone), compounds that have multiple functionality for modulating the activities of various combinations of PPARalpha, PPARgamma and PPARdelta, probucol or derivatives thereof (e.g., AGI-1067), cholesterol absorption inhibitors and/or Niemann-Pick Cl-like transporter inhibitors (e.g., ezetimibe), cholesterol ester transfer protein inhibitors (e.g., CP-529414), squalene synthase inhibitors and/or squalene epoxidase inhibitors or mixtures thereof, acyl coenzyme A: cholesteryl acyltransferase (ACAT) 1 inhibitors, ACAT2 inhibitors, dual ACAT1/2 inhibitors, ileal bile acid transport inhibitors (or apical sodium co-dependent bile acid transport inhibitors), microsomal triglyceride transfer protein inhibitors, liver-X-receptor (LXR) alpha modulators, LXRbeta modulators, LXR dual alpha/beta modulators, FXR modulators, omega 3 fatty acids (e.g., 3-PUFA), plant stanols and/or fatty acid esters of plant stanols (e.g., sitostanol ester used in BENECOL® margarine), endothelial lipase inhibitors, and HDL functional mimetics which activate reverse cholesterol transport (e.g., apoAI derivatives or apoAI peptide mimetics).

The compounds of the present invention are also useful as standard or reference compounds, for example as a quality standard or control, in tests or assays involving the inhibition of thrombin, Factor VIIa, IXa, Xa, XIa, and/or plasma kallikrein. Such compounds may be provided in a commercial kit, for example, for use in pharmaceutical research involving thrombin, Factor VIIa, IXa, Xa, XIa, and/or plasma kallikrein. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving thrombin, Factor VIIa, IXa, Xa, XIa, and/or plasma kallikrein. For example, the presence of thrombin, Factor VIIa, IXa, Xa XIa, and/or plasma kallikrein in an unknown sample could be determined by addition of the relevant chromogenic substrate, for example S2288 for Factor VIIa, to a series of solutions containing test sample and optionally one of the compounds of the present invention. If production of pNA is observed in the solutions containing test sample, but not in the presence of a compound of the present invention, then one would conclude Factor Via was present.

Extremely potent and selective compounds of the present invention, those having $K_i$ values less than or equal to 0.001 μM against the target protease and greater than or equal to 0.1 μM against the other proteases, may also be used in diagnostic assays involving the quantitation of thrombin, Factor VIIa, IXa, Xa, XIa, and/or plasma kallikrein in serum samples. For example, the amount of Factor Via in serum samples could be determined by careful titration of protease activity in the presence of the relevant chromogenic substrate, S2288, with a potent and selective Factor Via inhibitor of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic and/or inflammatory disorder (as defined previously). In another embodiment, the package insert states that the pharmaceutical composition can be used in combination (as defined previously) with a second therapeutic agent to treat a thromboembolic and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof.

EXAMPLES

The following Examples have been prepared, isolated and characterized using the methods disclosed herein. The following Examples demonstrate a partial scope of the invention and are not meant to be limiting of the scope of the invention.

Intermediate 1: (R)-methyl (4-(isopropylsulfonyl)-3-(pyrrolidin-2-yl)phenyl)carbamate hydrochloride

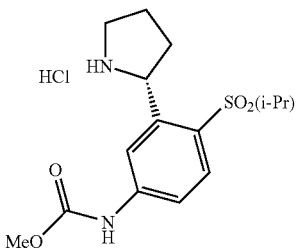

Intermediate 1A

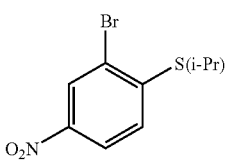

To 3-bromo-4-fluoronitrobenzene (5.0 g, 22.7 mmol) and 2-thiopropane (2.3 mL, 24.9 mmol) in DMF (15 mL) was added potassium carbonate (3.44 g, 24.9 mmol). The reaction was heated to 50° C. overnight. After cooling, the crude reaction mixture was filtered over Celite® and washed with ethyl acetate. The combined filtrate and washings were concentrated. The residue was redissolved in ethyl acetate and washed with water (3×) and then dried over sodium sulfate. Some of the yellow solid (2.53 g) precipitated. The filtrate was concentrated and purified by flash column chromatography to give 3.65 g of Intermediate 1A (98% total yield). $^1$H NMR (400 MHz, CDCl$_3$) δ ppm 1.41 (d, J=6.60 Hz, 6 H) 3.69 (m, 1 H) 7.50 (d, J=8.80 Hz, 1 H) 8.15 (dd, J=8.80, 2.45 Hz, 1 H) 8.35 (d, J=2.45 Hz, 1 H).

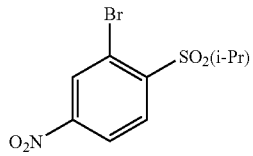

Intermediate 1B

To Intermediate 1A (1.6 g, 5.8 mmol) in methanol (7 mL) was added Oxone® (10.7 g, 17.4 mmol) in water (10 mL). The reaction was stirred at rt overnight. The reaction was quenched with 5% NaHSO$_3$ and then neutralized with 1M NaOH. The organic solvent was evaporated and the aqueous layer was extracted with dichloromethane (3×). The combined extracts were washed with brine and dried over sodium sulfate. The solvent was removed and the crude residue was purified by flash column chromatography to give 1.35 g of Intermediate 1B (76% yield). $^1$H NMR (400 MHz, Methanol-d$_4$) δ ppm 1.25 (d, J=6.85 Hz, 6 H) 3.92 (m, 1 H) 8.30 (d, J=8.56 Hz, 1 H) 8.39 (m, 1 H) 8.64 (d, J=1.96 Hz, 1 H).

Intermediate 1C

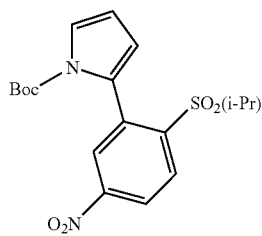

To a mixture of Intermediate 1B (3.0 g, 9.7 mmol), 1-(tert-butoxycarbonyl)-1H-pyrrol-2-ylboronic acid (2.5 g, 11.7 mmol, prepared according to the procedure in *Synthesis*, 1991, 613-615.) and sodium carbonate (19.5 mL, 2M, 38.9 mmol) in 1,2-dimethoxyethane (100 mL, flushed and degassed (3×) with nitrogen) was added Pd(PPh$_3$)$_4$ (2.2 g, 1.9 mmol) under nitrogen. The reaction was heated to 95° C. for 3 h. The catalyst was filtered over Celite®and washed with ethyl acetate. The organic layer was washed with water, brine and then dried over sodium sulfate. The solvent was removed and the crude residue was purified by flash column chromatography to give 3.68 g of Intermediate 1C (96% yield). $^1$H NMR (400 MHz, Methanol-d$_4$) δ ppm 1.01 (d, J=6.85 Hz, 3 H) 1.15 (d, J=6.85 Hz, 3 H) 1.20 (d, J=7.83 Hz, 9 H) 3.00 (m, 1 H) 6.29 (m, 2 H) 7.41 (dd, J=3.18, 1.71 Hz, 1 H) 8.20 (d, J=2.20 Hz, 1 H) 8.25 (d, J=8.56 Hz, 1 H), 8.41 (dd, J=8.68 Hz, 2.32 Hz, 1 H).

Intermediate 1D

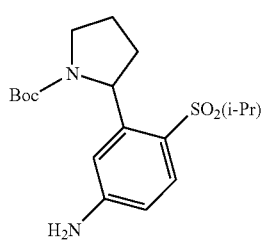

To platinum oxide (0.5 g) was added Intermediate 1C in ethanol and hydrogen chloride (0.45 mL) under nitrogen. The reaction was placed under hydrogen (40 psi). After 1.5 h the reaction was half done, additional platinum oxide (200 mg) was added and reaction was stirred under hydrogen (40 psi) for 2 h. The catalyst was filtered over Celite® and washed with ethanol. The filtrate was neutralized with diethylamine. The solvent was evaporated and the crude residue was redissolved in dichloromethane. The organic layer was washed with water, brine and dried over sodium sulfate. The solvent was removed and the crude product was purified by flash column chromatography to give a white solid Intermediate 1D (1.6 g, 88%). $^1$H NMR (400 MHz, Methanol-d$_4$) δ ppm 1.24 (m, 15 H) 1.84 (m, 3 H) 2.37 (m, 1 H) 3.15 (m, H) 3.62 (m, 2 H) 5.28 (s, 1 H) 6.53 (d, J=19.56 Hz, 2 H) 7.50 (d, J=8.56 Hz, 1 H).

Intermediate 1E

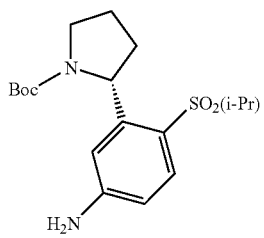

Racemate Intermediate 1D was separated using a preparative HPLC equipped with a Chiralpak® AD column (5 cm×50 cm, 20 μ). The separation was performed using an isocratic method of 15% isopropanol/heptane with 0.1% diethylamine for 100 min with a flow rate of 50 mL/min. The first peak is Intermediate 1E: $^1$H NMR (400 MHz, Methanol-d$_4$) δ ppm 1.20 (m, 15 H) 1.83 (s, 3H) 2.44 (s, 1 H) 3.26 (m, 1 H) 3.64 (m, 2 H) 5.29 (s, 1 H) 6.57 (m, 2 H) 7.52 (s, 1 H).

Intermediate 1

To Intermediate 1E (0.1 g, 0.27 mmol) in pyridine (1 mL) at 0° C. was added methyl chloroformate (57 (μL, 0.54 mmol). After 2.0 h of stirring at rt the reaction was acidified with 1M HCl to pH 3-4. The product was extracted with ethyl acetate and was washed with brine and dried over sodium sulfate. After evaporation of the solvent, the crude product was redissolved in ethyl acetate (1.5 mL) and hydrogen chloride (2 mL, 4M in dioxane) was added. The reaction was stirred for 3 h at rt. The solvent was removed and placed on the lyophilizer to give 0.15 g white solid Intermediate 1. $^1$H NMR (400 MHz, Methanol-d$_4$) δ ppm 1.25 (t, J=7.09 Hz, 3 H) 1.37 (d, J=6.85 Hz, 3 H) 2.13-2.31 (m, 1 H) 2.31-2.47 (m, 2 H) 2.47-2.63 (m, 1 H) 3.36-3.56 (m, 3 H) 3.73-3.91 (m, 3 H) 5.43 (t, J=7.70 Hz, 1 H) 7.66 (dd, J=8.80, 2.20 Hz, 1 H) 7.97 (d, J=8.80 Hz, 1 H) 8.11 (d, J=1.96 Hz, 1 H).

Intermediate 2: (2R,3S)-methyl 2-(2-(isopropylsulfonyl)-5-(methoxycarbonyl)phenyl)pyrrolidine-3-carboxylate HCl salt

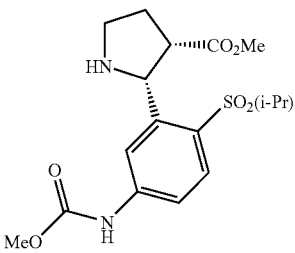

Intermediate 2A

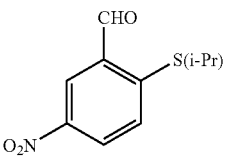

To 2-fluoro-5-nitrobenzaldehyde (5.8 g, 34.2 mmol) and 2-thiopropane (3.5 mL, 37.7 mmol) in DMF (20 mL) was added potassium carbonate (5.2 g, 37.7 mmol). The reaction mixture was stirred at 70° C. overnight. The crude reaction mixture was filtered and washed with ethyl acetate. The combined filtrate and washings were concentrated. The residue was redissolved in ethyl acetate and washed with water (3×) and then dried over sodium sulfate. Purification was performed by flash column chromatography to give 6.7 g of yellow oil Intermediate 2A. $^1$H NMR (400 MHz, DMSO-d$_6$) δ ppm 1.36 (d, J=6.60 Hz, 6 H) 3.73-3.93 (m, 1 H) 7.77 (d, J=9.05 Hz, 1 H) 8.36 (dd, J=9.05, 2.69 Hz, 1 H) 8.71 (d, J=2.69 Hz, 1 H) 10.20 (s, 1 H).

Intermediate 2B

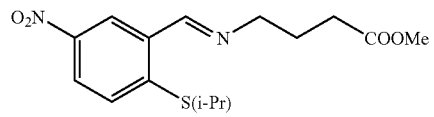

To the methyl aminobutyric ester (3.95 g, 25.7 mmol) in dichloromethane (200 mL) was added triethylamine (5.4 mL, 38.5 mmol) and then Intermediate 2A (5.8 g, 25.7 mmol) and 4 Å molecular sieves (5.0 g). The reaction was stirred overnight at rt. The reaction mixture was filtered to remove the molecular sieves and the solvent was evaporated to give 12.0 g of a solid Intermediate 2B together with triethylamine HCl salt. $^1$H NMR (400 MHz, Methanol-d$_4$) δ ppm 1.37 (t, J=6.24 Hz, 6 H) 1.93-2.11 (m, 2 H) 2.45 (t, J=7.21 Hz, 2 H) 7.68 (d, J=8.80 Hz, 1H) 8.21 (dd, J=8.80, 2.69 Hz, 1 H) 8.61 (d, J=2.69 Hz, 1 H) 8.79 (d, J=1.47 Hz, 1 H).

Intermediate 2C

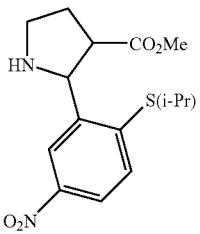

To Intermediate 2B (12.0 g, 28.2 mmol) and triethylamine (7.86 mL, 56.4 mmol) in dichloromethane at −10° C. was added titanium chloride (113 mL, IM in dichloromethane) dropwise under argon. The reaction was stirred at rt for 4 h and then quenched with saturated potassium carbonate. The mixture was filtered through Celite® and the aqueous layer was extracted with dichloromethane (2×). The organic extracts were combined, washed with brine and dried over sodium sulfate. The solvent was evaporated to give 7.3 g of crude pyrrolidine Intermediate 2C.

Intermediate 2D

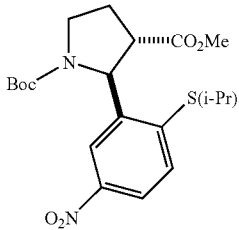

and Intermediate 2E:

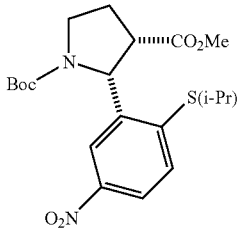

To the crude Intermediate 2C (7.3 g, 22.5 mmol) in methanol (100 mL) was added triethylamine (6.3 mL, 45 mmol) and then di-tert-butyl dicarbonate (5.9 g, 27 mmol). The reaction was stirred at rt for 2 h. The solvent was removed and crude residue was redissolved in ethyl acetate. The solution was washed with water and brine and dried over sodium sulfate. The solvent was evaporated and the crude residue was purified by flash column chromatography to give 4.3 g of yellow semi-solid Intermediate 2D and Intermediate 2E. $^1$H NMR analysis reveals approximately a 2:1 cis:trans ratio. Intermediate 2D and Intermediate 2E were separated in 95% purity by repeated (3×) trituration with EtOAc/hexanes (1:3). The solid collected was identified to be Intermediate 2D, the filtrate was Intermediate 2E. Intermediate 2D: $^1$H NMR (400 MHz, DMSO-$d_6$, 100° C.) δ ppm 1.24 (s, 9 H) 1.33 (d, J=6.60 Hz, 3 H) 1.36 (d, J=6.60 Hz, 3 H) 2.08-2.19 (m, 2 H) 2.92 (ddd, J=7.28, 3.85, 3.71 Hz, 1 H) 3.50-3.61 (m, 1 H) 3.67-3.73 (m, 4 H) 3.73-3.82 (m, 1H) 5.35 (d, J=3.30 Hz, 1 H) 7.65 (d, J=8.79 Hz, 1 H) 7.85 (d, J=2.20 Hz, 1 H) 8.07 (dd, J=8.52, 2.47 Hz, 1 H). Intermediate 2E: $^1$H NMR (400 MHz, DMSO-$d_6$, 100° C.) δ ppm 1.19 (s, 9 H) 1.34 (d, J=6.60 Hz, 3 H) 1.39 (d, J=6.60 Hz, 3 H) 2.17 (q, J=6.96 Hz, 2 H) 3.17-3.24 (s, 3 H) 3.56-3.67 (m, 2 H) 3.69-3.77 (m, 1 H) 3.77-3.83 (m, 1 H) 5.45 (d, J=8.25 Hz, 1 H) 7.60 (d, J=8.79 Hz, 1 H) 7.81 (d, J=2.20 Hz, 1H) 7.98-8.05 (m, 1 H).

Intermediate 2F

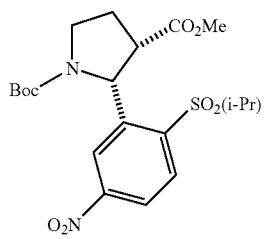

To Intermediate 2E (5.5 g, 13 mmol) in $CH_2Cl_2$ (100 mL) was added $NaHCO_3$ (3.28 g, 39 mmol) and MCPBA (75% purity, 7.4 g, 32 mmol). The mixture was stirred at rt for 4.0 h. It was quenched with sat. $NaHCO_3$ and extracted with $CH_2Cl_2$. The organic layer was dried over $Na_2SO_4$. After removal of solvent, the crude was purified with silica gel column chromatography eluting with gradient $CH_2Cl_2$ in hexanes to give Intermediate 2F (5.7 g, 95% yield). $^1$H NMR (500 MHz, DMSO-$d_6$, 100° C.) δ ppm 1.18 (d, J=6.60 Hz, 3 H) 1.27 (s, 9 H) 1.35 (d, J=6.60 Hz, 3 H) 2.18 (dd, J=17.86, 6.87 Hz, 2 H) 3.17 (s, 3 H) 3.61-3.72 (m, 3 H) 3.83 (m, 1 H) 5.82 (d, J=8.25 Hz, 1 H) 8.06 (s, 1 H) 8.13 (d, J=8.79 Hz, 1 H) 8.23-8.31 (m, 1 H).

Intermediate 2G

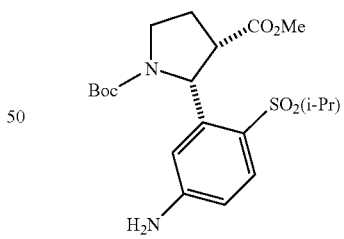

To 10% palladium on carbon (1.3 g) was added Intermediate 2F (5.7 g) in methanol (150 mL) and THF (50 mL) under a stream of nitrogen. The vessel was flushed and degassed with nitrogen gas (3×) and a balloon containing hydrogen gas was introduced. The reaction was stirred at rt for 4.0 h. The catalyst was filtered through Celite® and washed with methanol several times. The filtrate and the combined washings were evaporated and dried to give 5.5 g of Intermediate 2G. $^1$H NMR (400 MHz, DMSO-$d_6$, 100° C.) δ ppm 1.10 (d, J=6.60 Hz, 3 H) 1.21-1.30 (m, 12 H) 2.01-2.13 (m, 2 H) 3.20 (s, 3 H) 3.29-3.40 (m, 1 H) 3.44-3.53 (m, 1 H) 3.65 (ddd, J=10.17, 7.97, 5.50 Hz, 1 H) 3.70-3.78 (m, 1 H) 5.64 (d, J=8.25 Hz, 1 H) 6.46-6.55 (m, 2 H) 7.41 (d, J=7.70 Hz, 1 H).

Intermediate 2H

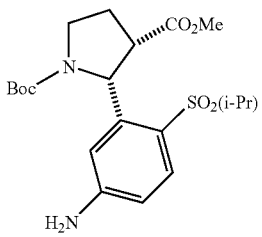

The enantiomers of the cis isomer Intermediate 2G were separated using a semi-preparative HPLC equipped with a Chiralpak® AD column. The separation was performed using an isocratic method of 15% isopropanol/heptane with 0.1% diethylamine for 30 min with a flow rate of 15 mL/min. The first peak corresponds to Intermediate 2H: $^1$H NMR (400 MHz, CDCl$_3$) δ ppm 1.06-1.53 (m, 15 H) 1.96-2.26 (m, 3 H) 3.19-3.31 (m, 3 H) 3.52-4.01 (m, 3 H) 5.69 (d, J=8.07 Hz, 1 H) 6.41-6.67 (m, 2 H) 7.66 (d, J=8.31 Hz, 1 H).

Intermediate 2

To Intermediate 2H (0.09 g, 0.21 mmol) in pyridine (1 mL) at 0° C. was added methyl chloroformate (32 μL, 0.42 mmol). After 2.0 h stirring at rt the reaction was acidified with 1M HCl to pH 3-4, The product was extracted with ethyl acetate and was washed with brine and dried over sodium sulfate. After evaporation of the solvent, the crude product was redissolved in ethyl acetate (1.5 mL) and hydrogen chloride (2 mL, 4M in dioxane) was added. The reaction was stirred for 3 h at rt. The solvent was removed and placed on the lyophilizer to give 0.11 g solid Intermediate 2I, $^1$H NMR (400 MHz, Methanol-d$_4$) δ ppm 1.22-1.40 (m, 6 H) 2.43-2.60 (m, 1 H) 2.62-2.80 (m, 1 H) 3.42 (s, 3 H) 3.45-3.65 (m, 2 H) 3.67-3.77 (m, 1 H) 3.78 (s, 3 H) 3.83-3.96 (m, 1 H) 5.84 (d, J=8.56 Hz, 1 H) 7.55-7.67 (m, 1 H) 7.81-7.90 (m, 1 H) 7.94 (d, J=8.80 Hz, 1 H).

Intermediate 3: (2R,3R)-ethyl 2-(2-(ethylsulfonyl)-5-(methoxycarbonylamino)phenyl)pyrrolidine-3-carboxylate hydrochloride Intermediate 4: (2R,3S)-ethyl 2-(2-(ethylsulfonyl)-5-(methoxycarbonylamino)phenyl)pyrrolidine-3-carboxylate hydrochloride Intermediate 3

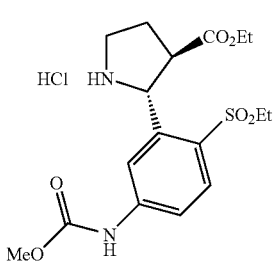

Intermediate 4

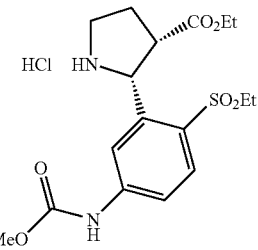

Intermediate 3A

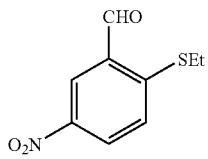

To 2-fluoro-5-nitrobenzaldehyde (25 g, 148 mmol) and ethyl thiol (15.1 mL, 203 mmol) in DMF (100 mL) was added potassium carbonate (35.8 g, 260 mmol). The reaction mixture was stirred at 60° C. for 8.0 h. After it cooled to rt, cold water (200 mL) was added and stirred at rt for 15 min. The precipitate was collected by filtration and washed with water. After drying, Intermediate 3A (25 g) was obtained as a yellow solid. The filtrate was extracted with EtOAc, washed with brine and dried over Na$_2$SO$_4$. After evaporation of solvent, the crude was triturated with EtOAc/hexane (1:3) to give a second crop of Intermediate 3A (3 g, total 90% yield). $^1$H NMR (400 MHz, CDCl$_3$) δ ppm 1.44 (t, J=7.47 Hz, 3 H) 3.08 (q, J=7.47 Hz, 2 H) 7.46 (d, J=8.79 Hz, 1 H) 8.30 (dd, J=8.79, 2.64 Hz, 1 H) 8.62 (d, J=2.20 Hz, 1 H) 10.25 (s, 1 H).

Intermediate 3B

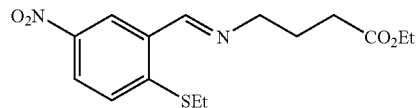

To ethyl aminobutyric ester (3.92 g, 23.4 mmol) in dichloromethane (100 mL) was added triethylamine (4.5 mL, 32.2 mmol) and then Intermediate 3A (4.94 g, 23.4 mmol) and 4 Å molecular sieves (3.0 g). The reaction was stirred overnight at rt and filtered to remove the molecular sieves. The solvent was evaporated to give a solid Intermediate 3B together with triethylamine HCl salt. $^1$H NMR (400 MHz, CDCl$_3$) δ ppm 1.10 (t, J=7.03 Hz, 3 H) 1.86-1.95 (m, 2 H) 2.29 (t, J=7.47 Hz, 2 H) 2.92 (q, J==7.47 Hz, 2 H) 3.56 (t, J=6.15 Hz, 2 H) 3.98 (q, J=7.32 Hz, 2 H) 7.99 (dd, J=8.79, 2.64 Hz, 1 H) 8.47 (d, J=2.64 Hz, 1 H) 8.51 (s, 1 H).

Intermediate 3C

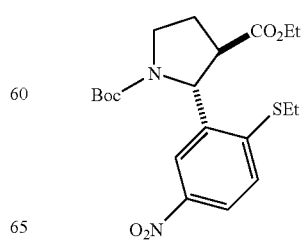

and Intermediate 3D:

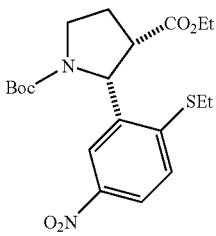

To Intermediate 3B (23.4 mmol) in CH$_2$Cl$_2$ (200 mL) at 45° C. was added Et$_3$N (5.7 mL, 41 mmol) followed by TiCl$_4$ (1.0 M in CH$_2$Cl$_2$, 41 mL, 41 mmol). The mixture was stirred from −15° C. to rt over 3.0 h before it was quenched with sat. K$_2$CO$_3$ (200 mL) at 0° C. and stirred at rt for 1.0 h. The mixture was filtered through a pad of wet Celite®, extracted with CH$_2$Cl$_2$ (3×60 mL). The organic layer was washed with water, dried over Na$_2$SO$_4$. A small portion of the dried organic layer was concentrated to give crude ethyl 2-(2-(ethylthio)-5-nitrophenyl)pyrrolidine-3-carboxylate: $^1$H NMR indicated a mixture of cis and trans isomer in ca. 1:1 ratio, LC-MS 325 (M+H). To the above ethyl 2-(2-(ethylthio)-5-nitrophenyl) pyrrolidine-3-carboxylate in THF (100 mL) was added Et$_3$N (3.3 mL) and di-tert-butyl dicarbonate (1.0 M in THF, 24 mL, 24 mmol). The mixture was stirred at rt for 3.0 h before it was washed with 0.5 N HCl (50 mL). The organic layer was washed with brine, dried (Na$_2$SO$_4$), filtered and concentrated. The crude product was first triturated with EtOAc, the precipitate was collected by filtration and washed with EtOAc to give the trans Intermediate 3C (1.7 g). The filtrate was concentrated and further purified by flash silica gel column chromatography using gradient EtOAc in hexane to give predominantly cis isomer Intermediate 3D ($^1$H NMR indicated presence of 30% trans isomer). To this cis isomer was added mixture of EtOAc/hexane (1:3), the precipitate was collected and washed with the same mixture of EtOAc/hexanes (1:3) to give a second crop of the trans Intermediate 3C (0.8 g, total 2.5 g, 25% yield). The filtrate was concentrated to give enriched cis isomer Intermediate 3D (3.0 g, > 92% purity, 30% yield). Intermediate 3C: $^1$H NMR (500 MHz, DMSO-d$_6$, 90° C.) δ ppm 1.20 and 1.23 (m, 12 H) 1.33 (t, J=7.42 Hz, 3 H) 2.08-2.19 (m, 2 H) 2.90 (br s, 1 H) 3.15 (q, J=7.15 Hz, 2 H) 3.48-3.58 (m, 1 H) 3.70 (m, 1 H) 4.10-4.19 (m, 2 H) 5.31 (brs, 1 H) 7.58 (d, J=8.79 Hz, 1 H) 7.84 (s, 1 H) 8.02-8.09 (m, 1 H). LC-MS 425 (M+H). Intermediate 3D: $^1$H NMR (500 MHz, DMSO-d$_6$, 90° C.) δ ppm 0.86 (t, J=6.87 Hz, 3 H) 1.18 (s, 9 H) 1.34 (t, J=7.15 Hz, 3 H) 2.12-2.22 (m, 2 H) 3.09-3.17 (m, 2 H) 3.56-3.67 (m, 3 H) 3.69-3.83 (m, 2 H) 5.43 (d, J=8.79 Hz, 1 H) 7.50-7.58 (ra, 1 H) 7.81 (s, 1 H) 8.03 (d, J=8.79 Hz, 1 H); LC-MS 425 (M+H).

Intermediate 3E

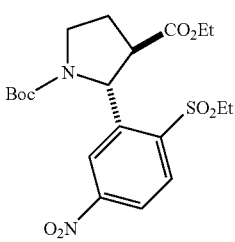

To Intermediate 3C (2.15 g, 5.06 mmol) in CH$_2$Cl$_2$ (100 mL) was added NaHCO$_3$ (1.28 g, 15.2 mmol) and MCPBA (75% purity, 2.9 g, 12.6 mmol). The mixture was stirred at rt overnight. It was quenched with sat. NaHCO$_3$ and extracted with CH$_2$Cl$_2$. The organic layer was dried over Na$_2$SO$_4$. After removal of solvent, the crude was purified with flash silica gel column chromatography eluting with gradient EtOAc in CH$_2$Cl$_2$ to give Intermediate 3E (2.1 g, 95% yield). $^1$H NMR (500 MHz, DMSO-d$_6$, 100° C.) δ ppm 1.16-1.25 (m, 6 H) 1.30 (s, 9 H) 2.07 (m, 1 H) 2.27 (m, 1 H) 2.97 (br s, 2 H) 3.45 (m, 3 H) 3.74-3.82 (m, 1 H) 4.14 (q, J=7.15 Hz, 2 H) 5.80 (s, 1 H) 8.09 (s, 1 H) 8.19 (d, J=8.79 Hz, 1 H) 8.32 (d, J=8.80 Hz, 1 H); LC-MS 401 (M−tert-Bn).

Intermediate 3F

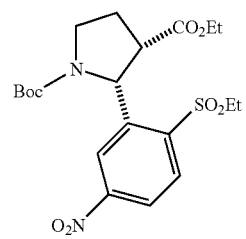

To Intermediate 3D (2.74 g, 6.45 mmol) in CH$_2$Cl$_2$ (100 mL) was added NaHCO$_3$ (1.63 g, 19.2 mmol) and MCPBA (75% purity, 3.7 g, 16.1 mmol). The mixture was stirred at rt overnight. It was quenched with sat. NaHCO$_3$ and extracted with CH$_2$Cl$_2$. The organic layer was dried over Na$_2$SO$_4$. After removal of solvent, the crude was purified with silica gel column chromatography eluting with gradient EtOAc in CH$_2$Cl$_2$ to give Intermediate 3F (2.1 g, 95% yield): $^1$H NMR (500 MHz, DMSO-d$_6$, 100° C.) δ ppm 0.82 (t, J=7.15 Hz, 3 H) 1.19-1.27 (m, 12 H) 2.13-2.23 (m, 2 H) 3.39-3.49 (m, 2 H) 3.62-3.73 (m, 4 H) 3.79-3.87 (m, 1 H) 5.86 (d, J=9.34 Hz, 1 H) 8.07 (s, 1 H) 8.15 (d, J=8.79 Hz, 1 H) 8.29 (d, J=8.79 Hz, 1H); LC-MS 401 (M−tert-Bn).

Intermediate 3G

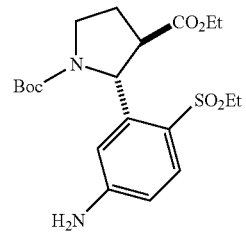

To Intermediate 3E (2.2 g) in methanol (50 mL) and THF (30 mL) was added 10% Pd/C (700 mg). The mixture was hydrogenated with a hydrogen balloon for 6.0 h. The Pd/C was removed by filtration and the filtrate was concentrated to afford Intermediate 3G (2.1 g, 95% yield). 5H NMR (500 MHz, DMSO-d$_6$, 100° C.) δ ppm 1.13 (t, J=7.42 Hz, 3 H) 1.16-1.23 (t, J=7.42 Hz, 3 H) 1.31 (s, 9 H) 1.93-2.01 (m, 1 H) 2.17 (m, 1 H) 2.78 (br s, 1 H) 3.14 (br s, 2 H) 3.38-3.47 (m, 1 H) 3.66 (t, J=8.52 Hz, 1 H) 4.10 (q, J=7.42 Hz, 2 H) 5.60 (s, 1 H) 5.83 (br s, 1 H) 6.51-6.58 (m, 2 H) 7.49 (d, J=9.34 Hz, 1 H); LC-MS 427 (M+H).

Intermediate 3H

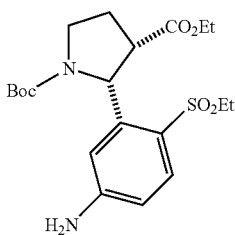

To Intermediate 3F (2.2 g) in methanol (50 mL) and THF (30 mL) was added 10% Pd/C (580 mg). The mixture was hydrogenated with a hydrogen balloon for 6.0 h. The Pd/C was removed by filtration and the filtrate was concentrated to afford Intermediate 3H (2.1 g, 95% yield). $^1$H NMR (500 MHz, DMSO-$d_6$, 100° C.) δ ppm 0.88 (t, J=6.87 Hz, 3 H) 1.16 (t, J=7.42 Hz, 3 H) 1.26 (s, 9H) 2.07-2.13 (m, 2 H) 3.13-3.21 (m, 2 H) 3.49 (br s, 1 H) 3.63-3.75 (m, 4 H) 5.69 (d, J=8.25 Hz, 1 H) 6.50-6.55 (m, 2 H) 7.44 (d, J=8.79 Hz, 1 H); LC-MS 427 (M+H).

Intermediate 3I

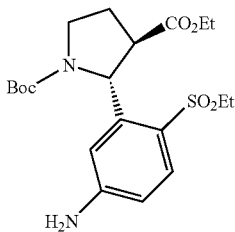

and Intermediate 3J:

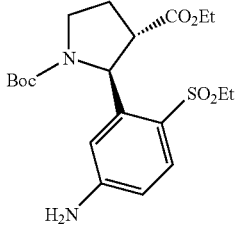

Intermediate 3I and Intermediate 3J were separated from Intermediate 3G using a preparative HPLC equipped with a Chiralpak® AD column (5 cm×50 cm, 20 μ). The separations were performed using an isocratic method of 5% MeOH-EtOH/heptane with 0.1% diethylamine with a flow rate of 50 mL/min. Alternatively, the isomers were separated by Berger SFC equipped with Chiralpak® AD column (25 cm×3 cm, 10 μ). The separations were performed using an isocratic method of $CO_2$/MeOH/DEA:90/10/0.1 with a flow rate of 65 mL/min at 35° C. The first peak is Intermediate 3I: $^1$H NMR (400 MHz, Methanol-$d_4$) δ ppm 1.15-1.34 (m, 12 H) 1.46 (s, 3 H) 1.96-2.11 (m, 1 H) 2.18-2.43 (m, 1 H) 2.80-3.00 (m, 1 H) 3.07-3.23 (m, 1 H) 3.24-3.34 (m, 1 H) 3.40-3.59 (m, 1 H) 3.77 (t, J=9.73 Hz, 1 H) 4.06-4.26 (m, 2 H) 5.61 (d, J=20.97 Hz, 1 H) 6.52-6.69 (m, 2 H) 7.53-7.66 (m, 1 H). LC-MS 327 (M−Boc). The second peak is Intermediate 3J: $^1$H NMR (400 MHz, Methanol-$d_4$) δ ppm 1.14-1.33 (m, 12 H) 1.45 (s, 3 H) 1.97-2.08 (m, 1 H) 2.15-2.41 (m, 1 H) 2.78-3.00 (m, 1 H) 3.08-3.22 (m, 1 H) 3.22-3.29 (m, 1 H) 3.38-3.58 (m, 1 H) 3.70-3.83 (m, 1 H) 4.18 (q, J=6.74 Hz, 2 H) 5.60 (d, J=21.22 Hz, 1 H) 6.51-6.68 (m, 2 H) 7.58 (dd, J=8.46, 5.43 Hz, 1 H). LC-MS 327 (M-Boc).

Intermediate 3K

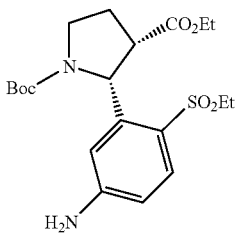

and Intermediate 3L:

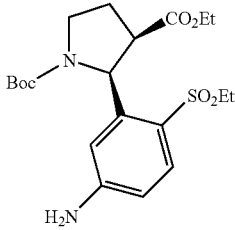

Intermediate 3K and Intermediate 3L were separated from Intermediate 3H using a preparative HPLC equipped with a Chiralpak® AD column (5 cm×50 cm, 20 μ). The separations were performed using an isocratic method of 10% MeOH-EtOH/heptane with 0.1% diethylamine with a flow rate of 50 mL/min. The first peak is Intermediate 3K: $^1$H NMR (400 MHz, Methanol-$d_4$) δ ppm 0.89 (t, J=7.07 Hz, 3 H) 1.04-1.58 (m, 12 H) 2.04-2.13 (m, 1 H) 2.15-2.31 (m, 1 H) 3.13-3.29 (m, 2 H) 3.57-3.69 (m, 2 H) 3.69-3.80 (m, 2 H) 3.82-3.98 (m, 1 H) 5.70 (d, J=8.08 Hz, 1 H) 6.48-6.70 (m, 2 H) 7.55 (d, J=8.59 Hz, 1 H). LC-MS 327 (M Boc). The second peak is Intermediate 3L: $^1$H NMR (400 MHz, Methanol-$d_4$) δ ppm 0.89 (t, J=7.20 Hz, 3 H) 1.07-1.56 (m, 12 H) 1.96-2.14 (m, 1 H) 2.22 (d, J=11.12 Hz, 1 H) 3.17-3.28 (m, 2 H) 3.58-3.70 (m, 2 H) 3.69-3.81 (m, 2 H) 3.81-3.94 (m, 1 H) 5.70 (d, J=8.34 Hz, 1 H) 6.48-6.68 (m, 2 H) 7.55 (d, J=8.59 Hz, 1 H). LC-MS 327 (M-Boc).

Intermediate 3 was prepared in a procedure similar to that of Intermediate 1 using Intermediate 3I and methyl chloroformate. $^1$H NMR (400 MHz, Methanol-$d_4$) δ ppm 1.17-1.33 (m, 6 H) 2.33-2.50 (m, 1 H) 2.63-2.79 (m, 1H) 3.35-3.45 (m, 2 H) 3.46-3.61 (m, 2 H) 3.75-3.89 (m, 4 H) 4.10-4.27 (m, 2 H) 5.74 (dd, J=8.84, 1.52 Hz, 1 H) 7.64-7.74 (m, 1 H) 7.95-8.04 (m, 1 H) 8.09 (d, J=1.77 Hz, 1 H), LC-MS 385 (M+H).

Intermediate 4 was prepared in a procedure similar to that of Intermediate 1 using Intermediate 3K and methyl chloroformate. $^1$H NMR (400 MHz, Methanol-$d_4$) δ ppm 0.89 (t, J=7.20 Hz, 3 H) 1.25-1.33 (m, 3 H) 2.45-2.60 (m, 1 H) 2.63-2.79 (m, 1 H) 3.31-3.41 (m, 2 H) 3.50-3.62 (m, 1 H) 3.67-3.75 (m, 1 H) 3.79 (s, 3 H) 3.83-3.96 (m, 3 H) 5.89 (d, J=8.59 Hz, 1 H) 7.57 (dd, J=8.84, 2.02 Hz, 1 H) 7.89 (d, J=2.02 Hz, 1 H) 7.96-8.02 (m, 1 H), LC-MS 385 (M+H).

Intermediate 5: 6-aminoquinazolin-4(3H)-one

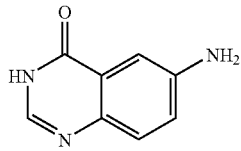

Intermediate 5A

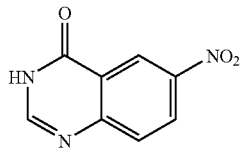

In a 2 mL microwave vial was placed formamide (1.5 mL, 37.8 mmol) and 5-nitroanthranilic acid (917 mg, 5.04 mmol) to give a yellow suspension. The mixture was heated under microwave at 150° C. for 60 min. The mixture was diluted with EtOAc (1 L) and washed with NaHCO$_3$ (Sat. 200 mL) and brine (200 mL). The organic layer was dried by MgSO$_4$ and concentrated to yield Intermediate 5A (760 mg, 79% yield). $^1$H NMR (400 MHz, DMSO-d$_6$) δ ppm 7.85 (d, J=8.79 Hz, 1 H) 8.31 (s, 1 H) 8.54 (dd, J=9.23, 2.64 Hz, 1 H) 8.79 (d, J=2.64 Hz, 1 H) 12.77 (s, 1 H).

Intermediate 5

In a 1 L flask was added Intermediate 5A (1 g, 5.23 mmol) in MeOH (500 ml) to give a yellow suspension. 10%> Pd/C (0.056 g, 0.523 mmol) was added. The mixture was stirred at r.t. under a hydrogen balloon for 4 hours. The reaction mixture was filtered and concentrated to a yellow solid 0.84 g (100%). $^1$H NMR (500 MHz, DMSO-d$_6$) δ ppm 5.60 (s, 2 H) 7.05 (dd, J=8.80, 2.75 Hz, 1 H) 7.16 (d, J=2.75 Hz, 1 H) 7.36 (d, J=8.80 Hz, 1 H) 7.74 (s, 1 H) 11.80 (s, 1 H).

Intermediate 6: 6-aminoisoindolin-1-one

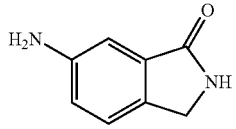

Intermediate 6A

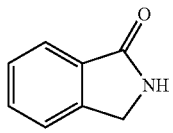

A solution of methyl 2-cyanobenzoate (9.2 g, 57 mmol) and Raney Ni (~1 g) in MeOH (200 mL) was stirred under H$_2$ (60 psi) for 16 h. The reaction mixture was filtered through Celite® and concentrated in vacuo to yield Intermediate 6A (7.5 g, 99% yield) as a white solid. $^1$H NMR (400 MHz, MeOD) δ ppm 4.53 (s, 2 H) 7.46-7.53 (m, J=7.42, 7.42 Hz, 1 H) 7.55-7.66 (m, 2 H) 7.78 (d, J=7.70 Hz, 1H).

Intermediate 6B

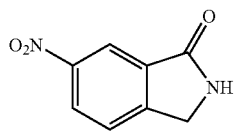

Potassium nitrate (1.215 g, 12.02 mmol) was added portionwise to a solution of Intermediate 6A (1.6 g, 12.02 mmol) in sulfuric acid (24 mL) at 0° C. over 10 min. The reaction mixture was stirred to 3 h at ambient temperature. The reaction mixture was poured onto ice and the resulting precipitate was washed with water and dried in vacuo to yield Intermediate 6B (1.85 g, 10.38 mmol, 86% yield) as a beige solid. $^1$H NMR (400 MHz, DMSO-d$_6$) δ ppm 4.53 (s, 2 H) 7.86 (d, J=8.25 Hz, 1 H) 8.33 (s, 1 H) 8.45 (dd, J=8.24, 2.20 Hz, 1 H) 8.97 (s, 1 H). MS (ESI) m/z 179.0 (M+H)$^+$.

Intermediate 6

A suspension of Intermediate 6B (1.6 g, 8.98 mmol) and Pd/C (0.18 g) in MeOH (100 mL) was stirred under H$_2$ (1 atm) for 4 h. The reaction mixture was filtered and the filter cake was washed with MeOH. The combined filtrates were concentrated in vacuo. The crude solid was triturated with MeOH (10 mL) and dried in vacuo to yield Intermediate 6 (800 mg, 5.40 mmol, 60.1% yield) as a beige solid. $^1$H NMR (400 MHz, DMSO-d$_6$) δ ppm 4.15 (s, 2 H) 5.26 (s, 2 H) 6.77 (dd, J=8.25, 2.20 Hz, 1 H) 6.80 (s, 1 H) 7.16 (d, J=8.79 Hz, 1 H) 8.29 (s, 1 H). MS (ESI) m/z 149.2 (M+H)$^+$.

Intermediate 7: 7-aminoisoquinolin-1(2H)-one

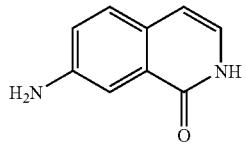

Intermediate 7A

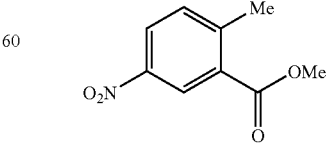

To 2-methyl-5-nitrobenzoic acid (2.69 g, 14.85 mmol) in CH$_2$Cl$_2$ (40 mL) was added thionyl chloride (5.42 mL, 74.2 mmol) and DMF (0.5 mL). The mixture was stirred at 80° C. (oil bath) for 3.5 h. After it was cooled to rt, the solvent was removed and the residue was azeotroped with toluene. The crude solid acyl chloride was dried in vacuo for 20 min. It was then dissolved in CH$_2$Cl$_2$ (20 mL) and MeOH (10 mL) and stirred at rt for 30 min. Solvent was removed and the residue was diluted in EtOAc/hexanes, washed with sat. NaHCO$_3$, brine, dried over Na$_2$SO$_4$. After evaporation of the solvent, Intermediate 7A (2.8 g) was obtained as a white solid. $^1$H NMR (400 MHz, CDCl$_3$) δ ppm 2.70 (s, 3 H) 3.93 (s, 3 H) 7.42 (d, J=8.35 Hz, 1 H) 8.22 (dd, J=8.57, 2.42 Hz, 1 H) 8.76 (d, J=2.20 Hz, 1 H). It was used for next step without purification.

Intermediate 7B

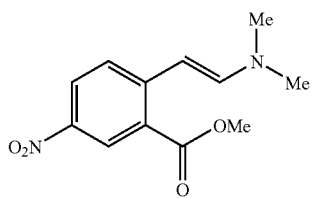

A mixture of Intermediate 7A (2.38 g, 12.19 mmol) and 1-tert-butoxy-N,N,N',N'-tetramethylmethanediamine (5.79 mL, 28.0 mmol) was heated at 115° C. (no solvent) for 3.5 h. After the mixture was cooled to rt, it was triturated with hexanes/EtOAc (6:1). After over night standing at room temperature, the precipitate was collected by filtration to give solid Intermediate 7B (2.73 g, 90% yield). $^1$H NMR (400 MHz, CDCl$_3$) δ ppm 2.99 (s, 6 H) 3.89 (s, 3 H) 6.39 (d, J=13.18 Hz, 1 H) 7.17 (d, J=13.62 Hz, 1 H) 7.43 (d, J=9.23 Hz, 1 H) 8.03 (dd, J=9.23, 2.64 Hz, 1 H) 8.70 (d, J=2.64 Hz, 1 H).

Intermediate 7C

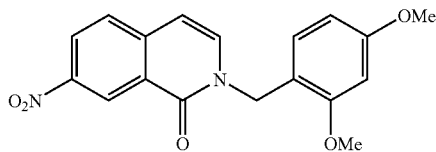

To Intermediate 7B (3.0 g, 11.99 mmol) in toluene (18 mL) was added (2,4-dimethoxyphenyl)methanamine (2.476 mL, 16.48 mmol). The mixture was stirred at 125° C. (oil bath) for 3.5 h. The color changed from deep red to yellow. After the mixture was cooled to rt, it was triturated with EtOAc/hexanes (1:2) and left standing overnight. The yellow precipitate was collected by filtration to give Intermediate 7C (3.92 g, 96% yield). $^1$H NMR (400 MHz, CDCl$_3$) δ ppm 3.79 (s, 3 H) 3.84 (s, 3 H) 5.13 (s, 2 H) 6.47-6.51 (m, 3 H) 7.39-7.48 (m, 2 H) 7.58 (d, J=8.79 Hz, 1 H) 8.37 (dd, J=8.79, 2.20 Hz, 1 H) 9.29 (d, J=2.64 Hz, 1 H).

Intermediate 7D

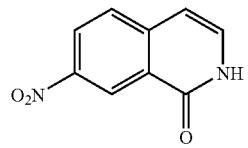

Intermediate 7C (1.2 g, 3.53 mmol) in TFA (20.0 mL) was stirred at 85° C. for 2.5 h. After the mixture was cooled to rt, TFA was removed under vacuum. The crude was chased with methanol once and dried under high vacuum to give a deep purple solid. The solid was further triturated with EtOAc and collected by filtration to give Intermediate 7D (1.0 g, 100%) as TFA solvate. $^1$H NMR (400 MHz, DMSO-d$_6$) δ ppm 6.72 (d, J=7.03 Hz, 1 H) 7.42-7.48 (m, 1 H) 7.90 (d, J=8.79 Hz, 1 H) 8.43 (dd, J=8.79, 2.64 Hz, 1 H) 8.88 (d, J=2.20 Hz, 1 H) 11.77 (s, 1H).

Intermediate 7

To Intermediate 7D (710 mg, 3.73 mmol) was added tetrahydrofuran (160 mL, stabilized with 25 ppm BHT) and water (0.95 mL). The solution was sonicated to near complete dissolution and 10% Pd/C (290 mg) was added. This solution was then hydrogenated with a hydrogen balloon for 50 min. Pd/C was removed by filtration and the filtrate was condensed to give slightly yellow solid Intermediate 7 (570 mg, 95% yield). $^1$H NMR (400 MHz, DMSO-d$_6$) δ ppm 5.47 (s, 2 H) 6.32 (d, J=7.15 Hz, 1 H) 6.78 (d, J=4.95 Hz, 1 H) 6.95 (dd, J=8.52, 2.47 Hz, 1H) 7.27-732 (m, 2 H) 10.81 (s, 1 H); LC-MS 161 (M+H).

General Coupling Procedure

Most of the final compounds described in the Examples were made according to the following general coupling scheme:

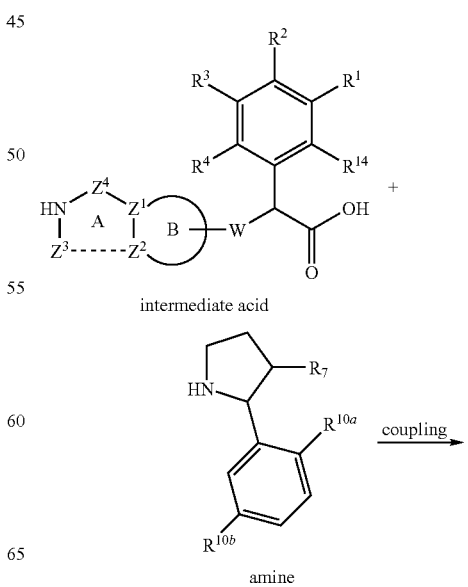

-continued

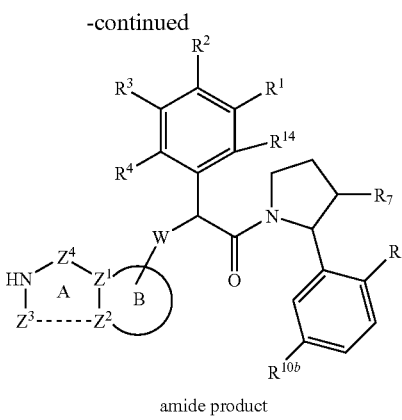

amide product

A mixture of intermediate acid (1 eq, preparation given in examples), amine (1.2-1.75 eq, preparation given in examples), EDCI (1.5-2.5 eq), HOAT (0.4-1.0 eq), DIEA (0-5 eq) in CH$_2$Cl$_2$ (0.01M) or CH$_2$Cl$_2$/DMF (0.03 M, 10:1) was stirred at rt for 4 h to overnight. The reaction product was concentrated and purified via preparative HPLC (MeOH/H$_2$O/TFA or CH$_3$CN/H$_2$O/TFA) to provide the desired amide. When the amine used was enantiomerically pure, the coupling gave a mixture of two diastereoisomers which were separated in chirally pure fractions by prep HPLC. In each case of examples where diastereomers were obtained, the more effective FVIIa inhibitor is listed first. In some cases, the less active diastereomer is actually inactive vs FVIIa, and is included to enable accurate identification of the more active diastereomer through comparison of spectroscopic data.

Example 1 methyl 3-((R)-1-((R)-2-(3,4-dimethoxyphenyl)-2-(3-oxoisoindolin-5-ylamino)acetyl)pyrrolidin-2-yl)-4-(isopropylsulfonyl)phenylcarbamate

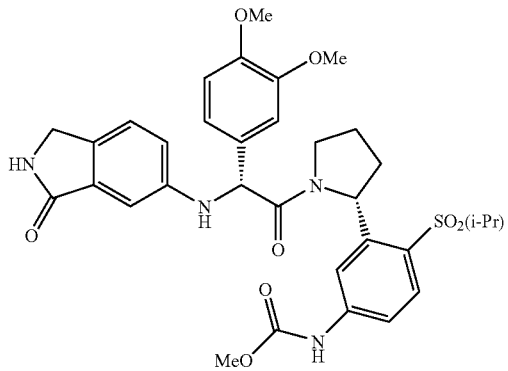

1A

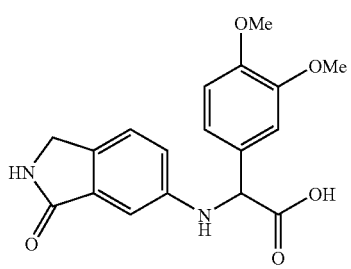

A solution of Intermediate 6 (300 mg, 2.0 mmol), 3,4-dimethoxyphenylboronic acid (370 mg, 2.0 mmol) and glyoxylic acid monohydrate (224 mg, 2.4 mmol) in acetonitrile/DMF (4 mL, 4:1) was heated in the microwave at 100° C. for 10 min. The reaction mixture was concentrated in vacuo and purified by flash chromatography (0% to 20% MeOH in CH$_2$Cl$_2$) to yield 1A (600 mg, 87%) as a yellow solid. MS (ESI) m/z 343.2 (M+H)$^+$.

Example 1

1A (64 mg, 0.19 mmol) and Intermediate 1 were reacted using the general coupling condition to yield Example 1 (24 mg) and its diastereomer (28 mg). $^1$H NMR (400 MHz, CD$_3$OD) δ ppm 1.15 (d, J=6.57 Hz, 3 H) 1.40 (d, J=6.82 Hz, 3H) 1.65-1.75 (m, 1 H) 2.01-2.15 (m, 2 H) 2.83-2.90 (m, 1 H) 3.66 (s, 3 H) 3.70 (s, 3 H) 3.83 (s, 3 H) 3.90-3.99 (m, 1 H) 4.14 (d, J=10.11 Hz, 1 H) 5.35 (s, 1 H) 5.61-5.71 (m, J=8.21, 4.93 Hz, 1 H) 6.86 (d, J=2.02 Hz, 1 H) 6.88-6.92 (m, 1 H) 6.93-6.97 (m, 1 H) 6.98-7.06 (m, 3 H) 7.23 (dd, J=8.72, 2.15 Hz, 1 H) 7.30 (d, J=8.34 Hz, 1 H) 7.73 (d, J=8.59 Hz, 1 H) 9.35 (s, 1 H). MS (ESI) m/z 651.4 (M+H)$^+$.

Example 2

(2R,3S)-methyl 1-((R)-2-(3,4-dimethoxyphenyl)-2-(3-oxoisoindolin-5-ylamino)acetyl)-2-(2-(isopropylsulfonyl)-5-(methoxycarbonylamino)phenyl)pyrrolidine-3-carboxylate

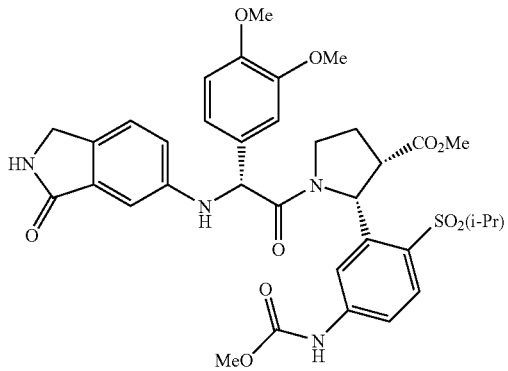

1A (100 mg, 0.29 mg) and Intermediate 2 were reacted using the general coupling condition to yield Example 2 (50 mg) and its diastereomer (30 mg). $^1$H NMR (400 MHz, CD$_3$OD) δ ppm 1.15 (d, J=6.82 Hz, 3 H) 1.39 (d, J=6.82 Hz, 3H) 2.17-2.47 (m, 2 H) 2.84-2.91 (m, 1 H) 3.67 (s, 3 H) 3.69 (s, 3 H) 3.74 (s, 3 H) 3.82 (s, 3 H) 3.84-3.90 (m, 3 H) 4.30 (s, 2 H) 5.35 (s, 1 H) 5.97 (d, J=2.27 Hz, 1 H) 6.86-6.91 (m, 2 H) 6.95-6.99 (m, 2 H) 7.08 (dd, J=5.94, 1.89 Hz, 2 H) 7.25 (dd, J=8.72, 2.15 Hz, 1 H) 7.30 (d, J=8.34 Hz, 1 H) 7.75 (d, J=8.59 Hz, 1 H) 9.41 (s, 1 H). MS (ESI) m/z 709.3 (M+H)$^+$.

Example 3

(2R,3S)-1-((R)-2-(3,4-dimethoxyphenyl)-2-(3-oxoisoindolin-5-ylamino)acetyl)-2(2-(isopropylsulfonyl)-5-(methoxycarbonylamino)phenyl)pyrrolidine-3-carboxylic acid

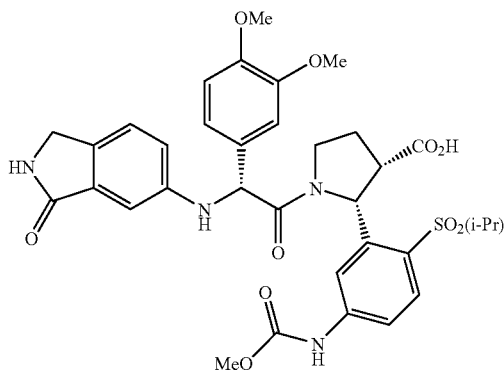

LiOH (1.0 M, 1 mL) was added to a solution of Example 2 (30 mg, 0.043 mmol) was in THF (2 mL) and the resulting mixture was stirred for 3 h at ambient temperature. HCl (0.25 mL, 4.0 M in dioxane) was added, the reaction mixture was concentrated in vacuo and purified by preparatory HPLC to yield Example 3 (16 mg, 55%) as a white solid. $^1$H NMR (400 MHz, CD$_3$OD) δ ppm 1.17 (d, J=6.60 Hz, 3 H) 1.41 (d, J=7.15 Hz, 3 H) 2.20-2.50 (m, 3 H) 2.85 (d, J=8.25 Hz, 1 H) 3.66 (s, 3 H) 3.68 (s, 3 H) 3.82-3.83 (m, 3 H) 3.84-3.96 (m, 3 H) 3.96-4.10 (m, 1 H) 4.33 (s, 2 H) 5.38 (s, 1 H) 6.04 (s, 1 H) 6.84-6.97 (m, 3 H) 7.03 (dd, J=8.25, 2.20 Hz, 1 H) 7.10-7.21 (m, 2 H) 7.24 (dd, J=8.79, 2.20 Hz, 1 H) 7.35 (d, J=8.25 Hz, 1 H) 7.77 (d, J=8.24 Hz, 1 H) 9.47 (s, 1 H). MS (ESI) m/z 695.65 (M+H)$^+$.

Example 4 methyl 3-((R)-1-((R)-2-(3,4-dimethoxyphenyl)-2(1-oxo-1,2,3,4-tetrahydroisoquinolin-7-ylamino)acetyl)pyrrolidin-2-yl)-4-(isopropylsulfonyl)phenylcarbamate

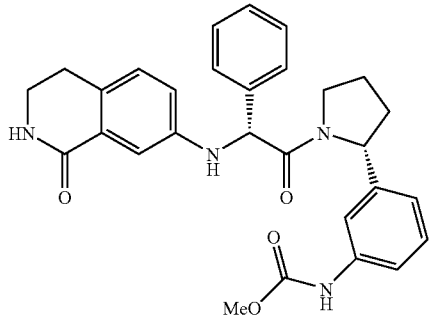

4A

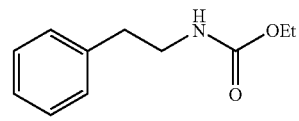

Ethyl chloroformate (20.8 g, 0.192 mol) was added dropwise to a solution of phenethylamine (15.5 g, 0.128 mol) and triethylamine (180 mL) in diethyl ether (500 mL) while maintaining the internal temperature of the reaction below 10° C. The reaction mixture was stirred two additional hours at ambient temperature and then filtered. The filtrate was concentrated in vacuo and the resulting oil was purified by flash chromatography (0-100% EtOAc in hexane) to yield 4A (23.1 g, 94%). MS (EST) m/z 193.4 (M+H)$^+$.

4B

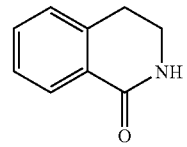

4A (4 g, 0.02 mol) was refluxed in a mixture of phosphorous pentoxide (5 g) and phosphorous oxychloride (25 mL) for 2 h. The reaction mixture was concentrated in vacuo to an oil, carefully quenched with wet ice followed by neutralization with sodium bicarbonate and extracted with diethyl ether. The combined organics were washed with water (2×50 mL), brine, dried (MgSO$_4$) and concentrated in vacuo. The crude product was purified by flash chromatography (0-100% EtOAc in hexane) to yield 4B (1.1 g, 38%). $^1$H NMR (400 MHz, CD$_3$OD) δppm 2.97 (t, J=6.59 Hz, 2 H) 3.44-3.53 (t, J=6.52 Hz, 2 H) 7.26-7.30 (m, J=7.91 Hz, 1 H) 7.31-7.38 (m, 1 H) 7.43-7.52 (m, 1 H) 7.92 (dd, J=7.69, 1.10 Hz, 1 H)

4C

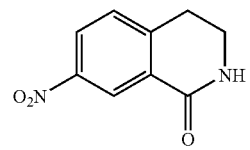

4B (1.1 g, 7.48 mmol) was added portionwise to a mixture of sulfuric acid (1 mL) and fuming nitric acid (5 mL) at 0° C. with stirring. The reaction was allowed to warm to ambient temperature and stirred for 2.5 h before pouring onto ice. The precipitate collected by filtration and dried in vacuo to yield 770 mg of 4C (770 mg, 55% yield) as white solid. $^1$H NMR (400 MHz, CD$_3$OD) δ ppm 2.81 (t, J=6.59 Hz, 2 H) 3.42 (t J=6.52 Hz, 2 H) 6.84 (dd, J=8.13, 2.42 Hz, 1 H) 7.02 (d, J=7.91 Hz, 1 H) 7.26 (d, J=2.64 Hz, 1 H).

4D

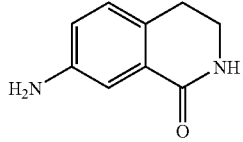

4C (700 mg, 3.6 mmol) was stirred in MeOH (25 mL) with 10% Pd/C (cat.) under H₂ (60 psi) for 1 h. The reaction was filtered through Celite® and concentrated in vacuo to give 4D (500 mg, 86% yield). ¹H NMR (400 MHz, CD₃OD) δ ppm 2.81 (t, J=6.59 Hz, 2 H) 3.42 (t, J=6.55 Hz, 2 H) 6.84 (dd, J=8.13, 2.42 Hz, 26H) 7.02 (d, J=7.91 Hz, 1 H) 7.26 (d, J=2.64 Hz, 1 H).

4E

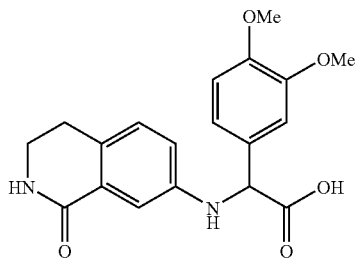

Using a procedure analogous to that used to prepare 1A, 4D (162 mg, 1.0 mmol) was reacted with 3,4-dimethoxyphenyl-boronic acid and glyoxylic acid monohydrate to yield 4E (290 mg, 80%). ¹H NMR (400 MHz, CD₃OD) δ ppm 2.80 (t, J=6.81 Hz, 2 H) 3.40 (t, J=6.59 Hz, 2 H) 3.80 (s, 3 H) 3.82 (s, 3 H) 5.02 (s, 1 H) 6.80 (dd, J=8.35, 2.64 Hz, 1 H) 6.91 (d, J=8.35 Hz, 1 H) 7.01 (d, J=8.35 Hz, 1 H) 7.07 (dd, J=8.35, 1.76 Hz, 1 H) 7.13 (d, J=1.76 Hz, 1 H) 7.20 (d, J=2.20 Hz, 1 H).

Example 4

4E (40 mg, 0.11 mmol) and Intermediate 1 were reacted using the general coupling condition to yield Example 4 (12 mg) and its diastereomer (11 mg), ¹H NMR (400 MHz, CD₃OD) δ ppm 1.17 (d, J=6.59 Hz, 3 H) 1.42 (d, J=7.03 Hz, 3H) 1.59-2.59 (m, 3 H) 2.87 (t, 2 H) 3.44 (t, J=6.59 Hz, 2 H) 3.65 (s, 3 H) 3.69 (s, 3H) 3.83 (s, 3 H) 3.86-4.14 (m, 2 H) 5.40 (s, 1 H) 5.62-5.70 (m, J=8.35, 4.83 Hz, 1H) 6.79-6.85 (m, 1 H) 6.88-6.91 (m, 2 H) 6.97 (dd, J=8.13, 2.42 Hz, 1 H) 7.06-7.11 (m, 1 H) 7.14 (d, J=8.35 Hz, 1 H) 7.23 (dd, J=8.79, 2.20 Hz, 1 H) 7.42 (d, J=2.64 Hz, 1 H) 7.74 (d, J=8.79 Hz, 1 H). MS (ESI) m/z 665.7 (M+H)⁺.

Example 5 methyl 3-((R)-1-((R)-2-(3,4-dimethoxyphenyl)-2-(1-oxo-1,2-dihydroisoquinolin-7-ylamino)acetyl)pyrrolidin-2-yl)-4-(isopropylsulfonyl)phenylcarbamate

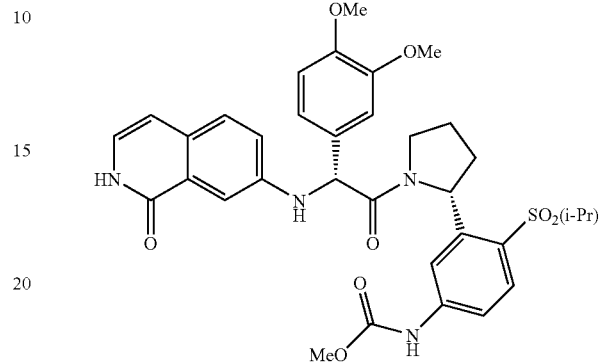

5A

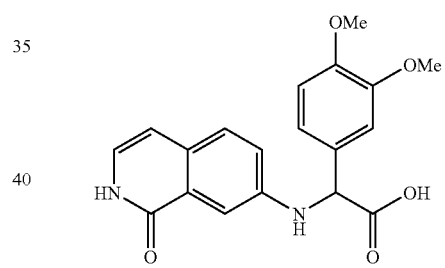

Using a procedure analogous to that used to prepare 1A, Intermediate 7 (200 mg, 1.25 mmol) was reacted with 3,4-dimethoxyphenylboronic acid and glyoxylic acid monohydrate to yield 5A (75 mg, 17%). MS (ESI) m/z 355.3 (M+H)⁺.

Example 5

5A (75 mg, 0.2 mmol) and Intermediate 1 were reacted using the general coupling condition to yield Example 5 (18 mg) and its diastereomer (14 mg). MS (ESI) m/z 663.5 (M+H)⁺. ¹H NMR (400 MHz, CD₃OD) δ ppm 1.13 (d, J=6.59 Hz, 3 H) 1.38 (d, J=7.03 Hz, 3 H) 1.63-1.78 (m, 1 H) 2.02-2.15 (m, 2 H) 2.44-2.58 (m, 1 H) 3.66 (s, 3 H) 3.69 (s, 3 H) 3.83 (s, 3 H) 3.85-4.02 (m, 2 H) 4.12-4.25 (m, 1H) 5.41 (s, 1 H) 5.63-5.74 (m, J=7.91, 4.83 Hz, 1 H) 6.56 (d, J=7.03 Hz, 1 H) 6.87-6.92 (m, 2 H) 6.93-7.00 (m, 2 H) 7.02-7.07 (m, 1 H) 7.17-7.28 (m, 2 H) 7.40-7.47 (m, 2 H) 7.73 (d, J=8.35 Hz, 1 H) 7.97 (s, 1 H) 9.37 (s, 1 H).

Example 6 methyl 3-((2R)-1-(2-(3,4-dimethoxyphenyl)-2-(7-fluoro-1-oxoisoindolin-4-ylamino)acetyl)pyrrolidin-2-yl)-4-(isopropylsulfonyl)phenylcarbamate

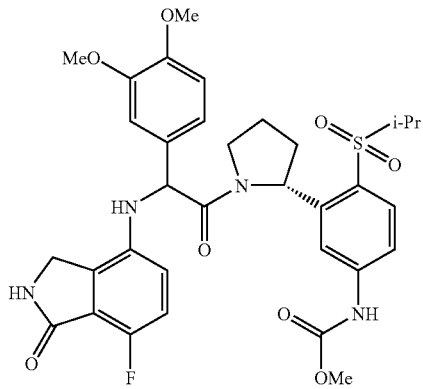

6A

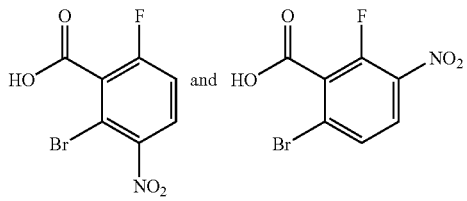

In a 50 mL round-bottomed flask 6-bromo-2-fluoro-benzoic acid (5 g, 22.8 mmol) and sulfuric acid (15 mL) were cooled to 0° C. before adding fuming nitric acid (2 mL, 22.83 mmol, 90%) drop wise over 10 min. The reaction was stirred for 2 hrs at rt. The reaction was poured onto ice and the solids were isolated by filtration. The crude solids were purified on SiO$_2$ (eluting with 0-100% EtOAc) to yield 6A as a 1:1 mixture of region-isomers 2-bromo-6-fluoro-3-nitrobenzoic acid and 6-bromo-2-fluoro-3-nitrobenzoic acid (3.7 g, 63% yield). $^1$H NMR (400 MHz, CD$_3$OD) δ ppm 7.48 (dd, J=9.23, 7.47 Hz, 1 H) 8.16 (dd, J=7.91, 2.64 Hz, 1 H) 8.26 (dd, J=9.23, 4.39 Hz, 1 H) 8.35-8.40 (m, 1 H).

6B

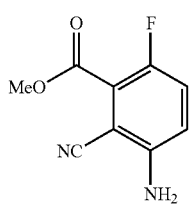

and 6C:

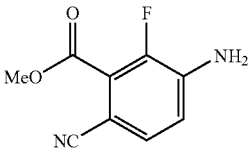

6A was refluxed for 1 hr in thionyl chloride (15 mL) and concentrated to an oil. MeOH (40 mL) was added slowly to the residue and the mixture refluxed for 1 h. The reaction was concentrated to dryness. The resulting crude residue was heated at 90° C. for 4 h in acetic acid (20 mL) with Fe powder (638 mg, 11.4 mmol). Upon cooling to rt the reaction was diluted with EtOAc (100 mL) and the resulting mixture filtered through Celite®. The filter cake washed with EtOAc (3×100 mL). The combined filtrates were washed with water, brine, dried with MgSO$_4$ and concentrated to an oil. The crude oil was purified on preparatory HPLC. Cu(I)CN (3.45 g, 38.5 mmol) was added to a solution of the product in DMF (25 mL) and the resulting mixture heated at 160° C. for 15 min under argon. The reaction was cooled to rt, quenched with a 50/50 mix NH$_4$OH/H$_2$O (50 mL), stirred 5 min and filtered through Celite®. The filter cake was washed with EtOAc (3×50 mL) and the combined filtrates were extracted with water (3×100 mL), brine and dried with MgSO$_4$. The filtrate was concentrated to an oil. The product was recrystallized from EtOH/Hexane and further purified on the preparatory HPLC to yield 6B (1.2 g, 6.11 mmol) and 6C (670 mg, 3.45 mmol) as a solids. MS (ESI) m/z 195.19 (M+H).

6D

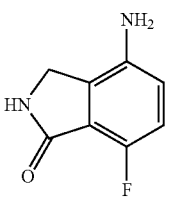

6B (450 mg, 2.31 mmol) was dissolved into MeOH (30 mL) and water (10 mL) and stirred with a catalytic amount of Raney Ni under 60 psi of hydrogen for 18 h. The reaction was filtered through Celite® and concentrated to an oil before purifying by preparatory HPLC to give explicitly 6D (300 mg, 1.8 mmol) as an oil in 78% yield. $^1$H NMR (400 MHz, MeOD) δ ppm 4.44 (s, 2 H) 7.25 (t, J=8.79 Hz, 1 H) 7.29-7.36 (m, 1 H), MS (ESI) M/Z 167.2 (M+H).

6E

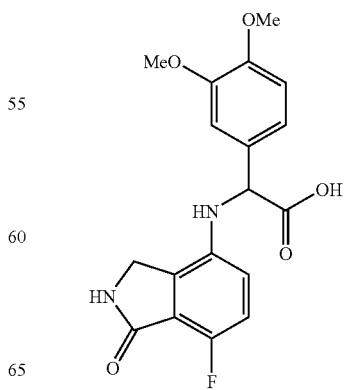

6D (300 mg, 1.806 mmol), 3,4-dimethoxyphenylboronic acid (361 mg, 1.986 mmol) and monohydrate glyoxylic acid (147 mg, 1.986 mmol) were diluted with acetonitrile/DMF (2 mL each). The reaction was heated at 110° C. for 10 min in a microwave. The reaction was concentrated to an oil and purified with reverse phase preparatory HPLC to yield 6E (220 mg, 0.611 mmol) in 34% yield. $^1$H NMR (400 MHz, DMF-$d_7$) δ ppm 3.79 (s, 6H) 4.60-4.77 (m, J=18.46 Hz, 2H) 6.08 (s, 1 H) 6.74-6.82 (m, J=8.35, 3.08 Hz, 1 H) 6.95 (d, J=8.35 Hz, 1 H) 6.98-7.06 (m, 1 H) 7.08-7.17 (m, 1 H) 7.22-7.29 (m, J=2.20 Hz, 1 H), MS (ESI) M/Z 361.3 (M+H).

Example 6

6E (110 mg, 0.3 mmol) and Intermediate 1 were reacted using the general coupling condition to yield diastereomer 1 (25 mg, 0.037 mmol) and Example 6 (18 mg, 0.027 mmol) as oils in 20% overall yield. MS (ESI) m/z 669.4 (M+H).

Example 7 methyl 3-((R)-1-((R)-2-(3,4-dimethoxyphenyl)-2-(4-oxo-3,4-dihydrophthalazin-6-ylamino)acetyl)pyrrolidin-2-yl)-4-(isopropylsulfonyl)phenylcarbamate

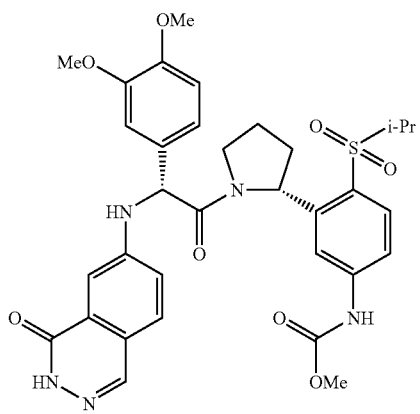

7A

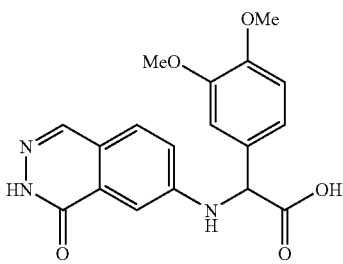

3-Hydroxy-6-nitroisobenzofuran-1(3H)-one (500 mg, prepared as in *JOC* 50(21) 2140, 1985)) was added slowly to a heated solution of hydrazine hydrate (500 μA) in isopropanol (6 mL) at 90° C. The solution was heated at 80° C. overnight. After cooling to rt, an orange precipitate was collected, washed with isopropanol and dried. A solution of the solid (200 mg) in MeOH was stirred under H$_2$ (55 psi) for 7 h. The reaction mixture was filtered through Celite and concentrated to yield 7A (118 mg) as an off-white solid. MS (ESI) m/z 162.1 (M+H)$^+$.

7B 3,4-Dimethoxyphenylboronic acid (62.1 mg, 0.341 mmol), 7A (55 mg, 0.341 mmol), and glyoxylic acid monohydrate (31.4 mg, 0.341 mmol) were dissolved in acetonitrile/DMF (1 mL each) and heated at 100° C. in the microwave for 10 min. The reaction mixture was concentrated in vacuo and purified by flash chromatography (0% to 20% MeOH in CH$_2$Cl$_2$) to yield 7B (120 mg, 0.338 mmol, 99% yield) as a yellow solid. MS (ESI) m/z 356.3 (M+H)$^+$.

Example 7

7B (50 mg, 0.14 mmol) and Intermediate 1 were reacted using the general coupling condition to yield Example 7 (10 mg, 0.015 mmol) as an oil in 11% yield. MS (ESI) M/Z 664.3 (M+H)$^1$H NMR (400 MHz, CD$_3$OD) δ ppm 1.09 (t, J=7.25 Hz, 3 H) 1.36-1.41 (m, 3 H) 2.40 (dd, J=12.52, 6.81 Hz, 1 H) 2.86 (d, J=2.64 Hz, 3 H) 2.99 (s, 1 H) 3.66-3.76 (m, 5 H) 3.77-3.82 (m, 5 H) 3.82-3.88 (m, 7 H) 5.43-5.47 (m, 1 H) 7.02 (d, J=8.35 Hz, 1 H) 7.09-7.18 (m, 2 H) 7.29 (d, J=2.20 Hz, 1 H) 7.45-7.49 (m, 1 H) 7.75-7.81 (m, 2 H) 8.06-8.12 (m, 1 H).

Example 8 methyl 3-((R)-1-((R)-2-(3,4-dimethoxyphenyl)-2-(1,2,3,4-tetrahydroisoquinolin-7-ylamino)acetyl)pyrrolidin-2-yl)-4-(isopropylsulfonyl)phenylcarbamate

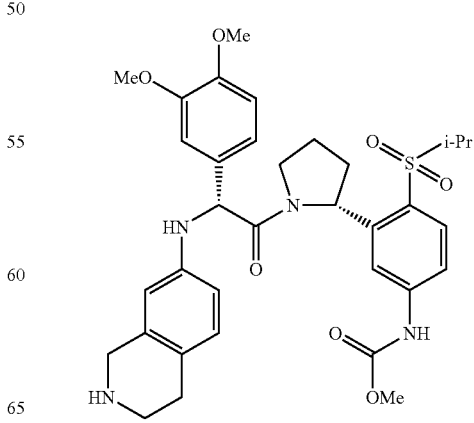

8A

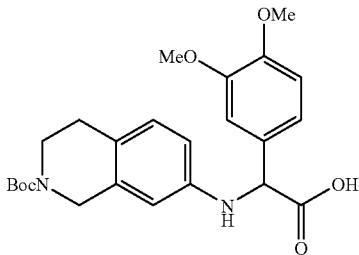

3,4-Dimethoxyphenylboronic acid (92 mg, 0.503 mmol), tert-butyl 7-amino-3,4-dihydroisoquinoline-2(1H)-carboxylate (125 mg, 0.503 mmol), and glyoxylic acid monohydrate (46.3 mg, 0.503 mmol) were dissolved in DMF/acetonitrile (2 mL each) and heated at 100° C. in the microwave for 10 min. The reaction mixture was concentrated in vacuo and purified by flash chromatography (0% to 15% MeOH in $CH_2Cl_2$) to yield 8A (220 mg, 0.497 mmol, 99% yield) as a yellow oil. MS (ESI) m/z 443.4 $(M+H)^+$. $^1H$ NMR (400 MHz, $CD_3OD$) δ ppm 1.46 (s, 9 H) 2.66 (t, J=5.77 Hz, 2 H) 2.85 (s, 3 H) 2.98 (s, 3 H) 3.49-3.60 (m, 2 H) 4.33-4.51 (m, 2 H) 4.97 (s, 1 H) 6.39 (s, 1 H) 6.51 (dd, J=8.24, 2.75 Hz, 1 H) 6.87 (d, J=8.24 Hz, 1 H) 6.92 (d, J=8.24 Hz, 1 H) 7.06 (dd, J=8.24, 2.20 Hz, 1 H) 7.11 (d, J=1.65 Hz, 1 H) 7.97 (s, 1H).

Example 8

8A (100 mg, 0.23 mmol) and Intermediate 1 were reacted using the general coupling condition to yield Example 8 (20 mg, 0.031 mmol) as an oil in 14% yield. MS (ESI) m/z 651.4 (M+H) $^1H$ NMR (400 MHz, $CD_3OD$) δ ppm 1.16 (d, J=6.59 Hz, 3 H) 1.42 (d, J=7.03 Hz, 3 H) 2.05 (dd, J=13.62, 7.03 Hz, 2 H) 2.69 (s, 4 H) 2.94-2.99 (m, 6 H) 3.42 (t, J=6.37 Hz, 2 H) 3.64 (s, 3 H) 3.67-3.71 (m, 3 H) 3.81-3.85 (m, 4 H) 3.89-3.97 (m, 1 H) 4.22 (s, 1 H) 6.86-6.96 (m, 2 H) 6.99-7.06 (m, 2 H) 7.20 (dd, J=8.57, 1.98 Hz, 1 H) 7.73 (d, J7=8.35 Hz, 1 H).

Example 9 methyl 3-((2R)-1-(2-(3,4-dimethoxyphenyl)-2-(7-fluoro-3-oxoisoindolin-5-ylamino)acetyl)pyrrolidin-2-yl)-4-(isopropylsulfonyl)phenylcarbamate

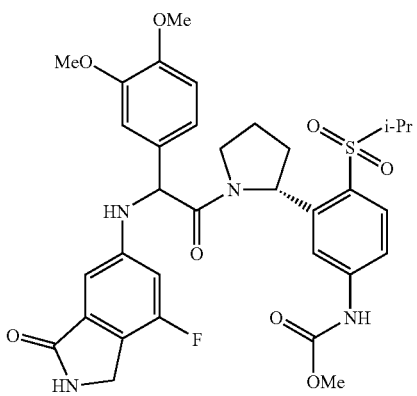

9A

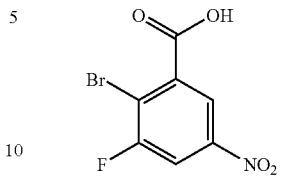

In a 50 mL round-bottomed flask 2-bromo-3-fluoro-benzoic acid (5 g, 22.8 mmol) and sulfuric acid (15 mL) were stirred at 0° C. before adding fuming nitric acid (2 mL, 22.83 mmol, 90%) drop wise over 10 min. The reaction was stirred for 2 h at rt. The reaction was poured onto ice and the solids were isolated by filtration. The crude solids were purified on $SiO_2$ (eluting with 0-100% EtOAc) to yield a 1:1 mixture of region-isomers 9A and 2-bromo-3-fluoro-6-nitrobenzoic acid (3.7 g, 63% yield). $^1H$ NMR (400 MHz, $CD_3OD$) δ ppm 7.48 (dd, J=9.23, 7.47 Hz, 1 H) 8.16 (dd, J=7.91, 2.64 Hz, 1 H) 8.26 (dd, J=9.23, 4.39 Hz, 1 H) 8.35-8.40 (m, 1 H).

9B

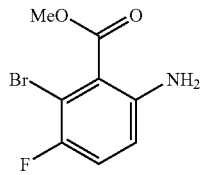

9A (3.7 g, 14 mmol) was refluxed for 1 h in thionyl chloride (15 mL) and concentrated to an oil. MeOH (40 mL) was added slowly to the residue and the mixture refluxed for 1 h. The reaction was concentrated to dryness. The residue was heated at 90° C. for 4 h in acetic acid (20 mL) with a Fe powder (365 mg, 6.7 mmol). Upon cooling to rt the reaction was diluted with EtOAc (100 mL) and the resulting mixture filtered through Celite®. The filter cake was washed with EtOAc (3×100 mL). The combined organics were washed with water and brine, dried w/ $MgSO_4$ and concentrated to give 9B (2.0 g, 54% yield) in a 1:1 mixture with a regioisomers. MS (ESI) m/z 248.1 (M+H)

9C

MeO, O
NC
F NH₂

9B (0.9 g, 3.6 mmol) was dissolved into DMF (25 mL). Cu(I)CN (3.45 g, 38.5 mmol) was added and the resulting mixture heated at 160° C. for 15 min. under argon. The reaction was cooled to rt., quenched with a 50/50 mix $NH_4OH/H_2O$ (50 mL), stirred 5 min and filtered through Celite®. The filter cake was washed with EtOAc (3×50 mL)

and the combined organics were extracted with water (3×100 mL), brine and dried with MgSO₄. The combined organics were concentrated and purified on preparatory HPLC to yield 9C (570 mg, 2.9 mmol) in a 1:1 mixture with a regioisomers in 81% yield MS (ESI) M/Z 195.2 (M+H)

9D

9C (390 mg, 2.0 mmol) was dissolved into MeOH (10 mL) and water (2 mL) and stirred with a catalytic amount of Raney Ni under 60 psi of hydrogen for 18 h. The reaction was filtered through Celite® and concentrated to an oil.

Preparatory HPLC was used to purify and separate the region-isomers, 9D (160 mg, 0.96 mmol) and 7-amino-4-fluoroisoindolin-1-one (100 mg, 0.60 mmol) in 78% yield. MS (ESI) m/z 167.2 (M+H). ¹H NMR (400 MHz, acetone) δ ppm 4.30 (s, 2 H) 6.67 (dd, J=11.42, 1.76 Hz, 1 H) 6.87 (d, J=1.76 Hz, 1 H).

9E

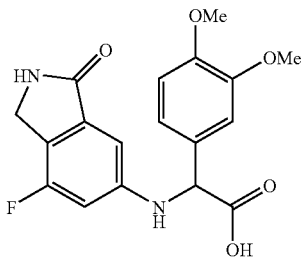

9D (150 mg, 0.90 mmol), 3,4-dimethoxyphenylboronic acid (181 mg, 0.903 mmol) and monohydrate glycolic acid (91 mg, 0.903 mmol) were dissolved in acetonitrile/DMF (2 mL each). The reaction was heated at 110° C. for 10 min in a microwave. The reaction was concentrated to an oil and purified with preparatory HPLC to yield 9E (115 mg, 0.319 mmol) in 36% yield. ¹H NMR (400 MHz, Solvent??) δ ppm 3.76-3.81 (m, 6 H) 4.24 (s, 2 H) 4.91 (s, 1 H) 6.39 (dd, J=11.21, 1.98 Hz, 1 H) 6.71-6.83 (m, 2 H) 6.88-6.96 (m, 1 H) 7.00 (dd, J=8.35, 2.20 Hz, 1 H), MS (ESI) M/Z 361.3 (M+H).

Example 9

9E (50 mg, 0.14 mmol) and Intermediate 1 were reacted using the general coupling condition to yield Example 9 (43 mg, 0.064 mmol) as an oil in 46% yield. MS (ESI) m/z 669.6 (M+H). ¹H NMR (400 MHz, CD₃OD) δ ppm 1.38 (t, J=6.81 Hz, 4 H) 1.69 (dd, J=12.08, 5.93 Hz, 1 H) 2.08 (dt, J=13.62, 6.81 Hz, 2 H) 2.49 (dd, J=12.74, 7.91 Hz, 1 H) 3.64-3.67 (m, 3 H) 3.68-3.72 (m, 4 H) 3.80-3.84 (m, 6 H) 4.29-4.35 (m, 3 H) 5.29-5.35 (m, 1 H) 5.66 (dd, J=8.35, 4.83 Hz, 1 H) 6.67 (dd, J=11.42, 1.76 Hz, 1 H) 6.81 (d, J=1.76 Hz, 1 H) 6.84-6.92 (m, 2 H) 6.95-7.02 (m, 2 H) 7.21 (dd, J=8.79, 2.20 Hz, 1 H) 7.68-7.78 (m, 2 H).

Example 10 methyl 3-((2R)-1-(2-(3,4-dimethoxyphenyl)-2-(7-methyl-3-oxoisoindolin-5-ylamino)acetyl)pyrrolidin-2-yl)-4-(isopropylsulfonyl)phenylcarbamate

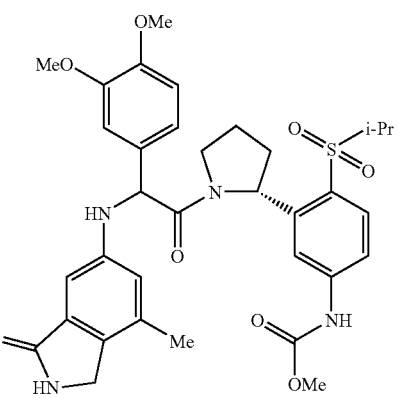

10A

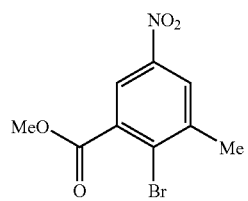

In a 50 mL round-bottomed flask 2-bromo-3-methyl-benzoic acid (5 g, 22.8 mmol) and sulfuric acid (15 mL) were stirred at 0° C. before adding fuming nitric acid (2 mL, 22.83 mmol, 90%) dropwise over 10 min. After stirring for 2 h at rt, the reaction mixture was poured onto ice and solids were isolated by filtration. The crude solids were purified on SiO₂ (eluting with 0-100% EtOAc). The residue was refluxed for 1 h in thionyl chloride (15 mL) and concentrated to an oil. MeOH (40 mL) was added slowly to the oil and the mixture refluxed for 1 h. The reaction mixture was concentrated to isolate a 9:1 ratio of desired regio-isomer 10A (3.85 g, 14.8 mmol) and another regioisomer in 65% yield. ¹H NMR (400 MHz, CD₃OD) δ ppm 2.47 (s, 3 H) 3.93 (s, 3 H) 7.45 (s, 1 H) 7.82 (s, 1 H) 7.96 (s, 1 H).

10B

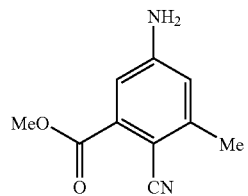

10A (3.4 g, 14.0 mmol) was heated at 90° C. for 4 h in acetic acid (20 mL) with Fe powder (6.7 mmol, 365 mg). Upon cooling to rt the reaction was diluted with EtOAc (100 mL) and the resulting mixture filtered through Celite®. The filter cake washed with EtOAc (3×100 mL). The combined organics were washed with water, brine and dried w/ $MgSO_4$ and concentrated to yield methyl 5-amino-2-bromo-3-methylbenzoate as an oil. The residue was dissolved into DMF (25 mL). Cu(I)CN (3.45 g, 38.5 mmol) was added and the resulting mixture heated at 160° C. for 15 min under argon. The reaction was cooled to rt, quenched with a 50/50 mixture of $NH_4OH/H_2O$ (50 mL), stirred 5 min. and filtered through Celite®. The filter cake was washed with EtOAc (3×50 mL) and the combined organics were extracted with water (3×100 mL), brine and dried with $MgSO_4$. The filtrate was concentrated to an oil and recrystallized from EtOH/Hexane. Further purification on preparatory HPLC yielded 10B as a 9:1 ratio of desired to undesired regioisomer (1.5 g, 7.9 mmol) as a solid in 56% overall yield. MS (ESI) m/z 191.3 (M+H).

10C

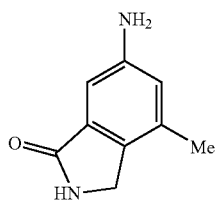

A solution of 10B (1.5 g, 7.9 mmol) in MeOH (20 mL) and water (6 mL) was stirred with a catalytic amount of Raney Ni under 60 psi of hydrogen for 18 h. The reaction was filtered through Celite® and conc. to an oil before purifying via preparatory HPLC to yield 10C (500 mg, 3.08 mmol) as a single regioisomer in 38% yield. MS (ESI) m/z 163.2 (M+H). $^1$H NMR (400 MHz, $CD_3OD$) δ ppm 2.40 (s, 3 H) 3.89 (s, 3 H) 6.73 (s, 1 H) 7.12 (d, J=2.20 Hz, 1 H).

10D

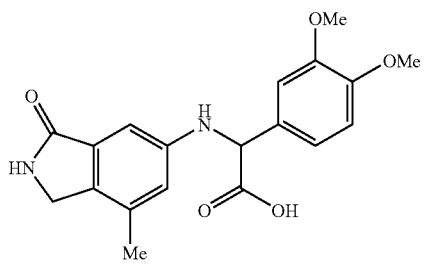

10C (500 mg, 3.08 mmol), 3,4-dimethoxyphenylboronic acid (617 mg, 3.39 mmol) and monohydrate glycolic acid (251 mg, 3.39 mmol) were diluted with acetonitrile/DMF (2 mL each). The reaction was heated at 110° C. for 10 min. in a microwave. Reaction concentrated to an oil and purified with preparatory HPLC to yield 10D in 5% yield. MS (ESI) m/z 357.4 (M+H). $^1$H NMR (400 MHz, MeOD-$d_4$) δ ppm 2.24 (s, 3 H) 3.80 (d, J=4.40 Hz, 6 H) 4.24 (s, 2 H) 5.10 (s, 1 H) 6.87 (s, 1 H) 6.91 (d, J=8.24 Hz, 1 H) 7.06 (d, 1 H) 7.09-7.14 (m, J=2.20 Hz, 1 H) 7.96 (s, 1 H).

Example 10

10D (50 mg, 0.14 mmol) and Intermediate 1 were reacted using the general coupling condition to yield Example 10 (37 mg, 0.054 mmol) as an oil in 39% yield. MS (ESI) m/z 665.6 (M+H). $^1$H NMR (400 MHz, $CD_3OD$) δ ppm 1.12-1.21 (m, 4 H) 1.26-1.37 (m, 1 H) 1.39-1.48 (m, 4 H) 1.70 (dd, J=12.52, 5.49 Hz, 1 H) 2.06 (td, J=13.29, 8.57 Hz, 2 H) 2.24-2.33 (m, 2 H) 2.84-2.87 (m, 1 H) 2.98 (s, 1 H) 3.66 (s, 2 H) 3.69-3.70 (m, 2 H) 3.83 (t, J=3.52 Hz, 4 H) 3.89-3.99 (m, 1 H) 4.09 (dd, J=6.81, 3.30 Hz, 1 H) 4.27-4.30 (m, 2 H) 5.67 (dd, J=8.13, 5.05 Hz, 1 H) 6.83-6.93 (m, 3 H) 6.95-7.04 (m, 2 H) 7.05-7.14 (m, 1 H) 7.15-7.25 (m, 1 H) 7.72-7.77 (m, 1 H).

Example 11 methyl 3-((2R)-1-(2-(3,4-dimethoxyphenyl)-2-(4-fluoro-3-oxoisoindolin-5-ylamino)acetyl)pyrrolidin-2-yl)-4-(isopropylsulfonyl)phenylcarbamate

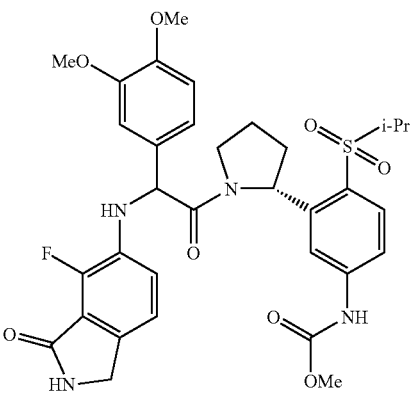

11A

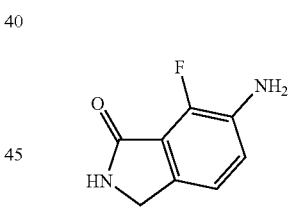

A solution of 6C (400 mg, 2.06 mmol) in MeOH (15 mL) and water (4 mL) was stirred with a catalytic amount of Raney Ni under 60 psi of hydrogen for 18 h. The reaction filtered through Celite® and concentrated to an oil before purifying via preparatory HPLC to yield 11A (275 mg, 1.65 mmol) as an oil in 80% yield. MS (ESI) m/z 167.1 (M+H).

11B

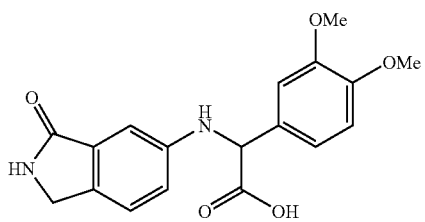

11A (150 mg, 0.903 mmol), 3,4-dimethoxyphenylboronic acid (163 mg, 0.903 mmol) and monohydrate glycolic acid (83 mg, 0.903 mmol) were dissolved in acetonitrile/DMF (2 mL each). The solution was heated at 110° C. for 10 min. in a microwave. The reaction concentrated to an oil and purified with preparatory HPLC to yield 11B in 11% yield. $^1$H NMR (400 MHz, DMF-$d_7$) δ ppm 3.61-3.66 (m, 6 H) 4.30-4.62 (m, 2 H) 5.06-5.11 (m, 1 H) 5.90-5.94 (m, 1 H) 6.63 (d, 1 H) 6.81 (d, 1 H) 6.84-6.92 (m, 1 H) 7.00 (d, 1 H) 7.11-7.18 (m, 1 H), MS (ESI) m/z 361.3 (M+H).

Example 11

11B (35 mg, 0.1 mmol) and Intermediate 1 were reacted using the general coupling condition to yield to a compound at peak 1 (10 mg, 0.015 mmol), $^1$H NMR (400 MHz, MeOD) δ ppm 1.15 (d, J=6.59 Hz, 3 H) 1.41 (d, J=7.03 Hz, 3 H) 1.65-1.75 (m, 2 H) 2.01-2.13 (m, 1 H) 2.42-2.54 (m, J=7.91 Hz, 1 H) 2.85 (d, J=3.08 Hz, 2 H) 2.98 (s, 1 H) 3.68 (d, J=10.11 Hz, 3H) 3.81-3.85 (m, 6 H) 4.09-4.17 (m, J=10.11 Hz, 1 H) 4.18-4.38 (m, 2 H) 5.37 (s, 1 H) 5.65 (dd, J=8.35, 4.83 Hz, 1 H) 6.80 (dd, J=8.79, 3.52 Hz, 1 H) 6.85-6.91 (m, 2 H) 6.93-6.99 (m, 2 H) 7.03 (s, 1 H) 7.20 (dd, J=8.57, 1.98 Hz, 1 H) 7.73 (d, J=8.35 Hz, 1 H) 7.97 (s, 1 H) 9.38 (s, 1 H) MS (ESI) M/Z 669.5 (M+H) and Example 11 (10 mg, 0.015 mmol), $^1$H NMR (400 MHz, MeOD) δ ppm 1.06-1.21 (m, 3 H) 1.35-1.52 (m, 3 H) 1.68-1.97 (m, 4 H) 2.26-2.44 (ra, 1 H) 2.76-3.04 (m, 3 H) 3.59-3.96 (m, 6 H) 4.07-4.39 (m, 2 H) 5.44 (s, 1 H) 5.52-5.77 (m, 1 H) 6.71-7.21 (m, 7 H) 7.65-7.85 (m, 1 H), MS (ESI) M/Z 669.5 (M+H) as an oil in 15% overall yield.

Example 12 methyl 3-((2R)-1-(2-(3,4-dimethoxyphenyl)-2-(isoindolin-5-ylamino)acetyl)pyrrolidin-2-yl)-4-(isopropylsulfonyl)phenylcarbamate

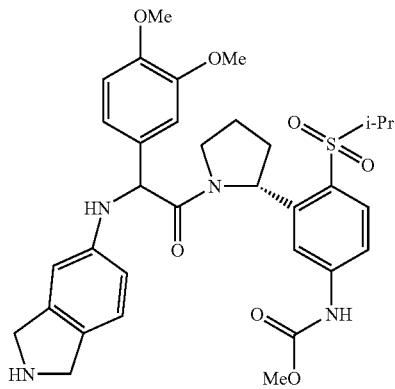

12A

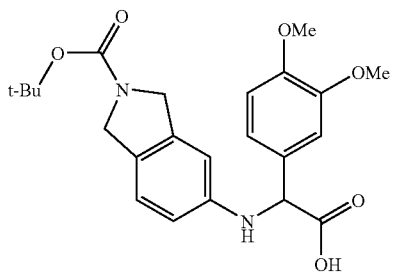

tert-Butyl 5-aminoisoindoline-2-carboxylate (200 mg, 0.854 mmol), 3,4-dimethoxyphenylboronic acid (155 mg, 0.854 mmol) and monohydrate glycolic acid (63 mg, 0.854 mmol) were dissolved in acetonitrile/DMF (2 mL each). The reaction was heated at 110° C. for 10 min. in a microwave. The reaction was concentrated to an oil and purified with preparatory HPLC to yield 12A (309 mg, 0.721 mmol) in 84% yield. $^1$H NMR (400 MHz, CDCl$_3$) δ ppm 1.45-1.51 (m, 9 H) 3.84-3.88 (m, 6 H) 4.48-4.56 (m, 4 H) 4.99 (d, J=6.59 Hz, 1 H) 6.36-6.55 (m, 2 H). MS (ESI) m/z 429.4 (M+H).

Example 12

12A (50 mg, 0.117 mmol), HABT (32 mg, 0.233 mmol), TEA (0.163 mL), N1-((ethylimino)methylene)-N3,N3-dimethylpropane-1,3-diamine hydrochloride (49 mg, 0.257 mmol) and Intermediate 1 (42 mg, 0.128 mmol) were dissolved in DMF (5 mL). The reaction was stirred at rt for 18 h under argon, diluted with MeOH and concentrated to an oil. The reaction mixture was concentrated to a dark oil, dissolved in a 1:1 mixture of dioxane/4M HCl dioxane and stirred at 40° C. for 2 h before concentrating. The residue was purified with preparatory HPLC to yield Example 12 (20 mg, 0.031 mmol), $^1$H NMR (400 MHz, CDCl$_3$) δ ppm 1.06 (d, J=6.59 Hz, 3 H) 1.33 (d, J=7.03 Hz, 3 H) 1.53-1.64 (m, 1 H) 1.81-1.97 (m, 2 H) 2.28-2.41 (m, 1 H) 3.54 (s, 3 H) 3.56 (s, 3 H) 3.72 (s, 3 H) 4.26 (d, J=5.27 Hz, 4 H) 4.96 (s, 1 H) 5.48 (dd, J=8.13, 5.05 Hz, 1 H) 6.37 (s, 1 H) 6.46 (dd, J=8.57, 1.98 Hz, 1 H) 6.55-6.58 (m, J=1.76 Hz, 1 H) 6.69-6.74 (m, 2 H) 6.82 (dd, J=8.13, 1.98 Hz, 1 H) 6.89 (d, J=8.35 Hz, 1 H) 7.07 (dd, J=8.35, 2.20 Hz, 1 H) 7.61 (d, J=8.35 Hz, 1 H), MS (ESI) m/z 637.5 (M+H) and peak 2 (10 mg, 0.016), $^1$H NMR (400 MHz, CDCl$_3$) δ ppm 1.01 (d, J=6.59 Hz, 3 H) 1.32 (d, J=6.59 Hz, 3 H) 1.56-1.79 (m, 2 H) 1.91-2.06 (m, 1 H) 2.10-2.26 (m, 1 H) 3.20 (s, 3 H) 3.65-3.76 (m, 6 H) 4.22 (d, J=15.38 Hz, 4 H) 5.42-5.54 (m, 1 H) 6.32 (s, 1 H) 6.46 (d, 1 H) 6.67-6.88 (m, 3 H) 7.04-7.24 (m, 2 H) 7.64 (d, J=8.79 Hz, 2 H), MS (ESI) m/z 637.5 (M+H) as solids in 40% overall yield.

Example 13 and Example 14 methyl 3-((2R)-1-((2R)-2-(3,4-dimethoxyphenyl)-2-(1-methyl-3-oxoisoindolin-5-ylamino)acetyl)pyrrolidin-2-yl)-4-(isopropylsulfonyl)phenylcarbamate (diastereomeric pair)

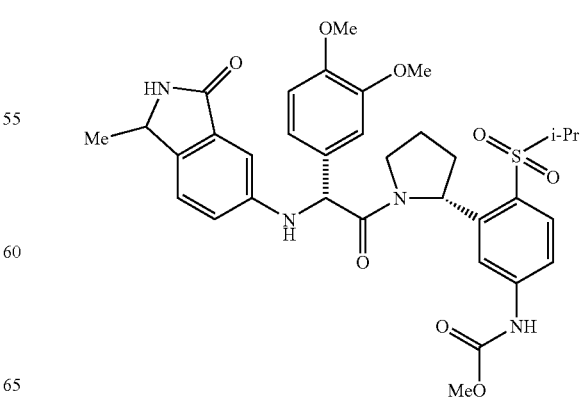

13A

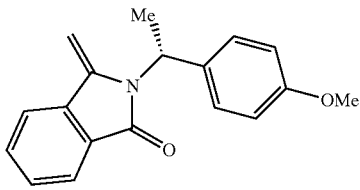

To a 20 mL microwave vial was added 2-acetylbenzoic acid (1.8 g, 10.97 mmol), (R)-1-(4-methoxyphenyl)ethanamine (2 mL, 13.23 mmol) and toluene (2 mL) The reaction was heated 25 min. at 200° C. in the microwave. The crude reaction was concentrated and purified on SiO$_2$, eluting w/0-100% EtOAc/Hex to yield 13A (3.0 g, 10.74 mmol) in 98% yield as an oil. $^1$H NMR (400 MHz, CDCl$_3$) δ ppm 1.82 (d, J=7.47 Hz, 3 H) 3.78 (s, 3 H) 4.60 (d, J=2.20 Hz, 1 H) 5.07 (d, J=2.20 Hz, 1 H) 5.87 (q, J=7.47 Hz, 1 H) 6.85 (d, 2 H) 7.50 (t, J=6.15 Hz, 1 H) 7.55 (t, J=6.81 Hz, 1 H) 7.61 (d, 1 H) 7.85 (d, J=7.47 Hz, 1 H), MS (ESI) m/z 280.3 (M+H).

13B

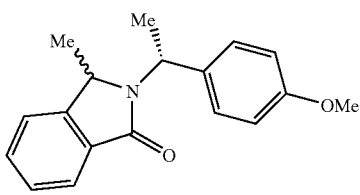

13A (3 g, 10.74 mmol) was dissolved in MeOH/DCM (20 mL/5 mL) and stirred at rt under 50 psi of H$_2$ for 2 h. The crude reaction was filtered through Celite® and purified on SiO$_2$, eluting with 0-100% EtOAc/Hexane. Separation of diastereomers was achieved via preparatory HPLC to yield an equal mixture of both diastereomers (800 mg, 1.80 mmol) as solids 27% yield. Characterization for 13B peak 1 ($^1$H NMR (400 MHz, CDCl$_3$) δ ppm 1.10 (d, J=6.60 Hz, 3 H) 1.78 (d, J=7.70 Hz, 3 H) 3.78 (s, 3 H) 4.70 (q, J=6.60 Hz, 1 H) 5.64 (q, J=7.15 Hz, 1 H) 6.84 (d, J=8.79 Hz, 2 H) 7.33-7.38 (m, 3 H) 7.46 (t, J=7.42 Hz, 1 H) 7.54 (t, J=7.70 Hz, 1 H) 7.88 (d, J=7.70 Hz, 1 H), MS (ESI) m/z 282.3 (M+H)) and 13B peak 2 ($^1$H NMR (400 MHz, CDCl$_3$) δ ppm 1.42 (d, J=6.60 Hz, 3 H) 1.75 (d, J=7.15 Hz, 3 H) 3.79 (s, 3 H) 4.26 (q, J=7.15 Hz, 1 H) 5.67 (q, J=7.15 Hz, 1 H) 6.89 (d, J=8.79 Hz, 2 H) 7.26-7.32 (m, J=8.24, 8.24 Hz, 3 H) 7.43 (t, J=7.15 Hz, 1 H) 7.51 (t, 1 H) 7.86 (d, J=7.15 Hz, 1 H), MS (ESI) m/z 282.3 (M+H)).

13C Peak 1

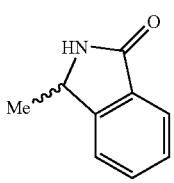

13B Peak 1 (200 mg, 0.711 mmol) was stirred in TFA (8 mL) at rt for 2 h. The reaction was concentrated and purified on SiO$_2$, eluting w/0-100% EtOAc/Hex to yield 13C (75 mg, 0.510 mmol) as a solid, 72% yield. $^1$H NMR (400 MHz, CDCl$_3$) δ ppm 1.50 (d, J=7.03 Hz, 3 H) 4.70 (q, J=6.59 Hz, 1 H) 7.39-7.47 (m, 2 H) 7.55 (t, J=6.81 Hz, 1 H) 7.83 (d, J=7.47 Hz, 1 H) 8.22 (s, 1 H), MS (ESI) m/z 148.2 (M+H).

13C Peak 2

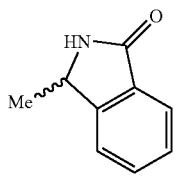

13B Peak 2 (400 mg, 1.4 mmol) was stirred in TFA (8 mL) at rt for 2 h. The reaction was concentrated and purified on SiO$_2$, eluting w/0-100% EtOAc/Hexane to isolate 3-Methyl-isoindolin-1-one (170 mg, 1.1 mmol) as a solid, 81% yield. $^1$H NMR (400 MHz, CDCl$_3$) δ ppm 1.50 (d, J=6.59 Hz, 3 H) 4.70 (q, J=6.59 Hz, 1 H) 7.38-7.48 (m, 2 H) 7.55 (t, J=7.47 Hz, 1 H) 7.83 (d, J=7.47 Hz, 1 H) 8.24 (s, 1 H), MS (ESI) M/Z 148.2 (M+H).

13D Peak 1

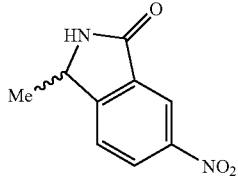

13C Peak 1 (160 mg, 1.1 mmol) was stirred in sulfuric acid (2 mL) at 0° C. for 5 min before adding potassium nitrate (110 mg, 1.1 mmol) portion wise. The reaction mixture was warmed to rt over 1 h, quenched with ice, and filtered resulting precipitate to yield 130 Peak 1 (170 mg, 0.885 mmol) as a white solid (81% yield), $^1$H NMR (400 MHz, CDCl$_3$) δ ppm 1.58 (d, J=6.59 Hz, 3 H) 4.85 (q, J=6.59 Hz, 1 H) 7.56-7.61 (m, 1 H) 8.48 (dd, J=8.35, 2.20 Hz, 1 H) 8.68 (d, J=1.76 Hz, 1 H), MS (ESI) M/Z 193.1 (M+H).

13D Peak 2

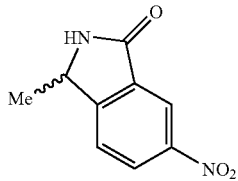

13C Peak 2 (160 mg, 1.1 mmol) was stirred in sulfuric acid (2 mL) at 0° C. for 5 min. before adding potassium nitrate (110 mg, 1.1 mmol) portion wise. Reaction warmed to rt. over 1 hr., quenched with ice, filtered resulting precipitate to yield 13D Peak 2 (170 mg, 0.885 mmol) as a white solid (81% yield), $^1$H NMR (400 MHz, CDCl$_3$) δ ppm 1.59 (d, J=7.03 Hz, 3 H) 4.86 (q, J=7.03 Hz, 1 H) 7.63 (d, J=8.35 Hz, 1 H) 8.48 (dd, J=8.35, 2.20 Hz, 1 H), MS (ESI) M/Z 193.1 (M+H)

13E Peak 1

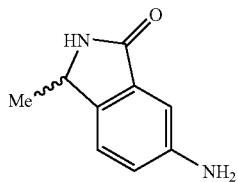

13D Peak 1 (170 mg, 0.885 mmol) was stirred in MeOH (10 mL) with a catalytic amount of 10% Pd/C with hydrogen (1 atm) for 2 h. The reaction was filtered and concentrated to yield 13E Peak 1 (135 mg, 0.832 mmol) as a solid in 94% yield. $^1$H NMR (400 MHz, MeOD) d ppm 1.44 (d, J=7.03 Hz, 3 H) 4.74 (q, J=6.59 Hz, 1 H) 4.93 (s, 3 H) 7.65 (d, 1 H) 7.72 (s, 1 H) 7.74 (d, J=2.20 Hz, 1 H), MS (ESI) m/z 163.2 (M+H).

13E Peak 2

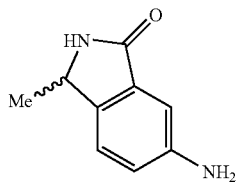

13D Peak 2 (170 mg, 0.885 mmol) was stirred in MeOH (10 mL) with a catalytic amount of 10% Pd/C with Hydrogen (1 atm) for 2 h. The reaction mixture was filtered and concentrated to yield 13E Peak 2 (130 mg, 0.802 mmol) as a solid in 91% yield. $^1$H NMR (400 MHz, MeOD) d ppm 1.44 (d, J=6.59 Hz, 3 H) 4.74 (q, J=7.03 Hz, 1 H) 5.01 (s, 2 H) 7.66 (d, 1 H) 7.72 (s, 1 H) 7.74 (d, 1 H). MS (ESI) m/z 163.3 (M+H).

13F

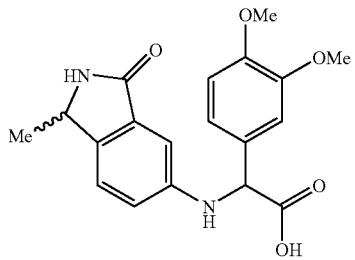

13E Peak 1 (150 mg, 0.925 mmol), 3,4-dimethoxyphenylboronic acid (168 mg, 0.925 mmol) and monohydrate glycolic acid (68 mg, 0.925 mmol) were dissolved in acetonitrile/DMF (2 mL each). The solution was heated at 110° C. for 10 min in a microwave. The reaction mixture was concentrated to a yellow oil and purified on silica gel eluting with MeOH/DCM (0-20%) to yield 13F Peak 1 (210 mg, 0.589 mmol) as a solid in 64% yield. $^1$H NMR (400 MHz, MeOD) δ ppm 1.34 (dd, J=6.59, 1.76 Hz, 3 H) 3.77 (s, 3 H) 3.79 (s, 3 H) 4.50 (q, J=6.59, 1.76 Hz, 1 H) 6.88 (d, J=8.35 Hz, 2 H) 6.91 (d, J=2.20 Hz, 1 H) 6.96 (d, J=8.35 Hz, 1 H) 7.08 (dd, 1 H) 7.13 (d, J=2.20 Hz, 1 H) 7.21 (d, J=8.35 Hz, 1 H), MS (ESI) M/Z 357.2 (M+H).

13F Peak 2

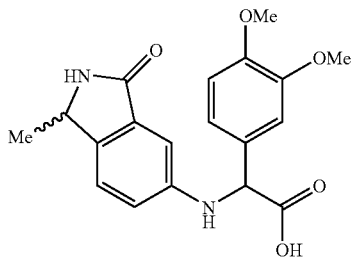

E Peak 2 (150 mg, 0.925 mmol), 3,4-dimethoxyphenylboronic acid (168 mg, 0.925 mmol) and monohydrate glycolic acid (68 mg, 0.925 mmol) were diluted with acetonitrile/DMF (2 mL each). The reaction was heated at 110° C. for 10 min in a microwave. The reaction was concentrated to a yellow oil and purified on silica gel eluting with MeOH/DCM (0-20%) to yield 13F Peak 2 (220 mg, 0.62 mmol) as a solid in 67% yield. $^1$H NMR (400 MHz, MeOD) δ ppm 1.34 (dd, J=6.59, 1.76 Hz, 3 H) 3.75-3.78 (m, 3 H) 3.79 (s, 3 H) 4.50 (q, J=6.59, 1.76 Hz, 1 H) 6.89 (d, J=8.35 Hz, 1 H) 6.91 (d, J=2.20 Hz, 1 H) 6.96 (dd, J=8.35, 2.20 Hz, 1 H) 7.07 (dd, J=8.35, 1.76 Hz, 2 H) 7.13 (d, J=1.76 Hz, 1 H) 7.21 (d, J=8.35 Hz, 1 H), MS (ESI) m/z 357.2 (M+H).

Example 13

13F Peak 1 (110 mg, 0.3 mmol) and Intermediate 1 were reacted using the general coupling condition to yield to yield Example 13 (15 mg, 0.023 mmol, 32% yield), $^1$H NMR (400 MHz, MeOD) δ ppm 1.16 (d, J=6.59 Hz, 3 H) 1.39 (dd, J=12.52, 6.81 Hz, 6 H) 1.70 (dd, J=11.64, 6.37 Hz, 1 H) 1.99-2.14 (m, 2 H) 2.48 (dd, J=12.96, 7.69 Hz, 1 H) 3.65 (s, 3 H) 3.69 (s, 3 H) 3.82-3.85 (m, 3 H) 3.90-4.00 (m, 1 H) 4.06-4.16 (m, 1 H) 4.57 (q, J=6.59 Hz, 1 H) 5.67 (dd, J=7.91, 4.83 Hz, 1 H) 6.84 (s, 1 H) 6.90-6.93 (m, 2 H) 7.02-7.08 (m, 4 H) 7.22 (dd, J=8.79, 2.20 Hz, 1 H) 7.32 (d, J=7.91 Hz, 1 H) 7.74 (d, J=8.79 Hz, 1 H), MS (ESI) m/z 665.4 (M+H) and diastereomer B (10 mg, 0.015 mmol, 22% yield), $^1$H NMR (400 MHz, MeOD) d ppm 1.14 (d, 3 H) 1.37 (d, 3 H) 1.41 (d, 3 H) 1.71-1.79 (m, 1 H) 1.82-1.92 (m, 1 H) 1.98-2.18 (m, 2 H) 2.35 (dd, J=13.18, 7.03 Hz, 1 H) 3.79 (s, 3 H) 3.82 (s, 3 H) 3.83 (s, 3 H) 4.12-4.20 (m, 1 H) 4.53-4.63 (m, 1 H) 5.43 (s, 1 H) 5.59 (q, J=8.35, 3.95 Hz, 1 H) 6.99-7.01 (m, 1 H) 7.05-7.09 (m, 2 H) 7.10-7.13 (m, J=2.20 Hz, 2 H) 7.26 (d, J=8.35 Hz, 1 H) 7.51 (dd, J=8.79, 2.20 Hz, 1 H) 7.62 (d, J=2.20 Hz, 1 H) 7.77 (d, J=8.79 Hz, 1 H), MS (ESI) m/z 665.3 (M+H).

Example 14

13F Peak 2 (110 mg, 0.3 mmol) and Intermediate 1 were reacted using the general coupling condition to yield Example 14 as a mixture of two diastereomers arbitrarily labeled isomer A (13 mg, 0.020 mmol, 28% yield), $^1$H NMR (400 MHz, MeOD) δ ppm 1.15 (d, J=6.59 Hz, 3 H) 1.38 (d, J=6.59 Hz, 3 H) 1.40 (d, J=7.03 Hz, 3 H) 1.65-1.76 (m, 1 H) 2.00-2.13 (m, 2 H) 2.48 (dd, J=13.18, 7.91 Hz, 1 H) 3.64 (s, 3 H) 3.69 (s, 3 H) 3.82-3.84 (m, 3 H) 3.90-3.99 (m, 1 H) 4.06-4.17 (m, 1 H) 4.57 (q, J=6.74 Hz, 1 H) 5.37 (s, 1 H) 5.67 (dd, J=8.35, 4.83 Hz, 1 H) 6.83 (s, 1 H) 6.88-6.92 (m, 2 H) 7.02-7.06 (m, 2 H) 7.06-7.09 (m, 1 H) 7.22 (dd, 1 H) 7.32 (d, J=8.35 Hz, 1 H) 7.74 (d, 1 H), MS (ESI) m/z 665.4 (M+H) and diastereomer B (8 mg, 0.012 mmol, 17% yield), $^1$H NMR (400 MHz, MeOD) S ppm 1.13 (d, J=6.59 Hz, 3 H) 1.35 (d, J=6.59 Hz, 3 H) 1.40 (dd, 3 H) 1.70-1.79 (m, 1 H) 1.82-1.92 (m, J=7.03 Hz, 1 H) 2.07-2.19 (m, 1 H) 2.36 (dd, J=12.74 Hz, 1 H) 3.78 (s, 3 H) 3.82 (s, 3 H) 3.83 (s, 3 H) 4.11-4.21 (m, J=7.03 Hz, 1 H) 4.56 (q, J=6.59 Hz, 1 H) 5.42 (s, 1 H) 5.58 (dd, J=8.35, 4.39 Hz, 1 H) 6.95-7.01 (m, 2 H) 7.07 (dd, J=8.35, 1.76 Hz, 1 H) 7.09-7.13 (m, 2 H) 7.21 (d, J=8.35 Hz, 1 H) 7.50 (dd, 1 H) 7.62 (s, 1 H) 7.76 (d, J=8.35 Hz, 1 H), MS (ESI) m/z 665.3 (M+H).

Example 15 methyl 3-((2R)-1-(2-(3,4-dimethoxyphenyl)-2-((S)-4-methyl-1-oxo-1,2,3,4-tetrahydroisoquinolin-7-ylamino)acetyl)pyrrolidin-2-yl)-4-(isopropylsulfonyl)phenylcarbamate

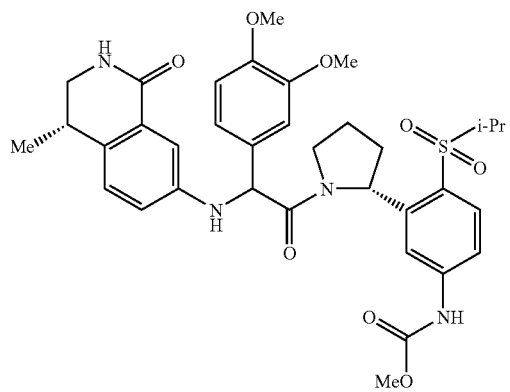

15A

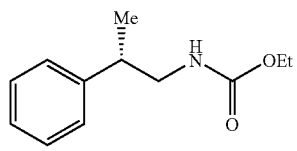

To a solution of S(−) β-methylphenylethylamine 1 (1 of what?—Intermediate or Example?) (0.5 g, 3.6 mmol) in diethyl ether (15 mL) at 0° C., was added triethylamine (5 mL) followed by ethyl chloroformate (0.6 g, 5.5 mmol) dropwise. The white precipitate formed was stirred for 30 min. The reaction mixture filtered and the solid was washed with diethyl ether. The combined filtrate was concentrated to yield ISA and taken for next step without further purification. Yield: 0.4 g, 53%. $^1$H NMR (CDCl$_3$, 400 MHz) δ 7.16-7.3 (m, 5H), 4.5 (s, 1H), 4.1 (m, 2H), 3.5 (m, 1H), 3.26 (m, 1H), 2.9 (m, 1H), 1.4 (m, 3H). LCMS-(M+1)$^+$ 208.

15B

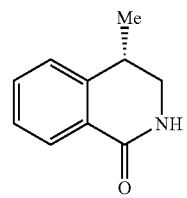

Eaton's reagent was prepared by stirring P$_2$O$_5$ (1.0 g) in methane sulfonic acid (10 mL) at rt for 12 h. ISA (2 g) was added to the Eatons reagent and heated at 120° C. for 2 h. The reaction mixture was cooled to rt, quenched with ice and extracted with ethyl acetate. Combined organic layer was washed with 10% NaHCO$_3$ solution (2×100 mL), water (1×100 mL), brine (1×100 mL), dried over anhydrous Na$_2$SO$_4$ and concentrated. The crude product was purified by flash column chromatography using silica gel column using hexane:ethyl acetate as eluent to yield 15B (1.5 g, 75% yield). $^1$H NMR (CDCl$_3$, 400 MHz) δ 8.05 (d, 1H), 7.5 (m, 1H), 7.3 (m, 1H), 7.2 (m, 1H), 3.67 (m, 1H), 3.3 (m, 1H), 3.14 (m, 1H), 1.3 (d, 3H). LCMS-(M+1)$^+$ 162.

15C

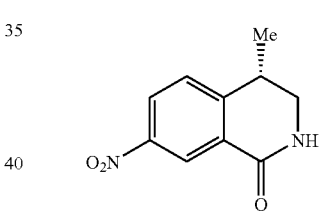

Conc. H$_2$SO$_4$ was added drop wise to 15B (4 g, 24.3 mmol) at 0° C. and stirred for 10 min. KNO$_3$ (2.7 g, 27.3 mmol) was added portion wise and stirred for 30 min. The reaction mixture was quenched with ice and extracted with ethyl acetate. The organic layer was washed with water (1×100 ml), brine (100 ml), dried over anhydrous Na$_2$SO$_4$ and concentrated. Yield: 3 g, 60%. 15C obtained was pure and taken as such for the next step. $^1$H NMR (DMSO-d$_6$, 400 MHz) δ 8.5 (d, 1H), 8.3 (m, 1H), 8.2 (bs, 1H), 7.6 (d, 1H), 3.5 (m, 1H), 3.2 (m, 2H), 1.3 (d, 3H). LCMS-(M+1)$^+$ 207.

15D

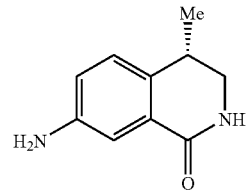

To a solution of 15C (0.5 g) in methanol (100 mL), was added Pd/C (0.5 g) and hydrogenated at 3 Kg pressure for 2 h. The catalyst was filtered through Celiete bed, washed with methanol. The filtrate was concentrated and purified by flash chromatography using neutral alumina using CHCl$_3$: MeOH as eluent to yield 15D (0.3 g, 70%). $^1$H NMR (DMSO-d$_6$, 400 MHz) δ 7.7 (s, 1H), 7.1 (d, 1H), 6.9 (m, 1H), 7.6 (d, 1H), 6.7 (m, 1H), 5.2 (d, 2H), 3.17 (d, 1H), 3.0 (m, 1H), 2.8 (m, 1H), 1.2 (d, 3H). LCMS-(M+1)$^+$ 177.

15E

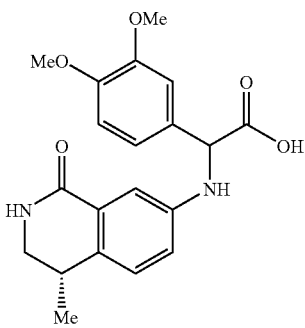

15D (300 mg, 1.7 mmol), 3,4-dimethoxyphenylboronic acid (310 mg, 1.7 mmol) and monohydrate glycolic acid (126 mg, 1.7 mmol) were stirred in acetonitrile/DMF (1 mL each) and heated in the microwave at 110° C. for 10 min. The reaction was concentrated and purified on silica gel eluting with MeOH/DCM (0-20%). 15E (510 mg, 1.38 mmol) was isolated in 81% yield as a solid. $^1$H NMR (400 MHz, MeOD) δ ppm 1.21 (d, J=7.15 Hz, 3 H) 2.91 (d, J=7.15 Hz, 1 H) 3.08-3.16 (m, 1 H) 3.43-3.51 (m, 1 H) 3.78 (s, 3 H) 3.80 (s, 3 H) 5.03 (s, 1 H) 6.83 (dd, J=8.24, 2.75 Hz, 1 H) 6.89 (d, J=8.25 Hz, 1 H) 7.01-7.09 (m, 2 H) 7.13 (s, 1 H) 7.19-7.24 (m, 1 H), MS (ESI) m/z 371.3 (M+H).

Example 15

15E (110 mg, 0.3 mmol) and Intermediate 1 were reacted using the general coupling condition to yield Example 15 (12 mg, 0.017 mmol), $^1$H NMR (400 MHz, MeOD) δ ppm 1.17 (d, J=6.59 Hz, 3 H) 1.25 (d, J=7.03 Hz, 3 H) 1.41 (d, 3 H) 1.64-1.76 (m, J=12.96, 5.05 Hz, 1 H) 1.97-2.13 (m, 2 H) 2.41-2.54 (m, J=13.18, 7.91 Hz, 1 H) 2.96-3.05 (m, 1 H) 3.18 (dd, J=12.52, 6.37 Hz, 1 H) 3.52 (dd, J=12.74, 4.83 Hz, 1 H) 3.65 (s, 3 H) 3.69 (s, 3 H) 3.82-3.84 (m, 3 H) 3.91-4.00 (m, 1 H) 4.01-4.10 (m, 1 H) 5.38-5.41 (m, 1 H) 5.66 (dd, J=7.91, 4.83 Hz, 1 H) 6.82 (s, 1 H) 6.89 (s, 2 H) 7.01 (dd, J=8.35, 2.64 Hz, 1 H) 7.08 (s, 1 H) 7.19 (d, J=8.35 Hz, 1 H) 7.22 (dd, J=8.79, 2.20 Hz, 1 H) 7.42 (d, J=2.64 Hz, 1 H) 7.74 (d, J=8.79 Hz, 1 H), MS (ESI) m/z 679.5 (M+H) and diastereomer 2 (8 mg, 0.012 mmol), $^1$H NMR (400 MHz, MeOD) δ ppm 1.13 (d, J=6.59 Hz, 3 H) 1.21 (d, J=7.03 Hz, 3 H) 1.41 (d, 3 H) 1.69-1.92 (m, 2 H) 2.07-2.20 (m, 1 H) 2.31-2.43 (m, 1 H) 2.92-3.00 (m, 1 H) 3.17-3.25 (m, 1 H) 3.52-3.60 (m, 2 H) 3.79 (s, 3 H) 3.83 (s, 3 H) 3.84 (s, 3 H) 4.15-4.25 (m, 1 H) 5.39 (s, 1 H) 5.57 (dd, J=8.35, 4.39 Hz, 1 H) 6.92 (dd, J=8.35, 2.64 Hz, 1 H) 7.00 (d, 1 H) 7.04-7.13 (m, 3 H) 7.34 (d, J=2.64 Hz, 1 H) 7.53 (d, J=2.20 Hz, 1 H) 7.68 (dd, 1 H) 7.77 (d, 1 H), MS (ESI) m/z 619.4 (M+H), as solids in 21% yield.

Example 16 methyl 3-((2R)-1-(2-(3,4-dimethoxyphenyl)-2-((R)-4-methyl-1-oxo-1,2,3,4-tetrahydroisoquinolin-7-ylamino)acetyl)pyrrolidin-2-yl)-4-(isopropylsulfonyl)phenylcarbamate

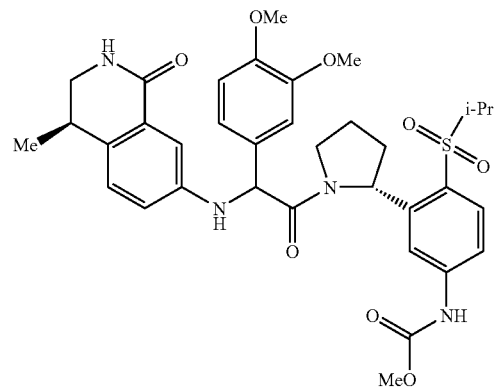

16A

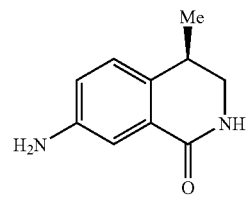

16A was synthesized from (R)-2-phenylpropan-1-amine using an analogous procedure to the one used for 15D.

16B

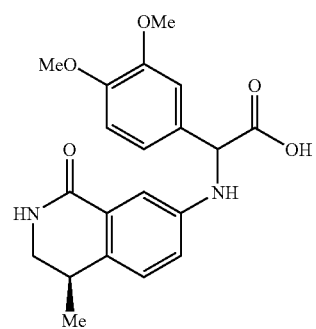

16A (300 mg, 1.7 mmol), 3,4-dimethoxyphenylboronic acid (310 mg, 1.7 mmol) and monohydrate glycolic acid (126 mg, 1.7 mmol) were stirred in acetonitrile/DMF (1 mL each) and heated in the microwave at 110° C. for 10 min. The reaction was concentrated and purified on silica gel, eluting with MeOH/DCM (0-20%). 16B was isolated in 82% yield as a solid. ¹H NMR (400 MHz, MeOD) δ ppm 1.22 (d, J=4.95 Hz, 3 H) 2.90-2.96 (m, 1 H) 3.09-3.17 (m, 1 H) 3.48 (dd, J=14.29, 4.95 Hz, 1 H) 3.79 (s, 3 H) 3.81 (s, 3 H) 5.04 (s, 1 H) 6.83 (dd, J=8.25, 2.75 Hz, 1 H) 6.91 (d, J=8.24 Hz, 1 H) 7.03-7.09 (m, 2 H) 7.13 (s, 1 H) 7.19-7.24 (m, 1 H), MS (ESI) m/z 371.3 (M+H).

Example 16

16B (28 mg, 0.08 mmol) and Intermediate 1 were reacted using the general coupling conditions to yield Example 16 (10 mg, 0.014 mmol), ¹H NMR (400 MHz, MeOD) δ ppm 1.17 (d, J=6.59 Hz, 3 H) 1.26 (d, 3 H) 1.41 (d, J=7.03 Hz, 3 H) 1.69 (dd, J=12.74, 5.27 Hz, 1 H) 1.97-2.13 (m, 2 H) 2.40-2.53 (m, J=12.96, 7.69 Hz, 1 H) 2.95-3.05 (m, 1 H) 3.18 (dd, J=12.74, 6.15 Hz, 1 H) 3.48-3.56 (m, 1 H) 3.64 (s, 3 H) 3.68 (s, 3 H) 3.82-3.84 (m, 3 H) 3.99-4.10 (m, 1 H) 5.40 (s, 1 H) 5.66 (dd, J=8.35, 4.83 Hz, 1 H) 6.82 (s, 1 H) 6.89 (s, 2 H) 7.01 (dd, J=8.35, 2.64 Hz, 1 H) 7.09 (s, 1 H) 7.17-7.26 (m, 2 H) 7.46 (d, J=2.20 Hz, 1H) 7.74 (d, J=8.79 Hz, 1 H), MS (ESI) M/Z 679.4 (M+H) and diasteromer 2 (6 mg, 0.09 mmol), ¹H NMR (400 MHz, MeOD) δ ppm 1.12 (d, J=5.93 Hz, 3 H) 1.24 (d, J=7.03 Hz, 3 H) 1.40 (d, J=7.03 Hz, 3 H) 1.70-1.81 (m, 1 H) 1.81-1.93 (m, 1 H) 2.08-2.21 (m, 1 H) 2.27-2.42 (m, 1 H) 2.94-3.02 (m, 1 H) 3.11-3.19 (m, 1 H) 3.45-3.53 (m, 1 H) 3.80 (s, 3 H) 3.82 (s, 3 H) 3.84 (s, 3 H) 4.12-4.23 (m, 1 H) 5.37-5.41 (m, 1 H) 5.59 (dd, J=8.35, 3.95 Hz, 1 H) 6.86 (dd, J=8.35, 2.64 Hz, 1 H) 6.98-7.06 (m, 2 H) 7.07-7.12 (m, 2 H) 7.37 (d, J=2.64 Hz, 1 H) 7.56 (d, J=2.20 Hz, 1 H) 7.62 (dd, J=8.79, 1.76 Hz, 1 H) 7.77 (d, J=8.79 Hz, 1 H), MS (ESI) M/Z 679.4 (M+H), as solids in 17% yield.

Example 17 methyl 3-((2R)-1-(2-(3,4-dimethoxyphenyl)-2-((S)-4-ethyl-1-oxo-1,2,3,4-tetrahydroisoquinolin-7-ylamino)acetyl)pyrrolidin-2-yl)-4-(isopropylsulfonyl)phenylcarbamate

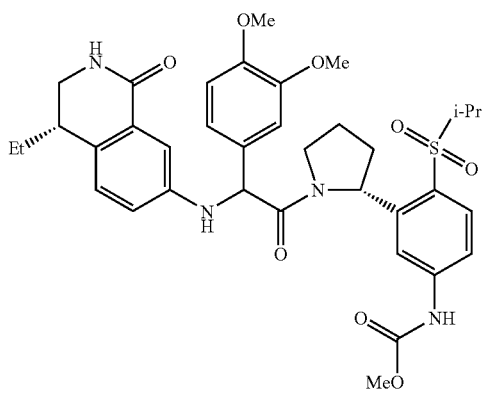

17A

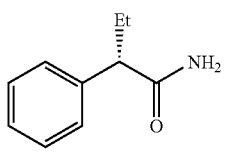

To a solution of S(+)-2-Phenyl butyric acid (0.5 g, 3.04 mmol) in DMF (5 mL), was added HOBt (0.45 g, 3.3 mmol), EDCI.HCl (0.7 g, 3.6 mmol) and cooled to 0° C. Aqueous NH₃ (10 mL) was added drop wise and stirred at rt for 12 h. Excess water was added and extracted with ethyl acetate. The organic layer was washed with brine, dried over Na₂SO₄ and concentrated to give 17A (0.4 g, 80% yield). ¹H NMR (CDCl₃, 400 MHz) δ 7.4-7.2 (m, 5H), 5.8 (bs, 1H), 5.5 (bs, 1H), 3.3 (m, 1H), 2.2 (m, 2H), 1.8 (m, 1H), 0.9 (m, 3H). LCMS-(M+1)+163.

17B

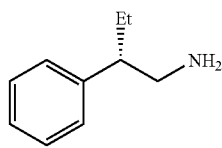

To a solution of 17A (0.2 g, 1.2 mmol) in THF (5 mL), at 0° C. was added BH₃.(CH₃)₂S complex (0.18 g, 2.4 mmol) drop wise. The reaction mixture was stirred at rt for 30 min and then refluxed for 12 h. The reaction mixture was cooled to 0° C., quenched with methanol (few drops) and 1.5N HCl (2 mL), THF was evaporated and the aqueous layer was basified with NaHCO₃ and extracted with ethyl acetate, washed with water, brine, dried and concentrated to give 17B. (0.13 g, 70% yield). ¹H NMR (CDCl₃, 400 MHz) 7.3 (m, 2H), 7.1 (m, 3H), 2.9 (bs, 1H), 2.5 (m, 2H), 1.7 (m, 1H), 1.5 (m, 1H), 0.8 (m, 3H).

17C

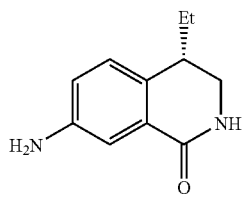

17B was converted to 17C using similar procedures to those used to make 15D from S(−) β-methylphenylethylamine. ¹H NMR (DMSO-d₆, 400 MHz) δ 7.6 (d, 1H), 7.1 (d, 1H), 6.9 (m, 1H), 6.7 (m, 1H), 5.6 (bs, 2H), 3.5 (m, 1H), 3.2 (m, 1H), 2.6 (m, 1H), 1.5 (m, 2H) 0.8 (m, 3H). LCMS−(M+1)⁺ 191.

17D

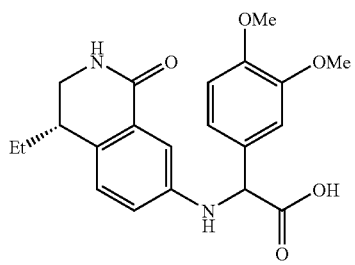

17C (75 mg, 0.394 mmol), 3,4-dimethoxyphenylboronic acid (72 mg, 0.394 mmol) and monohydrate glycolic acid (29 mg, 0.394 mmol) were stirred in acetonitrile/DMF (1 mL each) and heated in the microwave at 110° C. for 10 min. The reaction was concentrated and purified on silica gel eluting with MeOH/DCM (0-20%). 17D (125 mg, 0.319 mmol) was isolated in 81% yield as a solid. $^1$H NMR (400 MHz, MeOD) δ ppm 1.20-1.27 (m, 3 H) 1.86-1.95 (m, 2 H) 2.85-2.97 (m, 1H) 3.62-3.66 (m, 1 H) 3.79-3.89 (m, 1 H) 4.11 (d, J=2.20 Hz, 3 H) 4.13 (d, J=2.20 Hz, 3 H) 5.37 (s, 1 H) 7.12-7.18 (m, 1 H) 7.22 (dd, J=8.24, 2.75 Hz, 1 H) 7.33 (d, J=8.24 Hz, 1 H) 7.40 (dd, J=8.25, 2.20 Hz, 1 H) 7.46 (s, 1 H) 7.55 (dd, J=15.39, 2.75 Hz, 1 H) 8.29 (s, 1 H), MS (ESI) m/z 386.3 (M+H).

Example 17

17D (110 mg, 0.3 mmol) and Intermediate 1 were reacted using the general coupling condition to yield Example 17 (40 mg, 0.050 mmol), $^1$H NMR (400 MHz, MeOD) δ ppm 0.92 (t, J=7.42 Hz, 3 H) 1.17 (d, J=6.60 Hz, 3 H) 1.41 (d, J=6.60 Hz, 3 H) 1.57-1.66 (m, 2 H) 1.66-1.75 (m, J=12.09, 6.05 Hz, 1 H) 1.98-2.13 (m, 2 H) 2.41-2.54 (m, J=13.19, 7.70 Hz, 1 H) 2.65-2.73 (m, 1 H) 3.36 (dd, J=12.64, 3.30 Hz, 1 H) 3.56 (dd, J=12.92, 4.67 Hz, 2 H) 3.65 (s, 3 H) 3.69 (s, 3 H) 3.83 (s, 3 H) 3.91-4.00 (m, 1 H) 4.06 (dd, J=6.60, 3.30 Hz, 1 H) 5.40 (s, 1 H) 6.82 (s, 1 H) 6.89 (s, 2 H) 7.00 (dd, J=8.24, 2.75 Hz, 1 H) 7.09 (s, 1 H) 7.15 (d, J=8.24 Hz, 1H) 7.24 (dd, J=8.79, 2.20 Hz, 1 H) 7.42 (d, J=2.75 Hz, 1 H) 7.75 (d, J=8.79 Hz, 1 H), MS (ESI) M/Z 693.4 (M+H) and peak 2 (40 mg, 0.050 mmol), $^1$H NMR (400 MHz, MeOD) δ ppm 0.92 (t, 3 H) 1.12 (d, 3 H) 1.39 (d, J=7.15 Hz, 3 H) 1.43-1.66 (m, 4H) 1.74 (dd, J=12.09, 5.50 Hz, 1 H) 1.80-1.91 (m, 1 H) 2.07-2.19 (m, 1 H) 2.37 (dd, J=12.92, 6.87 Hz, 1 H) 2.55-2.66 (m, 1 H) 3.36-3.43 (m, 1 H) 3.54-3.65 (m, 3H) 3.77 (s, 3 H) 3.82 (s, 3 H) 3.83 (s, 3 H) 4.21 (dd, J=5.77, 3.02 Hz, 1 H) 5.37 (s, 1H) 5.55 (dd, J=8.24, 4.95 Hz, 1 H) 6.87 (dd, J=8.25, 2.20 Hz, 1 H) 6.96-7.08 (m, 3H) 7.08-7.14 (m, 1 H) 7.30 (d, J=2.75 Hz, 1 H) 7.49 (s, 1 H) 7.71-7.78 (m, 2 H), MS (ESI) m/z 693.4 (M+H) as solids in 36% yield.

Example 18 methyl 3-((2R)-1-(2-(3,4-dimethoxyphenyl)-2-((R)-4-ethyl-1-oxo-1,2,3,4-tetrahydroisoquinolin-7-ylamino)acetyl)pyrrolidin-2-yl)-4-(isopropylsulfonyl)phenylcarbamate

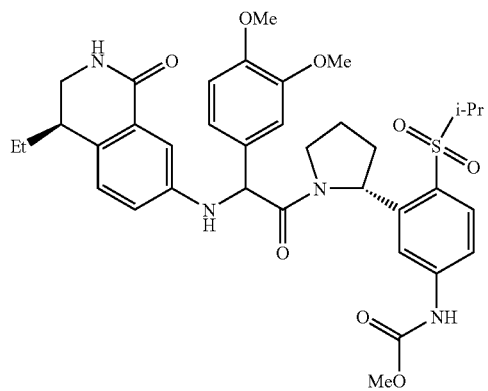

18A

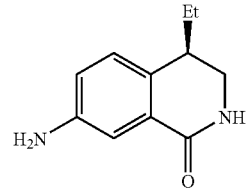

18A was synthesized from (R)-(−)-2-Phenylbutyric acid using similar procedures to those used to convert S(+)-2-phenyl butyric acid to 17C.

18B

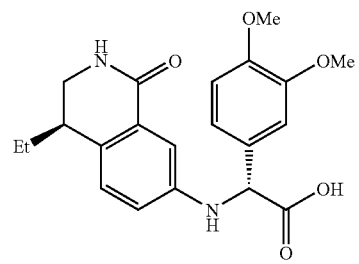

18A (300 mg, 1.577 mmol), 3,4-dimethoxyphenylboronic acid (287 mg, 1.577 mmol) and monohydrate glycolic acid (117 mg, 1.577 mmol) were stirred in acetonitrile/DMF (1 mL each) while heating in the microwave at 110° C. for 10 min. The reaction was concentrated and purified on silica gel eluting with MeOH/DCM (0-20%). 18B (560 mg, 1.47 mmol) was isolated in 92% yield as a solid. $^1$H NMR (400 MHz, MeOD) δ ppm 1.52-1.63 (m, 3 H) 2.53-2.62 (m, 1 H) 3.47-3.56 (m, 1 H) 3.78 (d, J=1.76 Hz, 3 H) 3.80 (d, J=1.76 Hz, 3 H) 3.82 (d, J=2.64 Hz, 1 H) 5.03 (d, J=1.76 Hz, 1 H) 6.78-6.84 (m, 1 H) 7.00 (d, J=8.35 Hz, 1 H) 7.06 (dd, J=8.35, 2.20 Hz, 1 H) 7.13 (d, J=1.76 Hz, 1 H) 7.20 (dd, J=15.82, 2.64 Hz, 1H), MS (ESI) m/z 384.4 (M+H).

Example 18

18B (50 mg, 0.3 mmol) and Intermediate 1 were reacted using the general coupling condition to yield Example 18 (8 mg, 0.012 mmol), $^1$H NMR (400 MHz, Solvent??) δ ppm 0.94 (t, J=7.42 Hz, 3 H) 1.19 (d, J=6.60 Hz, 3 H) 1.43 (d, J=6.60 Hz, 3 H) 1.59-1.66 (m, 2 H) 1.71 (s, 1 H) 2.01-2.11 (m, 2 H) 2.48 (s, 1 H) 2.67-2.74 (m, 1 H) 3.38 (dd, J=12.92, 3.02 Hz, 1 H) 3.55-3.63 (m, 2 H) 3.66 (s, 3H) 3.70 (s, 3 H) 3.85 (s, 3 H) 3.94-4.06 (m, 2 H) 5.43 (s, 1 H) 5.68 (dd, J=7.97, 5.22 Hz, 1 H) 6.83 (s, 1 H) 6.91 (s, 2 H) 7.02 (dd, J=8.24, 2.20 Hz, 1 H) 7.11 (s, 1 H) 7.19 (d, J=8.25 Hz, 1 H) 7.24 (dd, J=8.79, 2.20 Hz, 1 H) 7.50 (d, J=2.20 Hz, 1 H) 7.76 (d, J=8.79 Hz, 1 H), MS (ESI) m/z 695.5 (M+H) and diasteromer 2 (8 mg, 0.012 mmol) $^1$H NMR (400 MHz, MeOD) δ ppm 0.93 (ddd, J=10.72, 7.70, 7.42 Hz, 4 H) 1.10-1.17 (m, 4 H) 1.42 (t, J=6.05 Hz, 3 H) 1.56-1.67 (m, 2 H) 1.74 (td, J=11.41, 5.77 Hz, 1 H) 1.80-1.88 (m, 1 H) 2.06-2.17 (m, 1 H) 2.34 (dd, J=12.64, 7.15 Hz, 1 H) 2.61-2.70 (m, 1 H) 3.49-3.59 (m, 2 H) 3.62 (s, 1 H) 3.68-3.76 (m, 2 H) 3.78-3.84 (m, 7 H) 5.37-5.41 (m, 1 H) 5.61 (dd, J=8.25, 4.40 Hz, 1 H) 6.83-6.91 (m, 1 H) 6.98-7.06 (m, 3 H) 7.06-7.11 (m, 1 H) 7.56-7.61 (m, 2 H) 7.78 (d, J=8.79 Hz, 1 H), MS (ESI) M/Z 695.5 (M+H) as solids in 18% yield.

Example 19 methyl 3-((R)-1-((R)-2-(3,4-dimethoxyphenyl)-2-(3-oxo-2,3-dihydro-1H-indazol-5-ylamino)acetyl)pyrrolidin-2-yl)-4-(isopropylsulfonyl)phenylcarbamate trifluoroacetate

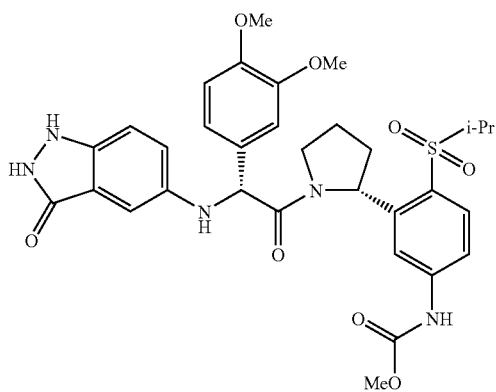

19A

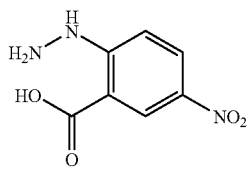

2-chloro-5-nitrobenzoic acid (5,000 g, 24.81 mmol) was dissolved in ethanol (10 mL), and hydrazine hydrate (12.08 mL, 248 mmol) was added. The mixture was heated at 100° C. for 3.5 h. The reaction mixture was cooled to rt, diluted with water and acidified to pH ~5.0 with HCl (12 N). The resultant bright-yellow solid was filtered, washed with water (2×), ether and dried to give 19A (3.968 g, 20.13 mmol, 81% yield) as a bright-yellow solid. LC-MS: (Phenom. Luna C18 30×4.6 mm 5μ; sol. A 10% MeCN-90% H$_2$O-0.1% TFA; sol. B 90% MeCN-10% H$_2$O-0.1% TFA; wavelength 220 nm; flow rate 5 mL/min; gradient time 2 min; start % B=0%, final % B=100%) 0.503 min, [M+1]$^+$=198.0. Purity >95%. $^1$H-NMR: (400 MHz, DMSO-d$_6$) δ ppm 7.38 (d, J=9.34 Hz, 1 H) 8.18 (dd, J=9.34, 2.75 Hz, 1H) 8.59 (d, J=2.75 Hz, 1 H) 9.53 (s, 1 H). $^{13}$C-NMR: (101 MHz, DMSO-d6) δ ppm 107.30, 111.70, 128.63, 129.13, 134.22, 156.51, 168.47.

19B

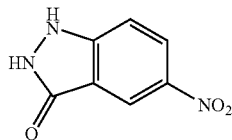

19A (8.515 g, 43.2 mmol) was mixed with water (325 mL) and then hydrochloric acid (12 N) (165 mL) was added. The resulting solution/suspension was brought to reflux (oil bath 150° C.). After ~15 min a clear solution was obtained. After refluxing was continued for 2.5 h, the reaction mixture was cooled to 0° C. The crystalline precipitate was filtered off, washed with a small amount of cold water (1×), ether (3×), and dried in vacuo to give 19B (6.469 g, 30.0 mmol, 69.5% yield) as yellow needles. LC-MS: (Phenom. Luna C18 30×4.6 mm 5u; sol. A 10% MeCN-90% H$_2$O-0.1% TFA; sol. B 90% MeCN-10% H$_2$O-0.1% TFA; wavelength 220 nm; flow rate 5 mL/min; gradient time 2 min; start % B=0%, final % B=100%) 0.550 min, [M+1]$^+$=180.0. Purity >95%. $^1$H-NMR: (400 MHz, DMSO-d$_6$) δ ppm 7.47 (d, J=8.79 Hz, 1 H) 8.13 (dd, J=9.34, 2.20 Hz, 1 H) 8.69 (d, J=2.20 Hz, 1 H)

19C

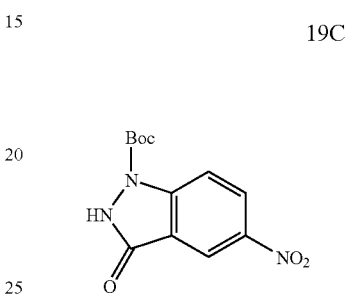

19B (0.500 g, 2.319 mmol) was mixed with water (10 mL). To this solution/suspension sodium bicarbonate (0.214 g, 2.55 mmol) was added portionwise. The mixture was stirred for 30 min. BOC-Anhydride (0.700 mL, 3.01 mmol) was added, the mixture was heated to 45° C. and stirred at this temperature for 30 min. Additional portions of sodium bicarbonate (totaling 1.5 g) and Boc$_2$O (totaling 1 g) were added and the mixture was stirred overnight at 45° C. The reaction mixture was diluted with water (100 mL), and extracted with EtOAc (3×25 mL). The combined organic phase was washed with water (2×50 mL), brine (1×50 mL) and dried (Na$_2$SO$_4$). After filtration, the solvent removed under reduced pressure and the resulting solid was washed with ether/hexanes (3×) and dried to give 19C (0.395 g, 1.415 mmol, 61.0% yield) as a yellowish solid. LC-MS: (Phenom. Luna C18 30×4.6 mm 5u; sol. A 10% MeCN-90% H$_2$O-0.1% TFA; sol. B 90% MeCN-10% H$_2$O-0.1% TFA; wavelength 220 nm; flow rate 5 mL/min; gradient time 2 min; start % B=0%, final % B=100%) 1.217 min, [M+1]$^+$=280.02. Purity >95%. $^1$H-NMR; (400 MHz, DMSO-d$_6$) δ ppm 1.61 (s, 9 H) 8.13 (d, J=9.34 Hz, 1 H) 8.40 (dd, J=9.34, 2.20 Hz, 1 H) 8.57 (d, J=2.20 Hz, 1 H) 12.60 (s, 1 H). $^{13}$C-NMR: (101 MHz, DMSO-d$_6$) δ ppm 27.69, 84.56, 114.97, 116.99, 117.24, 124.60, 143.02, 148.21, 158.48.

19D

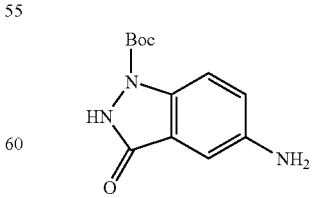

19C (0.100 g, 0.358 mmol) was partially dissolved in THF (5 mL) and water (0.6 mL), then the mixture was degassed (3×Ar/vacuum). To this solution, Pd—C (10% wt) (0.057 g, 0.054 mmol) was added. The mixture was degassed again (3×Ar) and allowed to stir at rt under hydrogen (1 atm) for 2 h. The Pd—C was filtered and the solvent was removed under reduced pressure to give 19D (0.080 g, 0.321 mmol, 90% yield) as a yellowish glass. LC-MS: (Phenom. Luna C18 30×4.6 mm 5u; sol. A 10% MeCN-90% H$_2$O-0.1% TFA; sol. B 90% MeCN-10% H$_2$O-0.1% TFA; wavelength 220 nm; flow rate 5 mL/min; gradient time 2 min; start % B=0%, final % B=100%) 0.562 min, [M+1]$^+$=250.1. Purity >95% $^1$H-NMR: (400 MHz, DMSO-d$_6$) δ ppm 1.55 (s, 9 H) 5.15 (s, 2 H) 6.73 (d, J=2.20 Hz, 1 H) 6.86 (dd, J=8.79, 2.20 Hz, 1 H) 7.63 (d, J=7.70 Hz, 1 H).

19E

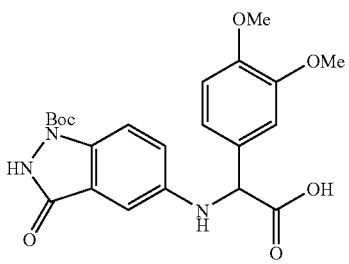

In a microwave reaction vial, 19D (0.077 g, 0.309 mmol), 3,4-dimethoxyphenylboronic acid (0.062 g, 0.340 mmol), and glyoxylic acid monohydrate (0.028 g, 0.309 mmol) were suspended in acetonitrile (4.5 mL) and DMF (1.5 mL). The mixture was irradiated in a microwave reactor at 100° C. for 10 min, and then was concentrated. The crude product was dissolved in dichloromethane with a couple of drops of MeOH, loaded onto a 12 g column and eluted with a gradient from 1 to 20% methanol/methylene chloride. The product containing peak that eluted (~10% MeOH) was concentrated to give 19E (0.120 g, 0.271 mmol, 88% yield) as a yellow glass. LC-MS: (Phenom. Luna C18 30×4.6 mm 5u; sol. A 10% MeCN-90% H$_2$O-0.1% TFA; sol. B 90% MeCN-10% H$_2$O-0.1% TFA; wavelength 220 nm; flow rate 5 mL/min; gradient time 2 min; start % B=0%, final % B=100%) 1.028 min, [M+1]$^+$=444.1. Purity >95%. $^1$H-NMR: (400 MHz, CD$_3$OD) δ ppm 1.62 (s, 9 H) 3.80 (s, 3 H) 3.82 (s, 3 H) 5.03 (s, 1 H) 6.78 (s, 1 H) 6.92 (d, J=8.24 Hz, 1 H) 7.05-7.16 (m, 3 H) 7.68 (d, J=8.24 Hz, 1 H) 7.96 (s, 1 H).

Example 19

To 19E (0.060 g, 0.135 mmol), HOAt (0.018 g, 0.135 mmol), and Intermediate 1 (0.049 g, 0.135 mmol) in dichloromethane (10 mL), was added N-methylmorpholine (0.045 mL, 0.406 mmol) and then EDC (0.052 g, 0.271 mmol). The reaction was stirred overnight at room temperature. A mixture of water and saturated sodium chloride was added to the reaction. The product was extracted with dichloromethane and dried over sodium sulfate. The reaction was filtered and the solvent was removed. The crude residue was dissolved in TFA. The reaction mixture was agitated for 15 min at rt, then was concentrated, and the residue was purified by preparative HPLC (Phenomenex Luna 5 μ, C1830×250 mm column; sol. A 10% MeCN-90% H$_2$O-0.1% TFA; sol. B 90% MeCN-10% H$_2$O-0.1% TFA; wavelength 220 nm; flow rate 40 mL/min; gradient time 20 min; start % B=0%, final % B=50%) 17.5 min. The isolated material was resubmitted to HPLC purification (Phenomenex Synergi 4u Polar-RP 80A 21.2×150 mm column; sol. A 10% MeCN-90% H$_2$O-0.1% TFA; sol. B 90% MeCN-10% H$_2$O-0.1% TFA; wavelength 220 nm; flow rate 20 mL/min; gradient time 10 min; start % B=0%, final % B=50%, rt=8.10 min) to afford Example 19 (0.020 g, 0.026 mmol, 38.6% yield). LC-MS: (Phenom. Luna C18 30×4.6 mm 5u; sol. A 10% MeCN-90% H$_2$O-0.1% TFA; sol. B 90% MeCN-10% H$_2$O-0.1% TFA; wavelength 220 nm; flow rate 5 mL/min; gradient time 2 min; start % B=0%, final % B=100%) 0.835 min, [M+1]$^+$=652.2. $^1$H NMR: (400 MHz, CD$_3$OD) δ ppm 1.21 (d, J=6.60 Hz, 3 H) 1.44 (d, J=6.60 Hz, 3 H) 1.67-1.78 (m, 1 H) 1.95-2.12 (m, 2 H) 2.42-2.54 (m, J=12.64, 7.70 Hz, 1 H) 3.45-3.54 (m, 1 H) 3.63 (s, 3 H) 3.70 (s, 3 H) 3.76 (d, J=10.44 Hz, 1H) 3.80-3.90 (m, 3 H) 3.93-4.06 (m, 4 H) 5.46 (s, 1 H) 5.71 (dd, J=8.24, 4.95 Hz, 1H) 6.76-6.84 (m, 2 H) 6.88-6.94 (m, 1 H) 7.13-7.21 (m, 2 H) 7.23-7.28 (m, 2 H) 7.34 (s, 1 H) 7.78 (d, J=8.79 Hz, 1 H) 9.53 (s, 1 H).

Example 20 methyl 3-((R)-1-((R)-2-(3,4-dimethoxyphenyl)-2-(2-methyl-4-oxo-3,4-dihydroquinazolin-6-ylamino)acetyl)pyrrolidin-2-yl)-4-(isopropylsulfonyl)phenylcarbamate trifluoroacetate

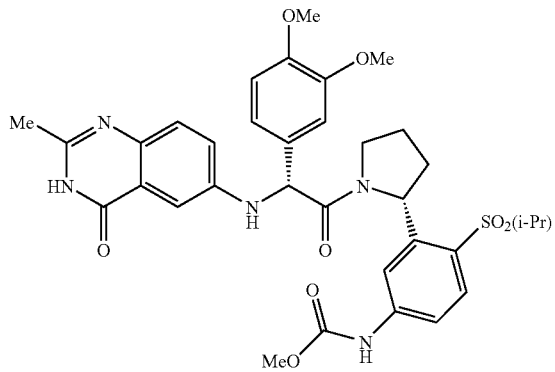

20A

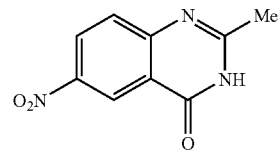

A mixture of 2-amino-5-nitrobenzoic acid (1.00 g, 5.49 mmol), ammonium acetate (0.550 g, 7.14 mmol) and triethyl orthoacetate (1.316 mL, 7.14 mmol) in a sealed microwave vessel was heated at 160° C. for 5 min in a microwave reactor, followed by 180° C. for 5 min. The reaction mixture was diluted with 10 mL H$_2$O and filtered. The resultant yellow solid was suspended in 10 mL Et$_2$O, then collected by filtration. The resultant 600 mg of solid (~1:1 pdt/impurity LCMS rt=1.28 min) was recrystallized from EtOAc (~60 mL). The flask was allowed to cool to rt, then was placed in a refrigerator o.n. The precipitate was collected by filtration and sucked dry to afford 20A (225 mg, 1.097 mmol, 19.97% yield) as a tan solid. LC-MS: (Phenom. Luna C18 30×4.6 mm 5 m; A: 10% MeCN-90% H$_2$O-0.1% TFA; B: 90% MeCN-10% H$_2$O-

0.1% TFA; wavelength 220 nm; flow rate 5 mL/min; gradient time 2 min; 0 to 100% B) 0.61 min, [M+H]⁺=206.0. ¹H NMR (400 MHz, CD₃OD) δ ppm 8.97 (d, J=2.75 Hz, 1 H) 8.55 (dd, J=8.79, 2.75 Hz, 1 H) 7.75 (d, J=8.79 Hz, 1 H) 2.49 (s, 3 H).

2 H) 6.94 (d, J=8.35 Hz, 1 H) 6.64 (s, 1 H) 5.05 (s, 1 H) 3.74 (s, 3 H) 3.72 (s, 3 H) 2.24 (s, 3 H).

20B

To a solution of 20A (105 mg, 0.512 mmol) in MeOH (15 mL) and THF (5 mL), was added 10% Pd—C (30 mg, 0.028 mmol). The mixture was evacuated and flushed with H₂ (3×), then was stirred under a balloon of H₂ for 2.5 h. The mixture was filtered and concentrated to afford 20B (90 mg, 0.514 mmol, 100% yield) as a white solid. LC-MS: (Phenom. Luna C18 30×4.6 mm 5 m; A: 10% MeCN-90% H₂O-0.1% TFA; B: 90% MeCN-10% H₂O-0.1% TFA; wavelength 220 nm; flow rate 5 mL/min; gradient time 2 min; 0 to 100% B) 0.17 min, [M+H]⁺=176.0. ¹H NMR (400 MHz, CD₃OD) δ ppm 7.38 (d, J=8.79 Hz, 1 H) 7.32 (d, J=2.75 Hz, 1H) 7.17 (dd, J=8.52, 2.47 Hz, 1 H) 2.38 (s, 3 H).

20C

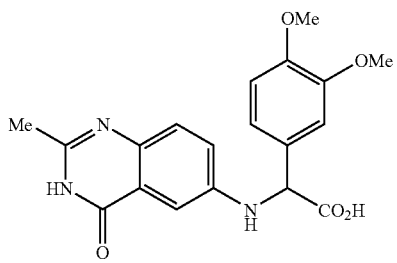

To a suspension of 20B (64 mg, 0.365 mmol) and 3,4-dimethoxyphenylboronic acid (69.8 mg, 0.384 mmol) in DMF (0.5 mL) and acetonitrile (1.5 mL), was added glyoxylic acid monohydrate (33.6 mg, 0.365 mmol). The mixture was sonicated to give a fine suspension, and then was heated in a microwave reactor at 100° C. for 10 min. When the reaction cooled to rt, a white precipitate formed. The mixture was diluted with CH₂Cl₂ (3 mL), then was filtered. The collected precipitate was washed with CH₂Cl₂ and sucked dry, and dried in vacuo to afford 20C (125 mg, 0.338 mmol, 93% yield) as a white solid. LC-MS: (Phenom. Luna C18 30×4.6 mm 5 m; A: 10% MeCN-90% H₂O-0.1% TFA; B: 90% MeCN-10% H₂O-0.1% TFA; wavelength 220 nm; flow rate 5 mL/min; gradient time 2 min; 0 to 100% B) 0.62 min, [M+H]⁺=370.0. ¹H NMR (400 MHz, DMSO-d₆) δ ppm 12.88 (s, 1 H) 11.87 (s, 1 H) 7.25-7.35 (m, 2 H) 7.13 (s, 1 H) 7.00-7.09 (m,

20D

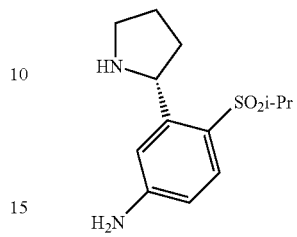

To a solution of Intermediate 1D (494 mg, 1.34 mmol) in EtOAc (5 mL), was added 4 N HCl in dioxane (10 mL). The mixture was stirred for 2 h, then was concentrated. The resultant residue was dried in vacuo over KOH (s) to afford 420 mg of 20D.

20E

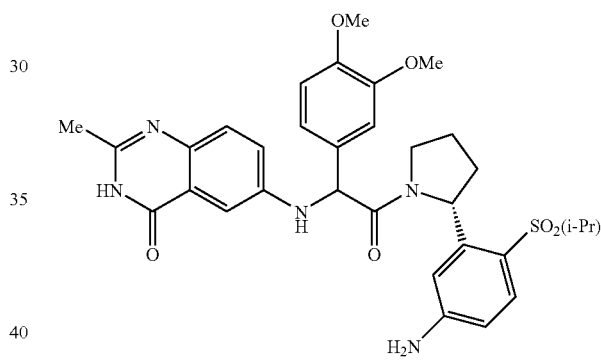

20C (60 mg, 0.162 mmol) and 20D (61 mg, 0.179 mmol) were dissolved in DMF (2 mL) at rt, 1-Hydroxy-7-azabenzotriazole (26.5 mg, 0.195 mmol), DIEA (0.113 mL, 0.650 mmol) and EDCI (34.3 mg, 0.179 mmol) were added. The yellow solution was stirred at rt. After 1 h, additional EDCI (10 mg) was added. The mixture was stirred at rt for 16.5 h, then was diluted with EtOAc. The mixture was washed with water, sat. NaHCO₃ and brine, dried (Na₂SO₄) and concentrated to afford 20E (96 mg, 0.155 mmol, 95% yield) as an orange glass. LC-MS: (Phenom. Luna C18 30×4.6 mm 5 μ; A: 10% MeCN-90% H₂O-0.1% TFA; B: 90% MeCN-10% H₂O-0.1% TFA; wavelength 220 nm; flow rate 5 mL/min; gradient time 2 min; 0 to 50% B) 1.26 min, [M+H]⁺=620.2 (major diastereomer) 1.34 min, [M+H]⁺=620.2 (minor diastereomer) (~2:1 ratio).

Example 20

To a solution of 20E (96 mg, 0.155 mmol) and pyridine (0.030 mL, 0.371 mmol) in dichloromethane (2 mL) at 0° C., was added methyl chloroformate (0.018 mL, 0.232 mmol). Then mixture was stirred at 0° C. for 10 min, then was quenched with water and evaporated. The crude product was purified by preparative HPLC (Phenomenex Luna 5 μ C18 30×250 (20% to 60% B, 20 min grad, 30 mL/min); solvent A=10% CH₃CN/90% H₂O/0.1% TFA; solvent B=90% CH₃CN/10% H₂O/0.1% TFA) to afford Example 20 (29.1 mg, 0.043 mmol, 27.7% yield) as a white powder. LC-MS: (Phenom. Luna C18 30×4.6 mm 5 µ; A: 10% MeCN-90% H₂O-0.1% TFA; B: 90% MeCN-10% H₂O-0.1% TFA; wavelength 220 nm; flow rate 5 mL/min; gradient time 2 min; 0 to 100% B) 0.91 min, [M+H]⁺=678.2. ¹H NMR (400 MHz, CD₃OD) δ ppm 9.36 (s, 1 H) 7.73 (d, J=8.79 Hz, 1 H) 7.35-7.41 (m, 1 H) 7.28-7.33 (m, 1 H) 7.25 (d, J=2.20 Hz, 1 H) 7.21 (d, J=8.79 Hz, 1 H) 7.01 (d, J=10.44 Hz, 2 H) 6.89-6.93 (m, 2 H) 5.67 (dd, J=8.25, 4.95 Hz, 1 H) 5.40 (s, 1 H) 4.14-4.23 (m, 1 H) 3.92 (dt, J=13.74, 6.87 Hz, 1 H) 3.81-3.86 (m, 3 H) 3.72-3.78 (m, 1 H) 3.70 (s, 3 H) 3.68 (s, 3 H) 2.57 (s, 3 H) 2.44-2.55 (m, 1 H) 2.10 (dq, J=13.88, 6.73 Hz, 2 H) 1.66-1.77 (m, 1 H) 1.40 (d, J=6.60 Hz, 3 H) 1.15 (d, J=6.60 Hz, 3 H).

Example 21 methyl 3-((R)-1-((R)-2-(3,4-dimethoxyphenyl)-2-(6-fluoro-3-oxoisoindolin-5-ylamino)acetyl)pyrrolidin-2-yl)-4-(isopropylsulfonyl)phenylcarbamate

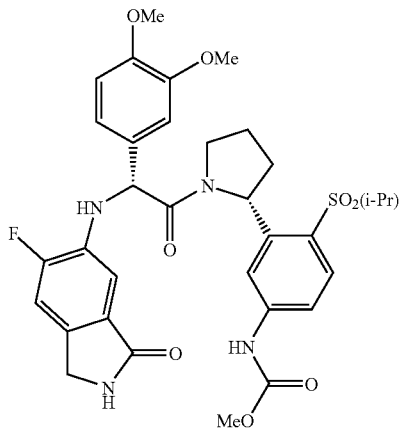

21A

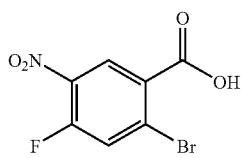

Potassium nitrate (11.54 g, 114 mmol) was added portionwise to a solution of 2-bromo-4-fluorobenzoic acid (25 g, 114 mmol) in sulfuric Acid (228 mL) at 0° C. over 10 min. The reaction mixture was stirred for 3 h at ambient temperature. The reaction mixture was poured onto ice. The resulting precipitate was washed with water and dried in vacuo to yield a mixture of 21A and 2-Br-4-F-6-nitrobenzoic acid (9:1) as a white solid (19.5 g). 7 g of this solid was purified by prep HPLC (0.1% TFA, H₂O/MeOH, 35% to 60%) to yield 21A (5.6 g, 21.21 mmol) as a white solid. MS (ESI) m/z 262.1/264.1 (M−H)⁻. ¹H NMR (400 MHz, CD₃OD) δ ppm 7.91 (d, J=10.44 Hz, 1 H) 8.61 (d, J=8.25 Hz, 1 H).

21B

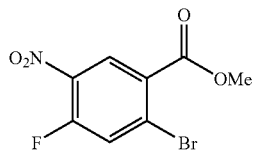

Thionyl chloride (1.673 mL, 22.92 mmol) was added to methanol (100 mL) at 0° C. and stirred for 30 min. 21A (5.5 g, 20.83 mmol) was added and the mixture was heated at 60° C. for 18 h. The reaction mixture was concentrated to a white solid and purified by column chromatography (0 to 50% EtOAc in hexanes, 120 g column) to yield 21B (5.03 g, 18.09 mmol, 87% yield) as a white solid. MS (ESI) m/z 279.0/281.0 (M+H)⁺. ¹H NMR (400 MHz, CDCl₃) δ ppm 3.97 (s, 3 H) 7.67 (d, J=9.89 Hz, 1 H) 8.62 (d, J=7.70 Hz, 1 H).

21C

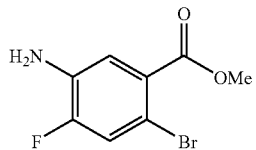

Iron (5.02 g, 90 mmol) was added portionwise to a solution of 21B (5.0 g, 17.98 mmol) in ethanol (138 mL)/water (34.6 mL)/AcOH (6.92 mL) at 110° C. (bath temp). The reaction mixture was refluxed for 1 h. The reaction mixture was neutralized with NaHCO₃ (aq, sat'd), diluted with H₂O (250 mL) and extracted with EtOAc (2×400 mL). The organics were combined, washed with brine, dried over Na₂SO₄ and concentrated to yield 21C (2.45 g, 9.88 mmol, 54.9% yield) as a white solid. MS (ESI) m/z 248.1/250.1 (M+H)⁺. ¹H NMR (400 MHz, CDCl₃) δ ppm 3.89 (s, 3 H) 7.26-7.35 (m, 2 H).

21D

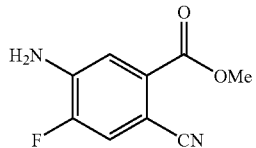

A solution of copper(I) cyanide (0.812 g, 9.07 mmol) and 21C (1.5 g, 6.05 mmol) in DMF (24.19 mL) was divided into two vessels and microwaved at 180° C. for 10 min. The reaction mixture was diluted with NH₄OH (50 mL) and H₂O (50 mL) and extracted with EtOAc (1×200 mL). The organics were washed with NaHCO₃, brine, dried over Na₂SO₄ and concentrated. Purification by column chromatography (0 to 100% EtOAc in Hexanes) yielded 21D (650 mg, 3.35 mmol, 55.4% yield) as a yellow solid. MS (ESI) m/z 195.2 (M+H)⁺.

¹H NMR (400 MHz, CD₃OD) δ ppm 3.91 (s, 3 H) 7.43 (d, J=10.99 Hz, 1 H). 7.48 (d, J=8.79 Hz, 1 H).

21E

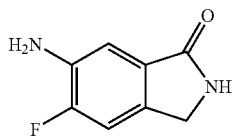

A mixture of 21D (200 mg, 1.030 mmol) and Raney Ni in MeOH and NH₃ (20 mL, 7.0 M) was stirred under H₂ (50 psi) for 16 h. The reaction mixture was diluted with acteone (100 mL), filtered through Celite and concentrated. The resulting solid was titurated with H₂O (20 mL) and dried in vacuo to yield 21E (100 mg, 0.602 mmol, 58.4% yield) as a white solid. MS (ESI) m/z 166.9 (M+H)⁺. ¹H NMR (400 MHz, dmso-d₆) δ ppm 5.14-5.43 (m, 2 H) 6.92-7.11 (m, 1 H) 7.10-7.28 (m, 1 H) 8.17-8.46 (m, 1 H).

21F

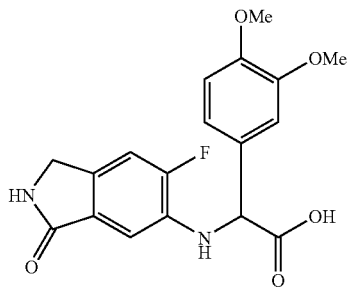

A solution of 21E (85 mg, 0.512 mmol), 3,4-dimethoxyphenylboronic acid (93 mg, 0.512 mmol), and glyoxylic acid monohydrate (51.8 mg, 0.563 mmol) in DMF (1.3 mL)/acetonitrile (1.3 mL) was microwaved at 100° C. for 10 min. The reaction mixture was concentrated and purified by column chromatography (12 g column, 5% to 20% MeOH in CH₂Cl₂) to yield 21F (141 mg, 0.391 mmol, 76% yield) as a yellow glass. MS (ESI) m/z 361.3 (M+H)⁺. ¹H NMR (400 MHz, MeOD) δ ppm 3.80 (s, 3 H) 3.82 (s, 3 H) 5.12 (s, 1 H) 6.86-6.96 (m, 2 H) 7.07 (dd, J=8.34, 2.02 Hz, 1 H) 7.12 (d, J=2.02 Hz, 1 H) 7.22 (d, J=10.86 Hz, 1 H).

Example 21

A cloudy solution of Intermediate 1 (47.3 mg, 0.130 mmol) and triethylamine (0.109 mL, 0.783 mmol) in DMF (1 mL) was added to a solution of 21F (47 mg, 0.130 mmol) and 1-Hydroxy-7-azabenzotriazole (17,75 mg, 0.130 mmol) in DMF (1 mL). 1-(3-(Dimethylamino)propyl)-3-ethyl-carbodiimide hydrochloride (50.0 mg, 0.261 mmol) was added and the reaction mixture was stirred for 15 h at 40° C. The reaction mixture was diluted with EtOAc (100 mL), washed with brine (50 mL), dried over Na₂SO₄ and concentrated. The crude mixture was purified by prep HPLC (Phenom. AXIA Luna, 75×30 mm, 5 micron, flow rate 40 mL/min, A: H₂O/acetonitrile (9:1), B: H₂O/acetonitrile (1:9), 0.1% TFA, 20 to 40% B, 10 min gradient) to yield Example 21 (19 mg, 0.28 mmol, 43.7% yield) and its diasteromer (11 mg). Characterization for Example 21: MS (ESI) m/z 669.4 (M+H)⁺. ¹H NMR (400 MHz, CD₃OD) δ ppm 1.13-1.22 (m, 3 H) 1.41-1.46 (m, 3 H) 1.65-1.75 (m, 1H) 1.91-2.15 (m, 3 H) 2.42-2.57 (m, 1 H) 3.67 (s, 3 H) 3.70 (s, 3 H) 3.71-3.76 (m, 1 H) 3.82 (s, 3 H) 3.91-4.03 (m, 1 H) 4.11-4.24 (m, 1 H) 4.27 (s, 2 H) 5.39 (s, 1 H) 5.66 (dd, J=8.24, 4.95 Hz, 1 H) 6.86 (s, 1 H) 6.89 (d, J=8.24 Hz, 1 H) 6.96-7.03 (m, 2 H) 7.11 (d, J=7.70 Hz, 1 H) 7.16 (d, J=10.99 Hz, 1 H) 7.21 (dd, J=8.79, 2.20 Hz, 1H) 7.73 (d, J=8.79 Hz, 1 H) 9.33 (s, 1 H). Analytical HPLC: 7.61 min, 99% purity (SunFire C18; 3.5 tan; 4.6×150 mm; H₂O/acetonitrile/0.05% TFA, 10% to 95% over 10 min, hold 5 min, wavelength 220 and 254 nm); 7.51 min, 99% purity (XBridge Phenyl 3.5 um; 4.6×150 mm; H₂O/acetonitrile/0.05% TFA, 10% to 95% over 10 min, hold 5 min, wavelength 220 and 254 nm).

Example 22 methyl 4-(cyclopropylsulfonyl)-3-((R)-1-((R)-2-(4-fluoro-3-methoxyphenyl)-2-(4-oxo-3,4-dihydroquinazolin-6-ylamino)acetyl)pyrrolidin-2-yl)phenylcarbamate

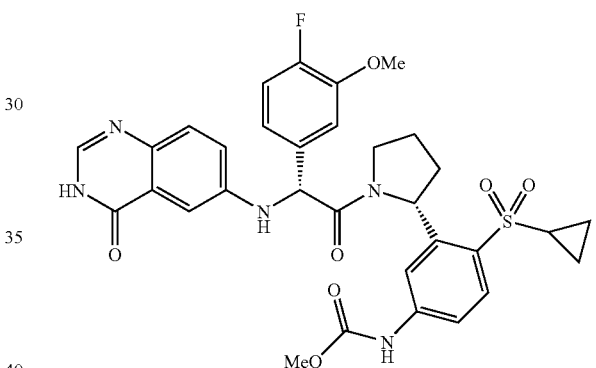

22A

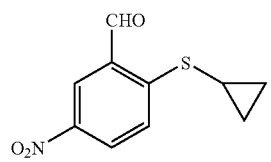

Freshly prepared cyclopropyl thiol in THF/diethyl ether (J. Am. Chem. Soc. 1992, 114(9), 3497) was added to 2-fluoro-5-nitrobenzaldehyde (3.4 g, 20 mmol, 1.0 eq.) and K₂CO₃ (4.83 g, 35 mmol) in DMF (20 mL). The mixture was stirred at 45° C. for 1.0 h and at rt over night. It was diluted with EtOAc and washed with water. The aqueous was extracted with EtOAc and the combined organic layers were washed with brine and dried over Na₂SO₄. After evaporation of solvent, the crude was triturated with EtOAc/hexanes (70/120). The solid was collected to give 22A (3.2 g). The filtrate was condensed and triturated again to give a second crop of 22A (0.5 g, total yield 85%). ¹H NMR (400 MHz, CDCl₃) δ ppm 0.74-0.83 (m, 2 H) 1.20-1.28 (m, 2 H) 2.13-2.19 (m, 1 H) 7.95

(d, J=9.23 Hz, 1 H) 8.33 (dd, J=8.79, 2.64 Hz, 1 H) 8.62 (d, J=2.64 Hz, 1 H) 10.15 (s, 1 H).

22B

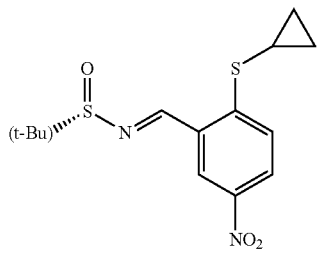

To 22A (2.02 g, 9.0 mmol), (S)-tert-butylsulfinamide (1.21 g, 10 mmol) in CH$_2$Cl$_2$ (40 mL) was added Ti(OEt)$_4$ (10 mL, 45 mmol). The mixture was heated at 73° C. for 6.0 h. CH$_2$Cl$_2$ was removed in vacuo and the residue was suspended in EtOAc. To this suspension was added brine. The mixture was stirred at rt for 15 min before it was filtered through a pad of wet Celite®. The filtrate was extracted with EtOAc (3×50 mL). The organic layer was washed with brine and dried over Na$_2$SO$_4$. After removal of solvent, 22B (3.0 g, 100% yield) was obtained as a solid. $^1$H NMR (400 MHz, CDCl$_3$) δ ppm 0.72-0.81 (m, 2 H) 1.21 (m, 2 H) 1.28 (s, 9 H) 2.14-2.21 (m, 1 H) 7.89 (d, J=8.79 Hz, 1 H) 8.24 (dd, J=8.79, 2.64 Hz, 1 H) 8.60 (d, J=2.64 Hz, 1 H) 8.77 (s, 1 H).

22C

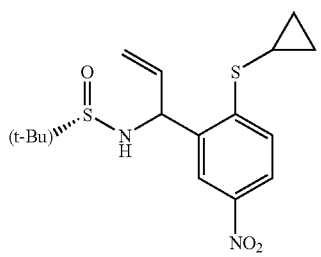

To 22B (3.0 g, 9.2 mmol) in THF (30 mL) and methyl tert-butylether (50 mL) at −78° C. was added vinylmagnesium bromide (1.0 M in THF, 20 mL, 20 mmol) dropwise. The mixture was stirred at −78° C. for 1.0 h before it was quenched with sat. NH$_4$Cl (50 mL) at −78° C. The mixture was extracted with EtOAc (3×50 mL), the organic layer was washed with brine and dried over Na$_2$SO$_4$. After removal of solvent, the crude was purified by silica gel column chromatography using gradient EtOAc in hexanes to give 22C (2.45 g, 78% yield). HPLC and $^1$H NMR indicated 22C is a mixture of two diastereoisomers in a ratio of 5:1. Major isomer: $^1$H NMR (400 MHz, CDCl$_3$) δ ppm 0.70-0.81 (m, 2 H) 1.17-1.24 (m, 2 H) 1.26 (s, 9 H) 2.17 (m, 1 H) 3.53 (d, J=2.64 Hz, 1 H) 5.21-5.32 (m, 3 H) 5.91 (m, 1 H) 7.72 (d, J=8.79 Hz, 1 H) 8.09 (dd, J=8.79, 2.64 Hz, 1 H) 8.26 (d, J=2.64 Hz, 1 H), LC-MS 355 (M+H).

22D

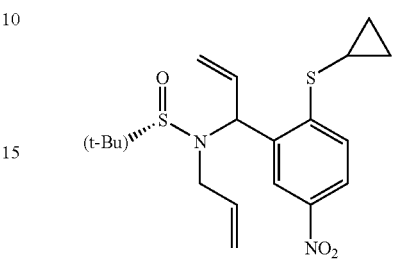

To 22C (2.46 g, 6.95 mmol) in DMF (20 mL) at −20° C. was added lithium bis(trimethylsilyl)amide (1.0 M in THF, 12.2 mL, 12.2 mmol) dropwise. The mixture was stirred at −20° C. for 20 min followed by addition of allyl bromide (3.0 mL, 34.8 mmol). After 1.0 h stirring at −20° C., the reaction was quenched with sat. NH$_4$Cl and warmed to rt. It was extracted with EtOAc (3×50 mL), the organic layer was washed with brine and dried over Na$_2$SO$_4$. After removal of solvent, the crude was purified by silica gel column chromatography using gradient EtOAc in hexanes to give 22D (2.2 g, 80% yield). HPLC and $^1$H NMR indicated 22D is a mixture of two diastereoisomers in a ratio of 5:1. Major isomer: $^1$H NMR (400 MHz, CDCl$_3$) δ ppm 0.67-0.76 (m, 2 H) 1.15-1.20 (m, 2 H) 1.25 (s, 9 H) 2.12-2.20 (m, 1 H) 3.02 (dd, J=17.14, 6.59 Hz, 1 H) 4.05 (dd, J=17.14, 4.83 Hz, 1 H) 5.06-5.26 (m, 5 H) 6.00 (ddd, J=17.03, 10.22, 7.03 Hz, 1 H) 7.70 (t, J=8.13 Hz, 1 H) 8.10 (dd, J=8.79, 2.64 Hz, 1 H) 8.49 (d, J=2.64 Hz, 1 H), LC-MS 395 (M+H).

22E

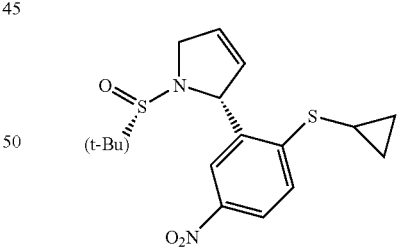

A solution of 22D (2.2 g, 5.5 mmol) in CH$_2$Cl$_2$ (200 mL) was degassed by bubbling argon for 8 min. To this solution was added Grubb's catalyst (2$^{nd}$ generation, 380 mg, 0.45 mmol). The mixture was heated at 72° C. for 5.0 h. After removal of solvent, the crude was purified by silica gel column chromatography using gradient EtOAc in hexanes to give 22E as a major product (1.66 g, 82% yield): $^1$H NMR (400 MHz, CDCl$_3$) δ ppm 0.71-0.80 (m, 2 H) 1.15-1.19 (s, 9 H) 1.19-1.25 (m, 2 H) 2.14-2.22 (m, 1 H) 3.78 (dt, J=14.50, 2.64 Hz, 1 H) 4.69 (dd, J=14.50, 2.64 Hz, 1 H) 5.73 (dd, J=6.15, 2.20 Hz, 1 H) 5.85 (dd, J=5.05, 2.42 Hz, 1 H) 5.88

(ddd, J=4.06, 2.20, 2.09 Hz, 1 H) 7.69 (d, J=8.79 Hz, 1 H) 8.06 (dd, J=8.57, 2.42 Hz, 1 H) 8.19 (d, J=2.20 Hz, 1 H), LC-MS 367 (M+H).

22F

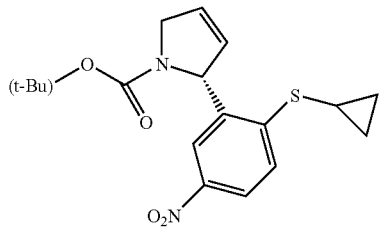

To 22E (1.6 g, 4.37 mmol) in MeOH (20 mL) at rt was added 4.0 N HCl in dioxane (4.37 mL, 17.5 mmol). The mixture was stirred at rt for 20 min. Solvent was evaporated and the crude (R)-2-(2-(cyclopropylthio)-5-nitrophenyl)-2,5-dihydro-1H-pyrrole HCl salt (LC-MS 263) was dried under high vacuum for 1.0 h. To the crude HCl salt in THF (20 mL) and MeOH (5.0 mL) was added di-tert-butyl dicarbonate (1.0 M in THF, 6.0 mL, 6.0 mmol) and triethylamine (1.28 mL, 9.18 mmol). The mixture was stirred at rt for 1.0 h. It was diluted and extracted with EtOAc. The organic layer was washed with 0.5 N HCl, sat. NaHCO$_3$, brine and dried over Na$_2$SO$_4$. After evaporation of solvent, the crude was purified by silica gel column chromatography eluting with gradient EtOAc in hexanes to give 22F (1.52 g, 95% yield) as a solid. $^1$H NMR (400 MHz, CDCl$_3$) δ ppm 0.73-0.80 (m, 2 H) 1.15 (s, 9 H) 1.18-1.27 (m, 2 H) 2.13-2.20 (m, 1 H) 4.33-4.42 (m, 2 H) 5.68-5.90 (m, 3 H) 7.68 (d, J=8.79 Hz, 1 H) 7.93 (dd, J=8.13, 2.42 Hz, 1 H) 8.05 (td, J=8.90, 2.42 Hz, 1 H), LC-MS 307 (M−tert-Bu).

22G

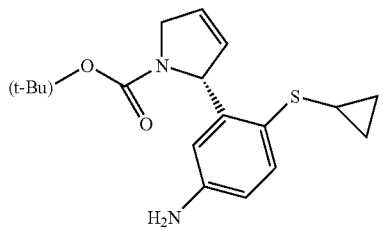

22F (1.52 g, 4.19 mmol) and 10% Pd/C (560 mg) in MeOH (100 mL) was hydrogenated under 45 psi for 3.5 h. TLC and LC-MS indicate a clean conversion to the product. Pd/C was removed by filtration through a pad of Celite®. The filtrate was concentrated to give 22G (1.37 g, 97% yield) as a solid. $^1$H NMR (400 MHz, Methanol-d$_4$) δ ppm 0.52-0.64 (m, 2 H) 0.85-0.95 (m, 2 H) 1.16-1.24 (s, 7 H) 1.45 (s, 2 H) 1.71 (m, 1 H) 1.82-1.94 (m, 2 H) 2.09-2.19 (m, 1 H) 2.32 (m, 1 H) 3.47-3.57 (m, 1 H) 3.59-3.69 (m, 1 H) 5.18-5.25 (m, 1 H) 6.48 (d, J=2.20 Hz, 1 H) 6.58 (dd, J=8.13, 2.42 Hz, 1 H) 7.30 (t, J=8.35 Hz, 1 H), LC-MS 235 (M−Boc).

22H

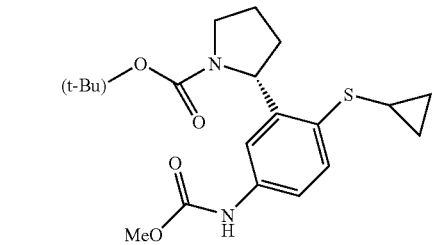

To 22G (1.25 g, 3.74 mmol) in pyridine (8.0 mL) at 0° C. was added methyl chloroformate (0.4 mL, 5.23 mmol). After 30 min, the reaction was quenched by MeOH (2.0 mL). Pyridine was removed under high vacuum. The crude was suspended in EtOAc and washed by 1.0 N HCl (2×20 mL), sat. NaHCO$_3$ and brine. The organic layer was dried over Na$_2$SO$_4$. After evaporation of solvent, 22H (1.6 g, 95% yield) was obtained as a solid used for next step without purification. $^1$H NMR (400 MHz, DMSO-d$_6$, 100° C.) δ ppm 0.52-0.64 (m, 2 H) 0.94-1.05 (m, 2 H) 1.17-1.28 (s, 9 H) 1.54-1.63 (m, 1 H) 1.77-1.86 (m, 2 H) 2.18-2.29 (m, 2 H) 3.46-3.57 (m, 2 H) 3.62-3.68 (s, 3 H) 5.05 (dd, J=7.70, 3.85 Hz, 1 H) 7.23 (s, 1 H) 7.32-7.40 (m, 1 H) 7.40-7.47 (m, 1 H) 9.26 (s, 1 H), LC-MS 293 (M−Boc).

22I

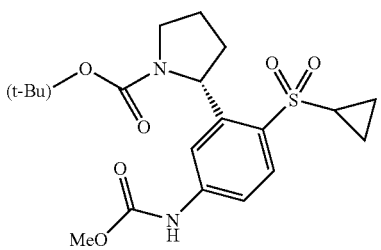

To 22H (1.60 g, 4.0 mmol) in CH$_2$Cl$_2$ (50 mL) was added NaHCO$_3$ (1.0 g, 11.9 mmol) and MCPBA (75% purity, 2.15 g, 9.4 mmol). The mixture was stirred at rt for 5.0 h. It was quenched with sat. NaHCO$_3$ and extracted with CH$_2$Cl$_2$. The organic layer was dried over Na$_2$SO$_4$. After removal of solvent, the crude was purified with silica gel column chromatography eluting with gradient EtOAc in hexanes to give 22I (1.64 g, 96%). $^1$H NMR (400 MHz, DMSO-d$_6$, 100° C.) δ ppm 0.95-1.00 (m, 1 H) 1.03-1.11 (m, 2 H) 1.20 (s, 9 H) 1.17-1.28 (m, 1 H) 1.72 (m, 1H) 1.81-1.92 (m, 2 H) 2.83 (m, 1 H) 3.52-3.64 (m, 2 H) 3.74 (s, 3 H) 5.56 (dd, J=8.24, 4.40 Hz, 1 H) 7.52 (d, J=2.20 Hz, 1 H) 7.59 (dd, J=8.79, 2.20 Hz, 1 H) 7.74 (d, J=8.79 Hz, 1 H) 9.80 (s, 1 H); LC-MS 425 (M+H).

119

22J

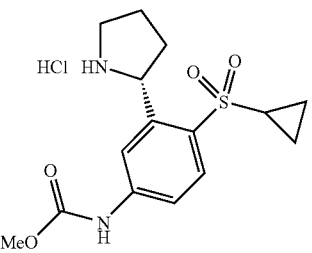

To 22I (1.63 g, 3.84 mmol) in EtOAc (15.0 mL) at rt was added 4.0 N HCl in dioxane (30 mL, 120 mmol). The mixture was stirred at rt for 4.0 h. TLC and LC-MS indicated a clean formation of the product. After evaporation of solvent, 22J (1.31 g, 95% yield) was obtained as a white solid. $^1$H NMR (400 MHz, Methanol-$d_4$) δ ppm 0.98-1.10 (m, 3 H) 1.21-1.33 (m, 1 H) 2.10-2.20 (m, 1 H) 2.24-2.34 (m, 2H) 2.41-2.50 (m, 1 H) 2.80-2.89 (m, 1 H) 3.31-3.41 (m, 2 H) 3.70 (s, 3 H) 5.45 (t, J=7.69 Hz, 1 H) 7.54 (dd, J=8.79, 2.20 Hz, 1 H) 7.85 (d, J=8.79 Hz, 1 H) 7.99 (d, J=2.20 Hz, 1 H), LC-MS 325 (M+H).

22K

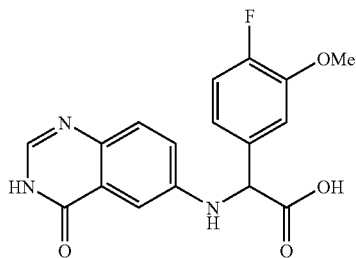

To 4-fluoro-3-methoxyphenylboronic acid (100 mg, 0.588 mmol, WO2007002313), Intermediate 5 (95 mg, 0.588 mmol) and glyoxylic acid monohydrate (59.6 mg, 0.647 mmol) was added acetonitrile (2.0 mL) and DMF (1.2 mL). The mixture was sonicated for 2 min, heated at 65° C. for 2.0 h then stirred at rt over night. Solvent was removed by high vacuum and the crude was purified by prep HPLC purification: C18 Phenomenex Luna AXIA column (30 mm×100 cm, 5 μ) with the UV detector set at 254 nm. The separations were performed using a gradient method: 15-80% B in 15 mins; then 80% B in 2 mins with a flow rate of 40 mL/min. Solvent B is 90% acetonitrile-10% water-0.1% TFA and solvent A is 10% acetonitrile-90% water-0.1% TFA. The desired fractions were collected to give 22K (68 mg, 34% yield) as a solid after lyophilization. $^1$H NMR (400 MHz, DMSO-$d_6$) δ ppm 3.83 (s, 3 H) 5.23 (s, 1 H) 7.06-7.11 (m, 1 H) 7.13 (d, J=2.20 Hz, 1 H) 7.21 (dd, J=11.43, 8.35 Hz, 1 H) 7.37 (td, J=5.60, 2.42 Hz, 2 H) 7.42-7.49 (m, 1 H) 8.17 (s, 1 H); LC-MS 343 (M+H)

Example 22

To 22K (40 mg, 0.117 mmol), 22J (46.2 mg, 0.128 mmol), HOAt (19.03 mg, 0.140 mmol) in DMF (1.5 mL) was added TEA (0.098 ml, 0.7 mmol) and EDC (44.7 mg, 0.233 mmol). The mixture was stirred at 40° C. for 3.0 h and then at rt over night. DMF was removed under high vacuum. The crude residue was purified using a preparative HPLC equipped with a C18 Phenomenex Luna AXIA column (30 mm×100 cm, 5 μ) with the UV detector set at 254 nm. The separations were performed using a gradient method: 15-80% B in 15 mins; then 80% B in 2 mins with a flow rate of 40 mL/min. Solvent B is 90% acetonitrile-10% water-0.1% TFA and solvent A is 10% acetonitrile-90% water-0.1% TFA. The fractions from the first peak (25 mg) were collected to give Example 22: $^1$H NMR (400 MHz, methanol-$d_4$) δ ppm 0.89-0.93 (m, 1 H) 0.94-1.01 (m, 3 H) 1.27-1.38 (m, 1 H) 1.72 (dd, J=12.64, 5.50 Hz, 1 H) 2.09 (dd, J=11.27, 6.87 Hz, 2 H) 2.51 (dd, J=12.92, 7.97 Hz, 1 H) 3.12-3.20 (m, 1 H) 3.69 (s, 3 H) 3.71 (s, 3 H) 3.73-3.77 (m, 1 H) 4.20 (dd, J=6.87, 3.57 Hz, 1 H) 5.47 (s, 1 H) 5.87 (dd, J=7.97, 5.22 Hz, 1 H) 7.01-7.12 (m, 5H) 7.25 (d, J=2.75 Hz, 1 H) 7.28-7.33 (m, 1 H) 7.45 (d, J=8.79 Hz, 1 H) 7.65 (d, J=8.79 Hz, 1 H) 8.64 (s, 1 H), 9.45 (s, 1 H). $^{19}$F NMR (376 MHz, Solvent) δ ppm −137.6; LC-MS 650 (M+H). The fractions from second peak is the diastereoisomer of Example 22: $^1$H NMR (400 MHz, methanol-$d_4$) δ ppm a mixture of two rotamers: 0.85-1.25 (m, 4 H), 1.25-1.45 (m, 2 H), 1.71-2.12 (m, 3 H), 2.30-3.00 (m, 2 H), 3.56-3.81 (m, 1 H), 3.70 3.74 and 3.81 (s, 6 H), 4.18 (m, 1 H), 5.33 and 5.48 (s, 1 H), 5.78 (m, 1 H), 6.41-6.70 (m, 2 H), 7.04-7.24 (m, 7 H), 7.65-7.73 (m, 2 H), 8.44 and 8.60 (s, 1 H); LC-MS 650 (M+H).

Example 23 methyl 3-((R)-1-((R)-2-(3,4-dimethoxyphenyl)-2-(4-oxo-3,4-dihydroquinazolin-6-ylamino)acetyl)pyrrolidin-2-yl)-4-(isopropylsulfonyl)phenylcarbamate

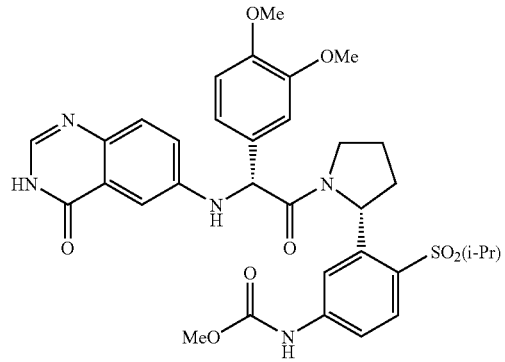

23A

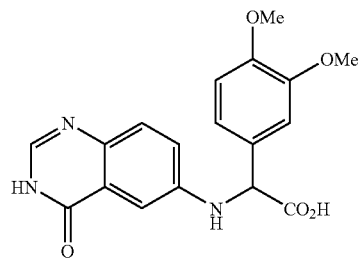

In a 25 mL flask was added glyoxylic acid monohydrate (38.4 mg, 0.417 mmol), Intermediate 5 (56 mg, 0.347 mmol), and 3,4-dimethoxybenzeneboronic acid (76 mg, 0.417 mmol) in MeCN (1.1 ml)/DMF(0.122 mL) to give a brown suspension. The reaction was stirred at 60° C. overnight. Solvent was removed and the crude residue was dissolved in a small amount of acetonitrile/water and purified by prep HPLC using AXIA column (2 injections) eluted with 90% water to 10% water in acetonitrile with 0.1% TFA. 23A (50 mg) was obtained as a solid. $^1$H NMR (400 MHz, CDCl$_3$) δ ppm 3.81 (s, 3 H) 3.83 (s, 3 H) 5.14 (s, 1 H) 6.94 (d, J=8.35 Hz, 1 H) 7.10 (dd, J=8.35, 2.20 Hz, 1 H) 7.15 (d, J=1.76 Hz, 1 H) 7.24 (d, J=2.64 Hz, 1 H) 7.37 (dd, J=9.01, 2.86 Hz, 1 H) 7.47-7.51 (m, 1 H) 8.47 (s, 1 H). LCMS 356 (M+H).

Example 23

To a 10 mL flask was added 23A (20 mg, 0.043 mmol), Intermediate 1 (15.46 mg, 0.043 mmol), and HOAt (0.580 mg, 4.26 µmol) in DMF (1 mL) to give a yellow solution. DIEA (0.045 ml, 0.256 mmol) and EDC (16.34 mg, 0.085 mmol) were added. The reaction was stirred at rt overnight under nitrogen. Solvent was removed. The crude product was dissolved in a small amount of acetonitrile/water and purified by prep HPLC using AXIA column eluted with 90% water to 10% water in acetonitrile with 0.1% TFA in 22 min. Fractions from the first peak (RT=8.02 min) was identified to be Example 23 (10 mg): $^1$H NMR (400 MHz, methanol-d4) δ ppm 1.00 (t, J=6.81 Hz, 3 H) 1.27 (t, J=6.81 Hz, 3 H) 1.58 (dd, J=13.18, 5.27 Hz, 1 H) 1.91-2.06 (m, 2 H) 2.37 (dd, J=13.18, 7.91 Hz, 1 H) 3.55 (s, 3 H) 3.57 (s, 3H) 3.60-3.64 (m, 1 H) 3.71 (s, 3 H) 3.75-3.84 (m, 1 H) 3.97-4.15 (m, 1 H) 5.28 (s, 1 H) 5.55 (dd, J=7.91, 4.83 Hz, 1 H) 6.76-6.80 (m, 2 H) 6.86-6.91 (m, 2 H) 7.09 (dd, J=8.57, 1.98 Hz, 1 H) 7.14 (d, J=2.64 Hz, 1 H) 7.16-7.21 (m, 1 H) 7.33 (d, J=9.23 Hz, 1 H) 7.60 (d, J=8.79 Hz, 1 H) 8.34 (s, 1 H) 9.24 (s, 1 H). LCMS 663 (M+H). The fractions from second peak is the diastereoisomer of Example 23: $^1$H NMR (400 MHz, methanol-d$_4$) δ ppm 0.98 (d, J=6.59 Hz, 3 H) 1.27 (d, J=7.03 Hz, 3H) 1.60-1.69 (m, 1 H) 1.70-1.82 (m, 1 H) 1.96-2.11 (m, 1 H) 2.16-2.30 (m, 1 H) 3.49-3.54 (m, 1 H) 3.63-3.69 (m, 1 H) 3.68 (s, 3 H) 3.71 (s, 3 H) 3.72 (s, 3 H) 4.05-4.18 (m, 1 H) 5.33 (s, 1 H) 5.48 (dd, J=8.13, 4.17 Hz, 1 H) 6.39 (s, 1 H) 6.85-6.90 (m, 1 H) 6.96-7.00 (m, 1 H) 7.03 (d, J=2.20 Hz, 1 H) 7.10-7.14 (m, 1 H) 7.19 (d, J=2.64 Hz, 1 H) 7.27 (d, J=9.23 Hz, 1 H) 7.43 (dd, J=8.79, 2.20 Hz, 1 H) 7.55 (d, J=2.20 Hz, 1 H) 7.62-7.69 (m, 1 H) 8.24 (s, 1 H). LCMS 663 (M+H).

Example 24 methyl 3-((R)-1-((R)-2-(4-fluoro-3-methoxyphenyl)-2-(3-oxoisoindolin-5-ylamino)acetyl)pyrrolidin-2-yl)-4-(isopropylsulfonyl)phenylcarbamate

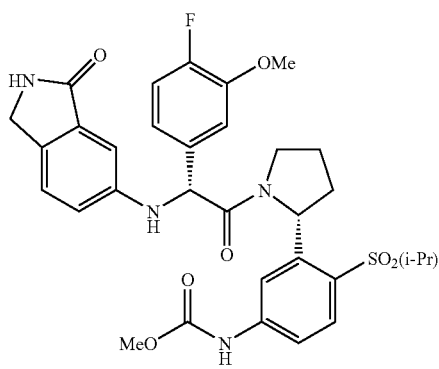

24A

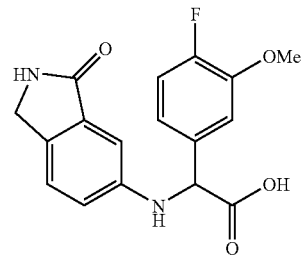

To Intermediate 6 (0.1 g, 0.675 mmol) and 4-fluoro-3-methoxyphenylboronic acid (0.115 g, 0.675 mmol) in acetonitrile (1.8 mL) and DMF (0.50 mL) was added 2-oxoacetic acid (0.062 g, 0.675 mmol). The reaction was mixture was sonicated for 5 minutes and heated to 90° C. for 20 min on a biotage microwave. The solvent was concentrated and the crude product was dissolved in a small amount of chloroform and charged to a 40 g silica gel cartridge which was eluted with a 40 min gradient time from 0-20% methanol/dichloromethane. The product peak was isolated and dried to give 24A (0.086 g, 39%) brown solid product. $^1$H NMR (400 MHz, methanol-d$_4$) δ ppm 3.82-3.88 (m, 3 H) 4.25-4.31 (m, 2 H) 5.10 (s, 1 H) 6.88-7.01 (m, 2 H) 7.02-7.13 (m, 2 H) 7.23-7.32 (m, 2 H); MS (ESI) (m/z) 331.3 [M+H]$^+$.

Example 24

To 24A (0.05 g, 0.151 mmol), HOAt (0.021 g, 0.151 mmol), and Intermediate 1 (0.055 g, 0.151 mmol) in dichloromethane (5 mL) was added N-methylmorpholine (0.050 mL, 0.454 mmol) and then EDC (0.058 g, 0.303 mmol). The reaction was stirred overnight at rt. A mixture of water and saturated sodium chloride was added to the reaction. The product was extracted with dichloromethane and dried over sodium sulfate. The reaction was filtered and the solvent was removed. The crude residue was purified and the diastereomers separated using a preparative HPLC equipped with a C18 Phenomenex Luna column (30 mm×75 mm, 5 µ). The separations were performed using a gradient method: 20-60% B in 12 mins; then 60% B in 3 mins with a flow rate of 40 mL/min. Solvent B is 90% acetonitrile-10% water-0.1% TFA and solvent A is 10% acetonitrile-90% water-0.1% TFA. Fractions from the first peak was identified to be Example 24 (17 mg, 35% yield): $^1$H NMR (400 MHz, methanol-d$_4$) δ ppm The product fractions were combined, solvent removed and lyophilized to give first diastereomer 1, 0.017 g (35%) white amorphous solid. 1.07 (d, J=6.57 Hz, 3 H) 1.33 (d, J=7.07 Hz, 3 H) 1.57-1.70 (m, 1 H) 1.93-2.09 (m, 2 H) 2.36-2.51 (m, 1 H) 3.61 (s, 3 H) 3.64 (s, 3 H) 3.65-3.70 (m, 1 H) 3.79-3.93 (m, 1 H) 4.05-4.16 (m, 1 H) 4.22 (s, 2 H) 5.31 (s, 1 H) 5.59 (dd, J=8.21, 5.18 Hz, 1 H) 6.86-7.00 (m, 5 H) 7.02 (d, J=1.77 Hz, 1 H) 7.08 (dd, J=8.59, 2.27 Hz, 1 H) 7.19 (d, J=8.84 Hz, 1 H) 7.65 (d, J=8.59 Hz, 1 H). MS (ESI) (m/z) 639.3 [M+H]$^+$. The fractions from second peak is the diastereoisomer of Example 24: $^1$H NMR (400 MHz, methanol-d$_4$) δ ppm 1.05 (t, J=6.32 Hz, 3 H) 1.28-1.43 (m, 3 H) 1.62-1.74 (m, 1 H) 1.78-1.88 (m, 1 H) 2.01-2.17 (m, 1 H) 2.23-2.41 (m, 1 H) 3.31 (dd, J=13.52, 6.69 Hz, 1 H) 3.69-3.74 (m, 3 H) 3.77-3.81 (m, 3 H) 4.09-4.18 (m, 1 H) 4.18-4.26 (m, 2 H) 5.26-5.42 (m, 1 H) 5.51 (dd, J=8.21, 4.17 Hz, 1 H) 6.83-7.08 (m, 4 H) 7.08-7.30 (m, 2 H)

7.44 (dd, J=8.72, 2.15 Hz, 1 H) 7.55 (d, J=2.02 Hz, 1 H) 7.63-7.74 (m, 1 H) 9.45 (s, 1 H); MS (ESI) (m/z) 639.2 [M+H]⁺.

Example 25 methyl 3((R)-1-((R)-2-(4-fluoro-3-methoxyphenyl)-2-(1-oxo-1,2-dihydroisoquinolin-7-ylamino)acetyl)pyrrolidin-2-yl)-4-(isopropylsulfonyl)phenylcarbamate

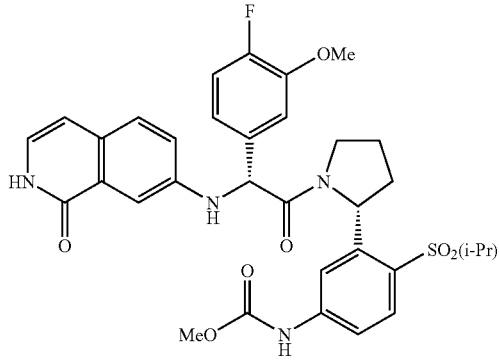

25A

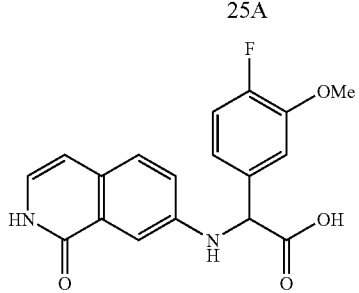

To Intermediate 7 (0.125 g, 0.780 mmol) and 4-fluoro-3-methoxyphenylboronic acid (0.106 g, 0.624 mmol) in acetonitrile (1.5 mL) and DMF (0.5 mL) was added 2-oxoacetic acid (0.057 g, 0.624 mmol). The reaction was heated to 90° C. for 20 min in a microwave. The solvent was concentrated and the crude residue was loaded into a 40 g ISCO column which was eluted with a 40 min gradient time from 0-15% methanol/dichloromethane. The desired fractions were combined and evaporated to give 25A (0.086 g, 40%) as a brown solid. ¹H NMR (400 MHz, methanol-d₄) δ ppm 3.80-3.85 (m, 3 H) 5.17 (s, 1 H) 6.35 (d, J=6.82 Hz, 1 H) 6.84 (dd, J=6.82, 5.81 Hz, 1 H) 7.05-7.12 (m, 1 H) 7.15-7.25 (m, 3 H) 7.32-7.41 (m, 2 H); MS (ESI) (m/z) 343.0 [M+H]⁺.

Example 25

To 25A (0.03 g, 0.088 mmol), HOAt (0.012 g, 0.088 mmol), and Intermediate 1 (0.032 g, 0.088 mmol) in dichloromethane (5 mL) was added N-methylmorpholine (0.029 mL, 0.263 mmol) and then EDC (0.034 g, 0.175 mmol). The reaction was stirred overnight at rt. A mixture of water and saturated sodium chloride was added to the reaction. The product was extracted with dichloromethane and dried over sodium sulfate. The reaction was filtered and solvent was removed. The crude residue was purified and the diastereomers separated using a preparative HPLC equipped with a C18 Phenomenex Luna column (30 mm×75 mm, 5 µ). The separations were performed using a gradient method: 20-100% B in 12 mins; then 100% B in 3 min with a flow rate of 40 mL/min. Solvent B is 90% acetonitrile-10% water-0.1% TFA and solvent A is 10% acetonitrile-90% water-0.1% TFA. Fractions from the first peak was identified to be Example 25 (38 mg, 67% yield): ¹H NMR (400 MHz, methanol-d₄) δ ppm 1.07 (d, J=6.57 Hz, 3 H) 1.32 (d, J=7.07 Hz, 3H) 1.59-1.71 (m, 1 H) 2.04 (dd, J=10.61, 6.57 Hz, 2 H) 2.38-2.52 (m, 1 H) 3.62 (s, 3 H) 3.65 (s, 3 H) 3.68 (dd, J=6.95, 3.41 Hz, 1 H) 3.81-3.92 (m, 1 H) 4.10-4.21 (m, 1 H) 5.36 (s, 1 H) 5.61 (dd, J=8.08, 5.05 Hz, 1 H) 6.49 (d, J=7.07 Hz, 1 H) 6.86 (d, 7=7.07 Hz, 1 H) 6.92-7.00 (m, 3 H) 7.04 (d, J=1.77 Hz, 1 H) 7.06-7.15 (m, 2 H) 7.30 (d, J=2.53 Hz, 1 H) 7.35 (d, J=8.59 Hz, 1 H) 7.66 (d, J=8.59 Hz, 1 H) 9.37 (s, 1H). MS (ESI) (m/z) 651.3 [M+H]⁺. The fractions from second peak (16 mg, 28% yield) is the diastereoisomer of Example 25: ¹H NMR (400 MHz, methanol-d₄) δ ppm 1.07 (d, J=6.06 Hz, 3 H) 1.36 (d, J=6.82 Hz, 3 H) 1.66-1.80 (m, 1 H) 1.81-1.92 (m, 1 H) 2.07-2.23 (m, 1 H) 2.28-2.45 (m, 1 H) 3.60-3.76 (m, 5 H) 3.85 (s, 3H) 4.24-4.41 (m, 1 H) 5.33-5.43 (m, 1 H) 5.47-5.59 (m, 1 H) 6.56 (d, J=6.82 Hz, 1H) 6.96 (d, 1 H) 7.02-7.15 (m, 3 H) 7.33 (s, 3 H) 7.38-7.48 (m, 1 H) 7.66-7.84 (m, 2 H) 9.47 (s, 1 H); MS (ESI) (m/z) 651.3 [M+H]⁺.

Example 26

(2R,3S)-ethyl 2-(2-(cyclopropylsulfonyl)phenyl)-1-((R)-2-(4-fluoro-3-methoxyphenyl)-2-(1-oxo-1,2-dihydroisoquinolin-7-ylamino)acetyl)pyrrolidine-3-carboxylate

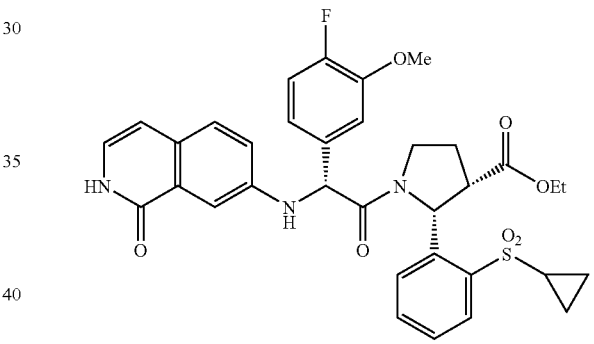

To 25A (0.04 g, 0.117 mmol), HOAt (0.016 g, 0.117 mmol), and (2R,3S)-ethyl 2-(2-(cyclopropylsulfonyl)phenyl)pyrrolidine-3-carboxylate hydrochloride (0.042 g, 0.117 mmol, WO 2006076246) in dichloromethane (5 mL) was added N-methylmorpholine (0.039 mL, 0.351 mmol) and then EDC (0.045 g, 0.234 mmol). The reaction was stirred over the weekend at room temperature. A mixture of water and saturated sodium chloride was added to the reaction. The product was extracted with dichloromethane and dried over sodium sulfate. The reaction was filtered and the solvent was removed. The crude residue was purified using a preparative HPLC equipped with a C18 Phenomenex Luna column (30 mm×75 mm, 5 µ). The separations were performed using a gradient method: 20-80% B in 12 mins; then 80% B in 3 mins with a flow rate of 40 mL/min. Solvent B is 90% acetonitrile-10% water-0.1% TFA and solvent A is 10% acetonitrile-90% water-0.1% TFA. Fractions from the first peak was identified to be Example 26 (22 mg, 58% yield): ¹H NMR (400 MHz, methanol-d₄) δ ppm 0.86-0.99 (m, 1 H) 1.04 (dd, J=19.71, 4.55 Hz, 1 H) 1.21 (s, 1 H) 1.32-1.43 (m, 1 H) 2.12-2.36 (m, 2 H) 2.82 (d, J=7.33 Hz, 1H) 2.97-3.14 (m, 1 H) 3.68-3.84 (m, 3 H) 3.85-3.93 (m, 1 H) 3.93-4.13 (m, 1 H) 5.40 (s, 1 H) 6.20 (s, 1 H) 6.48 (d, J=7.07 Hz, 1 H) 6.62 (d, J=7.07 Hz, 1 H) 6.74-6.87 (m, 1 H) 6.98-7.18 (m, 4 H) 7.23-7.48 (m, 4 H) 7.81 (dd, J=7.83, 1.52 Hz, 1 H); MS (ESI) (m/z) 648.3 [M+H]⁺.

Example 27

(2R,3S)-2-(2-(cyclopropylsulfonyl)phenyl)-1-((R)-2-(4-fluoro-3-methoxyphenyl)-2-(1-oxo-1,2-dihydroisoquinolin-7-ylamino)acetyl)pyrrolidine-3-carboxylic acid

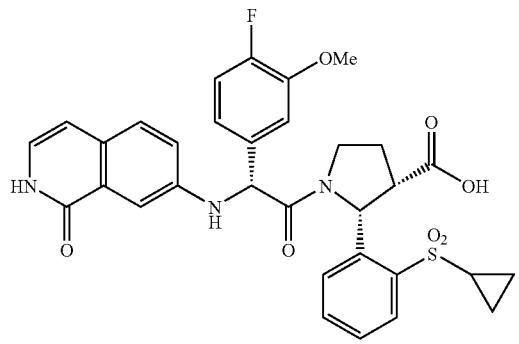

To Example 26 (0.019 g, 0.029 mmol) in ethanol (1.0 mL) and THF (1.0 mL) was added lithium hydroxide (0.293 mL, 0.293 mmol). The reaction was stirred at rt for 4 h. The crude residue was purified using a preparative HPLC equipped with a C18 Phenomenex Luna column (30 mm×75 mm, 5 μ). The separations were performed using a gradient method: 10-100% B in 12 mins; then 100% B in 3 mins with a flow rate of 40 mL/min. Solvent B is 90% acetonitrile-10% water-0.1% TFA and solvent A is 10% acetonitrile-90% water-0.1% TFA. The product fractions were combined, solvent removed and lyophilized to give Example 27 (3 mg, 18% yield) as a white amorphous solid. $^1$H NMR (400 MHz, methanol-$d_4$) δ ppm 0.86-0.99 (m, 1 H) 1.04 (dd, J=19.71, 4.55 Hz, 1 H) 1.21 (s, 1 H) 1.32-1.43 (m, 1 H) 2.12-2.36 (m, 2 H) 2.82 (d, J=7.33 Hz, 1 H) 2.97-3.14 (m, 1 H) 3.68-3.84 (m, 3 H) 3.85-3.93 (m, 1 H) 3.93-4.13 (m, 1 H) 5.40 (s, 1 H) 6.20 (s, 1 H) 6.48 (d, J=7.07 Hz, 1 H) 6.62 (d, J=7.07 Hz, 1 H) 6.74-6.87 (m, 1 H) 6.98-7.18 (m, 4 H) 7.23-7.48 (m, 4 H) 7.81 (dd, J=7.83, 1.52 Hz, 1 H); MS (ESI) (m/z) 620.2 [M+H]$^+$.

Example 28

(2R,3S)-2-(2-(cyclopropylsulfonyl)phenyl)-1-((R)-2-(4-fluoro-3-methoxyphenyl)-2-(3-oxoisoindolin-5-ylamino)acetyl)pyrrolidine-3-carboxylic acid

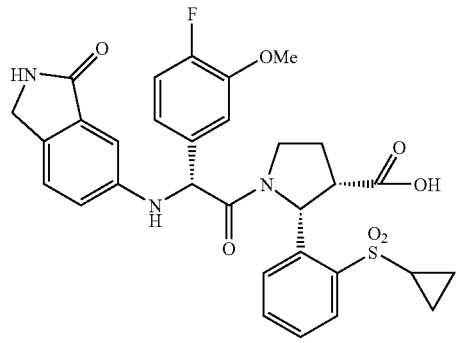

28A

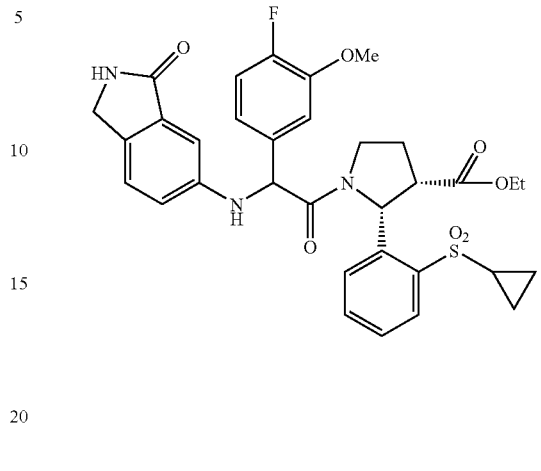

To 24A (0.08 g, 0.242 mmol), HOAt (0.033 g, 0.242 mmol) and (2R,3S)-ethyl 2-(2-(cyclopropylsulfonyl)phenyl)pyrrolidine-3-carboxylate hydrochloride (0.087 g, 0.242 mmol, WO2006076246) in dichloromethane (5 mL) was added N-methylmorpholine (0.080 mL, 0.727 mmol) and then EDC (0.093 g, 0.484 mmol). The reaction was stirred at rt for 3 days. A mixture of water and saturated sodium chloride was added to the reaction. The product was extracted with dichloromethane and dried over sodium sulfate. The reaction was filtered and the solvent was removed. The crude residue was dissolved in a small amount of dichloromethane and charged to a 12 g silica gel cartridge which was eluted with a 40 min gradient time from 0-20% methanol/dichloromethane. The product peak was isolated and dried to give 28A (0.138 g, 90% yield) as an off white solid. MS (ESI) (m/z) 636.3 [M+H]$^+$.

Example 28

To 28A (0.13 g, 0.204 mmol) in methanol (1.0 mL) and THF (1.0 mL) was added lithium hydroxide (4.0 mL, 4.00 mmol). The reaction was stirred at rt for 4 h. The solvent was removed and the crude residue was purified and diastereomers separated using a preparative HPLC equipped with a C18 Phenomenex Luna column (30 mm×75 mm, 5 μ). The separations were performed using a gradient method: 0-100% B in 12 mins; then 100% B in 3 mins with a flow rate of 40 mL/min. Solvent B is 90% acetonitrile-10% water-0.1% TFA and solvent A is 10% acetonitrile-90% water-0.1% TFA. The product fractions were combined, solvent removed and lyophilized to give Example 28 (0.036 g, 27% yield) as a white amorphous solid. $^1$H NMR (400 MHz, methanol-$d_4$) δ ppm 0.87-0.99 (m, 2 H) 1.00-1.12 (m, 1 H) 1.19-1.43 (m, 1 H) 2.10-2.36 (m, 2 H) 2.81 (d, J=7.33 Hz, 1 H) 2.98-3.09 (m, 1 H) 3.63-3.89 (m, 4 H) 3.93-4.08 (m, 1 H) 4.13-4.27 (m, 2 H) 5.00-5.38 (m, 1 H) 6.19 (s, 1H) 6.55-6.67 (m, 1 H) 6.84-7.12 (m, 5 H) 7.17-7.47 (m, 4 H) 7.76-7.91 (m, 1 H); MS (ESI) (m/z) 608.2 [M+H]$^+$.

Example 29 methyl 3-((R)-1-((R)-2-(3,4-dimethoxyphenyl)-2-(7-fluoro-4-oxo-3,4-dihydroquinazolin-6-ylamino)acetyl)pyrrolidin-2-yl)-4-(isopropylsulfonyl)phenylcarbamate

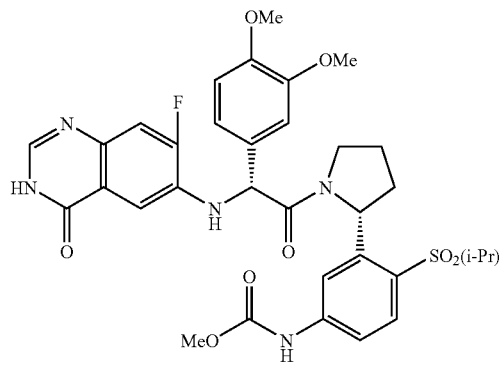

29A

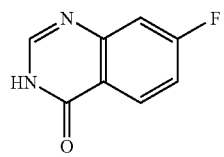

2-Amino-4-fluorobenzoic acid (0.3 g, 1.934 mmol) in methoxyethanol (2.0 mL) in a microwave vessel was irradiated at 210° C. for 20 min. After cooling white crystals were observed. The sample was concentrated and diluted with 0.01 M ammonia. The white solid was filtered and washed with 0.01M ammonia. The brown solid was collected and dried to give 29A (0.24 g, 75% yield). $^1$H NMR (400 MHz, DMSO-$d_6$) δ ppm 7.31-7.50 (m, 2 H) 8.12 (s, 1 H) 8.17 (dd, J=8.84, 6.32 Hz, 1 H) 12.33 (s, 11 H); LCMS at 1.475 min showed (ESI) (m/z) 164.9 [M+H]$^+$. The sample was analyzed using an LCMS equipped with a C18 Phenomenex Luna column (4.6 mm×50 mm, 5 μ) with the UV detector set at 254 nm. The analysis was performed using a gradient method: 0-100% B in 4 mins; then 100% B in 1 min with a flow rate of 4 mL/min. Solvent B is 90% methanol-10% water-0.1% TFA and solvent A is 10% methanol-90% water-0.1% TFA.

29B

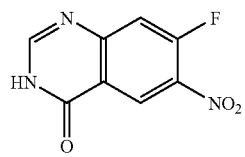

To 29A (0.2 g, 1.218 mmol) at 0° C. in sulfuric acid (4.87 mL, 1.218 mmol) was added potassium nitrate (0.058 mL, 1.218 mmol) portion wise over 10 min. The reaction was then allowed to warm to rt and stirred overnight. LCMS showed mostly starting material and about 10% prod. More potassium nitrate (0.058 mL, 1.218 mmol) was added and reaction was heated to 80° C. for 1 h. LCMS-showed mostly the product. Saturated sodium bicarbonate was slowly added in the cooled reaction (ice water bath) and yellow solid precipitate was observed. This was filtered and washed with water. The solid was dried to give 29B (0.14 g, 55% yield) as a yellow solid. $^1$H NMR (400 MHz, DMSO-$d_6$) δ ppm 7.78 (d, J=12.09 Hz, 1 H) 8.31 (s, 1 H) 8.72 (d, J=8.24 Hz, 1 H) 12.79 (s, 1 H); $^{19}$F NMR (376 MHz, Solvent??) δ ppm –111.75 (s, 1 H); LCMS at 1.695 min showed (ESI) (m/z) 209.9[M+H]$^+$. The sample was analyzed using an LCMS equipped with a C18 Phenomenex Luna column (4.6 mm×50 mm, 5 μ) with the UV detector set at 254 nm. The analysis was performed using a gradient method: 0-100% B in 4 mins; then 100% B in 1 min with a flow rate of 4 mL/min. Solvent B is 90% methanol-10% water-0.1% TFA and solvent A is 10% methanol-90% water-0.1% TFA.

29C

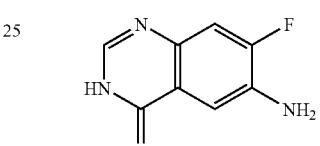

A solution of 29B (0.12 g, 0.574 mmol) in methanol (5 mL) with a few drops of HCl was stirred until hydrogen at atmospheric pressure with palladium on carbon (0.02 g, 0.188 mmol) for 1.5 h. The catalyst was filtered off and washed with methanol. The filtrate was evaporated and dried under vacuum overnight to give 29C (0.1 g, 97% yield) as a yellow solid. $^1$H NMR (400 MHz, DMSO-$d_6$) δ ppm 7.39-7.51 (m, 2 H) 8.57 (s, 1 H), LCMS at 0.85 min showed (ESI) (m/z) 180 [M+H]$^+$. The sample was analyzed using an LCMS equipped with a C18 Phenomenex Luna column (4.6 mm×50 mm, 5 μ) with the UV detector set at 254 nm. The analysis was performed using a gradient method: 0-100% B in 4 mins; then 100% B in 1 min with a flow rate of 4 mL/min. Solvent B is 90% methanol-10% water-0.1% TFA and solvent A is 10% methanol-90% water-0.1% TFA.

29D

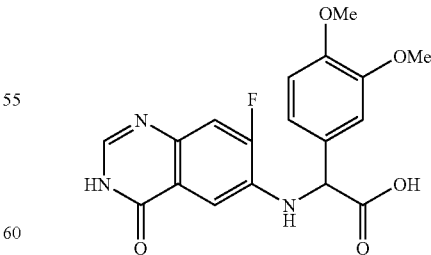

29C (0.1 g, 0.558 mmol), 3,4-dimethoxyphenylboronic acid (0.102 g, 0.558 mmol) and 2-oxoacetic acid (0.051 g, 0.558 mmol) dissolved in acetonitrile (1 mL) and DMF (0.100 mL) (partially soluble) were heated to 55° C. overnight. The solvent was removed by high vacuum. The crude product was dissolved in a small amount of dichloromethane and charged to a 12 g silica gel cartridge which was eluted with a gradient of 0%-20% CH$_2$Cl$_2$/MeOH. The fractions containing product was collected and combined and solvent was removed to give 29D (0.11 g, 57% yield) as a yellow solid. $^1$H NMR (400 MHz, DMSO-d$_6$) δ ppm 3.73 (d, J=7.07 Hz, 6 H) 5.21 (s, 1 H) 6.93 (d, J=8.34 Hz, 1 H) 7.04 (dd, J=8.21, 1.89 Hz, 1 H) 7.14-7.20 (m, 2 H) 7.43 (d, J=12.13 Hz, 1 H) 8.14 (s, 1 H); LCMS at 1.928 min showed (ESI) (m/z) 374 [M+H]$^+$. The sample was analyzed using an LCMS equipped with a C18 Phenomenex Luna column (4.6 mm×50 mm, 5 μ) with the UV detector set at 254 nm. The analysis was performed using a gradient method: 0-100% B in 4 mins; then 100% B in 1 min with a flow rate of 4 mL/min. Solvent B is 90% methanol-10% water-0.1% TFA and solvent A is 10% methanol-90% water-0.1% TFA.

Example 29

To 29D (0.06 g, 0.161 mmol), HOAt (0.022 g, 0.161 mmol), and Intermediate 1 (0.058 g, 0.161 mmol) in dichloromethane (5 mL) was added N-methylmorpholine (0.053 mL, 0.482 mmol) and then EDC (0.062 g, 0.321 mmol). The reaction was stirred overnight at rt. A mixture of water and saturated sodium chloride was added to the reaction. The product was extracted with dichloromethane and dried over sodium sulfate. The reaction was filtered and solvent was evaporated. The sample was purified and the diastereomers separated using a preparative HPLC equipped with a C18 Phenomenex Luna column (30 mm×100 mm, 5 μ). The UV detector was set at 254 nm. The separations were performed using a gradient method: 15-45% B in 15 mins; then 45% B in 5 mins with a flow rate of 40 mL/min. Solvent B is 90% acetonitrile-10% water-0.1% TFA and solvent A is 10% acetonitrile-90% water-0.1% TFA. Fractions from the first peak was identified to be Example 29 (48 mg, 88% yield): $^1$H NMR (400 MHz, methanol-d$_4$) δ ppm 1.19 (d, J=6.82 Hz, 3 H) 1.43 (d, J=7.07 Hz, 3 H) 1.70 (dd, J=12.88, 5.81 Hz, 1 H) 2.08 (dd, J=14.91, 7.58 Hz, 2 H) 2.50 (dd, J=13.01, 7.96 Hz, 1 H) 3.64-3.75 (m, 7 H) 3.79-3.86 (m, 3 H) 3.91-4.03 (m, 1 H) 4.07-4.26 (m, J=10.36 Hz, 1 H) 5.45 (s, 1 H) 5.67 (dd, J=8.21, 5.43 Hz, 1 H) 6.84-6.96 (m, 2 H) 6.96-7.08 (m, 2 H) 7.21 (dd, J=8.59, 2.27 Hz, 1 H) 7.28 (d, J=11.87 Hz, 1 H) 7.43 (d, J=9.09 Hz, 1 H) 7.74 (d, J=8.59 Hz, 1 H) 8.10 (s, 1 H) 9.32 (s, 1 H); LCMS at 2.678 min showed (ESI) (m/z) 682.2[M+H]$^+$. The sample was analyzed using an LCMS equipped with a C18 Phenomenex Luna column (4.6 mm×50 mm, 5 μ) with the UV detector set at 254 nm. The analysis was performed using a gradient method: 0-100% B in 4 mins; then 100% B in 1 min with a flow rate of 4 mL/min, Solvent B is 90% methanol-10% water-0.1% TFA and solvent A is 10% methanol-90% water-0.1% TFA. The fractions from second peak is the diastereoisomer of Example 29: $^1$H NMR (400 MHz, methanol-d$_4$) δ ppm 1.14-1.22 (m, 3 H) 1.37-1.56 (m, 3 H) 1.69-1.94 (m, 2 H) 1.96-2.21 (m, 1 H) 2.26-2.41 (m, 1 H) 3.68-3.76 (m, 3 H) 3.77-3.82 (m, 1 H) 3.83 (s, 3 H) 3.86 (s, 3 H) 4.18-4.30 (m, 1 H) 5.46-5.53 (m, 1 H) 5.60 (dd, J=8.34, 4.04 Hz, 1 H) 7.00 (d, J=8.34 Hz, 1 H) 7.13 (dd, J=8.34, 2.02 Hz, 1 H) 7.18 (d, J=2.02 Hz, 1 H) 7.23-7.32 (m, 1 H) 7.42-7.48 (m, 1 H) 7.51 (d, J=2.02 Hz, 1 H) 7.65 (dd, J=8.72, 2.15 Hz, 1 H) 7.73-7.85 (m, 1 H) 8.01-8.18 (m, 1 H) 9.22-9.37 (m, 1 H); LCMS at 2.718 min showed (ESI) (m/z) 682.2 [M+H]$^+$. The sample was analyzed using an LCMS equipped with a C18 Phenomenex Luna column (4.6 mm×50 mm, 5 μ) with the UV detector set at 254 nm. The analysis was performed using a gradient method: 0-100% B in 4 mins; then 100% B in 1 min with a flow rate of 4 mL/min. Solvent B is 90% methanol-10% water-0.1% TFA and solvent A is 10% methanol-90% water-0.1% TFA.

Example 30 methyl 3-((R)-1-((R)-2-(3,4-dimethoxyphenyl)-2-(4-methyl-1-oxo-1,2-dihydroisoquinolin-7-ylamino)acetyl)pyrrolidin-2-yl)-4-(isopropylsulfonyl)phenylcarbamate

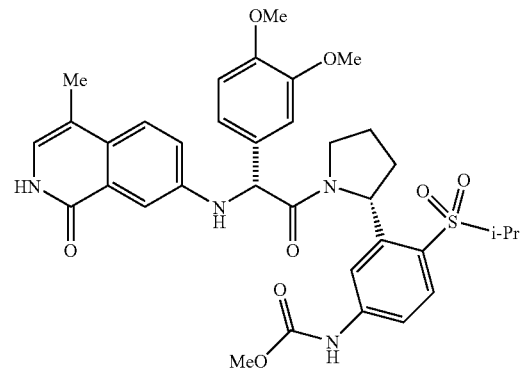

30A

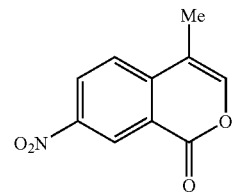

A mixture of methyl 2-ethyl-5-nitrobenzoate (785 mg, 3.75 mmol) and tert-butoxybis(dimethylamino)methane (1.78 mL, 8.63 mmol) was heated at 115° C. for 1 h 40 min. After cooling to rt, hexanes was added and an oily gum separated. The supernatant was concentrated and the residue was purified by silica gel chromatography, eluting with hexane:EtOAc:triethylamine, 70:30:1. 30A was obtained as an orange solid (477 mg, 62%). $^1$H NMR (400 MHz, CDCl$_3$) δ ppm 2.25 (s, 3 H), 7.30 (s, 1 H), 7.69 (d, J=8.79 Hz, 1 H), 8.59 (dd, J=8.79, 2.64 Hz, 1 H), 9.16 (d, J=2.64 Hz, 1 H). LC/MS RT=1.34 min, [M+H]$^+$=206.1. Gradient: 0 to 100% Solvent B in 2 min, hold 1 min. Flow rate: 5 mL/min. Solvent A: 10% methanol, 90% water, 0.1% trifluoroacetic acid. Solvent B: 90% methanol, 10% water, 0.1% trifluoroacetic acid. Column: Phenomenex Luna C18, 30×4.6 mm.

30B

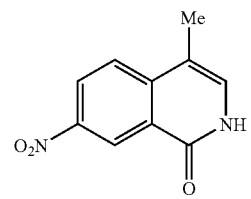

A mixture of 30A (214 mg, 1.04 mmol) and sat'd ammonia in ethylene glycol (4 mL, ~8M) was heated in a microwave from 100° C. to 170° C. in 10° C. increments for 10 min at each temperature to avoid over pressure (19 bar maximum pressure). Water was added to the resulting red suspension. The solid was filtered, washed with water, and air dried to give 30B as a yellow solid (173 mg, 81%). $^1$H NMR (400 MHz CDCl$_3$) δ ppm 2.35 (s, 3 H), 7.11 (s, 1 H), 7.78 (d, J=8.79 Hz, 1 H), 8.52 (dd, J=9.01, 2.42 Hz, 1 H), 9.30 (d, J=2.64 Hz, 1 H). LC/MS: RT=1.33 min, [M+H]$^+$=205.0. Gradient: 0 to 100% Solvent B in 2 min, hold 1 min. Flow rate: 5 mL/min. Solvent A: 10% methanol, 90% water, 0.1% trifluoroacetic acid. Solvent B: 90% methanol, 10% water, 0.1% trifluoroacetic acid. Column: Phenomenex Luna C18, 30×4.6 mm.

30C

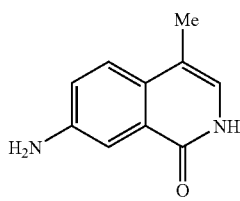

A suspension of 30B (204 mg, 0.999 mmol) in a mixture tetrahydrofuran (~15 mL, stabilized with 25 ppm BHT), MeOH (1 mL) and water (0.25 mL) was hydrogenated (20 psi) over palladium (10% on carbon, 81 mg, 0.076 mmol) for 55 min. Filtration and concentration of the filtrate gave 30C as a slightly yellow solid (183 mg, 100%). $^1$H NMR (400 MHz, DMSO-d$_6$) δ ppm 2.11 (s, 3 H), 5.48 (s, 2 H), 6.62 (s, 1 H), 7.02 (dd, J=8.57, 2.42 Hz, 1 H), 7.18-7.53 (m, 2 H), 10.66 (s, 1 H). LC/MS: RT=0.57 min, [M+H]$^+$=175.0. Gradient: 0 to 100% Solvent B in 2 min, hold 1 min. Flow rate: 5 mL/min. Solvent A: 10% methanol, 90% water, 0.1% trifluoroacetic acid. Solvent B: 90% methanol, 10% water, 0.1% trifluoroacetic acid. Column: Phenomenex Luna C18, 30×4.6 mm.

30D

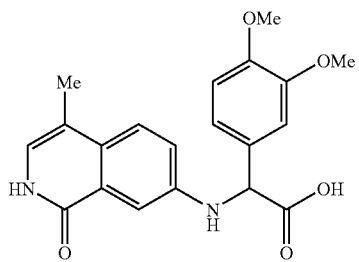

A suspension of 3,4-dimethoxyphenylboronic acid (52.2 mg, 0.287 mmol), 30C (50 mg, 0.287 mmol) and glyoxylic acid (26.4 mg, 0.287 mmol) in acetonitrile (0.5 mL) and DMF (0.05 mL) was heated by microwave at 100° C. for 10 min. The resulting clear orange solution was purified by preparative HPLC (Gradient: 20 to 100% Solvent B in 10 min. Flow rate: 40 mL/min. Solvent A: 10% methanol, 90% water, 0.1% trifluoroacetic acid. Solvent B: 90% methanol, 10% water, 0.1% trifluoroacetic acid. Column: YMC Sunfire 5 micron C18, 30×100 mm, RT=6.67 min) to give 30D as a yellow solid (82 mg, 78%). $^1$H NMR (400 MHz, methanol-d$_4$) δ ppm 2.22-2.24 (m, 3 H), 3.79-3.82 (m, 3 H), 3.82-3.84 (m, 3 H), 5.13-5.15 (m, 1 H), 6.74 (s, 1 H), 6.93 (d, J=8.35 Hz, 1 H), 7.12 (dd, J=8.13, 1.98 Hz, 1 H), 7.17 (d, 1 H), 7.27 (dd, J=8.79, 2.64 Hz, 1 H), 7.40 (d, J=2.20 Hz, 1 H), 7.53 (d, J=8.79 Hz, 1 H). LC/MS: RT=1.42 min, [M+H]$^+$=369.0. Gradient: 0 to 100% Solvent B in 2 min, hold 1 min. Flow rate: 5 mL/min. Solvent A: 10% methanol, 90% water, 0.1% trifluoroacetic acid. Solvent B: 90% methanol, 10% water, 0.1% trifluoroacetic acid. Column: Phenomenex Luna C18, 30×4.6 mm.

Example 30

DIEA (0.064 mL, 0.364 mmol) was added to a mixture of 30D (33.5 mg, 0.091 mmol), Intermediate 1 (33 mg, 0.091 mmol), 1-hydroxy-7-azabenzotriazole (12 mg, 0.091 mmol), and EDCI (34.9 mg, 0.182 mmol) in DMF (1 mL), and the reaction was stirred at rt overnight. The reaction mixture was concentrated and the residue was triturated with water and then purified by preparative HPLC (first run: Method A, except gradient: 20 to 100% Solvent B, RT=13.1 for 30, 14.4 for undesired diastereomer; second run: Method B, except gradient: 20 to 90% Solvent B, RT=7.1 min for 30, 10.4 min for undesired diastereomer) to give Example 30 as a yellow amorphous solid (11 mg, 18%). $^1$H NMR (400 MHz, methanol-d$_4$) δ ppm 1.15 (d, J=6.59 Hz, 3 H), 1.39 (d, J=6.59 Hz, 3 H), 1.67-1.79 (m, 1 H), 2.05-2.17 (m, 2 H), 2.24 (s, 3 H), 2.51 (dd, J=13.18, 7.91 Hz, 1 H), 3.68 (s, 3 H), 3.70 (s, 3 H), 3.71-3.77 (m, 1 H), 3.84 (s, 3 H), 3.89-3.99 (m, 1 H), 4.17-4.25 (m, 1 H), 5.42 (s, 1 H), 5.69 (dd, J=8.35, 4.83 Hz, 1 H), 6.80 (s, 1 H), 6.88-6.93 (m, 2 H), 6.96-7.01 (m, 1 H), 7.04 (s, 1 H), 7.21-7.27 (m, 2 H), 7.33 (s, 1 H), 7.48 (d, J=2.20 Hz, 1 H), 7.54 (d, J=8.79 Hz, 1 H), 7.74 (d, J=8.35 Hz, 1 H), 9.36 (s, 1 H). LC/MS: RT=1.70 min, [M+H]$^+$=677.0. Gradient: 0 to 100% Solvent B in 2 min, hold 1 min. Flow rate: 5 mL/min. Solvent A: 10% methanol, 90% water, 0.1% trifluoroacetic acid. Solvent B: 90% methanol, 10% water, 0.1% trifluoroacetic acid. Column: Phenomenex Luna C18, 30×4.6 mm. Analytical HPLC: RT 9.92 min, 94% purity, Xbridge Phenyl 3.5 micron, 4.6×150 mm, 220 nm, 254 nm; RT 10.07 min, 99% purity, Sunfire C18 3.5 micron, 4.6×150 mm, 220 nm, 254 nm, Gradient: 10 to 100% Solvent B in 15 min. Flow rate: 1 mL/min. Solvent A: 5% acetonitrile, 95% water, 0.05% trifluoroacetic acid. Solvent B: 95% acetonitrile, 5% water, 0.05% trifluoroacetic acid.

Example 31 methyl 3-((R)-1-((R)-2-(4-chloro-1-oxo-1,2-dihydroisoquinolin-7-ylamino)-2-(3,4-dimethoxy phenyl)acetyl)pyrrolidin-2-yl)-4-(isopropylsulfonyl)phenyl-carbamate

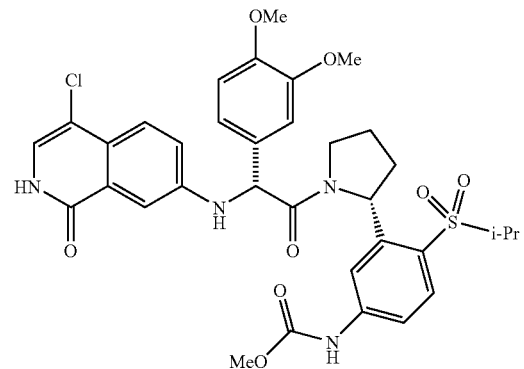

31A

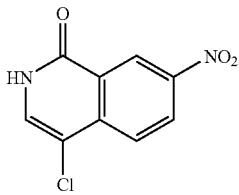

A solution of Intermediate 7D (299.7 mg, 1.576 mmol) and N-chlorosuccinimide (235 mg, 1.760 mmol) in DMA (4.5 mL) was heated by microwave at 200° C. for 10 min. The reaction mixture was poured into water (40 mL). The product was isolated by filtration, air dried, and then dried under vacuum to give 31A as a yellow green solid (328.3 mg, 93%). $^1$H NMR (400 MHz, THF-$d_8$) δ ppm 7.60 (s, 1 H) 8.02 (d, J=8.79 Hz, 1 H) 8.55 (dd, J=8.79, 2.64 Hz, 1 H) 9.08 (d, J=2.20 Hz, 1 H) 11.02 (br. s., 1 H). LC/MS: RT=0.99 min, [M+H]$^+$=225.1, 227.1. Gradient: 0 to 100% Solvent B in 2 min, hold 1 min. Flow rate: 5 mL/min. Solvent A: 10% acetonitrile, 90% water, 0.1% trifluoroacetic acid. Solvent B: 90% acetonitrile, 10% water, 0.1% trifluoroacetic acid. UV: 220 nM. Column: Phenomenex Luna C18, 30×4.6 mm, 5 micron.

31B

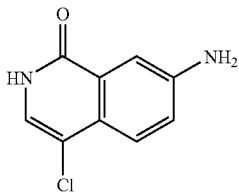

Tin(II) chloride dihydrate (1.25 g, 5.54 mmol) was added to a suspension of 31A (312 mg, 1.389 mmol) and ammonium chloride (370 mg, 6.92 mmol) in MeOH (10 mL) and the reaction mixture was stirred at rt for 7 h. The reaction mixture was then placed in a 50° C. oil bath overnight. Sat'd sodium bicarbonate was added and the mixture was extracted with ethyl acetate (4×). The combined organic layers were washed with brine, dried (MgSO$_4$) and then concentrated in vacuo to give 31B as a brown solid (244 mg, 90%). LC/MS: RT=0.84 min, [M+H]$^+$=195.2, 197.1. Gradient: 0 to 100% Solvent B in 2 min, hold 1 min. Flow rate: 5 mL/min. Solvent A: 10% methanol, 90% water, 0.1% trifluoroacetic acid. Solvent B: 90% methanol, 10% water, 0.1% trifluoroacetic acid. UV: 220 nM. Column: Phenomenex Luna C18, 30×4.6 mm, 5 micron.

31C

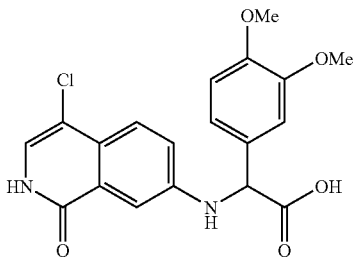

Using a procedure analogous to that described for preparation of 30D, 31B (47 mg, 0.241 mmol) was reacted with 3,4-dimethoxyphenylboronic acid and glyoxylic acid to give 31C (41 mg, 43%) as a red solid. $^1$H NMR (400 MHz, methanol-$d_4$) δ ppm 3.81 (s, 3 H), 3.83 (s, 3 H), 5.14 (s, 1 H), 6.92 (d, J=8.35 Hz, 1H), 7.00-7.05 (m, 1 H), 7.10 (dd, J=8.13, 1.98 Hz, 1 H), 7.15 (s, 1 H), 7.29 (dd, J=8.79, 2.64 Hz, 1 H), 7.37 (d, J=2.64 Hz, 1 H), 7.68 (d, J=8.79 Hz, 1 H).

Example 31

Using a procedure analogous to that described for preparation of Example 30, 31C (36 mg, 0.093 mmol) was reacted with Intermediate 1 to give Example 31 (15 mg, 23%) as a peach colored amorphous solid, along with its diastereomer. Preparative HPLC RT=10.4 min for 31, 10.9-11.7 min for its diastereomer using Method C, except gradient: 20 to 90% Solvent B. $^1$H NMR (400 MHz, methanol-$d_4$) δ ppm 1.11 (d, J=6.59 Hz, 3 H), 1.37 (d, J=6.59 Hz, 3 H), 1.71 (dd, J=12.74, 4.83 Hz, 1 H), 2.04-2.18 (m, 2 H), 2.51 (dd, J=13.18, 7.91 Hz, 1 H), 3.67 (s, 3 H), 3.70 (s, 3 H), 3.72-3.81 (m, 1 H), 3.83 (s, 3 H), 3.87-3.99 (m, 1 H), 4.15-4.28 (m, 1 H), 5.40 (s, 1 H), 5.69 (dd, J=7.91, 4.83 Hz, 1 H), 6.89 (d, J=8.35 Hz, 1 H), 6.93 (d, J=1.76 Hz, 1 H), 6.99 (d, J=2.20 Hz, 1 H), 7.02 (s, 1 H), 7.03-7.06 (m, 1 H), 7.23 (dd, J=8.79, 2.64 Hz, 1 H), 7.39 (d, J=2.64 Hz, 1 H), 7.64 (d, J=8.79 Hz, 1 H), 7.73 (d, J=8.79 Hz, 1 H), 9.34 (s, 1 H). LC/MS: RT=1.81 min, [M+H]$^+$=697.0. Gradient: 0 to 100% Solvent B in 2 min, hold 1 min. Flow rate: 5 mL/min. Solvent A: 10% methanol, 90% water, 0.1% trifluoroacetic acid. Solvent B: 90% methanol, 10% water, 0.1% trifluoroacetic acid. Column: Phenomenex Luna C18, 30×4.6 mm. Analytical HPLC: RT 10.42 min, 96% purity, Xbridge Phenyl 3.5 micron, 4.6×150 mm, 220 nm, 254 nm; RT 10.69 min, 94% purity, Sunfire C18 3.5 micron, 4.6×150 mm, 220 nm, 254 nm, Gradient: 10 to 100% Solvent B in 15 min. Flow rate: 1 mL/min. Solvent A: 5% acetonitrile, 95% water, 0.05% trifluoroacetic acid. Solvent B: 95% acetonitrile, 5% water, 0.05% trifluoroacetic acid.

Example 32 methyl 3-((R)-1-((R)-2-(4-bromo-1-oxo-1,2-dihydroisoquinolin-7-ylamino)-2-(3,4-dimethoxyphenyl)acetyl)pyrrolidin-2-yl)-4-(isopropylsulfonyl)phenylcarbamate

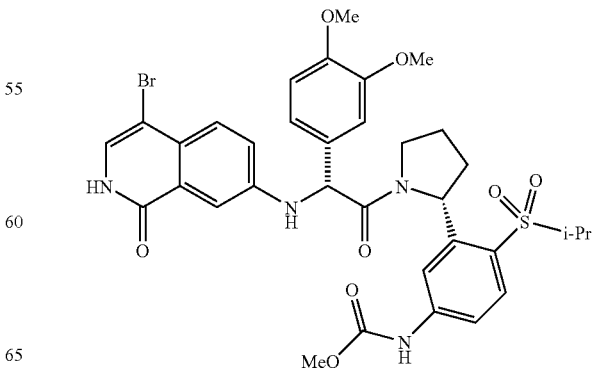

135

32A

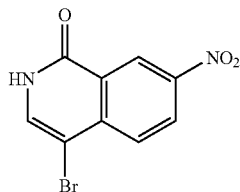

A solution of NBS (94 mg, 0.526 mmol) was added to Intermediate 7D (100 mg, 0.526 mmol) in DMA (0.5 mL). The mixture was heated by microwave at 200° C. for 10 min. Water was added to the resulting dark green solution. The precipitate was filtered, washed with water and air dried to give 32A (117 mg, 83%) as a mustard yellow solid. $^1$H NMR (400 MHz, DMSO-$d_6$) δ ppm 7.84 (d, J=3.08 Hz, 1 H), 7.94 (d, J=9.23 Hz, 1 H), 8.56 (dd, J=8.79, 2.64 Hz, 1 H), 8.87 (d, J=2.64 Hz, 1 H), 12.10 (s, 1 H). LC/MS: RT=1.56 min, [M+H]$^+$=271.0. Gradient: 0 to 100% Solvent B in 2 min, hold 1 min. Flow rate: 5 mL/min. Solvent A: 10% methanol, 90% water, 0.1% trifluoroacetic acid. Solvent B: 90% methanol, 10% water, 0.1% trifluoroacetic acid. Column: Phenomenex Luna C18, 30×4.6 mm.

32B

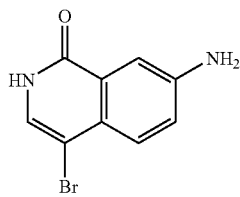

Using a procedure analogous to that described for preparation of 31B, 32A (112 mg, 0.416 mmol) was reacted with tin(II) chloride dihydrate to give 32B (88 mg, 0.368 mmol, 88%) as an orange colored amorphous solid. $^1$H NMR (400 MHz, DMSO-$d_6$) δ ppm 5.76 (s, 2 H), 7.07 (dd, J=8.57, 2.42 Hz, 1 H), 7.11 (d, J=5.71 Hz, 1 H), 7.33 (d, J=2.20 Hz, 1 H), 7.44 (d, J=8.79 Hz, 1 H), 11.11 (d, J=3.96 Hz, 1 H).

32C

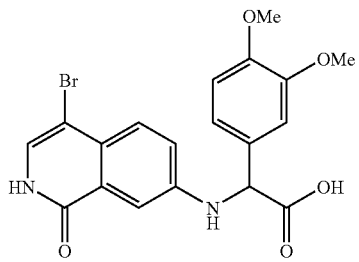

Using a procedure analogous to that described for preparation of 30D, 32B (47 mg, 0.197 mmol) was reacted with 3,4-dimethoxyphenylboronic acid and glyoxylic acid to give 32C (70 mg, 82%) as a yellow solid. $^1$H NMR (400 MHz, methanol-$d_4$) δ ppm 3.83 (s, 3 H), 5.15 (s, 1 H), 6.94 (d, J=8.35 Hz, 1 H), 7.10-7.13 (m, 1 H), 7.15 (s, 1 H), 7.17 (d, J=1.76 Hz, 1 H), 7.30 (dd, J=8.79, 2.64 Hz, 1 H), 7.37 (d, J=2.20 Hz, 1 H), 7.65 (d, J=9.23 Hz, 1 H). LC/MS: RT=1.60 min, [M+H]$^+$=435.0. Gradient: 0 to 100% Solvent B in 2 min, hold 1 min. Flow rate: 5 mL/min. Solvent A: 10% methanol, 90% water, 0.1% trifluoroacetic acid. Solvent B: 90% methanol, 10% water, 0.1% trifluoroacetic acid. Column: Phenomenex Luna C18, 30×4.6 mm.

Example 32

Using a procedure analogous to that described for preparation of Example 30, 32C (43 mg, 0.099 mmol) was reacted with Intermediate 1 to give Example 32 (19 mg, 26%) as a yellow amorphous solid, along with its diastereomer. Preparative HPLC RT=9.7 min for 32, 12.3 min for its diastereomer using Method B, except gradient: 30 to 90% Solvent B. $^1$H NMR (400 MHz, methanol-$d_4$) δ ppm 1.09 (d, J=6.59 Hz, 3 H), 1.36 (d, J=7.03 Hz, 3 H), 1.68-1.77 (m, 1 H), 2.05-2.16 (m, 2 H), 2.51 (dd, J=13.18, 7.91 Hz, 1 H), 3.67 (s, 3 H), 3.70 (s, 3 H), 3.72-3.78 (m, 1 H), 3.83 (s, 3 H), 3.85-3.95 (m, 1 H), 4.15-4.26 (m, 1 H), 5.41 (s, 1 H), 5.69 (dd, J=8.35, 4.83 Hz, 1 H), 6.86-6.94 (m, 2 H), 6.96-7.06 (m, 2 H), 7.16 (s, 1 H), 7.18-7.28 (m, 2 H), 7.40 (d, J=2.20 Hz, 1 H), 7.58 (d, J=8.79 Hz, 1 H), 7.72 (d, J=8.35 Hz, 1 H), 9.35 (s, 1 H). LC/MS: RT=1.83 min, [M+H]$^+$=742.6. Gradient: 0 to 100% Solvent B in 2 min, hold 1 min. Flow rate: 5 mL/min. Solvent A: 10% methanol, 90% water, 0.1% trifluoroacetic acid. Solvent B: 90% methanol, 10% water, 0.1% trifluoroacetic acid. Column: Phenomenex Luna C18, 30×4.6 mm. Analytical HPLC: RT 10.54 min, 98% purity, Xbridge Phenyl 3.5 micron, 4.6× 150 mm, 220 nm, 254 nm; RT 10.8 min, 99% purity, Sunfire C18 3.5 micron, 4.6×150 mm, 220 nm, 254 nm, Gradient: 10 to 100% Solvent B in 15 min. Flow rate: 1 mL/min. Solvent A: 5% acetonitrile, 95% water, 0.05% trifluoroacetic acid. Solvent B: 95% acetonitrile, 5% water, 0.05% trifluoroacetic acid.

Example 33 methyl 3-((R)-1-((R)-2-(3,4-dimethoxyphenyl)-2-(4-ethyl-1-oxo-1,2-dihydroisoquinolin-7-ylamino)acetyl)pyrrolidin-2-yl)-4-(isopropylsulfonyl)phenylcarbamate

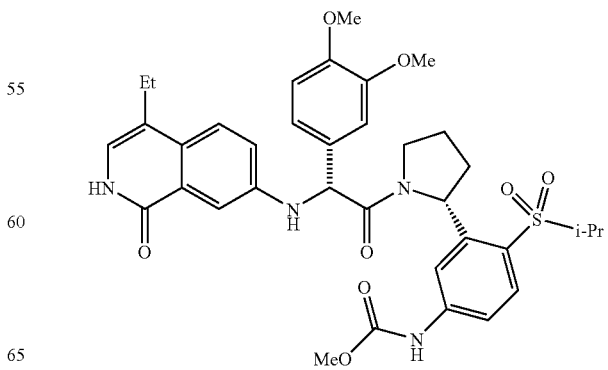

33A

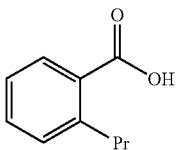

To a solution of 2-methylbenzoic acid (0.5 g, 3.67 mmol) in THF at −78° C. was added sec-butyllithium (9.62 mL, 8.08 mmol, 0.84 M in cyclohexane/hexene) dropwise. The resulting orange red solution was stirred at −78° C. for 1 h, and then iodoethane (2.08 mL, 25.7 mmol) was added. The reaction mixture was allowed to warm slowly to rt and stirred overnight. The solution was then cooled in an ice bath and quenched with conc. HCl. Volatile organic solvents were removed in vacuo, and the residue was diluted with HCl (1M) and extracted with ether (3×). The combined organic layers were washed with water, brine, dried, and concentrated to give 33A (0.68 g, 100%) as a brown oil. $^1$H NMR (400 MHz, chloroform-d) δ ppm 0.98 (t, J=7.47 Hz, 3 H), 1.60-1.72 (m, 2 H), 2.90-3.10 (m, 2H), 7.21-7.34 (m, 2 H), 7.47 (t, J=6.81 Hz, 1 H), 8.03 (d, J=7.03 Hz, 1 H).

33B

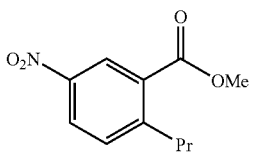

Potassium nitrate (369 mg, 3.65 mmol) was added in small portions to a solution of 33A (600 mg, 3.65 mmol) in sulfuric acid (7 mL) at 0° C. over 5 min. The mixture was stirred for 1 h and then poured into ice water. A solid was isolated by filtration, dissolved in EtOAc, washed with water and brine, dried (MgSO$_4$, and concentrated. The crude solid (559 mg) was dissolved in dichloromethane (10 mL) and methanol (8 mL), and (trimethylsilyl)diazomethane (2.38 mL, 4.75 mmol) was added drop wise at rt. The reaction mixture was stirred for 30 min and then concentrated. The residue was purified by silica gel chromatography (gradient of 5 to 15% EtOAc in hexane) to give 33B (241 mg, 30%). $^1$H NMR (400 MHz, chloroform-d) δ ppm 0.86-1.06 (m, 3 H), 1.59-1.80 (m, 2 H), 2.95-3.16 (m, 2 H), 3.96 (s, 3H), 7.40-7.52 (m, 1 H), 8.06-8.37 (m, 1 H), 8.74 (d, J=2.64 Hz, 1 H).

33C

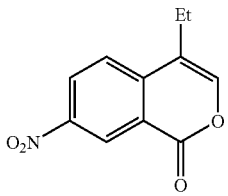

A mixture of 33B (380 mg, 1.702 mmol) and tert-butoxybis(dimethylamino)methane (809 μL, 3.92 mmol) was heated at 115° C. for 3.5 h. The reaction was cooled to rt, and hexanes was added to give a gummy precipitate. This material purified by silica gel chromatography (Hexane:EtOAc:Et$_3$N 70:30:1) to give 33C as an orange foam (346 mg, 93%). $^1$H NMR (400 MHz, chloroform-d) δ ppm 1.32 (t, J=7.47 Hz, 3 H), 2.68 (q, J=7.47 Hz, 2 H), 7.28 (s, 1 H), 7.74 (d, J=8.79 Hz, 1 H), 8.58 (dd, J=8.79, 2.64 Hz, 1 H), 9.17 (d, J=2.64 Hz, 1 H). LC/MS: RT=1.57 min, [M+H]$^+$=220.1. Gradient: 0 to 100% Solvent B in 2 min, hold 1 min. Flow rate: 5 mL/min. Solvent A: 10% methanol, 90% water, 0.1% trifluoroacetic acid. Solvent B: 90% methanol, 10% water, 0.1% trifluoroacetic acid. Column: Phenomenex Luna C18, 30×4.6 mm.

33D

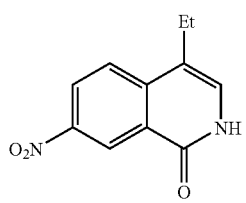

Using a procedure analogous to that described for preparation of 30B, 33C (340 mg, 1.551 mmol) was reacted with sat'd ammonia in ethylene glycol to give 33D (200 mg, 59%) as a yellow solid. $^1$H NMR (400 MHz, DMSO-d$_6$) δ ppm 1.18 (t, J=7.25 Hz, 3 H), 2.70 (q, J=7.18 Hz, 2 H), 7.24 (s, 1 H), 7.94 (d, J=9.23 Hz, 1 H), 8.46 (dd, J=9.23, 2.64 Hz, 1 H), 8.92 (d, J=2.64 Hz, 1 H), 11.03 (s, 1 H). LCMS. RT=1.52 min, [M+H]$^+$=219.1. Gradient: 0 to 100% Solvent B in 2 min, hold 1 min. Flow rate: 5 mL/min. Solvent A: 10% methanol, 90% water, 0.1% trifluoroacetic acid. Solvent B: 90% methanol, 10% water, 0.1% trifluoroacetic acid. Column: Phenomenex Luna C18, 30×4.6 mm.

33E

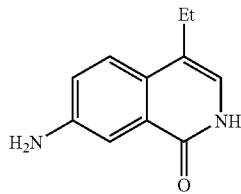

To a suspension of 33D (200 mg, 0.917 mmol) in THF (stabilized) and water was added palladium (79 mg, 0.074 mmol, 10% on carbon). The suspension was hydrogenated at 20 psi. The reaction mixture was filtered and the filtrate was concentrated to give 33E (170 mg, 99%) as a yellow solid. $^1$H NMR (400 MHz, DMSO-d$_6$) δ ppm 1.14 (t, J=7.42 Hz, 3 H), 2.56 (q, J=7.70 Hz, 2 H), 5.46 (s, 2 H), 6.58 (d, J=5.50 Hz, 1 H), 7.01 (dd, J=8.52, 2.47 Hz, 1 H), 7.34 (d, J=2.20 Hz, 1 H), 7.41 (d, J=8.79 Hz, 1 H), 10.67 (d, J=4.40 Hz, 1 H). LC/MS: RT=0.75 min, [M+H]$^+$=189.2. Gradient: 0 to 100% Solvent B in 2 min, hold 1 min. Flow rate: 5 mL/min. Solvent A: 10% methanol, 90% water, 0.1% trifluoroacetic acid. Solvent B:

90% methanol, 10% water, 0.1% trifluoroacetic acid. Column: Phenomenex Luna C18, 30×4.6 mm.

33F

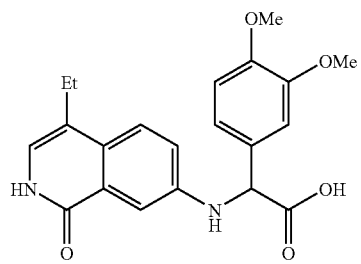

Using a procedure analogous to that described for preparation of 30D, 33E (50 mg, 0.266 mmol) was reacted with 3,4-dimethoxyphenylboronic acid and glyoxylic acid to give 33F (70 mg, 69%) as a white solid. $^1$H NMR (400 MHz, DMSO-d$_6$) δ ppm 1.14 (t, J=7.42 Hz, 3 H), 2.57 (d, J=7.15 Hz, 2 H), 3.73 (s, 3 H), 3.75 (s, 3 H), 5.08 (s, 1 H), 6.94 (d, J=8.24 Hz, 1 H), 7.01-7.08 (m, 1 H), 7.14 (s, 1H), 7.25-7.29 (m, 1 H), 7.31 (d, J=2.75 Hz, 1 H), 7.47 (d, J=8.79 Hz, 1 H), 10.78 (d, J=5.50 Hz, 1 H). LC/MS: RT=1.56 min, [M+H]$^+$=383.1. Gradient: 0 to 100% Solvent B in 2 min, hold 1 min. Flow rate: 5 mL/min. Solvent A: 10% methanol, 90% water, 0.1% trifluoroacetic acid. Solvent B: 90% methanol, 10% water, 0.1% trifluoroacetic acid. Column: Phenomenex Luna C18, 30×4.6 mm.

Example 33

Using a procedure analogous to that described for preparation of Example 30, 33F (40 mg, 0.10 mmol) was reacted with Intermediate 1 to give Example 33 (19 mg, 26%) as a yellow amorphous solid, along with its diastereomer. Preparative HPLC RT=8.3 min for 33, 11.2 min for its diastereomer using Method B, except gradient: 20 to 90% Solvent B. $^1$H NMR (400 MHz, methanol-d$_4$) δ ppm 1.12 (d, J=6.59 Hz, 3 H), 1.22 (t, J=7.47 Hz, 3 H), 1.37 (d, J=7.03 Hz, 3 H), 1.65-1.78 (m, 1 H), 2.02-2.15 (m, 2 H), 2.45-2.57 (m, 1 H), 2.67 (q, J=7.32 Hz, 2 H), 3.66 (s, 3 H), 3.68-3.74 (m, 1 H), 3.70 (s, 3 H), 3.83 (s, 3 H), 3.88-3.98 (m, 1 H), 4.13-4.23 (m, 1 H), 5.44 (s, 1 H), 5.69 (dd, J=7.91, 4.83 Hz, 1 H), 6.80 (s, 1 H), 6.85-6.92 (m, 2 H), 6.92-7.00 (m, 1 H), 7.06 (s, 1 H), 7.24 (dd, J=8.57, 1.98 Hz, 2 H), 7.53-7.63 (m, 2 H), 7.74 (d, J=8.79 Hz, 1 H), 9.39 (s, 1 H). LC/MS: RT=1.79 min, [M+H]$^+$=691.0. Gradient: 0 to 100% Solvent B in 2 min, hold 1 min. Flow rate: 5 mL/min. Solvent A: 10% methanol, 90% water, 0.1% trifluoroacetic acid. Solvent B: 90% methanol, 10% water, 0.1% trifluoroacetic acid. Column: Phenomenex Luna C18, 30×4.6 mm. Analytical HPLC: RT 10.32 min, 98% purity, Xbridge Phenyl 3.5 micron, 4.6×150 mm, 220 nm, 254 nm; RT 10.56 min, 99% purity, Sunfire C18 3.5 micron, 4.6×150 mm, 220 nm, 254 nm, Gradient: 10 to 100% Solvent B in 15 min. Flow rate: 1 mL/min. Solvent A: 5% acetonitrile, 95% water, 0.05% trifluoroacetic acid. Solvent B: 95% acetonitrile, 5% water, 0.05% trifluoroacetic acid.

Example 34 methyl 3-((R)-1-((R)-2-(3,4-dimethoxyphenyl)-2-(4-fluoro-1-oxo-1,2-dihydroisoquinolin-7-ylamino)acetyl)pyrrolidin-2-yl)-4-(isopropylsulfonyl)phenylcarbamate

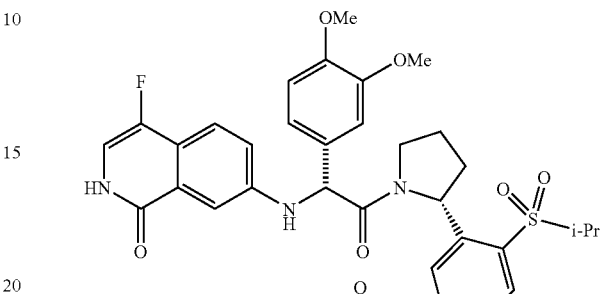

34A

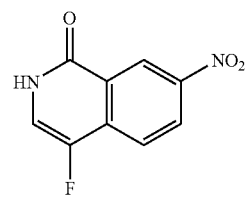

A 20 mL microwave tube was charged with Intermediate 7D (1.0 g, 5.25 mmol), Selectflor (1.86 g, 5.25 mmol) and dimethylacetamide (10 mL) and the brown solution was microwaved at 150° C. for 15 min. The reaction mixture was cooled to rt and the DMA was removed under high vacuum. Twenty 1.0 g scale reactions were carried out and purified by preparative HPLC to give 34A as yellow solid (5.0 g, 23% yield). $^1$H NMR (DMSO-d$_6$, 400 MHz) δ 11.7 (s, 1H), 8.8 (s, 1H), 8.6 (d, 1H), 7.9 (d, 1H), 7.6 (d, 1H). LCMS-(M+1)$^+$ 208.8.

34B

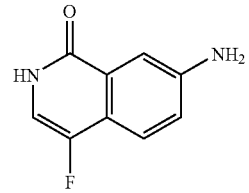

To a solution of 34A (1.5 g, 7.2 mmol) in a methanol and THF mixture (1:1, 20 mL) was added palladium on carbon (150 mg) and the resulting mixture was stirred for 3 h at bladder hydrogen pressure. The reaction mixture was filtered and concentrated. The crude product was purified by silica gel column chromatography to give 34B as yellow solid. Yield: 1.2 g, 88%. $^1$H NMR (DMSO-d$_6$, 400 MHz) δ 10.7 (s, 1H), 7.5 (d, 1H), 7.3 (d, 1H), 7.2 (d, 1H), 6.9 (d, 1H), 5.8 (s, 1H). LCMS-(M+1)$^+$ 178.8.

34C

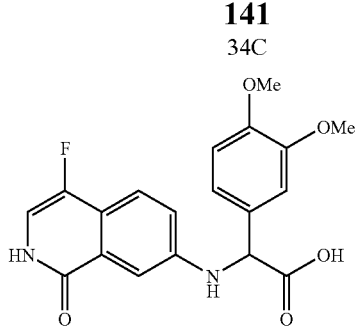

Using a procedure analogous to that described for preparation of 30D, 34B (47 mg, 0.264 mmol) was reacted with 3,4-dimethoxyphenylboronic acid and glyoxylic acid to give 34C (41 mg, 42%) as a red solid. $^1$H NMR (400 MHz, methanol-$d_4$) δ ppm 3.81 (s, 3 H), 3.83 (s, 3 H), 5.15 (s, 1 H), 6.90 (d, J=5.71 Hz, 1H), 6.94 (d, J=8.35 Hz, 1 H), 7.11 (dd, J=8.13, 1.98 Hz, 1 H), 7.17 (d, J=1.76 Hz, 1H), 7.29-7.33 (m, 1 H), 7.34 (d, J=2.20 Hz, 1 H), 7.60 (d, J=8.79 Hz, 1 H).

Example 34

Using a procedure analogous to that described for preparation of Example 30, 34C (50 mg, 0.134 mmol) was reacted with Intermediate 1 to give Example 34 (20 mg, 22%) as a yellow amorphous solid, along with its diastereomer. $^1$H NMR (400 MHz, methanol-$d_4$) δ ppm 1.14 (d, J=6.59 Hz, 3 H), 1.39 (d, J=7.03 Hz, 3 H), 1.71 (dd, J=12.08, 5.93 Hz, 1 H), 2.04-2.21 (m, 2 H), 2.52 (dd, J=13.18, 7.91 Hz, 1 H), 3.68 (s, 3 H), 3.70 (s, 3 H), 3.73-3.79 (m, 1 H), 3.84 (s, 3 H), 3.91-3.97 (m, 1 H), 4.19-4.24 (m, 1 H), 5.40 (s, 1 H), 5.69 (dd, J=8.13, 4.61 Hz, 1 H), 6.87-6.93 (m, 3 H), 7.01 (dd, J=8.35, 2.20 Hz, 2 H), 7.18-7.29 (m, 2 H), 7.33 (s, 1H), 7.34-7.38 (m, 1 H), 7.58 (d, J=8.79 Hz, 1 H), 7.73 (d, J=8.79 Hz, 1 H), 9.35 (s, 1H). LC/MS: RT=1.73 min, [M+H]$^+$=681.1. Gradient: 0 to 100% Solvent B in 2 min, hold 1 min. Flow rate: 5 mL/min. Solvent A: 10% methanol, 90% water, 0.1% trifluoroacetic acid. Solvent B: 90% methanol, 10% water, 0.1% trifluoroacetic acid. Column: Phenomenex Luna C18, 30×4.6 mm. Analytical HPLC: RT 10.07 min, 98% purity, Xbridge Phenyl 3.5 micron, 4.6×150 mm, 220 nm, 254 nm; RT 10.20 min, 97% purity, Sunfire C18 3.5 micron, 4.6×150 mm, 220 nm, 254 nm, Gradient: 10 to 100% Solvent B in 15 min. Flow rate: 1 mL/min. Solvent A: 5% acetonitrile, 95% water, 0.05% trifluoroacetic acid. Solvent B: 95% acetonitrile, 5% water, 0.05%) trifluoroacetic acid.

Example 35 methyl 3-((R)-1-((R)-2-(4-cyclopropyl-1-oxo-1,2-dihydroisoquinolin-7-ylamino)-2-(3,4-dimethoxyphenyl)acetyl)pyrrolidin-2-yl)-4-(isopropylsulfonyl)phenylcarbamate

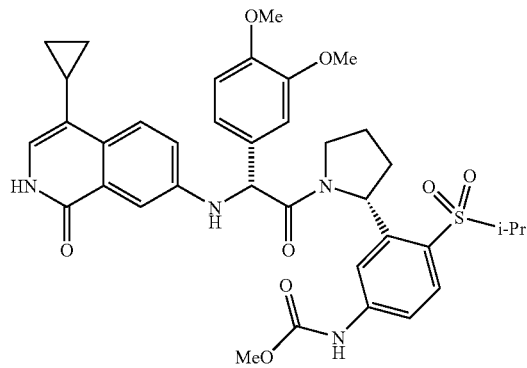

35A

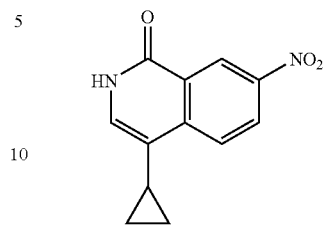

A solution of 32A (300 mg, 1.12 mmol), cyclopropyl boronic acid (144 mg, 1.67 mmol), potassium phosphate (830 mg, 3.9 mmol), and tricyclohexylphosphine (31 mg, 0.11 mmol) in a mixture of toluene (6 mL) and water (0.15 mL) was deoxygenated by sparging with nitrogen. Palladium acetate was added (12 mg, 0.056 mmol) and the reaction was heated by microwave at 140° C. for 10 min. The reaction was diluted with water and extracted with EtOAc (3×). The combined organic layers were washed with brine and concentrated to give 35A (240 mg) as a crude orange solid. LC/MS: RT=1.53 min, [M+H]$^+$=231.2. Gradient: 0 to 100% Solvent B in 2 min, hold 1 min. Flow rate: 5 mL/min. Solvent A: 10% methanol, 90% water, 0.1% trifluoroacetic acid. Solvent B: 90% methanol, 10% water, 0.1% trifluoroacetic acid. Column: Phenomenex Luna C18, 30×4.6 mm.

35B

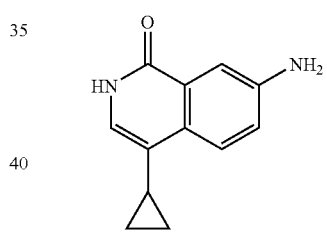

A suspension of 35A (240 mg, 1.042 mmol) and palladium (100 mg, 0.094 mmol, 10% on carbon) in THF (40 mL, stabilized) and water (0.25 mL) was hydrogenated (20 psi) for 3 h. The reaction mixture was filtered and concentrated. The residue was purified by preparative HPLC (Method A, except gradient from 20 to 100% B, RT=3.45 min) to give 35B as a white solid (25 mg, 12% yield).

35C

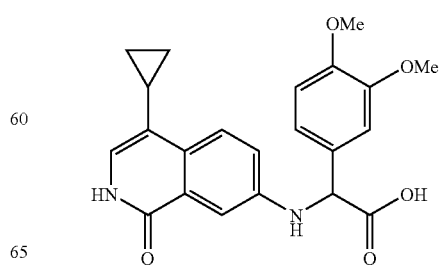

Using a procedure analogous to that described for preparation of 30D, 35B (25 mg, 0.125 mmol) was reacted with 3,4-dimethoxyphenylboronic acid and glyoxylic acid to give 35C (23 mg, 46%) as a solid. MS: [M+H]⁺=395.1.

Example 35

Using a procedure analogous to that described for preparation of Example 30, 35C (23 mg, 0.058 mmol) was reacted with Intermediate 1 to give Example 35 (6 mg, 15%) as a pale yellow amorphous solid, along with its diastereomer. Preparative HPLC Method A, except gradient: 30 to 100% Solvent B over 20 min. ¹H NMR (400 MHz, methanol-d₄) δ ppm 0.44-0.57 (m, 2 H), 0.86-0.97 (m, 2 H), 1.14 (d, J=6.59 Hz, 3 H), 1.39 (d, J=6.96 Hz, 3 H), 1.71 (dd, J=12.08, 5.86 Hz, 1 H), 1.82-1.92 (m, 1 H), 2.10 (dd, J=11.17, 6.77 Hz, 2 H), 2.51 (dd, J=13.00, 7.87 Hz, 1 H), 3.67 (s, 3 H), 3.69-3.74 (m, 1 H), 3.70 (s, 3 H), 3.84 (s, 3 H), 3.93 (dd, J=13.55, 6.59 Hz, 1 H), 4.12-4.25 (m, 1 H), 5.44 (s, 1 H), 5.69 (dd, J=8.06, 4.76 Hz, 1 H), 6.77 (s, 1 H), 6.86-6.93 (m, 2 H), 6.95-7.00 (m, 2 H), 7.06 (d, J=1.83 Hz, 1 H), 7.20-7.31 (m, 2 H), 7.50 (d, J=2.56 Hz, 1 H), 7.74 (d, J=8.79 Hz, 1 H), 7.94 (d, J=8.79 Hz, 1 H), 9.38 (s, 1 H). LC/MS: RT=1.81 min, [M+H]⁺=703.1. Gradient: 0 to 100% Solvent B in 2 min, hold 1 min. Flow rate: 5 mL/min. Solvent A: 10% methanol, 90% water, 0.1% trifluoroacetic acid. Solvent B: 90% methanol, 10% water, 0.1% trifluoroacetic acid. Column: Phenomenex Luna C18, 30×4.6 mm. Analytical HPLC: RT 10.72 min, 97% purity, Xbridge Phenyl 3.5 micron, 4.6×150 mm, 220 nm, 254 nm; RT 10.53 min, 98% purity, Sunfire C18 3.5 micron, 4.6×150 mm, 220 nm, 254 nm, Gradient: 10 to 100% Solvent B in 15 min. Flow rate: 1 mL/min. Solvent A: 5% acetonitrile, 95% water, 0.05% trifluoroacetic acid. Solvent B: 95% acetonitrile, 5% water, 0.05% trifluoroacetic acid.

Table 1 below lists Factor VIIa $K_i$ values for the following examples of this invention measured in the Factor VIIa assay described above.

TABLE 1

| Example Number | Factor VIIa Ki (nM) |
|---|---|
| 4 | 51, 132, 158, 160 |
| 6 | >13000 |
| 11 | 6600 |
| 18 | 41, 88 |
| 22 | <5, 3.5 |
| 28 | 60 |
| 31 | 17, 9.2, 9.0 |

While the foregoing specification teaches the principles of the present invention, which examples provided for the purpose of illustration, it will be understood that the practice of the invention encompasses all of the usual variations, adaptations and/or modifications as come within the scope of the following claims and their equivalents.

What is claimed is:
1. A compound of Formula (I):

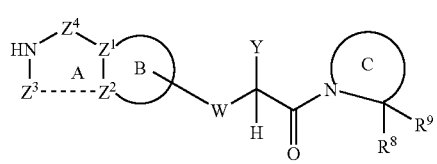

(I)

or stereoisomers, tautomers, or pharmaceutically acceptable salts thereof, wherein:

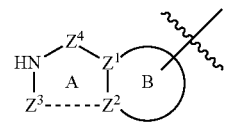

is selected from:

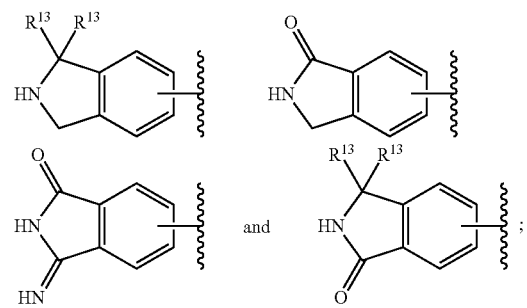

wherein ring A is substituted with 0-2 $R^{11}$; and ring B is substituted with 0-2 $R^6$;

ring C is a 4- to 8-membered heterocycle comprising: the nitrogen atom shown in the ring, carbon atoms and 0-1 additional heteroatom selected from N, $NR^c$, O, and $S(O)_p$, 0-1 carbonyl, and 0-2 double bonds, wherein said heterocycle is substituted with 0-2 $R^7$;

W is $NR^j$, O or S;
Y is selected from:

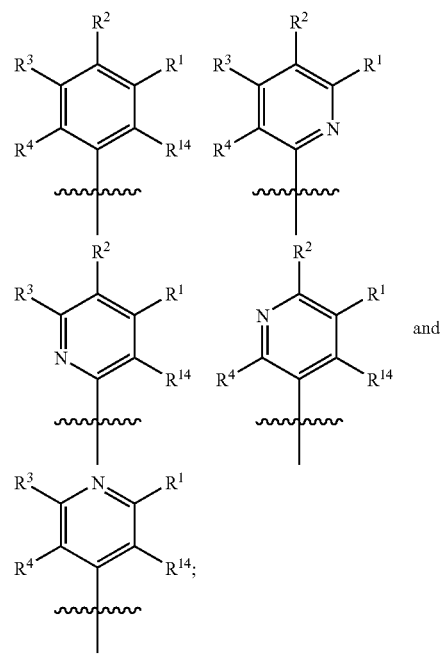

$R^1$ is, independently at each occurrence, H, F, Cl, Br, I, $C_{1-5}$ alkyl substituted with 0-1 OH, $C_{1-5}$ haloalkyl, $C_{2-5}$ alkenyl, $C_{2-5}$ alkynyl, —O—$C_{1-5}$ alkyl, —O—$C_{1-5}$ haloalkyl, —S—$C_{1-5}$ alkyl, or $C_{3-6}$ cycloalkyl;

$R^2$, $R^3$ and $R^4$ are, independently at each occurrence, H, F, Cl, Br, I, —$(CH_2)_sOR^a$, —$(CH_2)_sSR^b$, —$(CH_2)_sCF_3$, —$(CH_2)_sOCF_3$, —$(CH_2)_sOCHF_2$, —$(CH_2)_sOCH_2F$, —$(CH_2)_sCN$, —$(CH_2)_sNO_2$, —$(CH_2)_sNR^bR^c$, —$(CH_2)_sC(O)R^a$, —$(CH_2)_sCO_2R^a$, —$(CH_2)_sNR^dC(O)R^a$, —$(CH_2)_sC(O)NR^cR^d$, —$(CH_2)_sNR^cC(O)OR^a$, —$(CH_2)_sOC(O)R^a$, —$(CH_2)_sOC(O)OR^a$, —$(CH_2)_sNR^cC(O)NR^cR^d$, —$(CH_2)_sOC(O)NR^cR^d$, —$(CH_2)_sSO_2NR^cR^d$, —$(CH_2)_sNR^cSO_2NR^cR^d$, —$(CH_2)_sNR^cSO_2R^i$, —$(CH_2)_sNR^cSO_2CF_3$, —$(CH_2)_sSO_2CF_3$, —$(CH_2)_sS(O)_pR^i$, —$O(CH_2)_nCO_2R^a$, —$(CH_2)_sSO_2NHCOR^a$, —$(CH_2)_sCONHSO_2R^i$, —$(CF_2)_rCF_3$, $C_{1-6}$ alkyl substituted with 0-2 $R^e$, $C_{1-4}$ haloalkyl, $C_{2-6}$ alkenyl substituted with 0-2 $R^e$, $C_{2-6}$ alkynyl substituted with 0-2 $R^e$, —O(benzyl substituted with $CO_2R^a$), —$(CH_2)_sC_{3-10}$ carbocycle substituted with 0-3 $R^f$, —$(CH_2)_s$-(5- to 10-membered heterocycle), comprising: carbon atoms and 1-4 heteroatoms selected from N, $NR^c$, O, and $S(O)_p$, wherein said heterocycle is substituted with 0-3 $R^f$;

alternatively, $R^2$ and $R^3$ may combine to form a 5- to 7-membered carbocycle or heterocycle comprising: carbon atoms and 0-4 heteroatoms selected from N, $NR^c$, O, and $S(O)_p$, wherein said carbocycle and heterocycle are substituted with 0-3 $R^f$;

alternatively, $R^3$ and $R^4$ may combine to form a 5- to 7-membered carbocycle or heterocycle comprising: carbon atoms and 0-4 heteroatoms selected from N, $NR^c$, O, and $S(O)_p$, wherein said carbocycle and heterocycle are substituted with 0-3 $R^f$;

$R^6$ is, independently at each occurrence, F, Cl, Br, I, CN, OH, $CF_3$, $C_{1-4}$ alkyl, $C_{1-4}$ haloalkyl, $C_{1-4}$ alkoxy, or $C_{3-6}$ cycloalkyl;

$R^7$ is, independently at each occurrence, F, Cl, Br, I, —$(CH_2)_rOR^a$, —$(CH_2)_rSR^b$, —$(CH_2)_sCF_3$, —$(CH_2)_rOCF_3$, —$(CH_2)_rOCHF_2$, —$(CH_2)_rOCH_2F$, —$(CH_2)_sCN$, —$(CH_2)_sNO_2$, —$(CH_2)_sNR^bR^c$, —$(CH_2)_sC(O)R^a$, —$(CH_2)_sCO_2R^a$, —$(CH_2)_sNR^dC(O)R^a$, —$(CH_2)_sC(O)NR^cR^d$, —$SO_2NR^cR^d$, —$NR^cSO_2R^i$, —$(CH_2)_rNR^cC(O)OR^b$, —$(CH_2)_rOC(O)OR^b$, —$(CH_2)_rNR^cC(O)NR^cR^d$, —$(CH_2)_rOC(O)NR^cR^d$, —$(CH_2)_rSO_2NR^cR^d$, —$(CH_2)_rNR^cSO_2NR^cR^d$, —$(CH_2)_rNR^cSO_2R^b$, —$(CH_2)_rNR^cSO_2CF_3$, —$(CH_2)_rSO_2CF_3$, —$(CH_2)_rS(O)_pR^b$, —$SO_2NHC(O)R^b$, —$C(O)NHSO_2R^b$, —$NR^cSO_2CF_3$, —$SO_2CF_3$, —$S(O)_pR^i$, —$(CF_2)_rCF_3$, tetrazole, —$(CH_2)_r$-phenyl substituted with 0-3 $R^f$, or —$(CH_2)_r$-5- to 6-membered heterocycle comprising: carbon atoms and 1-4 heteroatoms selected from N, $NR^c$, O, and $S(O)_p$, wherein said heterocycle is substituted with 0-3 $R^f$;

$R^8$ is H, CN, —$CO_2R^a$, —$C(O)NR^cR^d$, tetrazolyl, or $C_{1-4}$ alkyl substituted with 0-2 $R^{8a}$;

$R^{8a}$ is, independently at each occurrence, =O, $OR^a$, F, Cl, Br, I, CN, $NO_2$, $SR^b$, $CF_3$, —$OCF_3$, —$OCHF_2$, —$OCH_2F$, —$NR^bR^c$, —$C(O)R^a$, —$CO_2R^a$, —$OC(O)R^a$, —$OC(O)NR^cR^d$, —$NR^dC(O)R^a$, —$C(O)NR^cR^d$, —$NR^cC(O)NR^cR^d$, —$NR^cC(O)OR^b$, —$SO_2NR^cR^d$, —$NR^cSO_2R^i$, —$NR^cSO_2NR^cR^d$, —$SO_2NHC(O)R^b$, —$C(O)NHSO_2R^b$, —$NR^cSO_2CF_3$, —$SO_2CF_3$, —$S(O)_pR^i$, —$O(CH_2)_nCO_2R^a$, —$(CF_2)_rCF_3$, tetrazole, $C_{3-6}$ cycloalkyl substituted with 0-3 $R^f$, phenyl substituted with 0-3 $R^f$, or 5- to 6-membered heterocycle comprising: carbon atoms and 1-4 heteroatoms selected from N, $NR^c$, O, and $S(O)_p$, wherein said heterocycle is substituted with 0-3 $R^f$;

$R^9$ is phenyl or pyridyl substituted with 1-3 $R^{10}$;

$R^{10}$ is, independently at each occurrence, F, Cl, Br, I, —$(CH_2)_rOR^a$, —$(CH_2)_sSR^b$, —$(CH_2)_rCF_3$, —$(CH_2)_sOCF_3$, —$(CH_2)_sOCHF_2$, —$(CH_2)_sOCH_2F$, —$(CH_2)_sCN$, —$(CH_2)_sNO_2$, —$(CH_2)_sSCF_3$, —$(CH_2)_sNR^bR^c$, —$(CH_2)_sC(O)R^a$, —$(CH_2)_sCO_2R^a$, —$(CH_2)_sNR^cCO_2R^a$, —$(CH_2)_sNR^dC(O)R^a$, —$(CH_2)_sC(O)NR^cR^d$, —$(CH_2)_sNR^cC(O)OR^b$, —$(CH_2)_sOC(O)OR^b$, —$(CH_2)_sNR^cC(O)NR^cR^d$, —$(CH_2)_sSO_2NR^cR^d$, —$(CH_2)_sOSO_2NR^cR^d$, —$(CH_2)_sNR^cSO_2NR^cR^d$, —$(CH_2)_sNR^cSO_2R^i$, —$(CH_2)_sNR^cSO_2CF_3$, —$(CH_2)_sSO_2CF_3$, —$(CH_2)_sS(O)_pR^i$, —$(CF_2)_rCF_3$, $C_{1-6}$ alkyl substituted with 0-2 $R^e$, $C_{1-4}$ haloalkyl, $C_{2-6}$ alkenyl substituted with 0-2 $R^e$, $C_{2-6}$ alkynyl substituted with 0-2 $R^e$, —$(CH_2)_r$—$C_{3-10}$ carbocycle substituted with 0-3 $R^f$, or —$(CH_2)_r$-5- to 10-membered heterocycle comprising: carbon atoms and 1-4 heteroatoms selected from N, $NR^c$, O, and $S(O)_p$, wherein said heterocycle are substituted with 0-3 $R^f$;

$R^{11}$ is, independently at each occurrence, H, F, Cl, Br, I, $CF_3$, $OCF_3$, $OCHF_2$, $OCH_2F$, CN, $C_{1-4}$ alkyl, $C_{1-4}$ alkoxy, $C_{1-4}$ haloalkyl, $C_{2-4}$ alkenyl, $C_{2-4}$ alkynyl, or $C_{3-6}$ cycloalkyl;

$R^{13}$ is, independently at each occurrence, H, $CF_3$, CN, —$C(O)R^a$, —$CO_2R^a$, —$C(O)NR^cR^d$, $C_{1-6}$ alkyl substituted with 0-2 $R^e$, $C_{1-4}$ haloalkyl, $C_{2-4}$ alkenyl substituted with 0-2 $R^e$, $C_{2-4}$ alkynyl substituted with 0-2 $R^e$, —$(CH_2)_s$—$C_{3-6}$ carbocycle substituted with 0-2 $R^f$, —$(CH_2)_s$-(5- to 6-membered heterocycle), —$NR^c$-(5- to 6-membered heterocycle), or —O-(5- to 6-membered heterocycle); wherein said heterocycle comprises carbon atoms and 1-3 heteroatoms selected from N, $NR^c$, O, and $S(O)_p$ and is substituted with 0-2 $R^f$;

$R^{14}$ is, independently at each occurrence, H, F, Cl, Me, Et, or OMe;

$R^a$ is, independently at each occurrence, H, $C_{1-6}$ alkyl substituted with 0-4 $R^h$, fluoroalkyl, —$(CH_2)_r$—$C_{3-7}$ carbocycle substituted with 0-4 $R^f$, or —$(CH_2)_r$-5- to 10-membered heterocycle comprising: carbon atoms and 1-4 heteroatoms selected from N, $NR^g$, O, and $S(O)_p$, wherein said heterocycle is substituted with 0-4 $R^f$;

$R^b$ is, independently at each occurrence, H, $C_{1-6}$ alkyl, fluoroalkyl, —$(CH_2)_n$-phenyl, $(C_{1-6}$ alkyl)$C(O)$—, $(C_{3-6}$ cycloalkyl)-$C_{0-4}$ alkyl-$C(O)$—, $(C_{6-10}$ aryl)-$C_{0-4}$ alkyl-$C(O)$—, (5- to 10-membered heteroaryl)-$C_{0-4}$ alkyl-$C(O)$—, $(C_{1-6}$ alkyl)-$NHC(O)$—, $(C_{1-6}$ alkyl)$_2$-$NHC(O)$—, $(C_{6-10}$ aryl)-$C_{0-4}$ alkyl-$NHC(O)$—, (5- to 10-membered heteroaryl)-$C_{0-4}$ alkyl-$NHC(O)$—, $(C_{1-6}$ alkyl)-$SO_2$—, $(C_{6-10}$ aryl)-$C_{0-4}$ alkyl-$SO_2$—, or (5- to 10-membered heteroaryl)-$C_{0-4}$ alkyl-$SO_2$—, wherein said phenyl, aryl and heteroaryl are substituted with 0-2 $R^f$;

$R^c$ is, independently at each occurrence, H, $C_{1-6}$ alkyl substituted with 0-3 $R^h$, fluoroalkyl, —$(CH_2)_n$—$C_{3-7}$ cycloalkyl substituted with 0-3 $R^h$, or —$(CH_2)_n$-phenyl substituted with 0-3 $R^h$;

alternatively, $R^b$ and $R^c$, when attached to the same nitrogen atom, may be taken together with the nitrogen atom to form a 4- to 10-membered heterocycle comprising: carbon atoms and 1-4 heteroatoms selected from N, $NR^g$, O, and $S(O)_p$, wherein heterocycle are substituted with 0-3 $R^f$;

$R^d$ is, independently at each occurrence, H, $C_{1-6}$ alkyl, fluoroalkyl, —$(CH_2)_r$—$C_{3-10}$ carbocycle substituted with 0-3 $R^f$, or a —$(CH_2)_r$-5- to 12-membered heterocycle comprising: carbon atoms and 1-4 heteroatoms selected from N, NR$^g$, O, and S(O)$_p$, wherein said heterocycle is substituted with 0-3 R$^f$;

alternatively, R$^c$ and R$^d$, when attached to the same nitrogen atom, may be taken together with the nitrogen atom to form a 4- to 10-membered heterocycle comprising: carbon atoms and 1-4 heteroatoms selected from N, NR$^g$, O, and S(O)$_p$, wherein heterocycle are substituted with 0-3 R$^f$;

R$^e$ is, independently at each occurrence, =O, OR$^a$, F, Cl, Br, I, CN, NO$_2$, —SR$^a$, —OCF$_3$, —NR$^b$R$^c$, —C(O)R$^a$, —CO$_2$R$^a$, —NR$^d$C(O)R$^a$, —C(O)NR$^c$R$^d$, —OC(O)R$^a$, O—NR$^d$C(O)OR$^a$, —NR$^d$C(O)NR$^c$R$^d$, —OC(O)NR$^c$R$^d$, —SO$_2$NR$^c$R$^d$, —NC(O)OR$^a$, —NR$^c$SO$_2$NR$^c$R$^d$, —NR$^c$SO$_2$R$^i$, —CONHSO$_2$R$^i$, —CH$_2$CONHSO$_2$R$^i$, —NR$^c$SO$_2$CF$_3$, —SO$_2$CF$_3$, —S(O)$_p$R$^i$, —(CF$_2$)$_r$CF$_3$, C$_{3-10}$ carbocycle substituted with 0-3 R$^f$, or a 5- to 12-membered heterocycle comprising: carbon atoms and 1-4 heteroatoms selected from N, NR$^g$, O, and S(O)$_p$, wherein said heterocycle is substituted with 0-3 R$^f$;

R$^f$ is, independently at each occurrence, =O, OR$^g$, F, Cl, Br, I, CN, NO$_2$, —SR$^g$, —OCF$_3$, —NR$^c$R$^c$, —C(O)R$^g$, —CO$_2$R$^g$, —NR$^c$C(O)R$^g$, —C(O)NR$^c$R$^c$, —OC(O)R$^g$, —NR$^c$C(O)OR$^g$, —NR$^c$C(O)NR$^c$R$^c$, —OC(O)NR$^c$R$^c$, —SO$_2$NR$^c$R$^c$, —NR$^c$SO$_2$NR$^c$R$^c$, —NR$^c$SO$_2$R$^i$, —CONHSO$_2$R$^i$, —CH$_2$CONHSO$_2$R$^i$, —NR$^c$SO$_2$CF$_3$, —SO$_2$CF$_3$, —S(O)$_p$R$^i$, —(CF$_2$)$_r$CF$_3$, C$_{1-6}$ alkyl, C$_{2-6}$ alkenyl, C$_{2-6}$ alkynyl, C$_{3-10}$ carbocycle substituted with 0-3 R$^h$, or a 5- to 12-membered heterocycle comprising: carbon atoms and 1-4 heteroatoms selected from N, NR$^g$, O, and S(O)$_p$, and substituted with 0-3 R$^h$;

R$^g$ is, independently at each occurrence, H, C$_{1-6}$ alkyl, or —(CH$_2$)$_n$-phenyl;

R$^h$ is, independently at each occurrence, =O, —(CH$_2$)$_r$OR$^g$, F, Cl, Br, I, CN, NO$_2$, —OCF$_3$, —NR$^g$R$^g$, —C(O)R$^g$, —CO$_2$R$^g$, —NR$^g$C(O)R$^g$, —C(O)NR$^g$R$^g$, —SO$_2$NR$^g$R$^g$, —NR$^g$SO$_2$NR$^g$R$^g$, —NR$^g$SO$_2$—C$_{1-4}$ alkyl, —NR$^g$SO$_2$CF$_3$, —NR$^g$SO$_2$-phenyl, —SO$_2$CF$_3$, —S(O)$_p$—C$_{1-4}$ alkyl, —S(O)$_p$-phenyl, —(CF$_2$)$_r$CF$_3$, C$_{1-6}$ alkyl, C$_{2-6}$ alkenyl, C$_{2-6}$ alkynyl, (C$_{1-6}$ alkyl)C(O)—, (C$_{3-6}$ cycloalkyl)-C$_{0-4}$ alkyl-C(O)—, (C$_{6-10}$ aryl)(C$_{0-4}$ alkyl)-C(O)—, (5-10 membered heteroaryl)-C$_{0-4}$ alkyl-C(O)—, (C$_{1-6}$ alkyl)-NHC(O)—, (C$_{1-6}$ alkyl)$_2$-NHC(O)—, (C$_{6-10}$ aryl)-C$_{0-4}$ alkyl-NHC(O)—, (5-10 membered heteroaryl)-C$_{0-4}$ alkyl-NHC(O)—, (C$_{1-6}$ alkyl)-SO$_2$—, (C$_{6-10}$ aryl)-C$_{0-4}$ alkyl-SO$_2$—, (5-10 membered heteroaryl)-C$_{0-4}$ alkyl-SO$_2$—, —(CH$_2$)$_r$C$_{3-10}$ carbocycle, or a —(CH$_2$)$_r$-5- to 12-membered heterocycle comprising: carbon atoms and 1-4 heteroatoms selected from N, NR$^g$, O, and S(O)$_p$;

R$^i$ is, independently at each occurrence, H, C$_{1-6}$ alkyl substituted with 0-3 R$^h$, C$_{3-6}$ cycloalkyl substituted with 0-3 R$^h$, —(CH$_2$)$_n$-phenyl substituted with 0-3 R$^h$, —(CH$_2$)$_r$-5- to 10-membered heterocycle comprising: carbon atoms and 1-4 heteroatoms selected from N, NR$^g$, O, and S(O)$_p$, wherein said heterocycle is substituted with 0-3 R$^h$;

R$^j$ is, independently at each occurrence, H or C$_{1-3}$ alkyl;

n, at each occurrence, is selected from 0, 1, 2, 3, and 4;

p, at each occurrence, is selected from 0, 1, and 2;

r, at each occurrence, is selected from 0, 1, 2, 3, and 4; and s, at each occurrence, is selected from 0, 1, and 2.

2. A compound according to claim 1, wherein:

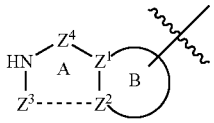

is selected from:

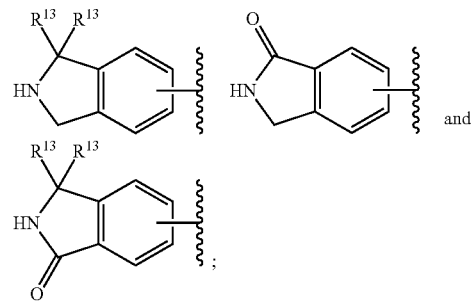

wherein ring A is substituted with 0-2 R$^{11}$; and ring B is substituted with 0-2 R$^6$;

ring C is a 5- or 6-membered heterocycle comprising: the nitrogen atom shown in the ring, carbon atoms and 0-1 additional heteroatom selected from N, NR$^c$, O, and S(O)$_p$, wherein said heterocycle is substituted with 0-2 R$^7$;

W is NH or O; and

R$^1$ is, independently at each occurrence, H, F, Cl, Br, C$_{1-3}$ alkyl substituted with 0-1 OH, C$_{1-3}$ haloalkyl, C$_{2-3}$ alkenyl, C$_{2-3}$ alkynyl, —O—C$_{1-3}$ alkyl, or C$_{3-5}$ cycloalkyl.

3. A compound according to claim 1, wherein the compound is of Formula (II):

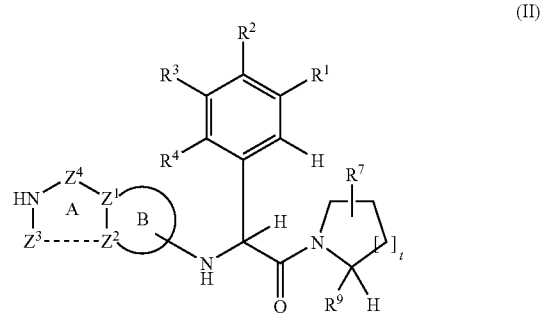

or stereoisomers, tautomers, or pharmaceutically acceptable salts thereof, wherein:

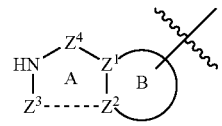

is selected from:

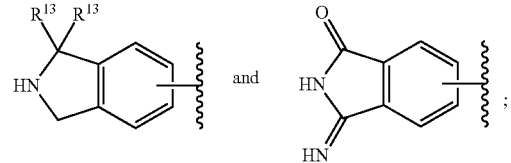

wherein ring A is substituted with 0-2 $R^{11}$ and ring B is substituted with 0-2 $R^6$;

$R^1$ is H, F, Cl, Br, $C_{1-2}$ alkyl substituted with 0-1 OH, $C_{1-2}$ haloalkyl, $C_{2-3}$ alkenyl, $C_{2-3}$ alkynyl, —O—$C_{1-2}$ alkyl, or $C_{3-5}$ cycloalkyl;

$R^2$, $R^3$ and $R^4$ are, independently at each occurrence, H, F, Cl, Br, I, $OR^a$, $OCF_3$, $OCHF_2$, $OCH_2F$, CN, $NO_2$, —$NR^bR^c$, —$C(O)R^a$, —$CO_2R^a$, —$NR^dC(O)R^a$, —$C(O)NR^cR^d$, —$NR^cC(O)OR^a$, —$NR^cC(O)NR^cR^d$, —$SO_2NR^cR^d$, —$NR^cSO_2NR^cR^d$, —$NR^cSO_2R^i$, —$NR^cSO_2CF_3$, —$SO_2CF_3$, —$S(O)_pR^i$, —$(CF_2)_rCF_3$, $C_{1-6}$ alkyl substituted with 0-2 $R^e$, $C_{1-4}$ haloalkyl, $C_{2-6}$ alkenyl substituted with 0-2 $R^e$, $C_{2-6}$ alkynyl substituted with 0-2 $R^e$, $C_{3-10}$ carbocycle substituted with 0-3 $R^f$, or a 5- to 10-membered heterocycle comprising: carbon atoms and 1-4 heteroatoms selected from N, $NR^c$, O, and $S(O)_p$, wherein said heterocycle are substituted with 0-3 $R^f$;

alternatively, $R^2$ and $R^3$ may combine to form a 5- to 7-membered carbocycle or heterocycle comprising: carbon atoms and 0-4 heteroatoms selected from N, $NR^c$, O, and $S(O)_p$, wherein said carbocycle and heterocycle are substituted with 0-3 $R^f$;

alternatively, $R^3$ and $R^4$ may combine to form a 5- to 7-membered carbocycle or heterocycle comprising: carbon atoms and 0-4 heteroatoms selected from N, $NR^c$, O, and $S(O)_p$, wherein said carbocycle and heterocycle are substituted with 0-3 $R^f$;

$R^6$ is, independently at each occurrence, F, Cl, OH, $CF_3$, $C_{1-2}$ alkyl, or $C_{1-2}$ alkoxy;

$R^7$ is, independently at each occurrence, $OR^a$, F, Cl, Br, I, CN, $NO_2$, —$OCF_3$, —$NR^bR^c$, —$C(O)R^a$, —$CO_2R^a$, —$NR^dC(O)R^a$, —$C(O)NR^cR^d$, —$SO_2NR^cR^d$, —$NR^cSO_2R^i$, —$SO_2NHC(O)R^b$, —$C(O)NHSO_2R^b$, —$NR^cSO_2CF_3$, —$SO_2CF_3$, —$S(O)_pR^i$, —$(CF_2)_rCF_3$, tetrazole, —$(CH_2)_r$-phenyl substituted with 0-3 $R^f$, or a —$(CH_2)_r$-5- to 6-membered heterocycle comprising: carbon atoms and 1-4 heteroatoms selected from N, $NR^c$, O, and $S(O)_p$, wherein said heterocycle is substituted with 0-3 $R^f$;

$R^9$ is selected from:

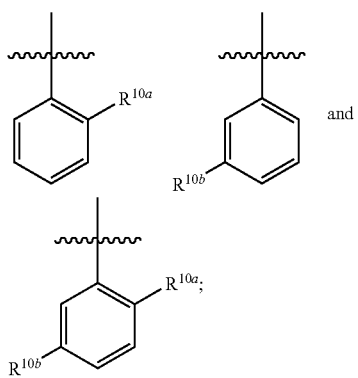

$R^{10a}$ and $R^{10b}$ are, independently at each occurrence, H, F, Cl, Br, I, —$(CH_2)_r$—$OR^a$, $OCF_3$, $SCF_3$, CN, $NO_2$, —$(CH_2)_r$—$NR^bR^c$, —$C(O)R^a$, —$(CH_2)_r$—$CO_2R^a$, —$(CH_2)_r$—$NR^cCO_2R^a$, —$NR^dC(O)R^a$, —$(CH_2)_r$—$C(O)NR^cR^d$, —$NR^cC(O)NR^cR^d$, —$SO_2NR^cR^d$, —$OSO_2NR^cR^d$, —$NR^cSO_2NR^cR^d$, —$NR^cSO_2R^i$, —$NR^cSO_2CF_3$, —$SO_2CF_3$, —$S(O)_pR^i$, —$(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, —$(CH_2)_r$—$C_{3-10}$ carbocycle substituted with 0-3 $R^f$, or —$(CH_2)_r$-5- to 10-membered heterocycle comprising: carbon atoms and 1-4 heteroatoms selected from N, $NR^c$, O, and $S(O)_p$, wherein said heterocycle are substituted with 0-3 $R^f$; and t is selected from 1 and 2.

4. A compound according to claim 3, wherein:

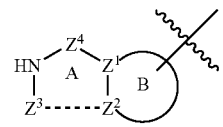

is selected from:

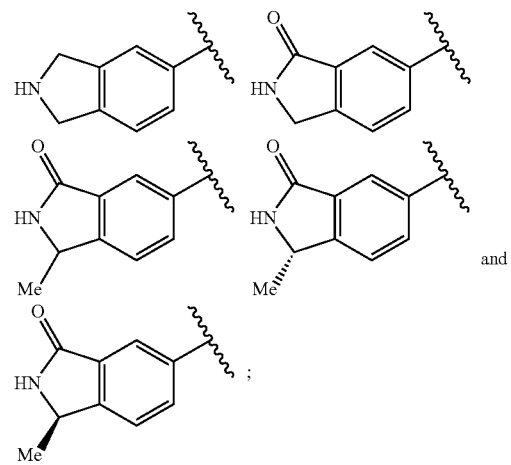

wherein ring B is substituted with 0-1 $R^6$; and $R^6$ is, independently at each occurrence, F, Cl, Me or Et.

5. A compound according to claim 3, wherein:

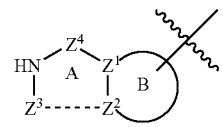

is selected from:

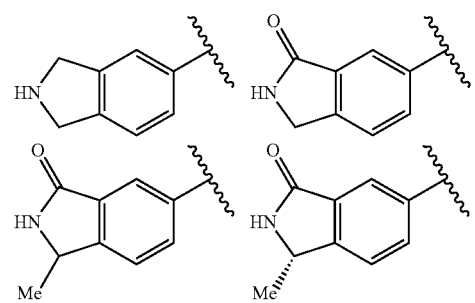

-continued

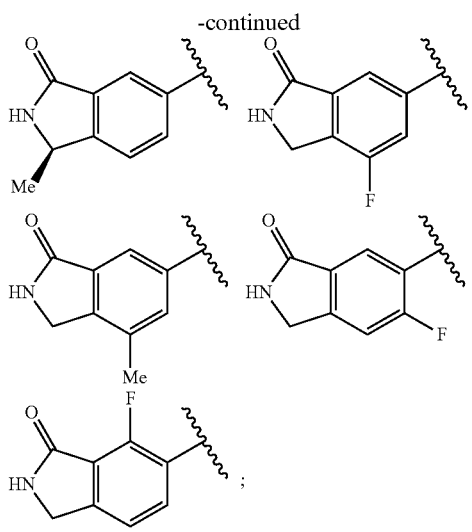

R[1] is Cl, Br, Me, Et, vinyl, 2-propenyl, ethynyl, —CH(OH)Me, OMe, OEt, cyclopropyl, —OCHF$_2$, or —OCF$_2$CHF$_2$;
R[2] is H, F, Cl, C$_{1-4}$ alkyl, C$_{1-4}$ alkoxy, or —OCHF$_2$;
R[3] is H, C$_{1-4}$ alkyl, or C$_{1-4}$ alkoxy;
R[4] is H or F;
R[7] is H, CO$_2$H, CO$_2$Me, CO$_2$Et, or CONMe$_2$;
R[9] is selected from:

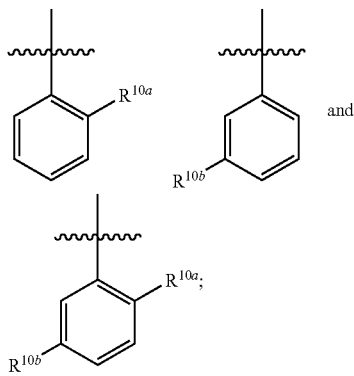

R[10a] is, independently at each occurrence, H, —SO$_2$Me, —SO$_2$Et, —SO$_2$Pr, —SO$_2$(i-Pr), —SO$_2$(i-Bu), —SO$_2$-cyclopropyl, —SO$_2$-cyclobutyl, —SO$_2$-cyclopentyl, —SO$_2$Ph, —SO$_2$-(1-pyrrolidinyl), —SO$_2$-(1-piperidyl), —SO$_2$-(1-azepanyl), —SO$_2$-(4-morpholinyl), —SO$_2$-(4-thiamorpholinyl), —SO$_2$-(4-Me-1-piperazinyl), —SO$_2$NH$_2$, —SO$_2$NHMe, —SO$_2$NHEt, —SO$_2$NH(i-Pr), —SO$_2$NH-cyclopropyl, —SO$_2$NH-cyclohexyl, —SO$_2$NH(t-Bu), —SO$_2$N(Me)Bn, —SO$_2$NMe$_2$, —OSO$_2$NH$_2$, —NHSO$_2$NH$_2$, —NHSO$_2$Me, Ph, 4-F-Ph, 1-piperidyl, 4-morpholinyl, 3,5-diethyl-1H-pyrazol-1-yl, NO$_2$; and
R[10b] is, independently at each occurrence, H, CONH$_2$, NH$_2$, NHMe, NHEt, NMe$_2$, —NHCOH, —NHCOMe, —NHCOEt, —NHCOPr, —NHCO(i-Pr), —NHCO(i-Bu), —NHCO-cyclopropyl, —N(Me)COMe, —NHCO$_2$Me, —NHCO$_2$Et, —NHCONH$_2$, —NHCONHMe, —NHCONMe$_2$, —NHCON(Me)Et, —NHCON(Me)(i-Pr), —NHCO-(1-azetidinyl), —NHCO-(1-pyrrolidinyl), or —NHCO-(3-thiazolidinyl).

6. A compound according to claim 3, wherein:

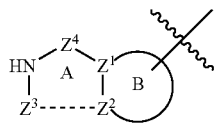

is selected from:

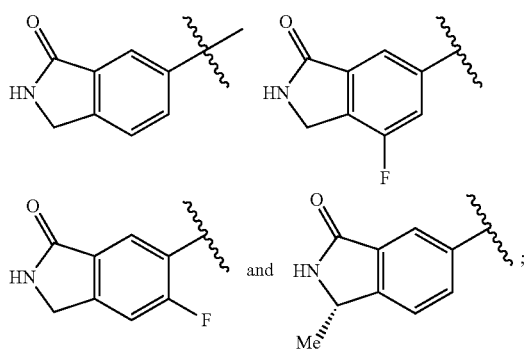

R[1] is Cl, Br, Me, Et, vinyl, 2-propenyl, ethynyl, —CH(OH)Me, OMe, OEt, cyclopropyl, —OCHF$_2$, or —OCF$_2$CHF$_2$;
R[2] is H, F, Cl, C$_{1-4}$ alkyl, C$_{1-4}$ alkoxy, or —OCHF$_2$;
R[3] is H, C$_{1-4}$ alkyl, or C$_{1-4}$ alkoxy;
R[4] is H or F;
R[7] is H, CO$_2$H, CO$_2$Me, CO$_2$Et, or CONMe$_2$;
R[9] is selected from:

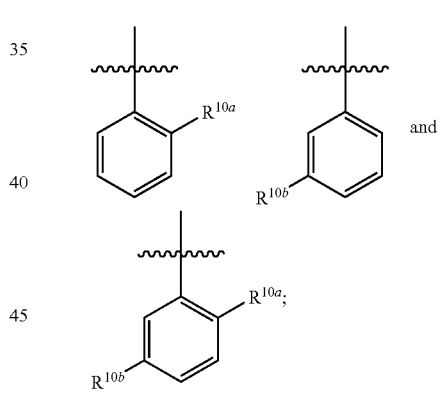

R[10a] is, independently at each occurrence, H, —SO$_2$Me, —SO$_2$Et, —SO$_2$Pr, —SO$_2$(i-Pr), —SO$_2$(i-Bu), —SO$_2$-cyclopropyl, —SO$_2$-cyclobutyl, —SO$_2$-cyclopentyl, —SO$_2$Ph, —SO$_2$-(1-pyrrolidinyl), —SO$_2$-(1-piperidyl), —SO$_2$-(1-azepanyl), —SO$_2$-(4-morpholinyl), —SO$_2$-(4-thiamorpholinyl), —SO$_2$-(4-Me-1-piperazinyl), —SO$_2$NH$_2$, —SO$_2$NHMe, —SO$_2$NHEt, —SO$_2$NH(i-Pr), —SO$_2$NH-cyclopropyl, —SO$_2$NH-cyclohexyl, —SO$_2$NH(t-Bu), —SO$_2$N(Me)Bn, —SO$_2$NMe$_2$, —OSO$_2$NH$_2$, —NHSO$_2$NH$_2$, —NHSO$_2$Me, Ph, 4-F-Ph, 1-piperidyl, 4-morpholinyl, 3,5-diethyl-1H-pyrazol-1-yl, NO$_2$; and
R[10b] is, independently at each occurrence, H, CONH$_2$, NH$_2$, NHMe, NHEt, NMe$_2$, —NHCOH, —NHCOMe, —NHCOEt, —NHCOPr, —NHCO(i-Pr), —NHCO(i-Bu), —NHCO-cyclopropyl, N(Me)COMe, —NHCO$_2$Me, —NHCO$_2$Et, —NHCONH$_2$, —NHCONHMe, —NHCONMe$_2$, —NHCON(Me)Et, —NHCON(Me)(i-Pr), —NHCO-(1-azetidinyl), —NHCO-(1-pyrrolidinyl), or —NHCO-(3-thiazolidinyl).

7. A compound according to claim 4, wherein:
$R^1$ is Cl, Me, Et, OMe, or OEt;
$R^2$ is F, Cl, OMe or O(i-Pr);
$R^3$ is H;
$R^4$ is H or F;
$R^7$ is H, $CO_2H$, $CO_2Me$, or $CO_2Et$;
$R^9$ is:

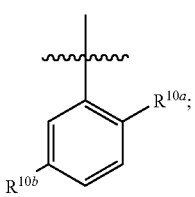

$R^{10a}$ is, independently at each occurrence, H, —$SO_2$—$C_{1-4}$ alkyl, —$SO_2$-cyclopropyl, —$SO_2$-cyclobutyl, —$SO_2$-cyclopentyl, —$SO_2Ph$, —$SO_2$-(1-pyrrolidinyl), —$SO_2$-(1-piperidyl), —$SO_2$-(1-azepanyl), —$SO_2NH$—$C_{1-4}$ alkyl, —$SO_2NH$-cyclopropyl, —$SO_2NMe_2$, $CONMe_2$, CO(1-pyrrolidinyl), CO(1-piperidinyl), 1-piperidyl, 4-morpholinyl, or 3,5-diethyl-1H-pyrazol-1-yl;

$R^{10b}$ is, independently at each occurrence, H, OH, $NH_2$, —NHCOH, —NHCOMe, —NHCOEt, —$NHCO_2Me$, —$NHCO_2Et$, —NHCONHMe, —$NHCONH_2$, —$NHCONMe_2$, —NHCON(Me)Et, —NHCON(Me)(i-Pr), —NHCO-(1-azetidinyl), —NHCO-(1-pyrrolidinyl), —NHCO-(3-thiazolidinyl), —$OSO_2NH_2$, —$NHSO_2NH_2$, —$NHSO_2Me$, —$SO_2NH_2$, or $NO_2$; and t is 1.

8. A compound according to claim 3, wherein the compound is of Formula (IIa):

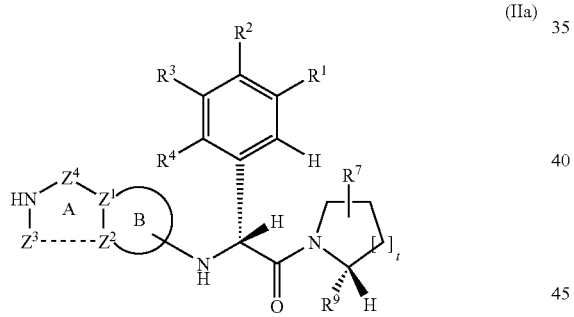

(IIa)

or stereoisomers, tautomers, pharmaceutically acceptable salts, thereof.

9. A compound according to claim 1, wherein the compound selected from the group consisting of:

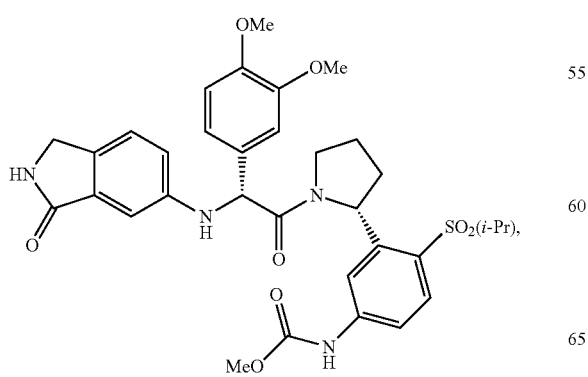

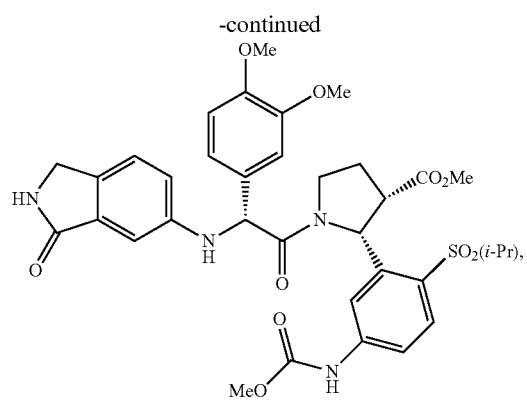

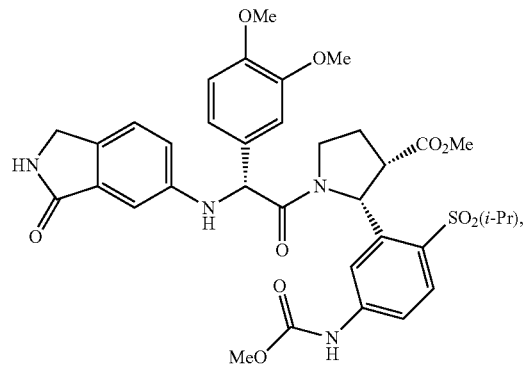

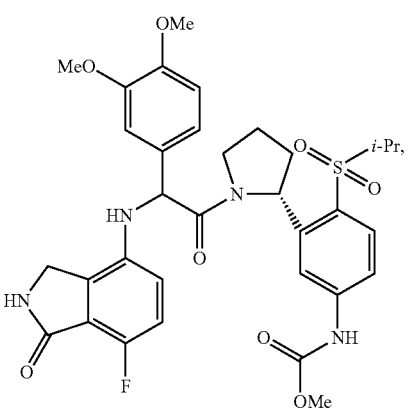

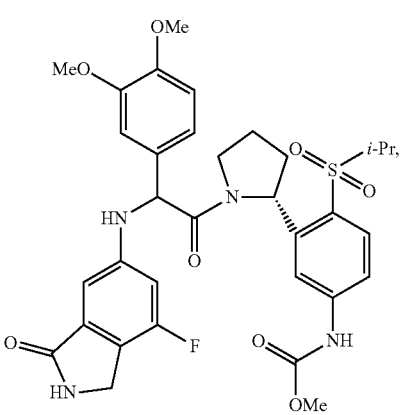

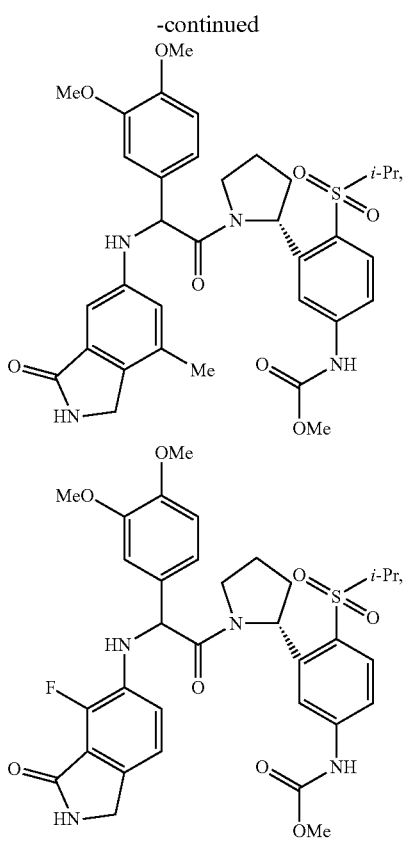
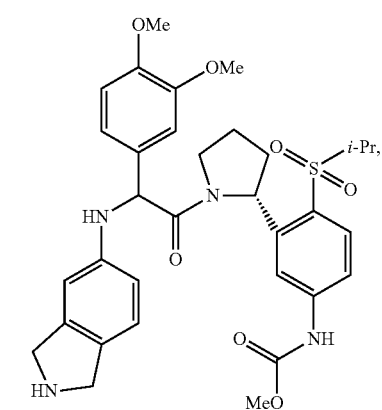
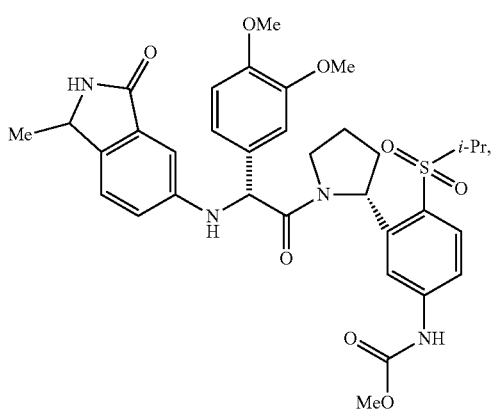
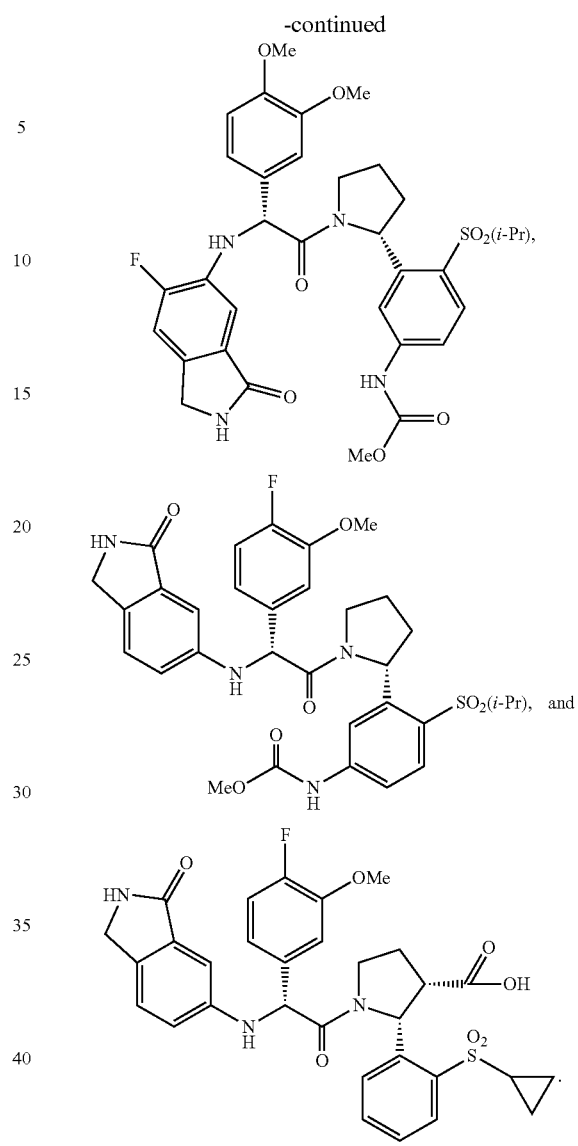

or stereoisomers, tautomers, or pharmaceutically acceptable salts, thereof.

10. A pharmaceutical composition, comprising: a pharmaceutically acceptable carrier and a compound of claim 3, or stereoisomers, tautomers, or pharmaceutically acceptable salts thereof.

11. A pharmaceutical composition, comprising: a pharmaceutically acceptable carrier and a compound of claim 4, or stereoisomers, tautomers, or pharmaceutically acceptable salts-thereof.

12. A pharmaceutical composition, comprising: a pharmaceutically acceptable carrier and a compound of claim 5, or stereoisomers, tautomers, or pharmaceutically acceptable salts-thereof.

13. A pharmaceutical composition, comprising: a pharmaceutically acceptable carrier and a compound of claim 6, or stereoisomers, tautomers, or pharmaceutically acceptable salts-thereof.

14. A pharmaceutical composition, comprising: a pharmaceutically acceptable carrier and a compound of claim 7, or stereoisomers, tautomers, or pharmaceutically acceptable salts-thereof.

15. A pharmaceutical composition, comprising: a pharmaceutically acceptable carrier and a compound of claim 8, or stereoisomers, tautomers, or pharmaceutically acceptable salts-thereof.

16. A pharmaceutical composition, comprising: a pharmaceutically acceptable carrier and a compound of claim 9, or stereoisomers, tautomers, or pharmaceutically acceptable salts-thereof.

* * * * *

UNITED STATES PATENT AND TRADEMARK OFFICE
CERTIFICATE OF CORRECTION

PATENT NO.        : 8,039,506 B2
APPLICATION NO.   : 12/519365
DATED             : October 18, 2011
INVENTOR(S)       : Nicholas Wurtz et al.

It is certified that error appears in the above-identified patent and that said Letters Patent is hereby corrected as shown below:

Column 1
Line 9, "Dec. 19, 2007" should read -- Dec. 17, 2007 --.

Column 147
Line 11, "O-NR$^d$C(O)OR$^a$," should read -- -NR$^d$C(O)OR$^a$ --.

Column 148
Line 5, before "and" insert -- 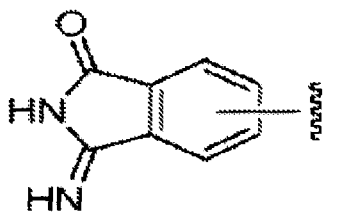 --.

Column 148
Line 60, before "and" insert -- 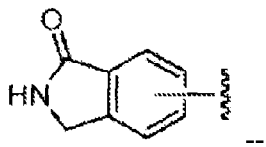 --.

Signed and Sealed this
Twenty-seventh Day of December, 2011

David J. Kappos
Director of the United States Patent and Trademark Office

CERTIFICATE OF CORRECTION (continued)

U.S. Pat. No. 8,039,506 B2

Column 154
Line 16-30,

" 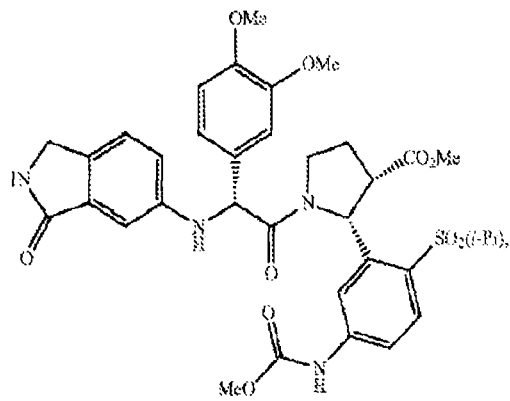 " should read

-- 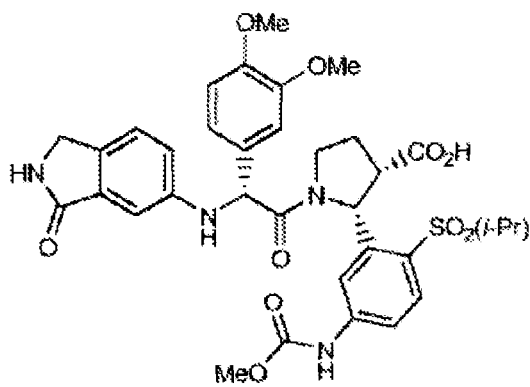 --.